United States Patent
Pooth et al.

(10) Patent No.: US 11,944,849 B2
(45) Date of Patent: Apr. 2, 2024

(54) SYSTEMS AND METHODS FOR COMBINED COSMETIC TREATMENT OF CELLULITE WITH ULTRASOUND

(71) Applicant: Ulthera, Inc., Mesa, AZ (US)

(72) Inventors: Rainer Pooth, Bad Soden (DE); Harry Frank Abts, Oberursel (DE); Charles D. Emery, Gilbert, AZ (US); Wojciech Danysz, Nidderau (DE)

(73) Assignee: Ulthera, Inc., Mesa, AZ (US)

( * ) Notice: Subject to any disclaimer, the term of this patent is extended or adjusted under 35 U.S.C. 154(b) by 820 days.

(21) Appl. No.: 16/970,772

(22) PCT Filed: Feb. 19, 2019

(86) PCT No.: PCT/US2019/018561
§ 371 (c)(1),
(2) Date: Aug. 18, 2020

(87) PCT Pub. No.: WO2019/164836
PCT Pub. Date: Aug. 29, 2019

(65) Prior Publication Data
US 2021/0093898 A1    Apr. 1, 2021

Related U.S. Application Data

(60) Provisional application No. 62/632,741, filed on Feb. 20, 2018, provisional application No. 62/662,394, filed on Apr. 25, 2018.

(51) Int. Cl.
*A61N 7/02*   (2006.01)
*A61K 41/00*  (2020.01)
*A61N 7/00*   (2006.01)

(52) U.S. Cl.
CPC .......... *A61N 7/02* (2013.01); *A61K 41/0028* (2013.01); *A61N 2007/0008* (2013.01); *A61N 2007/0034* (2013.01); *A61N 2007/0039* (2013.01)

(58) Field of Classification Search
CPC .............. A61N 7/02; A61N 2007/0008; A61N 2007/0034; A61N 2007/0039;
(Continued)

(56) References Cited

U.S. PATENT DOCUMENTS

| 2,427,348 A | 9/1947 | Bond et al. |
| 2,792,829 A | 2/1952 | Calosi |

(Continued)

FOREIGN PATENT DOCUMENTS

| CN | 2460061 | 11/2001 |
| CN | 1734284 | 12/2009 |

(Continued)

OTHER PUBLICATIONS

US 10,398,895 B2, 09/2019, Schwarz (withdrawn)
(Continued)

*Primary Examiner* — Hien N Nguyen
(74) *Attorney, Agent, or Firm* — Knobbe Martens Olson & Bear LLP

(57) ABSTRACT

Dermatological cosmetic combination treatments with high intensity focused ultrasound, dermal fillers, fat-reducing compounds, cavitation-prone fluids, and/or septa dissection are provided. A HIFU therapy system can include an imaging system, methods adapted to alter placement and position of a line focus band therapy, multiple simultaneous cosmetic ultrasound treatment zones in tissue, and dithering ultrasound beams from a transducer to alter placement and position of multiple cosmetic treatment zones in tissue. The HIFU systems can include a hand wand, removable trans- (Continued)

ducer modules, and a control module. The dermal fillers can include hydroxyapatite. The fat-reducing compounds can include adipocytolytic compounds, pentacyclic triterpenoid compounds, proapoptotic compounds, compounds impairing differentiation of pre-adipocytes, and combinations thereof. The cavitation-prone fluids can include molecules dissolved in fluids, ethanol, glycerin, and ethylene glycol. The septa dissecting can include using a cutting blade and/or cavitation HIFU. The cosmetic treatment system may be used in various cosmetic procedures, such as treating cellulite.

20 Claims, 26 Drawing Sheets

(58) Field of Classification Search
CPC .... A61N 2007/0052; A61N 2007/0082; A61N 2007/0095; A61N 2007/027; A61K 41/0028; A61K 31/045; A61K 33/42; A61B 8/4209; A61B 8/4245; A61B 8/4455; A61B 8/4461; A61B 8/4405; A61B 8/4411; A61B 8/4427; A61B 8/4477; A61L 27/52; A61L 27/54; A61L 27/46; A61L 2400/06; A61L 2430/34
See application file for complete search history.

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,151,834 A | 5/1979 | Sato et al. |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,417,170 A | 11/1983 | Benisncasa |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,587,971 A | 5/1986 | Stolfi |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,054,491 A | 10/1991 | Saito et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,142,511 A | 8/1992 | Kanai et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |

(56) References Cited

U.S. PATENT DOCUMENTS

| | | |
|---|---|---|
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,329,202 A | 7/1994 | Garlick et al. |
| 5,348,016 A | 9/1994 | Unger et al. |
| 5,358,466 A | 10/1994 | Aida et al. |
| 5,360,268 A | 11/1994 | Hayashi |
| 5,370,121 A | 12/1994 | Reichenberger |
| 5,370,122 A | 12/1994 | Kunig |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams |
| 5,413,550 A | 5/1995 | Castel |
| 5,417,216 A | 5/1995 | Tanaka |
| 5,423,220 A | 6/1995 | Finsterwald et al. |
| 5,435,311 A | 7/1995 | Umemura |
| 5,438,998 A | 8/1995 | Hanafy |
| 5,443,068 A | 8/1995 | Cline et al. |
| 5,445,611 A | 8/1995 | Eppstein et al. |
| 5,458,596 A | 10/1995 | Lax |
| 5,460,179 A | 10/1995 | Okunuki et al. |
| 5,460,595 A | 10/1995 | Hall et al. |
| 5,419,327 A | 11/1995 | Rohwedder |
| 5,469,854 A | 11/1995 | Unger et al. |
| 5,471,488 A | 12/1995 | Fujio |
| 5,472,405 A | 12/1995 | Buchholtz et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,511,296 A | 4/1996 | Dias et al. |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenchein |
| 5,524,624 A | 6/1996 | Tepper |
| 5,524,625 A | 6/1996 | Okazaki |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,573,497 A | 11/1996 | Chapelon |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,643,179 A | 1/1997 | Fujimoto |
| 5,601,526 A | 2/1997 | Chapelon |
| 5,603,323 A | 2/1997 | Pflugrath et al. |
| 5,605,154 A | 2/1997 | Ries et al. |
| 5,609,562 A | 3/1997 | Kaali |
| 5,615,091 A | 3/1997 | Palatnik |
| 5,618,275 A | 4/1997 | Bock |
| 5,620,479 A | 4/1997 | Diederich |
| 5,622,175 A | 4/1997 | Sudol et al. |
| 5,617,858 A | 5/1997 | Taverna et al. |
| 5,638,819 A | 6/1997 | Manwaring et al. |
| 5,644,085 A | 7/1997 | Lorraine et al. |
| 5,647,373 A | 7/1997 | Paltieli |
| 5,655,535 A | 8/1997 | Frlemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,740,804 A | 4/1998 | Cerofolini |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,866,024 A | 2/1999 | Villenueve |
| 5,869,751 A | 2/1999 | Bonin |
| 5,871,524 A | 2/1999 | Knowlton |
| 5,873,902 A | 2/1999 | Sanghvi |
| 5,876,341 A | 3/1999 | Wang et al. |
| 5,879,303 A | 3/1999 | Averkiou et al. |
| 5,882,557 A | 3/1999 | Hayakawa |
| 5,891,034 A | 4/1999 | Bucholz |
| 5,895,356 A | 4/1999 | Andrus et al. |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,964,707 A | 10/1999 | Fenster et al. |
| 5,967,980 A | 10/1999 | Ferre et al. |
| 5,968,034 A | 10/1999 | Fullmer |
| 5,971,949 A | 10/1999 | Levin |

(56) References Cited

U.S. PATENT DOCUMENTS

| | | |
|---|---|---|
| 5,977,538 A | 11/1999 | Unger et al. |
| 5,984,881 A | 11/1999 | Ishibashi et al. |
| 5,984,882 A | 11/1999 | Rosenchein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,014,473 A | 1/2000 | Hossack et al. |
| 6,016,255 A | 1/2000 | Bolan et al. |
| 6,019,724 A | 2/2000 | Gronningsaeter et al. |
| 6,022,308 A | 2/2000 | Williams |
| 6,022,317 A | 2/2000 | Cruanas et al. |
| 6,022,327 A | 2/2000 | Chang |
| 6,030,374 A | 2/2000 | McDaniel |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,148 A | 7/2000 | Fujimoto |
| 6,093,883 A | 7/2000 | Sanghvi |
| 6,100,626 A | 8/2000 | Frey et al. |
| 6,101,407 A | 8/2000 | Groezinger |
| 6,106,469 A | 8/2000 | Suzuki et al. |
| 6,113,558 A | 9/2000 | Rosenchein |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias |
| 6,190,336 B1 | 2/2001 | Duarte |
| 6,193,658 B1 | 2/2001 | Wendelken |
| 6,198,956 B1 | 3/2001 | Dunne |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,287,304 B1 | 9/2001 | Eggers et al. |
| 6,296,619 B1 | 10/2001 | Brisken |
| 6,301,989 B1 | 10/2001 | Brown et al. |
| 6,307,302 B1 | 10/2001 | Toda |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,447,443 B1 | 9/2002 | Keogh et al. |
| 6,450,979 B1 | 9/2002 | Miwa et al. |
| 6,451,013 B1 | 9/2002 | Bays et al. |
| 6,453,202 B1 | 9/2002 | Knowlton |
| 6,461,304 B1 | 10/2002 | Tanaka et al. |
| 6,461,378 B1 | 10/2002 | Knowlton |
| 6,470,216 B1 | 10/2002 | Knowlton |
| 6,338,716 B1 | 11/2002 | Hossack |
| 6,485,420 B1 | 11/2002 | Bullis |
| 6,488,626 B1 | 12/2002 | Lizzi |
| 6,491,657 B2 | 12/2002 | Rowe |
| 6,500,121 B1 | 12/2002 | Slayton |
| 6,500,141 B1 | 12/2002 | Irion |
| 6,506,171 B1 | 1/2003 | Vitek et al. |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk |
| 6,524,250 B1 | 2/2003 | Weber |
| 6,666,835 B2 | 3/2003 | Martin |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,547,788 B1 | 4/2003 | Maguire et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,605,043 B1 | 8/2003 | Dreschel |
| 6,605,080 B1 | 8/2003 | Altshuler et al. |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,145 B1 | 11/2003 | Dreschel et al. |
| 6,645,150 B2 | 11/2003 | Angelsen et al. |
| 6,645,162 B2 | 11/2003 | Friedman |
| 6,662,054 B2 | 12/2003 | Kreindel |

(56) References Cited

U.S. PATENT DOCUMENTS

| | | |
|---|---|---|
| 6,663,627 B2 | 12/2003 | Francischelli |
| 6,665,806 B1 | 12/2003 | Shimizu |
| 6,669,638 B1 | 12/2003 | Miller |
| 6,673,017 B1 | 1/2004 | Jackson |
| 6,685,639 B1 | 2/2004 | Wang et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,772,490 B2 | 8/2004 | Toda |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,825,176 B2 | 11/2004 | White |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,887,260 B1 | 5/2005 | McDaniel |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,713,203 B2 | 3/2010 | Lacoste et al. |
| 7,694,406 B2 | 4/2010 | Wildes et al. |
| 7,695,437 B2 | 4/2010 | Quistgaard et al. |
| 7,727,156 B2 | 6/2010 | Angelsen et al. |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,828,734 B2 | 10/2010 | Azhari et al. |
| 7,824,348 B2 | 11/2010 | Barthe |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,955,281 B2 | 6/2011 | Pedersen et al. |
| 7,967,764 B2 | 6/2011 | Lidgren et al. |
| 7,967,839 B2 | 6/2011 | Flock et al. |
| 7,955,262 B2 | 7/2011 | Rosenberg |
| 7,993,289 B2 | 8/2011 | Quistgaard et al. |
| 8,057,465 B2 | 9/2011 | Sliwa, Jr. et al. |
| 8,057,389 B2 | 11/2011 | Barthe et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |
| 8,333,700 B1 | 12/2012 | Barthe et al. |
| 8,334,637 B2 | 12/2012 | Crunkilton et al. |
| 8,337,407 B2 | 12/2012 | Quistgaard et al. |
| 8,343,051 B2 | 1/2013 | Desilets et al. |
| 8,454,540 B2 | 1/2013 | Eshel et al. |
| 8,366,622 B2 | 2/2013 | Slayton et al. |
| 8,398,549 B2 | 3/2013 | Palmeri et al. |
| 8,409,097 B2 | 4/2013 | Slayton et al. |
| 8,425,435 B2 | 4/2013 | Wing et al. |
| 8,388,535 B2 | 5/2013 | Weng et al. |
| 8,444,562 B2 | 5/2013 | Barthe et al. |

(56) References Cited

U.S. PATENT DOCUMENTS

| | | |
|---|---|---|
| 8,460,193 B2 | 6/2013 | Barthe et al. |
| 8,480,585 B2 | 7/2013 | Slayton et al. |
| 8,486,001 B2 | 7/2013 | Weyant |
| 8,506,486 B2 | 8/2013 | Slayton et al. |
| 8,512,250 B2 | 8/2013 | Quistgaard et al. |
| 8,523,775 B2 | 9/2013 | Barthe et al. |
| 8,523,849 B2 | 9/2013 | Liu et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |
| 8,622,937 B2 | 1/2014 | Weng et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 | 12/2014 | Barthe et al. |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |
| 8,926,533 B2 | 1/2015 | Bockenstedt et al. |
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,050,116 B2 | 6/2015 | Homer |
| 9,095,697 B2 | 8/2015 | Barthe et al. |
| 9,107,798 B2 | 8/2015 | Azhari et al. |
| 9,114,247 B2 | 8/2015 | Barthe et al. |
| 9,180,314 B2 | 11/2015 | Desilets et al. |
| 9,216,276 B2 | 12/2015 | Slayton et al. |
| 9,220,915 B2 | 12/2015 | Liu et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,295,607 B2 | 3/2016 | Rosenberg |
| 9,308,390 B2 | 4/2016 | Youngquist |
| 9,308,391 B2 | 4/2016 | Liu et al. |
| 9,314,650 B2 | 4/2016 | Rosenberg et al. |
| 9,320,537 B2 | 4/2016 | Slayton et al. |
| 9,345,910 B2 | 5/2016 | Slayton et al. |
| 9,421,029 B2 | 8/2016 | Barthe et al. |
| 9,427,600 B2 | 8/2016 | Barthe et al. |
| 9,427,601 B2 | 8/2016 | Barthe et al. |
| 9,433,803 B2 | 9/2016 | Lin et al. |
| 9,440,093 B2 | 9/2016 | Homer |
| 9,440,096 B2 | 9/2016 | Barthe et al. |
| 9,492,645 B2 | 11/2016 | Zhou et al. |
| 9,492,686 B2 | 11/2016 | Da Silva |
| 9,498,651 B2 | 11/2016 | Sapozhnikov et al. |
| 9,510,802 B2 | 12/2016 | Barthe et al. |
| 9,522,290 B2 | 12/2016 | Slayton et al. |
| 9,532,832 B2 | 1/2017 | Ron Edoute et al. |
| 9,533,174 B2 | 1/2017 | Barthe et al. |
| 9,533,175 B2 | 1/2017 | Slayton et al. |
| 9,545,529 B2 | 1/2017 | Britva et al. |
| 9,566,454 B2 | 2/2017 | Barthe et al. |
| 9,623,267 B2 | 4/2017 | Ulric et al. |
| 9,694,211 B2 | 7/2017 | Barthe et al. |
| 9,694,212 B2 | 7/2017 | Barthe et al. |
| 9,700,340 B2 | 7/2017 | Barthe et al. |
| 9,707,412 B2 | 7/2017 | Slayton et al. |
| 9,710,607 B2 | 7/2017 | Ramdas et al. |
| 9,713,731 B2 | 7/2017 | Slayton et al. |
| 9,802,063 B2 | 10/2017 | Barthe et al. |
| 9,827,449 B2 | 11/2017 | Barthe et al. |
| 9,827,450 B2 | 11/2017 | Slayton et al. |
| 9,833,639 B2 | 12/2017 | Slayton et al. |
| 9,833,640 B2 | 12/2017 | Barthe et al. |
| 9,895,560 B2 | 2/2018 | Barthe et al. |
| 9,907,535 B2 | 3/2018 | Barthe et al. |
| 9,919,167 B2 | 3/2018 | Domankevitz |
| 9,974,982 B2 | 5/2018 | Slayton et al. |
| 9,993,664 B2 | 6/2018 | Aviad et al. |
| 10,010,721 B2 | 7/2018 | Slayton et al. |
| 10,010,724 B2 | 7/2018 | Barthe et al. |
| 10,010,725 B2 | 7/2018 | Slayton et al. |
| 10,010,726 B2 | 7/2018 | Barthe et al. |
| 10,016,626 B2 | 7/2018 | Zovrin et al. |
| 10,046,181 B2 | 8/2018 | Barthe et al. |
| 10,046,182 B2 | 8/2018 | Barthe et al. |
| 10,070,883 B2 | 9/2018 | Barthe et al. |
| 10,183,183 B2 | 1/2019 | Burdette |
| 10,226,645 B2 | 3/2019 | Barthe |
| 10,238,894 B2 | 3/2019 | Slayton et al. |
| 10,245,450 B2 | 4/2019 | Slayton et al. |
| 10,252,086 B2 | 4/2019 | Barthe et al. |
| 10,265,550 B2 | 4/2019 | Barthe et al. |
| 10,272,272 B2 | 4/2019 | Lee et al. |
| 10,300,308 B2 | 5/2019 | Seip et al. |
| 10,328,289 B2 | 6/2019 | Barthe et al. |
| 10,363,440 B2 | 6/2019 | Cho et al. |
| 10,406,383 B2 | 9/2019 | Luebcke |
| 10,420,960 B2 | 9/2019 | Emery |
| 10,420,961 B2 | 9/2019 | Lacoste |
| 10,485,573 B2 | 11/2019 | Clark, III et al. |
| 10,492,862 B2 | 12/2019 | Domankevitz |
| 10,525,288 B2 | 1/2020 | Slayton et al. |
| 10,532,230 B2 | 1/2020 | Barthe et al. |
| 10,537,304 B2 | 1/2020 | Barthe et al. |
| 10,556,123 B2 | 2/2020 | Altshuler et al. |
| 10,583,287 B2 | 3/2020 | Schwarz |
| 10,603,519 B2 | 3/2020 | Slayton et al. |
| 10,603,521 B2 | 3/2020 | Emery et al. |
| 10,603,523 B2 | 3/2020 | Slayton et al. |
| 10,610,705 B2 | 4/2020 | Barthe et al. |
| 10,610,706 B2 | 4/2020 | Barthe et al. |
| 10,639,006 B2 | 5/2020 | Choi et al. |
| 10,639,504 B2 | 5/2020 | Kim |
| 10,751,246 B2 | 8/2020 | Kaila |
| 10,772,646 B2 | 9/2020 | Lu et al. |
| 10,780,298 B2 | 9/2020 | Cain et al. |
| 10,888,716 B2 | 1/2021 | Slayton et al. |
| 10,888,717 B2 | 1/2021 | Slayton et al. |
| 10,888,718 B2 | 1/2021 | Barthe et al. |
| 10,960,235 B2 | 3/2021 | Barthe et al. |
| 10,960,236 B2 | 3/2021 | Slayton et al. |
| 11,123,039 B2 | 9/2021 | Barthe et al. |
| 11,167,155 B2 | 11/2021 | Barthe et al. |
| 11,179,580 B2 | 11/2021 | Slayton et al. |
| 11,207,547 B2 | 12/2021 | Slayton et al. |
| 11,207,548 B2 | 12/2021 | Barthe et al. |
| 11,224,895 B2 | 1/2022 | Brown et al. |
| 11,235,179 B2 | 2/2022 | Barthe et al. |
| 11,235,180 B2 | 2/2022 | Slayton et al. |
| 11,241,218 B2 | 2/2022 | Emery et al. |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1 | 10/2001 | Weng |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |

(56) References Cited

U.S. PATENT DOCUMENTS

| | | |
|---|---|---|
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |
| 2002/0095143 A1 | 7/2002 | Key |
| 2002/0099094 A1 | 7/2002 | Anderson |
| 2002/0111569 A1 | 8/2002 | Rosenschien et al. |
| 2002/0115917 A1 | 8/2002 | Honda et al. |
| 2002/0128639 A1 | 8/2002 | Pless et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1 | 1/2003 | McDaniel |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055308 A1 | 3/2003 | Friemel et al. |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0066708 A1 | 4/2003 | Allison et al. |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0149366 A1 | 8/2003 | Stringer et al. |
| 2003/0153961 A1 | 8/2003 | Babaev |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0199794 A1 | 10/2003 | Sakurai et al. |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002658 A1 | 1/2004 | Marian, Jr. |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0030268 A1 | 2/2004 | Weng et al. |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Tosaya et al. |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0007879 A1 | 1/2005 | Nishida |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0085731 A1 | 4/2005 | Miller et al. |
| 2005/0091770 A1 | 5/2005 | Mourad et al. |
| 2005/0096542 A1 | 5/2005 | Weng |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0193820 A1 | 9/2005 | Sheljaskow et al. |
| 2005/0197681 A1 | 9/2005 | Barolet et al. |
| 2005/0228281 A1 | 10/2005 | Nefos |
| 2005/0240127 A1 | 10/2005 | Seip et al. |
| 2005/0240170 A1 | 10/2005 | Zhang et al. |
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |

(56) References Cited

U.S. PATENT DOCUMENTS

| | | |
|---|---|---|
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0106325 A1 | 5/2006 | Perrier |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0224090 A1 | 10/2006 | Ostrovsky et al. |
| 2006/0229514 A1 | 10/2006 | Wiener |
| 2006/0238068 A1 | 10/2006 | May et al. |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0016039 A1 | 1/2007 | Vortman et al. |
| 2007/0032784 A1 | 2/2007 | Gilklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0078290 A1 * | 4/2007 | Esenaliev ............. A61N 7/00 600/1 |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0018553 A1 | 8/2007 | Kennedy |
| 2007/0208253 A1 | 9/2007 | Slayton |
| 2007/0219448 A1 | 9/2007 | Seip et al. |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0015435 A1 | 1/2008 | Cribbs et al. |
| 2008/0027328 A1 | 1/2008 | Klopotek |
| 2008/0033458 A1 | 2/2008 | McLean et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0086056 A1 | 4/2008 | Chang et al. |
| 2008/0097214 A1 | 4/2008 | Meyers et al. |
| 2008/0097253 A1 | 4/2008 | Pedersen et al. |
| 2008/0114251 A1 | 5/2008 | Weymer et al. |
| 2008/0139943 A1 | 6/2008 | Deng et al. |
| 2008/0139974 A1 | 6/2008 | Da Silva |
| 2008/0146970 A1 | 6/2008 | Litman et al. |
| 2008/0167556 A1 | 7/2008 | Thompson |
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1 | 8/2008 | Randall et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0214988 A1 | 9/2008 | Altshuler et al. |
| 2008/0221491 A1 | 9/2008 | Slayton |
| 2008/0223379 A1 | 9/2008 | Stuker et al. |
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294072 A1 | 11/2008 | Crutchfield, III |
| 2008/0294073 A1 | 11/2008 | Barthe |
| 2008/0319356 A1 | 12/2008 | Cain |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0163807 A1 | 6/2009 | Sliwa |
| 2009/0171252 A1 | 7/2009 | Bockenstedt et al. |
| 2009/0171266 A1 * | 7/2009 | Harris ................. A61N 7/02 604/22 |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0230823 A1 | 9/2009 | Kushculey et al. |
| 2009/0240146 A1 | 9/2009 | Bockenstedt et al. |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1 | 2/2010 | Vortman et al. |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0056962 A1 | 3/2010 | Vortman et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Douglas et al. |
| 2011/0040171 A1 | 2/2011 | Foley et al. |
| 2011/0040190 A1 | 2/2011 | Jahnke et al. |
| 2011/0040213 A1 | 2/2011 | Dietz et al. |
| 2011/0040214 A1 | 2/2011 | Foley et al. |
| 2011/0066084 A1 | 3/2011 | Desilets et al. |
| 2011/0072970 A1 | 3/2011 | Slobodzian et al. |
| 2011/0077514 A1 | 3/2011 | Ulric et al. |
| 2011/0079083 A1 | 4/2011 | Yoo et al. |
| 2011/0087099 A1 | 4/2011 | Eshel et al. |
| 2011/0087255 A1 | 4/2011 | McCormack et al. |

(56) References Cited

U.S. PATENT DOCUMENTS

| | | |
|---|---|---|
| 2011/0112405 A1 | 5/2011 | Barthe et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0201976 A1 | 8/2011 | Sanghvi et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |
| 2011/0319793 A1 | 12/2011 | Henrik et al. |
| 2011/0319794 A1 | 12/2011 | Gertner |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035473 A1 | 2/2012 | Sanghvi et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0059288 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191019 A1 | 7/2012 | Desilets et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1 | 10/2012 | Barthe et al. |
| 2012/0277639 A1 | 11/2012 | Pollock et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0073001 A1 | 3/2013 | Campbell |
| 2013/0096471 A1 | 4/2013 | Slayton et al. |
| 2013/0096596 A1 | 4/2013 | Schafer |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0278111 A1 | 10/2013 | Sammoura |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0296743 A1 | 11/2013 | Lee et al. |
| 2013/0303904 A1 | 11/2013 | Barthe et al. |
| 2013/0303905 A1 | 11/2013 | Barthe et al. |
| 2013/0310714 A1 | 11/2013 | Eshel et al. |
| 2013/0310863 A1 | 11/2013 | Makin et al. |
| 2013/0345562 A1 | 12/2013 | Barthe et al. |
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |
| 2014/0155747 A1 | 6/2014 | Bennett |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |
| 2014/0236061 A1 | 8/2014 | Lee et al. |
| 2014/0243713 A1 | 8/2014 | Slayton et al. |
| 2014/0257145 A1 | 9/2014 | Emery |
| 2014/0276055 A1 | 9/2014 | Barthe et al. |
| 2014/0316269 A1 | 10/2014 | Zhang et al. |
| 2015/0000674 A1 | 1/2015 | Barthe et al. |
| 2015/0025420 A1 | 1/2015 | Slayton et al. |
| 2015/0064165 A1* | 3/2015 | Perry .............. A61B 17/3421 424/94.67 |
| 2015/0080723 A1 | 3/2015 | Barthe et al. |
| 2015/0080771 A1 | 3/2015 | Barthe et al. |
| 2015/0080874 A1 | 3/2015 | Slayton et al. |
| 2015/0088182 A1 | 3/2015 | Slayton et al. |
| 2015/0141734 A1 | 5/2015 | Chapelon et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0238258 A1 | 8/2015 | Palero et al. |
| 2015/0297188 A1 | 10/2015 | Konofagou |
| 2015/0321026 A1 | 11/2015 | Branson et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0001097 A1 | 1/2016 | Cho et al. |
| 2016/0016015 A1 | 1/2016 | Slayton et al. |
| 2016/0027994 A1 | 1/2016 | Toda et al. |
| 2016/0151618 A1 | 6/2016 | Powers et al. |
| 2016/0158580 A1 | 6/2016 | Slayton et al. |
| 2016/0175619 A1 | 6/2016 | Lee et al. |
| 2016/0206335 A1 | 7/2016 | Slayton |
| 2016/0206341 A1 | 7/2016 | Slayton |
| 2016/0256675 A1 | 9/2016 | Slayton |
| 2016/0296769 A1 | 10/2016 | Barthe et al. |
| 2016/0310444 A1* | 10/2016 | Dobak, III ............. A61K 47/10 |
| 2016/0361571 A1 | 12/2016 | Bernabei |
| 2016/0361572 A1 | 12/2016 | Slayton |
| 2017/0028227 A1 | 2/2017 | Emery et al. |
| 2017/0043190 A1 | 2/2017 | Barthe et al. |
| 2017/0050019 A1 | 2/2017 | Ron Edoute et al. |
| 2017/0080257 A1 | 3/2017 | Paunescu et al. |
| 2017/0090507 A1 | 3/2017 | Weiner et al. |
| 2017/0100585 A1 | 4/2017 | Hall et al. |
| 2017/0119345 A1 | 5/2017 | Levien et al. |
| 2017/0136263 A1 | 5/2017 | Reil |
| 2017/0209201 A1 | 7/2017 | Slayton et al. |
| 2017/0209202 A1 | 7/2017 | Friedrichs et al. |
| 2017/0304654 A1 | 10/2017 | Blanche et al. |
| 2017/0368574 A1 | 12/2017 | Sammoura |
| 2018/0001113 A1 | 1/2018 | Streeter |
| 2018/0015308 A1 | 1/2018 | Reed et al. |
| 2018/0043147 A1 | 2/2018 | Slayton |
| 2018/0099162 A1 | 4/2018 | Bernabei |
| 2018/0099163 A1 | 4/2018 | Bernabei |
| 2018/0126190 A1 | 5/2018 | Aviad et al. |
| 2018/0154184 A1 | 6/2018 | Kong et al. |
| 2018/0177912 A1* | 6/2018 | Kasioptas ............. A61L 27/025 |
| 2018/0207450 A1 | 7/2018 | Sanchez et al. |
| 2018/0272156 A1 | 9/2018 | Slayton et al. |
| 2018/0272157 A1 | 9/2018 | Barthe et al. |

(56) References Cited

U.S. PATENT DOCUMENTS

| | | | |
|---|---|---|---|
| 2018/0272158 | A1 | 9/2018 | Barthe et al. |
| 2018/0272159 | A1 | 9/2018 | Slayton et al. |
| 2018/0317884 | A1 | 11/2018 | Chapelon et al. |
| 2018/0333595 | A1 | 11/2018 | Barthe et al. |
| 2018/0360420 | A1 | 12/2018 | Vortman et al. |
| 2019/0000498 | A1 | 1/2019 | Barthe et al. |
| 2019/0009110 | A1 | 1/2019 | Gross et al. |
| 2019/0009111 | A1 | 1/2019 | Myhr et al. |
| 2019/0022405 | A1 | 1/2019 | Greenbaum et al. |
| 2019/0038921 | A1 | 2/2019 | Domankevitz |
| 2019/0060675 | A1 | 2/2019 | Krone et al. |
| 2019/0091490 | A1 | 3/2019 | Alexander et al. |
| 2019/0142380 | A1 | 5/2019 | Emery et al. |
| 2019/0143148 | A1 | 5/2019 | Slayton |
| 2019/0184202 | A1 | 6/2019 | Zereshkian et al. |
| 2019/0184203 | A1 | 6/2019 | Slayton et al. |
| 2019/0184205 | A1 | 6/2019 | Slayton et al. |
| 2019/0184207 | A1 | 6/2019 | Barthe et al. |
| 2019/0184208 | A1 | 6/2019 | Barthe et al. |
| 2019/0224501 | A1 | 7/2019 | Burdette |
| 2019/0262634 | A1 | 8/2019 | Barthe et al. |
| 2019/0282834 | A1 | 9/2019 | Zawada et al. |
| 2019/0290939 | A1 | 9/2019 | Watson et al. |
| 2019/0350562 | A1 | 11/2019 | Slayton et al. |
| 2019/0366126 | A1 | 12/2019 | Pahk et al. |
| 2019/0366127 | A1 | 12/2019 | Emery |
| 2019/0366128 | A1 | 12/2019 | Slayton et al. |
| 2020/0094083 | A1 | 3/2020 | Slayton et al. |
| 2020/0100762 | A1 | 4/2020 | Barthe et al. |
| 2020/0129759 | A1 | 4/2020 | Schwarz |
| 2020/0171330 | A1 | 6/2020 | Barthe et al. |
| 2020/0179727 | A1 | 6/2020 | Slayton et al. |
| 2020/0179729 | A1 | 6/2020 | Slayton et al. |
| 2020/0188703 | A1 | 6/2020 | Barthe et al. |
| 2020/0188704 | A1 | 6/2020 | Barthe et al. |
| 2020/0188705 | A1 | 6/2020 | Emery et al. |
| 2020/0206072 | A1 | 7/2020 | Capelli et al. |
| 2020/0222728 | A1 | 7/2020 | Khokhlova et al. |
| 2021/0038925 | A1 | 2/2021 | Emery |
| 2021/0378630 | A1 | 12/2021 | Slayton et al. |

FOREIGN PATENT DOCUMENTS

| | | |
|---|---|---|
| CN | 104027893 | 9/2014 |
| DE | 4029175 | 3/1992 |
| DE | 10140064 | 3/2003 |
| DE | 10219297 | 11/2003 |
| DE | 10219217 | 12/2004 |
| DE | 20314479 | 12/2004 |
| EP | 0142215 | 5/1984 |
| EP | 0344773 | 12/1989 |
| EP | 1479412 | 11/1991 |
| EP | 0473553 | 4/1992 |
| EP | 670147 | 2/1995 |
| EP | 0661029 | 7/1995 |
| EP | 724894 | 2/1996 |
| EP | 763371 | 11/1996 |
| EP | 1044038 | 10/2000 |
| EP | 1050322 | 11/2000 |
| EP | 1234566 | 8/2002 |
| EP | 1262160 | 12/2002 |
| EP | 0659387 | 4/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1283690 | 11/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| EP | 2527828 | 11/2012 |
| EP | 2709726 | 11/2015 |
| EP | 1538980 | 1/2017 |
| EP | 3124047 | 1/2017 |
| EP | 2897547 | 11/2017 |
| EP | 2173261 B1 | 8/2018 |
| EP | 3417911 | 12/2018 |
| FR | 2532851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 3053069 | 10/1998 |
| JP | 11123226 | 5/1999 |
| JP | 11505440 | 5/1999 |
| JP | 11506636 | 6/1999 |
| JP | 10248850 | 9/1999 |
| JP | 2000126310 | 5/2000 |
| JP | 2000166940 | 6/2000 |
| JP | 2000233009 | 8/2000 |
| JP | 2001-46387 | 2/2001 |
| JP | 2001136599 A | 5/2001 |
| JP | 2001170068 | 6/2001 |
| JP | 2002505596 | 2/2002 |
| JP | 2002078764 | 3/2002 |
| JP | 2002515786 | 5/2002 |
| JP | 2002537013 | 5/2002 |
| JP | 2002521118 | 7/2002 |
| JP | 2002537939 | 11/2002 |
| JP | 2003050298 | 7/2003 |
| JP | 2003204982 | 7/2003 |
| JP | 2004-504898 | 2/2004 |
| JP | 2004-507280 | 3/2004 |
| JP | 2004154256 | 3/2004 |
| JP | 2004-509671 | 4/2004 |
| JP | 2004-512856 | 4/2004 |
| JP | 2004130145 | 4/2004 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2008515559 | 5/2008 |
| JP | 2009518126 | 5/2009 |
| JP | 2010517695 | 5/2010 |
| KR | 2001-0019317 | 3/2001 |
| KR | 1020010024871 | 3/2001 |
| KR | 2002-0038547 | 5/2002 |
| KR | 100400870 | 10/2003 |
| KR | 20060121267 | 11/2006 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| KR | 10-2013-0124598 | 11/2013 |
| KR | 10-1365946 | 2/2014 |
| TW | 386883 | 9/2000 |
| TW | 201208734 A | 3/2012 |
| WO | WO9312742 | 7/1993 |
| WO | WO9524159 | 9/1995 |
| WO | WO9625888 | 8/1996 |

(56) References Cited

FOREIGN PATENT DOCUMENTS

| | | |
|---|---|---|
| WO | WO9634568 | 11/1996 |
| WO | WO9639079 | 12/1996 |
| WO | WO9735518 | 10/1997 |
| WO | WO9832379 | 7/1998 |
| WO | WO9852465 | 11/1998 |
| WO | WO9933520 | 7/1999 |
| WO | WO9939677 | 8/1999 |
| WO | WO9949788 | 10/1999 |
| WO | WO200006032 | 2/2000 |
| WO | WO0015300 | 3/2000 |
| WO | WO0021612 | 4/2000 |
| WO | WO0048518 | 8/2000 |
| WO | WO0053113 | 9/2000 |
| WO | WO200071021 | 11/2000 |
| WO | WO0128623 | 4/2001 |
| WO | WO01045550 | 6/2001 |
| WO | WO0182777 | 11/2001 |
| WO | WO0182778 | 11/2001 |
| WO | WO0187161 | 11/2001 |
| WO | WO01080709 | 11/2001 |
| WO | WO2001087161 | 11/2001 |
| WO | WO0209812 | 2/2002 |
| WO | WO0209813 | 2/2002 |
| WO | WO02015768 | 2/2002 |
| WO | WO0224050 | 3/2002 |
| WO | WO200149194 | 7/2002 |
| WO | WO2002054018 | 7/2002 |
| WO | WO02092168 | 11/2002 |
| WO | WO03053266 | 7/2003 |
| WO | WO03065347 | 8/2003 |
| WO | WO03070105 | 8/2003 |
| WO | WO03077833 | 9/2003 |
| WO | WO03086215 | 10/2003 |
| WO | WO03096883 | 11/2003 |
| WO | WO03099177 | 12/2003 |
| WO | WO03099382 | 12/2003 |
| WO | WO03101530 | 12/2003 |
| WO | WO2004000116 | 12/2003 |
| WO | WO2004080147 | 9/2004 |
| WO | WO2004110558 | 12/2004 |
| WO | WO2005/011804 | 2/2005 |
| WO | WO2005065408 | 7/2005 |
| WO | WO2005065409 | 7/2005 |
| WO | WO2005090978 | 9/2005 |
| WO | WO2005113068 | 12/2005 |
| WO | WO2006/042163 | 4/2006 |
| WO | WO2006036870 | 4/2006 |
| WO | WO2006042168 | 4/2006 |
| WO | WO2006042201 | 4/2006 |
| WO | WO2006065671 | 6/2006 |
| WO | WO2006082573 | 8/2006 |
| WO | WO2006104568 | 10/2006 |
| WO | WO2006110388 | 10/2006 |
| WO | WO2007067563 | 6/2007 |
| WO | WO2008036479 | 3/2008 |
| WO | WO2008036622 | 3/2008 |
| WO | WO2008144274 | 11/2008 |
| WO | WO2009013729 | 1/2009 |
| WO | WO2009149390 | 10/2009 |
| WO | WO2010006293 | 1/2010 |
| WO | WO2010102128 | 9/2010 |
| WO | WO2012134645 | 10/2012 |
| WO | WO2013048912 | 4/2013 |
| WO | WO2013178830 | 12/2013 |
| WO | WO2014043206 | 3/2014 |
| WO | WO2014045216 | 3/2014 |
| WO | WO2014055708 | 4/2014 |
| WO | WO2014057388 | 4/2014 |
| WO | WO2014127091 | 8/2014 |
| WO | WO 2014/137835 | 9/2014 |
| WO | WO2015160708 | 10/2015 |
| WO | WO2016054155 | 4/2016 |
| WO | WO2016115363 | 7/2016 |
| WO | WO2017127328 | 7/2017 |
| WO | WO2017149506 | 9/2017 |
| WO | WO2017165595 | 9/2017 |
| WO | WO 2017/212489 | 12/2017 |
| WO | WO2017212489 | 12/2017 |
| WO | WO2017223312 | 12/2017 |
| WO | WO2018035012 | 2/2018 |
| WO | WO2018158355 | 9/2018 |
| WO | WO2019008573 | 1/2019 |
| WO | WO 2019147596 | 8/2019 |
| WO | WO2019164836 | 8/2019 |
| WO | WO2020009324 | 1/2020 |
| WO | WO2020075906 | 4/2020 |
| WO | WO2020080730 | 4/2020 |
| WO | WO2020121307 | 6/2020 |

OTHER PUBLICATIONS

Adams et al., "High Intensity Focused Ultrasound Ablation of Rabbit Kidney Tumors" Sonablate High-Intensity Focused Ultrasound device; Journal of Endourology vol. 10, No. 1, (Feb. 1996).

Agren, Magnus S. et al., Collagenase in Wound Healing: Effect of Wound Age and Type. The Journal of Investigative Dermatology, vol. 99/No. 6, (Dec. 1992).

Alam, M., "The future of noninvasive procedural dermatology". Semin Cutan Med Surg. Mar. 2013; 32(1):59-61.

Alam, M., et al., "Ultrasound tightening of facial and neck skin: a rater-blinded prospective cohort study". J Am Acad Dermatol, 2010. 62(2): p. 262-9.

Alexiades-Armenakas, M., "Ultrasound Technologies for Dermatologic Techniques". J Drugs Derm. 2014. 12 (11): p. 1305.

Alster, T.S., et al., "Noninvasive lifting of arm, thigh, and knee skin with transcutaneous intense focused ultrasound". Dermatol Surg, 2012. 38(5): p. 754-9.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Arosarena, O., "Options and Challenges for Facial Rejuvenation in Patients With Higher Fitzpatrick Skin Phototypes". JAMA Facial Plastic Surgery, 2015.

Arthur et al., "Non-invasive estimation of hyperthermia temperatures with ultrasound," Int. J. Hyperthermia, Sep. 2005, 21(6), pp. 589-600.

Barthe et al., "Ultrasound therapy system and ablation results utilizing miniature imaging/therapy arrays," Ultrasonics Symposium, 2004 IEEE, Aug. 23, 2004, pp. 1792-1795, vol. 3.

Bozec, Laurent et al., Thermal Denaturation Studies of Collagen by Microthermal Analysis and Atomic Force Microscopy, Biophysical Journal, vol. 101, pp. 228-236. (Jul. 2001).

Brobst, R.W., et al., "Noninvasive Treatment of the Neck". Facial Plast Surg Clin North Am, 2014. 22(2): p. 191-202.

Brobst, R.W., et., al., "Ulthera: initial and six month results". Facial Plast Surg Clin North Am, 2012. 20(2): p. 163-76.

Brown J. A. et al.: "Fabrication and performance of 40-60 MHz annular arrays", 2003 IEEE Ultrasonics Symposium Proceedings. Honolulu, Hawaii, Oct. 5-8, 2003; [IEEE Ultrasonics Symposium Proceedings], New York, NY : IEEE, US, vol. 1, Oct. 5, 2003 (Oct. 5, 2003), pp. 869-872.

Calderhead et al., "One Mechanism Behind LED Photo-Therapy for Wound Healing and Skin Rejuvenation: Key Role of the Mast Cell" Laser Therapy 17.3: 141-148 (2008).

Carruthers et al., "Consensus Recommendations for Combined Aesthetic Interventions in the Face Using Botulinum Toxin, Fillers, and Energy-Based Devices" Dermatol Surg 2016 (pp. 1-12).

Casabona, G., et al., "Microfocused Ultrasound with Visualization and Calcium Hydroxylapatite for Improving Skin Laxity and Cellulite Appearance"; Plast Reconstr Surg Glob Open. Jul. 25, 2017;5(7):e1388, 8 pages.

Casabona, G., et al., "Microfocused Ultrasound With Visualization and Fillers for Increased Neocollagenesis: Clinical and Histological Evaluation". Dermatol Surg 2014;40:S194-S198.

Chan, N.P., et al., "Safety study of transcutaneous focused ultrasound for non-invasive skin tightening in Asians". Lasers Surg Med, 2011. 43(5): p. 366-75.

(56) References Cited

OTHER PUBLICATIONS

Chapelon et al., "Effects of Cavitation In The High Intensity Therapeutic Ultrasound", Ultrasonics Symposium-1357 (1991).
Chapelon, et al., "Thresholds for Tissue Ablation by Focused Ultrasound" (1990).
Chen, L. et al., "Effect of Blood Perfusion on the ablation of liver parenchyma with high intensity focused ultrasound," Phys. Med. Biol; 38:1661-1673; 1993b.
Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.
Corry, Peter M., et al., "Human Cancer Treatment with Ultrasound", IEEE Transactions on Sonics and Ultrasonics, vol. SU-31, No. 5, Sep. 1984, pp. 444, 456.
Damianou et al., "Application of the Thermal Dose Concept for Predicting the Necrosed Tissue Volume During Ultrasound Surgery," 1993 IEEE Ultrasound Symposium, pp. 1199-1202.
Daum et al., Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.
Davis, Brian J., et al., "An Acoustic Phase Shift Technique for the Non-Invasive Measurement of Temperature Changes in Tissues", 1985 Ultrasonics Symposium, pp. 921-924.
Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Décolletage". Plast Reconstr Surg. Oct. 2014; 134(4 Suppl 1):123-4.
Decision of the Korean Intellectual Property Tribunal dated Jun. 28, 2013 regarding Korean Patent No. 10-1142108, which is related to the pending application and/or an application identified in the Table on pp. 1-4 of the Information Disclosure Statement herein (English translation, English translation certification, and Korean decision included).
Delon Martin, C., et al., "Venous Thrombosis Generation By Means of High-Intensity Focused Ultrasound" Ultrasound in Med. & Biol., vol. 21, No. 1, pp. 113-119 (1995).
Dierickx, Christine C., "The Role of Deep Heating for Noninvasive Skin Rejuvenation" Lasers in Surgery and Medicine 38:799-807 (2006).
Dobke, M.K., et al., "Tissue restructuring by energy-based surgical tools". Clin Plast Surg, 2012. 39(4): p. 399-408.
Dong, Yuan-Lin et al., "Effect of Ibuprofen on the Inflammatory Response To Surgical Wounds" The Journal of Trauma, vol. 35, No. 3. (1993).
Driller et al., "Therapeutic Applications of Ultrasound: A Review" IEEE Engineering in Medicine and Biology; (Dec. 1987) pp. 33-40.
Dvivedi, Sanjay, et al. "Effect of Ibuprofen and diclofenac sodium on experimental wound healing" Indian Journal of Experimental Biology, vol. 35, pp. 1243-1245. (Nov. 1997).
Fabi, S.G., "Microfocused Ultrasound With Visualization for Skin Tightening and Lifting: My Experience and a Review of the Literature". Dermatol Surg. Dec. 2014; 40 Suppl 12:S164-7.
Fabi, S.G., "Noninvasive skin tightening: focus on new ultrasound techniques". Clin Cosmet Investig Dermatol. Feb. 5, 2015; 8:47-52.
Fabi, S.G., et al., "A prospective multicenter pilot study of the safety and efficacy of microfocused ultrasound with visualization for improving lines and wrinkles of the décolleté". Dermatol Surg. Mar. 2015; 41(3):327-35.
Fabi, S.G., et al., "Evaluation of microfocused ultrasound with visualization for lifting, tightening, and wrinkle reduction of the decolletage". J Am Acad Dermatol, 2013. 69(6): p. 965-71.
Fabi, S.G., et al., "Future directions in cutaneous laser surgery". Dermatol Clin, 2014. 32(1): p. 61-9.
Fabi, S.G., et al., "Retrospective Evaluation of Micro-focused Ultrasound for Lifting and Tightening the Face and Neck". Dermatol Surg, 2014.

Friedmann D.P., "Comments on evaluation of microfocused ultrasound system for improving skin laxity and tightening in the lower face". Aesthet Surg J. Mar. 2015;35(3):NP81-2.
Friedmann, D.P., et al., "Combination of intense pulsed light, Sculptra, and Ultherapy for treatment of the aging face". J Cosmet Dermatol, 2014. 13(2): p. 109-18.
Fry, W.J. et al., "Production of Focal Destructive Lesions in the Central Nervous System with Ultrasound," J. Neurosurg., 11:471-478; 1954.
Fujimoto, et al., "A New Cavitation Suppression Technique for Local Ablation Using High-Intensity Focused Ultrasound" Ultrasonics Symposium—1629 (1995).
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.
Gold, M.H., et al., "Use of Micro-Focused Ultrasound with Visualization to Lift and Tighten Lax Knee Skin". J Cosmet Laser Ther, 2014: p. 1-15.
Goldberg, D.J., et al., "Safety and Efficacy of Microfocused Ultrasound to Lift, Tighten, and Smooth the Buttocks". Dermatol Surg 2014; 40:1113-1117.
Greene, R.M., et al., "Skin tightening technologies". Facial Plast Surg. Feb. 2014; 30(1):62-7.
Greenhalgh, David G., "Wound healing and diabetes mellitus" Clinics in Plastic Surgery 30; 37-45. (2003).
Guo, S. et al., "Factors Affecting Wound Healing" Critical Reviews in Oral Biology & Medicine, J Dent Res 89(3), pp. 219-229. (2010).
Haar, G.R. et al., "Tissue Destruction with Focused Ultrasound in Vivo," Eur. Urol. 23 (suppl. 1):8-11; 1993.
Hantash, Basil M. et al., "Bipolar Fractional Radiofrequency Treatment Induces Neoelastogenesis and Neocollagenesis" Lasers in Surgery and Medicine 41:1-9 (2009).
Hantash, Basil M. et al., "In Vivo Histological Evaluation of a Novel Ablative Fractional Resurfacing Device" Lasers in Surgery and Medicine 39:96-107 (2007).
Harris, M.O., "Safety of Microfocused Ultrasound With Visualization in Patients With Fitzpatrick Skin Phototypes III to VI". Jama Facial Plast. Surg, 2015.
Hart, et. al., "Current Concepts in the Use of PLLA: Clinical Synergy Noted with Combined Use of Microfocused Ultrasound and Poly-I-Lactic Acid on the Face, Neck, and Décolletage". Amer. Soc. Plast. Surg. 2015. 136; 180-187S.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Hexsel et al., "A Validated Photonumeric Cellulite Severity Scale"; J Eur Acad Dermatol Venereol. May 2009; 23(5):523-8, 6 pages.
Hitchcock, T.M et al., "Review of the safety profile for microfocused ultrasound with Visualization". Journal of Cosmetic Dermatology, 13, 329-335. (2014).
Husseini et al., "The Role of Cavitation in Acoustically Activated Drug Delivery," J. Control Release, Oct. 3, 2005, pp. 253-261, vol. 107(2).
Husseini et al. "Investigating the mechanism of acoustically activated uptake of drugs from Pluronic micelles," BMD Cancer 2002, 2:20k, Aug. 30, 2002, pp. 1-6.
Hynynen et al., Temperature Distributions During Local Ultrasound Induced Hyperthermia In Vivo, Ultrasonics Symposium-745 (1982).
Jeffers et al., "Evaluation of the Effect of Cavitation Activity on Drug-Ultrasound Synergisms," 1993 IEEE Ultrasonics Symposium, pp. 925-928.
Jenne, J., et al., "Temperature Mapping for High Energy US-Therapy", 1994 Ultrasonics Symposium, pp. 1879-1882.
Jeong, K.H., et al., "Neurologic complication associated with intense focused ultrasound". J Cosmet Laser Ther, 2013.
Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).

(56) References Cited

OTHER PUBLICATIONS

Ketterling J. A et al: "Design and fabrication of a 40-MHz annular array transducer", IEEE Transactions On Ultrasonics, Ferroelectrics And Frequency Control, IEEE, US, vol. 52, No. 4, Apr. 1, 2005 (Apr. 1, 2005), pp. 672-681.
Kim, H.J., et al., "Coagulation and ablation patterns of high-intensity focused ultrasound on a tissue mimicking phantom and cadaveric skin". Laser Med Sci. Sep. 4, 2015.
Kornstein, A.N., "Ulthera for silicone lip correction". Plast Reconstr Surg, 2012. 129(6): p. 1014e-1015e.
Kornstein, A.N., "Ultherapy shrinks nasal skin after rhinoplasty following failure of conservative measures". Plast Reconstr Surg, 2013. 131(4): p. 664e-6e.
Krischak, G.D., et al., "The effects of non-steroidal anti-inflammatory drug application on incisional wound healing in rats" Journal of Wound Care, vol. 6, No. 2, (Feb. 2007).
Laubach, H.J., et al., "Confined Thermal Damage with Intense Ultrasound (IUS)" [abstr.] American Society for Laser Medicine and Surgery Abstracts, p. 15 #43 (Apr. 2006).
Laubach, H.J., et al., "Intense focused ultrasound: evaluation of a new treatment modality for precise microcoagulation within the skin". Dermatol Surg, 2008. 34(5): p. 727-34.
Lee, H.J., et al., "The efficacy and safety of intense focused ultrasound in the treatment of enlarged facial pores in Asian skin". J Dermatolog Treat, 2014.
Lee, H.S., et al., "Multiple Pass Ultrasound Tightening of Skin Laxity of the Lower Face and Neck". Dermatol Surg, 2011.
Lin, Sung-Jan, et al., "Monitoring the thermally induced structural transitions of collagen by use of second-harmonic generation microscopy" Optics Letters, vol. 30, No. 6, (Mar. 15, 2005).
MacGregor J.L., et al., "Microfocused Ultrasound for Skin Tightening". Semin Cutan Med Surg 32:18-25. (2013).
Madersbacher, S. et al., "Tissue Ablation in Benign Prostatic Hyperplasia with High Intensity Focused Ultrasound," Dur. Urol., 23 (suppl. 1):39-43; 1993.
Makin et al., "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.
Makin et al., "Confirmed Bulk Ablation and Therapy Monitoring Using Intracorporeal Image-Treat Ultrasound Arrays," 4th International Symposium on Therapeutic Ultrasound, Sep. 19, 2004.
Makin et al., "Miniaturized Ultrasound Arrays for Interstitial Ablation and Imaging," UltraSound Med. Biol. 2005, Nov. 1, 2005, pp. 1539-1550, vol. 31(11).
Manohar et al., "Photoacoustic mammography laboratory prototype: imaging of breast tissue phantoms," Journal of Biomedical Optics, Nov./Dec. 2004, pp. 1172-1181, vol. 9, No. 6.
Mast et al., "Bulk Ablation of Soft Tissue with Intense Ultrasound; Modeling and Experiments," J. Acoust. Soc. Am., Oct. 1, 2005, pp. 2715-2724, vol. 118(4).
Meshkinpour, Azin, et al., "Treatment of Hypertrophic Scars and Keloids With aRadiofrequency Device: A Study of Collagen Effects" Lasers in Surgery and Medicine 37:343-349 (2005).
MICROCHIP microID 125 KHz EFID System Design Guide, Microchip Technology Inc. (2004).
Minkis, K., et al., "Ultrasound skin tightening". Dermatol Clin, 2014. 32(1): p. 71-7.
Mitragotri, S., "Healing sound: the use of ultrasound in drug delivery and other therapeutic applications," Nature Reviews; Drug Delivery, pp. 255-260, vol. 4 (Mar. 2005).
Mosser, David M. et al., "Exploring the full spectrum of macrophage activation" Nat Rev Immunol; 8(12): 958-969. (Dec. 2008).
Murota, Sei-Itsu, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).
Murota, Sei-Itsu, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).
Nestor, M.S et al., "Safety and Efficacy of Micro-focused Ultrasound Plus Visualization for the Treatment of Axillary Hyperhidrosis". J Clin Aesthet Dermatol, 2014. 7(4): p. 14-21.
Oni, G., et al. "Response to 'comments on evaluation of microfocused ultrasound system|for improving skin laxity and tightening in the lower face'". Aesthet Surg J. Mar. 2015;35(3):NP83-4.
Oni, G., et al., "Evaluation of a Microfocused Ultrasound System for Improving Skin Laxity and Tightening in the Lower Face". Aesthet Surg J, 2014. 38:861-868.
Pak, C.S., et al., "Safety and Efficacy of Ulthera in the Rejuvenation of Aging Lower Eyelids: A Pivotal Clinical Trial". Aesthetic Plast Surg, 2014.
Paradossi et al., "Poly(vinyl alcohol) as versatile biomaterial for potential biomedical applications," Journal of Materials Science: Materials in Medicine, 2003, pp. 687-691, vol. 14.
Pritzker, R.N., et al., "Updates in noninvasive and minimally invasive skin tightening". Semin Cutan Med Surg. Dec. 2014;33(4):182-7.
Pritzker, R.N., et al., "Comparison of different technologies for noninvasive skin tightening". Journal of Cosmetic Dermatology, 13, 315-323. (2014).
Rappolee, Daniel A., et al., "Wound Macrophages Express TGF and Other Growth Factors in Vivo: Analysis by mRNA Phenotyping" Science, vol. 241, No. 4866 (Aug. 1988).
Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.
Righetti et al., "Elastographic Characterization of HIFU-Induced Lesions in Canine Livers," 1999, Ultrasound in Med & Bio, vol. 25, No. 7, pp. 1099-1113.
Rokhsar, C., et al., "Safety and efficacy of microfocused ultrasound in tightening of lax elbow skin". Dermatol Surg. 2015; 41(7):821-6.
Rosenberg, Carol S. "Wound Healing in the Patient with Diabetes Mellitus" Nursing Clinics of North America, vol. 25, No. 1, (Mar. 1990).
Saad et al., "Ultrasound-Enhanced Effects of Adriamycin Against Murine Tumors," Ultrasound in Med. & Biol. vol. 18, No. 8, pp. 715-723 (1992).
Sabet-Peyman, E.J et al., "Complications Using Intense Ultrasound Therapy to Treat Deep Dermal Facial Skin and Subcutaneous Tissues". Dermatol Surg 2014; 40:1108-1112.
Sandulache, Vlad C. et al., "Prostaglandin E2 inhibition of keloid fibroblast migration, contraction, and transforming growth factor (TGF)-B1-induced collagen synthesis" Wound Rep Reg 15 122-133, 2007. (2007).
Sanghvi, N.T., et al., "Transrectal Ablation of Prostate Tissue Using Focused Ultrasound," 1993 Ultrasonics Symposium, IEEE, pp. 1207-1210.
Sasaki, G.H. et al., "Clinical Efficacy and Safety of Focused-Image Ultrasonography: A 2-Year Experience". Aesthet Surg J, 2012.
Sasaki, G.H. et al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.
Sassen, Sander, "ATI's R520 architecture, the new king of the hill?" http://www.hardwareanalysis.com/content/article/1813, Sep. 16, 2005, 2 pages.
Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.
Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Simon et al., "Applications of Lipid-Coated Microbubble Ultrasonic Contrast to Tumor Therapy," Ultrasound in Med. & Biol. vol. 19, No. 2, pp. 123-125 (1993).

(56) References Cited

OTHER PUBLICATIONS

Sklar, L.R., et al., "Use of transcutaneous ultrasound for lipolysis and skin tightening: a review". Aesthetic Plast Surg, 2014. 38(2): p. 429-41.
Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.
Sonocare, Inc. Therapeutic Ultrasound System Model CST-100 Instruction Manual (1985).
Suh, D.H., et al., "A intense-focused ultrasound tightening for the treatment of infraorbital laxity". J Cosmet Laser Ther, 2012. 14(6): p. 290-5.
Suh, D.H., et al., "Comparative histometric analysis of the effects of high-intensity focused ultrasound and radiofrequency on skin". J Cosmet Laser Ther. Mar. 2015 24:1-7.
Suh, D.H., et al., "Intense Focused Ultrasound Tightening in Asian Skin: Clinical and Pathologic Results" American Society for Dermatologic Surgery, Inc.; 37:1595-1602. (2011).
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectrometry," Proceedings of the National Academy of Sciences of USA, National Academy of Science, Washington, DC, vol. 101, No. 26, Jun. 29, 2004, pp. 9528-9533.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions," American Chemical Society, Phys. Chem. 1992, 96, pp. 3548-3555.
Ueno, S., et al., "Ultrasound Thermometry in Hyperthermia", 1990 Ultrasonic Symposium, pp. 1645-1652.
Verhofstad, Michiel H.J. et al., "Collagen Synthesis in rat skin and ileum fibroblasts is affected differently by diabetes-related factors" Int. J. Exp. Path. (1998), 79, 321-328.
Wang, H., et al., "Limits on Focused Ultrasound for Deep Hyperthermia", 1994 Ultrasonic Symposium, Nov. 1-4, 1994, pp. 1869-1872, vol. 3.
Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.
Webster et al. "The role of ultrasound-induced cavitation in the 'in vitro' stimulation of collagen synthesis in human fibroblasts"; Ultrasonics pp. 33-37(Jan. 1980).
Weiss, M., "Commentary: noninvasive skin tightening: ultrasound and other technologies: where are we in 2011?" Dermatol Surg, 2012. 38(1): p. 28-30.
White et al."Selective Creating of Thermal Injury Zones in the Superficial Musculoaponeurotic System Using Intense Ultrasound Therapy," Arch Facial Plastic Surgery, Jan./Feb. 2007, vol. 9, No. 1 (pp. 22-29).
White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).
White, W. Matthew, et al., "Selective Transcutaneous Delivery of Energy to Porcine Soft Tissues Using Intense Ultrasound (IUS)" Lasers in Surgery and Medicine 40:67-75 (2008).
Woodward, J.A., et al. "Safety and Efficacy of Combining Microfocused Ultrasound WithFractional CO2 Laser Resurfacing for Lifting and Tightening the Face and Neck". Dermatol Surg, Dec. 2014 40:S190-S193.
Zelickson, Brian D. et al., "Histological and Ultrastructural Evaluation of the Effects of a Radiofrequency-Based Nonablative Dermal Remodeling Device, A Pilot Study" Arch Dermatol, vol. 140, (Feb. 2004).
PCT/US19/18561 International Search Report dated May 8, 2019, 41 pages.

U.S. Appl. No. 12/996,616, filed Jan. 12, 2011, Hand Wand For Ultrasonic Cosmetic Treatment And Imaging.
U.S. Appl. No. 16/703,019, filed Dec. 6, 2019, System and Method For Ultrasound Treatment.
U.S. Appl. No. 13/245,822, filed Sep. 26, 2011, System and Method For Cosmetic Treatment.
U.S. Appl. No. 13/245,852, filed Sep. 26, 2011, System For Cosmetic Treatment.
U.S. Appl. No. 13/245,864, filed Sep. 27, 2011, Methods For Non-Invasive Cosmetic Treatment Of The Eye Region.
U.S. Appl. No. 13/246,117, filed Sep. 27, 2011, Methods For Non-Invasive Lifting And Tightening Of The Lower Face And Neck.
U.S. Appl. No. 13/246,112, filed Sep. 27, 2011, Tissue Imaging And Treatment Method.
U.S. Appl. No. 14/193,234, filed Feb. 28, 2014, Devices and Methods for Multi-Focus Ultrasound Therapy.
U.S. Appl. No. 16/541,476, filed Aug. 15, 2019, Devices and Methods for Multi-Focus Ultrasound Therapy.
U.S. Appl. No. 15/302,436, filed Oct. 6, 2016, Band Transducer Ultrasound Therapy.
U.S. Appl. No. 15/855,949, filed Dec. 27, 2017, Band Transducer Ultrasound Therapy.
U.S. Appl. No. 16/797,393, filed Feb. 21, 2020, Band Transducer Ultrasound Therapy.
U.S. Appl. No. 15/562,384, filed Oct. 27, 2017, Systems And Methods For Cosmetic Ultrasound Treatment Of Skin.
U.S. Appl. No. 16/069,319, filed Jul. 11, 2018, Compact ultrasound device having annular ultrasound array peripherally electrically connected to flexible printed circuit board and method of assembly thereof.
U.S. Appl. No. 16/964,914, filed Jul. 24, 2020, Systems And Methods For Simultaneous Multi-Focus Ultrasound Therapy In Multiple Dimensions.
U.S. Appl. No. 08/950,353, filed Oct. 14, 1997, Imaging, Therapy And Temperature Monitoring Ultrasonic System.
U.S. Appl. No. 09/502,174, filed Feb. 10, 2000, Imaging, Therapy And Temperature Monitoring Ultrasonic System.
U.S. Appl. No. 10/193,419, filed Jul. 10, 2002, Imaging, Therapy And Temperature Monitoring Ultrasonic System.
U.S. Appl. No. 10/944,499, filed Sep. 16, 2004, Method And System For Ultrasound Treatment With A Multi-Directional Transducer.
U.S. Appl. No. 11/163,177, filed Oct. 7, 2005, Method And System For Treating Acne And Sebaceous Glands.
U.S. Appl. No. 10/950,112, filed Sep. 24, 2004, Method And System For Combined Ultrasound Treatment.
U.S. Appl. No. 11/163,178, filed Oct. 7, 2005, Method And System For Treating Stretch Marks.
U.S. Appl. No. 11/245,999, filed Oct. 6, 2005, System And Method For Ultra-High Frequency Ultrasound Treatment.
U.S. Appl. No. 10/944,500, filed Sep. 16, 2004, System And Method For Variable Depth Ultrasound Treatment.
U.S. Appl. No. 11/744,655, filed May 4, 2007, Imaging, Therapy And Temperature Monitoring Ultrasonic System.
U.S. Appl. No. 13/937,190, filed Jul. 8, 2013, Imaging, Therapy and Temperature Monitoring Ultrasonic System.
U.S. Appl. No. 12/135,962, filed Jun. 9, 2008, Method And System For Ultrasound Treatment With A Multi-Directional Transducer.
U.S. Appl. No. 12/792,934, filed Jun. 3, 2010, System And Method For Ultra-High Frequency Ultrasound Treatment.
U.S. Appl. No. 13/914,945, filed Jun. 11, 2013, System And Method For Ultra-High Frequency Ultrasound Treatment.
U.S. Appl. No. 12/834,754, filed Jul. 12, 2010, System And Method For Variable Depth Ultrasound Treatment.
U.S. Appl. No. 14/264,732, filed Apr. 29, 2014, System and Method For Variable Depth Ultrasound Treatment.
U.S. Appl. No. 11/126,760, filed May 11, 2005, Method And System For Three-Dimensional Scanning And Imaging.
U.S. Appl. No. 13/564,552, filed Aug. 1, 2012, Method And System For Controlled Scanning, Imaging And/Or Therapy.
U.S. Appl. No. 12/437,726, filed May 8, 2009, Method And System For Combined Ultrasound Treatment.

(56) References Cited

OTHER PUBLICATIONS

U.S. Appl. No. 11/163,148, filed Oct. 6, 2005, Method And System For Controlled Thermal Injury Of Human Superficial Tissue.
U.S. Appl. No. 13/444,688, filed Apr. 11, 2012, Customized Cosmetic Treatment.
U.S. Appl. No. 16/427,969, filed May 31, 2019, Customized Cosmetic Treatment.
U.S. Appl. No. 11/163,152, filed Oct. 6, 2005, Method And System For Treatment Of Sweat Glands.
U.S. Appl. No. 13/444,485, filed Apr. 11, 2012, Methods For Treatment Of Sweat Glands.
U.S. Appl. No. 13/603,159, filed Sep. 4, 2012, Methods For Treatment Of Hyperhidrosis.
U.S. Appl. No. 13/603,279, filed Sep. 4, 2012, Energy Based Hyperhidrosis Treatment.
U.S. Appl. No. 13/950,728, filed Jul. 25, 2013, Energy Based Hyperhidrosis Treatment.
U.S. Appl. No. 14/571,835, filed Dec. 16, 2014, Energy Based Hyperhidrosis Treatment.
U.S. Appl. No. 15/243,081, filed Aug. 22, 2016, Energy Based Hyperhidrosis Treatment.
U.S. Appl. No. 16/049,365, filed Jul. 30, 2018, Energy Based Hyperhidrosis Treatment.
U.S. Appl. No. 11/163,151, filed Oct. 6, 2005, Method And System For Noninvasive Face Lifts And Deep Tissue Tightening.
U.S. Appl. No. 13/444,336, filed Apr. 11, 2012, Treatment Of Sub-Dermal Regions For Cosmetic Effects.
U.S. Appl. No. 13/679,430, filed Nov. 16, 2012, Ultrasound Treatment Of Sub-Dermal Tissue For Cosmetic Effects.
U.S. Appl. No. 13/924,376, filed Jun. 21, 2013, Noninvasive Tissue Tightening For Cosmetic Effects.
U.S. Appl. No. 13/924,355, filed Jun. 21, 2013, Noninvasive Aesthetic Treatment For Tightening Tissue.
U.S. Appl. No. 13/924,323, filed Jun. 21, 2013, Energy-Based Tissue Tightening.
U.S. Appl. No. 14/200,852, filed Mar. 7, 2014, Noninvasive Tissue Tightening System.
U.S. Appl. No. 14/200,961, filed Mar. 7, 2014, Energy-Based Tissue Tightening System.
U.S. Appl. No. 16/543,137, filed Aug. 16, 2019, Noninvasive Tissue Tightening System.
U.S. Appl. No. 12/028,636, filed Feb. 8, 2008, Method And System For Noninvasive Face Lifts And Deep Tissue Tightening.
U.S. Appl. No. 13/964,820, filed Aug. 12, 2013, Methods For Noninvasive Skin Tightening.
U.S. Appl. No. 14/201,256, filed Mar. 7, 2014, System For Noninvasive Skin Tightening.
U.S. Appl. No. 15/098,139, filed Apr. 13, 2016, System and Method for Noninvasive Skin Tightening.
U.S. Appl. No. 15/958,939, filed Apr. 20, 2018, System and Method for Noninvasive Skin Tightening.
U.S. Appl. No. 16/698,122, filed Nov. 27, 2019, System and Method for Noninvasive Skin Tightening.
U.S. Appl. No. 14/685,390, filed Apr. 13, 2015, Energy-Based Tissue Tightening System.
U.S. Appl. No. 11/163,150, filed Oct. 6, 2005, Method And System For Photoaged Tissue.
U.S. Appl. No. 13/230,498, filed Sep. 12, 2011, Method And System For Photoaged Tissue.
U.S. Appl. No. 14/169,709, filed Jan. 31, 2014, Methods for Treating Skin Laxity.
U.S. Appl. No. 14/692,114, filed Apr. 21, 2015, Systems For Treating Skin Laxity.
U.S. Appl. No. 15/248,407, filed Aug. 26, 2016, Systems For Treating Skin Laxity.
U.S. Appl. No. 15/625,700, filed Jun. 16, 2017, Systems For Treating Skin Laxity.
U.S. Appl. No. 15/821,070, filed Nov. 22, 2017, Ultrasound Probe For Treating Skin Laxity.
U.S. Appl. No. 15/996,255, filed Jun. 1, 2018, Ultrasound Probe For Treating Skin Laxity.
U.S. Appl. No. 16/284,907, filed Feb. 25, 2019, Ultrasound Probe For Treating Skin Laxity.
U.S. Appl. No. 16/797,362, filed Feb. 21, 2020, Ultrasound Probe For Treating Skin Laxity.
U.S. Appl. No. 11/163,176, filed Oct. 7, 2005, Method And System For Treating Blood Vessel Disorders.
U.S. Appl. No. 13/601,742, filed Aug. 31, 2012, Method and System For Treating Blood Vessel Disorders.
U.S. Appl. No. 12/574,512, filed Oct. 6, 2009, Method And System For Treating Stretch Marks.
U.S. Appl. No. 14/554,668, filed Nov. 26, 2014, Method and System For Treating Stretch Marks.
U.S. Appl. No. 15/260,825, filed Sep. 12, 2016, Method and System For Ultrasound Treatment Of Skin.
U.S. Appl. No. 15/625,818, filed Jun. 16, 2017, Method and System For Ultrasound Treatment Of Skin.
U.S. Appl. No. 15/829,182, filed Dec. 1, 2017, Ultrasound Probe For Treatment Of Skin.
U.S. Appl. No. 15/996,263, filed Jun. 1, 2018, Ultrasound Probe For Treatment Of Skin.
U.S. Appl. No. 16/284,920, filed Feb. 25, 2019, Ultrasound Probe For Treatment Of Skin.
U.S. Appl. No. 16/797,387, filed Feb. 21, 2020, Ultrasound Probe For Treatment Of Skin.
U.S. Appl. No. 11/857,989, filed Sep. 19, 2007, Method And System For Treating Muscle, Tendon, Ligament And Cartilage Tissue.
U.S. Appl. No. 13/494,856, filed Jun. 12, 2012, Method and System For Treating Muscle, Tendon, Ligament and Cartilage Tissue.
U.S. Appl. No. 13/835,635, filed Mar. 15, 2013, Methods for Face and Neck Lifts.
U.S. Appl. No. 13/965,741, filed Aug. 13, 2013, Methods For Preheating Tissue For Cosmetic Treatment Of The Face And Body.
U.S. Appl. No. 14/740,092, filed Jun. 15, 2015, Methods For Rejuvenating Skin By Heating Tissue For Cosmetic Treatment Of The Face And Body.
U.S. Appl. No. 15/862,400, filed Jan. 4, 2018, Rejuvenating Skin By Heating Tissue For Cosmetic Treatment Of The Face And Body.
U.S. Appl. No. 16/409,678, filed May 10, 2019, Rejuvenating Skin By Heating Tissue For Cosmetic Treatment Of The Face And Body.
U.S. Appl. No. 14/628,198, filed Feb. 20, 2015, System and Method for Treating Cartilage and Injuries to Joints and Connective Tissue.
U.S. Appl. No. 14/554,571, filed Nov. 26, 2014, Methods for Face and Neck Lifts.
U.S. Appl. No. 15/248,454, filed Aug. 26, 2016, Methods for Face and Neck Lifts.
U.S. Appl. No. 16/049,293, filed Jul. 30, 2018, Methods for Face and Neck Lifts.
U.S. Appl. No. 16/697,970, filed Nov. 27, 2019, Methods for Lifting Skin Tissue.
U.S. Appl. No. 12/954,484, filed Nov. 24, 2010, Methods And Systems For Generating Thermal Bubbles For Improved Ultrasound Imaging And Therapy.
U.S. Appl. No. 12/350,383, filed Jan. 8, 2009, Method And System For Treating Acne And Sebaceous Glands.
U.S. Appl. No. 12/116,845, filed May 7, 2008, Method And System For Combined Energy Profile.
U.S. Appl. No. 14/643,749, filed Mar. 10, 2015, Method and System For Combined Energy Profile.
U.S. Appl. No. 08/766,083, filed Dec. 16, 1996, Method And Apparatus For Surface Ultrasound Imaging.
U.S. Appl. No. 09/113,227, filed Jul. 10, 1998, Method And Apparatus For Three Dimensional Ultrasound Imaging.
U.S. Appl. No. 08/944,261, filed Oct. 6, 1997, Wideband Acoustic Transducer.
U.S. Appl. No. 09/434,078, filed Nov. 5, 1999, Method And Apparatus For Three Dimensional Ultrasound Imaging.
U.S. Appl. No. 09/523,890, filed Mar. 13, 2000, Method And Apparatus For Three Dimensional Ultrasound Imaging.
U.S. Appl. No. 09/419,543, filed Oct. 18, 1999, Peripheral Ultrasound Imaging System.

(56) References Cited

OTHER PUBLICATIONS

U.S. Appl. No. 09/750,816, filed Dec. 28, 2000, Visual Imaging System For Ultrasonic Probe.
U.S. Appl. No. 10/358,110, filed Feb. 4, 2003, Visual Imaging System For Ultrasonic Probe.
U.S. Appl. No. 11/380,161, filed Apr. 25, 2006, Method And System For Enhancing Computer Peripheral Safety.
U.S. Appl. No. 11/554,272, filed Oct. 30, 2006, Visual Imaging System For Ultrasonic Probe.
U.S. Appl. No. 13/071,298, filed Mar. 24, 2011, Visual Imaging System For Ultrasonic Probe.
U.S. Appl. No. 13/854,936, filed Mar. 25, 2013, Visual Imaging System For Ultrasonic Probe.
U.S. Appl. No. 12/509,254, filed Jul. 24, 2009, Method And System For Enhancing Computer Peripheral Safety.
U.S. Appl. No. 13/453,847, filed Apr. 23, 2012, Method and System For Enhancing Computer Peripheral Safety.
U.S. Appl. No. 11/538,794, filed Oct. 4, 2006, Ultrasound System And Method For Imaging And/Or Measuring Displacement Of Moving Tissue And Fluid.
U.S. Appl. No. 09/502,175, filed Feb. 10, 2000, Method And Apparatus For Safely Delivering Medicants To A Region Of Tissue, Using Imaging, Therapy And Temperature Monitoring.
U.S. Appl. No. 08/943,728, filed Oct. 3, 1997, Method And Apparatus For Safely Delivering Medicants To A Region Of Tissue Using Ultrasound.
U.S. Appl. No. 12/415,945, filed Mar. 31, 2009, Method And System For Noninvasive Mastopexy.
U.S. Appl. No. 11/163,155, filed Oct. 6, 2005, Method And System For Noninvasive Mastopexy.
U.S. Appl. No. 11/163,154, filed Oct. 6, 2005, Method And System For Treatment Of Cellulite.
U.S. Appl. No. 13/356,405, filed Jan. 23, 2012, Method and System For Treatment Of Cellulite.
U.S. Appl. No. 13/789,562, filed Mar. 7, 2013, Method and System For Ultrasound Treatment Of Fat.
U.S. Appl. No. 14/164,598, filed Jan. 27, 2013, Method for Fat and Cellulite Reduction.
U.S. Appl. No. 14/550,720, filed Nov. 21, 2014, System and Method For Fat And Cellulite Reduction.
U.S. Appl. No. 15/041,829, filed Feb. 11, 2016, System and Method For Fat And Cellulite Reduction.
U.S. Appl. No. 15/374,918, filed Dec. 9, 2016, System and Method For Fat And Cellulite Reduction.
U.S. Appl. No. 15/650,246, filed Jul. 14, 2017, System and Method For Fat And Cellulite Reduction.
U.S. Appl. No. 15/821,281, filed Nov. 22, 2017, Ultrasound Probe For Fat And Cellulite Reduction.
U.S. Appl. No. 15/996,295, filed Jun. 1, 2018, Ultrasound Probe For Fat And Cellulite Reduction.
U.S. Appl. No. 16/272,453, filed Feb. 11, 2019, Ultrasound Probe For Tissue Treatment.
U.S. Appl. No. 16/794,717, filed Feb. 19, 2020, Ultrasound Probe For Tissue Treatment.
U.S. Appl. No. 11/738,682, filed Apr. 23, 2007, Method And System For Non-Ablative Acne Treatment And Prevention.
U.S. Appl. No. 12/116,810, filed May 7, 2008, Methods And Systems For Modulating Medicants Using Acoustic Energy.
U.S. Appl. No. 12/116,828, filed May 7, 2008, Methods And Systems For Coupling And Focusing Acoustic Energy Using A Coupler Member.
U.S. Appl. No. 12/646,609, filed Dec. 23, 2009, Methods and System For Fat Reduction And/Or Cellulite Treatment.
U.S. Appl. No. 14/192,520, filed Feb. 27, 2014, Energy Based Fat Reduction.
U.S. Appl. No. 14/550,772, filed Nov. 21, 2014, Energy Based Fat Reduction.
U.S. Appl. No. 15/401,804, filed Feb. 11, 2016, Energy Based Fat Reduction.
U.S. Appl. No. 15/380,267, filed Dec. 15, 2016, Energy Based Fat Reduction.
U.S. Appl. No. 15/650,525, filed Jul. 18, 2017, Energy Based Fat Reduction.
U.S. Appl. No. 15/829,175, filed Dec. 1, 2017, Energy Based Fat Reduction.
U.S. Appl. No. 15/996,249, filed Jun. 1, 2018, Energy Based Fat Reduction.
U.S. Appl. No. 16/272,427, filed Feb. 11, 2019, Energy Based Fat Reduction.
U.S. Appl. No. 16/794,701, filed Feb. 19, 2020, Energy Based Fat Reduction.
U.S. Appl. No. 13/291,312, filed Nov. 11, 2011, Devices and Methods for Acoustic Shielding.
U.S. Appl. No. 14/487,504, filed Sep. 16, 2014, Devices and Methods for Acoustic Shielding.
U.S. Appl. No. 13/136,538, filed Aug. 2, 2011, Systems and Methods for Treating Acute and/or Chronic Injuries in Soft Tissue.
U.S. Appl. No. 13/136,542, filed Aug. 2, 2011, System and Method for Treating Cartilage.
U.S. Appl. No. 13/163,541, filed Aug. 2, 2011, Methods and Systems for Treating Plantar Fascia.
U.S. Appl. No. 13/136,544, filed Aug. 2, 2011, Systems and Methods for Ultrasound Treatment.
U.S. Appl. No. 13/547,023, filed Jul. 11, 2012, Systems and Methods for Coupling an Ultrasound Source to Tissue.
U.S. Appl. No. 13/545,931, filed Jul. 10, 2012, Methods and Systems for Controlling Acoustic Energy Deposition Into A Medium.
U.S. Appl. No. 13/545,953, filed Jul. 10, 2012, Systems and Methods for Accelerating Healing of Implanted Material and/or Native Tissue.
U.S. Appl. No. 13/547,011, filed Jul. 11, 2012, Systems and Methods for Monitoring and Controlling Ultrasound Power Output and Stability.
U.S. Appl. No. 13/545,954, filed Jul. 10, 2012, Systems And Methods For Improving An Outside Appearance Of Skin Using Ultrasound As An Energy Source.
U.S. Appl. No. 13/545,945, filed Jul. 10, 2012, Systems And Methods For Treating Injuries To Joints And Connective Tissue.
U.S. Appl. No. 13/545,929, filed Jul. 10, 2012, Methods and Systems for Ultrasound Treatment.
U.S. Appl. No. 13/863,249, filed Apr. 15, 2013, Systems for Cosmetic Treatment.
U.S. Appl. No. 13/863,281, filed Apr. 15, 2013, Methods for Non-invasive Cosmetic Treatment.
U.S. Appl. No. 14/847,626, filed Sep. 8, 2015, Systems for Cosmetic Treatment.
U.S. Appl. No. 13/863,362, filed Apr. 15, 2013, Thick Film Transducer Arrays.
U.S. Appl. No. 14/217,110, filed Mar. 17, 2014, Ultrasound Treatment Device and Method of Use.
U.S. Appl. No. 14/217,382, filed Mar. 17, 2014, Ultrasound Treatment Device and Method of Use.
U.S. Appl. No. 14/225,189, filed Mar. 25, 2014, Reflective Ultrasound Technology for Dermatological Treatments.
U.S. Appl. No. 15/345,908, filed Nov. 8, 2016, Reflective Ultrasound Technology for Dermatological Treatments.
U.S. Appl. No. 15/719,377, filed Sep. 28, 2017, Reflective Ultrasound Technology for Dermatological Treatments.
U.S. Appl. No. 14/270,859, filed May 6, 2014, Methods And Systems For Generating Thermal Bubbles For Improved Ultrasound Imaging And Therapy.
U.S. Appl. No. 14/679,494, filed Apr. 6, 2015, Methods and Systems for Generating Thermal Bubbles for Improved Ultrasound Imaging and Therapy.
U.S. Appl. No. 14/405,368, filed Dec. 3, 2014, Devices And Methods For Ultrasound Focal Depth Control.
U.S. Appl. No. 14/568,954, filed Dec. 12, 2014, System And Method For Cosmetic Enhancement of Lips.
U.S. Appl. No. 14/569,001, filed Dec. 12, 2014, System And Method For Non-Invasive Treatment With Improved Efficiency.

(56) References Cited

OTHER PUBLICATIONS

U.S. Appl. No. 14/600,782, filed Jan. 20, 2015, Methods and Systems for Controlling and Acoustic Energy Deposition in Various Media.
U.S. Appl. No. 14/738,420, filed Jun. 12, 2015, Systems And Methods For Fast Ultrasound Treatment.
U.S. Appl. No. 14/751,349, filed Jun. 26, 2015, Methods and Systems for Tattoo Removal.
U.S. Appl. No. 15/001,712, filed Jan. 20, 2016, Methods and Systems for Removal of a Targeted Tissue from a Body.
U.S. Appl. No. 15/001,621, filed Jan. 20, 2016, Methods and Systems for Removal of a Foreign Object from Tissue.
U.S. Appl. No. 15/059,773, filed Mar. 3, 2016, Methods And Systems For Material Transport Across An Impermeable Or Semi-Permeable Membrane Via Artificially Created Microchannels.
U.S. Appl. No. 15/094,774, filed Apr. 8, 2016, System and Method for Increased Control of Ultrasound Treatments.
Narayanasamy et al., "Spatial registration of temporally separated whole breast 3D ultrasound images" Med Phys. Sep. 2009;36(9):4288-300. doi: 10.1118/1.3193678. PMID: 19810503; PMCID: PMC2749445 (2009).

\* cited by examiner

| Patient No. | Gender | Age | Treatment Group | Aesthetic Scale Cellulite Dimples at Rest | | | | Aesthetic Scale Skin Laxity at Rest | | | |
|---|---|---|---|---|---|---|---|---|---|---|---|
| | | | | Day 0 | Day 90 | Day 180 | Day 270 | Day 0 | Day 90 | Day 180 | Day 270 |
| 1 | W | 37 | Group I: Radiesse Day 0 and 90 +/- 10 days | 2 | 2 | 1 | 1 | 2 | 2 | 1 | 1 |
| 2 | W | 48 | Group II: Ultherapy 1.5mm and Radiesse Day 0 and Radiesse Day 90 +/- 10 days | 2 | 1 | 1 | 1 | 2 | 1 | 1 | 1 |
| 4 | W | 44 | Group IV: Ultherapy 1.5mm and Aethoxysklerol and Radiesse Day 0 and Aethoxysklerol Day 45 +/- 10 days | 2 | 2 | 2 | 2 | 2 | 1 | 1 | 1 |

*FIG. 20*

| | Patient 1 Radiesse | Patient 2 Ultherapy 1.5mm and Radiesse | Patient 4 Ultherapy 1.5mm and Aethoxysklerol and Radiesse |
|---|---|---|---|
| Day 0 | 1.137 | 1.187 | 1.172 |
| Day 90 | 1.172 | 1.565 | 1.083 |
| Day 180 | 1.412 | 1.540 | 1.169 |
| Day 270 | 1.237 | 1.452 | 1.285 |

*FIG. 21*

| Day | R0 | | | % | | |
|---|---|---|---|---|---|---|
| | Patient 1 | Patient 2 | Patient 4 | Patient 1 | Patient 2 | Patient 4 |
| 0 | 1,137 | 1,187 | 1,172 | 100,00 | 100,00 | 100,00 |
| 90 | 1,172 | 1,565 | 1,083 | 103,08 | 131,84 | 92,41 |
| 180 | 1,412 | 1,54 | 1,169 | 124,19 | 129,74 | 99,74 |
| 270 | 1,237 | 1,452 | 1,285 | 108,80 | 122,33 | 109,64 |

Illustration R0 value for skin firmness

| | R2 | | | % | | |
|---|---|---|---|---|---|---|
| | Patient 1 | Patient 2 | Patient 4 | Patient 1 | Patient 2 | Patient 4 |
| Day 0 | 0,916 | 0,921 | 0,889 | 100,00 | 100,00 | 100,00 |
| Day 90 | 0,935 | 0,96 | 0,927 | 102,07 | 104,23 | 104,27 |
| Day 180 | 0,939 | 0,917 | 0,92 | 102,51 | 99,57 | 103,49 |
| Day 270 | 0,930 | 0,897 | 0,928 | 101,53 | 97,39 | 104,39 |

Illustration R2 value for Gross elasticity

Patient 2: day 0 (a) day 90 (b) day 180 (c) day 270 (d)

Patient 4: day 0 (a) day 90 (b) day 180 (c) day 270 (d)

SYSTEMS AND METHODS FOR COMBINED COSMETIC TREATMENT OF CELLULITE WITH ULTRASOUND

INCORPORATION BY REFERENCE

This application is a U.S. National Phase application of Intl. App. No. PCT/US2019/018561 filed Feb. 19, 2019, which claims the benefit from U.S. Provisional Patent Application Nos. 62/632,741 filed on Feb. 20, 2018, and 62/662,394 filed on Apr. 25, 2018, each of which is incorporated herein by reference in its entirety for all purposes. Any and all applications for which a foreign or domestic claim is identified in the Application Data Sheet as filed with the present application are hereby incorporated by reference under 37 CFR 1.57.

BACKGROUND

Field

Several embodiments of the invention relate to obtaining aesthetically and/or cosmetically enhancing effects on skin and/or tissue near the skin of a human body through combined therapies of injectables, topical agents absorbed through the skin, energy-based noninvasive therapy treatments, and/or septa severing.

Description of the Related Art

Cellulite is a gender-related complex architectural and metabolic disorder of subcutaneous tissue which leads to an alteration of a subject's body shape. Cellulite mainly affects the pelvic region, buttocks, the lower limbs and/or the abdomen of a female body. Cellulite, or gynoid lipodystrophy, is a topographic alteration of the skin and subcutaneous adipose tissue. It manifests as a textured, dimpled, mattress-like, cottage cheese, or orange peel appearance of the skin, mainly in the buttocks, thighs and abdominal areas. Cellulite can be a result of weak connective tissue and special skin extracellular matrix structure. Notably, many post pubertal females are affected to different extents by cellulite. While not a pathologic condition, cellulite represents a significant cosmetic appearance problem for the affected individuals.

SUMMARY

Some cosmetic procedures involve invasive procedures that may require invasive surgery. Patients not only have to endure weeks of recovery time, but also are frequently required to undergo additional anesthetic procedures. Non-invasive energy-based therapeutic devices and treatments with various drugs are available, but may have various shortcomings with respect to efficiency, effectiveness, and patient comfort.

Non-invasive treatment cosmetic procedures are also available. For cellulite in particular, various topicals (such as creams) and other treatments are also available but show limited effectiveness.

Several embodiments of the invention advantageously treat cellulite using non-invasive energy (such as ultrasound) combined with one or more anti-cellulite agents to provide efficacious and visible results. Although cellulite is treated in some embodiments, other aesthetic treatments are also provided herein that synergistically combine energy (such as ultrasound) with one or more agents.

According to some embodiments, the combination of energy (such as ultrasound) together with an agent provides a synergetic result in which the energy enhances a structural, connective tissue aspect of cellulite treatment (e.g., altering the structure of septae and/or fat lobuli underlying an appearance of cellulite, modify the tissue matrix by altering collagen and/or elastic fibers via fillers and/or HIFU treatment for, e.g., promotion of neo-collagenesis) and/or the volume or viability of a fat cell aspect of cellulite treatment (e.g., removing fat in herniated areas to create uniform volume distribution, and thus increase tissue smoothness, such as via necrotic and/or apoptotic fat cell death).

According to some embodiments, the combination of energy (such as ultrasound) together with an agent provides a synergetic result in which the energy enhances the absorption, penetration, stability, localization, comfort, and/or efficiency of the agent. In some embodiments, an agent can enhance the efficacy, comfort, and/or location of the energy, or ultrasound therapy. Less energy may be required to obtain the same improving effect on the treated tissue. Consequently, the agent is able to act more quickly and/or with greater efficacy in some embodiments. In one embodiment, a reduced amount of the agent is needed when combined with energy (versus without energy). This reduction in dosage can help reduce side effects that sometimes accompany dermatological agents. Patient satisfaction may also be improved in one embodiment because the patient will see visible results more quickly and/or experience longer lasting cosmetic effects. In yet other embodiments, the agent enhances the efficacy of the energy. Thus, the unique synergy of the energy and the agent working together provides visible benefits to the patient according to several embodiments described herein.

FIGS. 16A-16D show embodiments of the disclosure with an Energy-Based Device ("EBD"), a Filler, each alone or in combination. FIG. 19A is a plot showing an embodiment of Efficacy of Filler (y-axis) and Amount of Filler (x-axis) for Filler Only and Filler Plus EBD is shown. FIG. 19B is a plot showing an embodiment of Safety of Filler (y-axis) and Amount of Filler (x-axis) for Filler Only and Filler Plus EBD is shown. FIG. 19C is a plot showing an embodiment of Efficacy of EBD (y-axis) and Amount of Energy (x-axis) for EBD Only and EBD Plus Filler is shown. FIG. 19D is a plot showing an embodiment of Safety of Filler (y-axis) and Amount of Energy (x-axis) for EBD Only and EBD Plus Filler is shown. In one embodiment, the EBD when added to filler delivery improves the efficacy or safety or both. This may be achieved by the capabilities of embodiments described in this disclosure which include modifying viscosity, releasing cross-linkers at the area of interest, shaping the filler, moving the filler, etc. Similarly, the filler when added to the EBD delivery improves the efficacy or safety or both. This may be achieved by the capabilities described in this disclosure which include modifying the attenuation, reflection, harmonic content, etc. of the ultrasound energy.

Several embodiments include a combination of energy-based devices (EBDs) with any one or more of an anti-cellulite agent, including for example any one or more of (i) dermal fillers, (ii) fat-reducing compounds, (iii) cavitation-prone fluids such as molecules dissolved in fluids, ethanol, glycerin, ethylene glycol, or (iv) energy absorptive fluids (e.g., ultrasound attenuation, electrical impedance). In some embodiments, dermal fillers and fat-reducing compounds are both used in combination with ultrasound. Some embodiments relate to the treatment and reduction in appearance of cellulite, which is also known as gynoid lipodystrophy. In one embodiment, non-dimple type female gynoid lipodystrophy is treated.

Some embodiments of the energy-based devices comprise an ultrasound device. One example is a high intensity focused ultrasound ("HIFU") device. In various embodiments, an ultrasound system is configured to treat aspects of cellulite via a "connective tissue aspect," a "fat cell aspect," or any combinations thereof. In various embodiments, an ultrasound system is configured to treat aspects of cellulite via focused ultrasound fractionation of tissue to selectively create low mechanical resistance channels to improve the localization of an anti-cellulite agent (e.g., a dermal filler and/or fat-reducing compound), which increases the probability to achieve the intended outcome.

Imaging is included in some embodiments. For example, in one embodiment, an ultrasound system is configured for imaging to visualize tissue (e.g., dermal and subdermal layers of tissue, such as fat) to, for example, confirm proper coupling of the transducer to the skin, target the energy and/or agent to a treatment location, and/or track the location of the agent. In various embodiments, an ultrasound system is configured for imaging to visualize tissue (e.g., dermal, fat, and other layers of tissue) to confirm appropriate depth of treatment such as to avoid certain tissues (e.g., in certain embodiments, nerves, blood vessels, or bone).

Examples of dermal fillers that are used with energy-based devices (such as HIFU) include, but are not limited to, collagen, hyaluronic acids, and/or calcium (hydroxy)phosphate (e.g., calcium hydroxyapatite, hydroxyapatite particles, calcium hydroxyapatite, calcium hydroxyapatite microspheres). One non-limiting example includes RADIESSE® (a registered trademark of Merz North America, Inc.). In several embodiments, the dermal filler comprises a sterile, latex-free, non-pyrogenic, semi-solid, cohesive subdermal, injectable synthetic calcium hydroxyapatite. The semi-solid nature of the product is created, in one embodiment, by suspending calcium hydroxyapatite microspheres of about 20-50 (e.g., 25-45) microns diameter in a gel carrier of carboxymethylcellulose. In other embodiments, cross-linked acids comprising calcium hydroxyapatite microspheres are used.

With respect to dermal fillers, in several embodiments, the use of a HIFU system in combination with a dermal filler provides an improved treatment of cellulite, which is well tolerated, leads to increased patient satisfaction, and improves the patient's quality of life. In one embodiment, the dermal filler is used to address the connective tissue aspect of cellulite by strengthening the tissue structure, e.g., the connective tissue in the skin (e.g., dermis) to reduce or prevent the protrusion of fat lobuli compartments to the skin surface. With use of energy (such as ultrasound), injection of small amounts of dermal filler significantly improves skin firmness, laxity and flaccidity. In one embodiment, injected dermal filler increases the in situ synthesis of extracellular matrix in general in conjunction with HIFU based collagen restructuring and synthesis, thereby increasing the firmness or strength of the tissue structure and providing beneficial long-lasting treatment effects that are enhanced through the use of ultrasound. In one embodiment, HIFU is used prior to the use of the injectable/topical agent because of the potential of interaction with the ultrasound. In one embodiment, the injectable/topical agent may be applied to the tissue prior to the HIFU, wherein the agent enhances the absorptive nature of the ultrasound either at the targeted tissue site, pre-focally to generate more harmonics, or post focally, to prevent ultrasound energy from getting to even deeper post focal tissues. In various embodiments, the use of ultrasound strengthens collagen structures, and initiates additional new collagen formation of the walls and "roof" of fat lobuli that intersperse into the dermal and near dermal layers that affect the textured appearance of cellulite. The combined application of HIFU energy with dermal fillers, in sequence or simultaneously, strengthens the connective tissue aspect of cellulite treatment. In one embodiment, ultrasound treatment alters the structural integrity of the connective tissue aspect by piercing the wall and/or roof of fat lobuli to release fat cells, e.g., by destroying the walls containing the fat compartments in the skin and reducing the bulges of fat lobuli and reduce the appearance of cellulite. In one embodiment the HIFU is used to selectively heat up the fat-cell mass of the subcutaneous fat tissue and induce necrotic and/or apoptotic cell death. In one embodiment, the HIFU is used at different depths in the dermal skin layer in order to induce in the deep dermis or in the upper dermis the formation of new collagen fibers and thus reinforcing the extracellular matrix network within the dermis. In one embodiment, ultrasound is used to decrease the amount of tissue stiffness by creating an inflammatory response which causes the generation of new collagen and elastin through necrosis. In one embodiment, ultrasound is used to generate new collagen and elastin with a reduced inflammatory response by promoting apoptosis. In one embodiment, ultrasound is used to sever the fibrous septae through non-invasive mechanical means. In one embodiment, dermal septae are addressed in a treatment. In another embodiment, ultrasound is used to sever the fibrous septae through non-invasive thermal means. In some embodiments, HIFU is used to more rapidly move, stabilize, harden and/or cross-link the dermal filler at targeted tissue locations. In some embodiments, HIFU is used to selectively alter the dermal filler into designed tissue support structures. In some embodiments, HIFU is used to release a cross-linker or another agent with the filler to improve or reduce viscosity. In some embodiments, HIFU is used to remove the filler through either thermal or mechanical techniques. In some embodiments, the HIFU degrades the filler through thermal means. In some embodiments, the HIFU 'breaks-up' the filler through mechanical means. In another embodiment, HIFU degrades or 'breaks-up' the filler through mechanical and thermal means. HIFU might also be used to heat-up the filler material for increasing the biostimulatory activity of the filler. In various embodiments, the HIFU treatment might also be used to trigger the release of stimulatory actives from loaded, functionalized dermal filler material, shape the filler, change the hardness of the filler, migrate the filler, remove the filler.

Examples of fat-reducing compounds that are used with energy-based devices (such as HIFU) include but are not limited to adipocytolytic compounds (such as polidocanol), pentacyclic triterpenoid compounds (such as ursolic acid or betulinic acid), proapoptotic compounds (such as resveratrol or phytoalexin), compounds impairing differentiation of pre-adipocytes, and combinations thereof. In one embodiment, HIFU is used to release compounds when coming into contact with sufficient ultrasound pressures.

With respect to fat-reducing compounds, in some embodiments, the use of a HIFU system in combination with a fat-reducing compound provides an improved treatment of cellulite, which is well tolerated, leads to increased patient satisfaction, and improves the patient's quality of life by reducing the volume of fat (e.g., fat cell aspect of cellulite) via induced elimination of adipocytes (necrotic and/or apoptotic cell death) by HIFU heating fat tissue, e.g., inducing elimination of adipocytes (e.g., necrotic and/or apoptotic fat cell death). In various embodiments, HIFU is used in combination with an adipocytolic or adipotoxic compound by sensitizing the adipocytes towards the applied active. With this lower concentration of the adipose-targeting compound could be used in order to reach an efficient elimination of fat-tissue.

Examples of cavitation-prone fluids that are used with energy-based devices (such as HIFU) include but are not limited water, an aqueous solution of ethanol, and an aqueous solution of glycerol other fluids include molecules dissolved in fluids, ethanol, glycerin, ethylene glycol. In one embodiment, gas is deliberately dissolved in fluids to create cavitation at known temperatures and pressures when exposed to ultrasound. In another embodiment, particles which act like nuclei (e.g., liposomes) for cavitation are added to the fluid to create cavitation at known temperatures and pressures. With respect to cavitation-prone fluids, the application of ultrasound energy amplifies a cavitation, or bubble bursting effect, which can reduce the volume of fat cells in lobuli compartments underlying the appearance of cellulite. In various embodiments, cavitation-prone fluids 1) limit the amount of ultrasound energy propagating to tissues behind where the cavitation occurs 2) increase the absorption locally where the absorption occurs, and/or 3) increase the backscattered energy so it is easier to visualize where the fluid is located in tissue and thus where the cavitation is occurring.

In some embodiments, two or all of (i) dermal fillers, (ii) fat-reducing compounds, (iii) cavitation-prone fluids (iv) reflective prone fluids (v) attenuative prone fluids and/or (vi) non-linear prone fluids are used in combination with the energy-based device (such as HIFU). For example, in one embodiment, a dermal filler and a fat-reducing compound are used in combination with ultrasound (e.g., HIFU) and/or other energy source.

Although various embodiments for aesthetic treatments are contemplated herein, the systems and procedures described herein are also used for non-aesthetic applications in some embodiments.

In various embodiments, use of high intensity focused (HIFU) ultrasound comprises at least one of the group consisting of: a dermal filler and a fat-reducing compound in the cosmetic treatment of gynoid lipodystrophy.

In one embodiment, the HIFU ultrasound therapy is targeted to a dermal tissue. In one embodiment, the HIFU ultrasound therapy is targeted to a dermal tissue to strengthen a connective tissue by improving a collagen-network in the dermal tissue. In one embodiment, the HIFU ultrasound therapy is targeted to a tissue in the upper dermis. In one embodiment, the HIFU ultrasound therapy is targeted to a tissue in the upper dermis to strengthen collagen in the upper dermal tissue. In one embodiment, the HIFU ultrasound therapy is targeted to a dermal tissue and a subcutaneous fat tissue. In one embodiment, the HIFU ultrasound therapy is simultaneously targeted to a dermal tissue and a subcutaneous fat tissue. In one embodiment, the HIFU ultrasound therapy is targeted to a subcutaneous fat tissue. In one embodiment, the HIFU ultrasound therapy is targeted to a fat lobuli within a subcutaneous fat tissue. In one embodiment, the HIFU ultrasound therapy is targeted to a subcutaneous fat tissue to induce cell-death in adipocytes. In one embodiment, the HIFU ultrasound therapy is targeted to a subcutaneous fat tissue to induce cell-death in adipocytes via apoptosis. In one embodiment, the HIFU ultrasound therapy is targeted to a subcutaneous fat tissue to increase lipolysis in adipocytes resulting in reduced cell diameter of affected adipocytes. In one embodiment, the HIFU ultrasound therapy is targeted to a fibrous septa to cut the fibrous septa. In one embodiment, the HIFU ultrasound therapy is provided at a depth of 1.5 mm below a skin surface. In one embodiment, the HIFU ultrasound therapy is provided at a depth of 4.5 mm and/or 3.0 mm below a skin surface. In one embodiment, the HIFU ultrasound therapy is provided at a depth of 1.5 mm and a depth of 4.5 mm and/or 3.0 mm below a skin surface. In one embodiment, the HIFU ultrasound therapy is provided at a depth of 1.5 mm and between 10 mm to 17 mm below a skin surface. In one embodiment, the HIFU ultrasound therapy is provided at a depth of 1.5 mm, 4.5 mm and/or 3.0 mm, and at least 10 mm below a skin surface. In one embodiment, the HIFU ultrasound therapy is provided at a depth of at least 10 mm below a skin surface. In one embodiment, the HIFU ultrasound therapy is provided at a depth of 17 mm below a skin surface. In one embodiment, the HIFU ultrasound therapy is provided at a frequency of 4 MHz. In one embodiment, the HIFU ultrasound therapy is provided at a frequency of 7 MHz. In one embodiment, the HIFU ultrasound therapy is provided at a frequency of 10 MHz. In one embodiment, the HIFU ultrasound therapy is provided at a frequency of 2 MHz or less. In one embodiment, the HIFU ultrasound therapy is provided at a power of at least 5 kW/cm$^2$. In one embodiment, the HIFU ultrasound therapy is provided at a power of at least 10 kW/cm$^2$. In one embodiment, the HIFU ultrasound therapy is provided at a power of at least 15 kW/cm$^2$. In one embodiment, the HIFU ultrasound therapy is provided with a spherically focused transducer. In one embodiment, the HIFU ultrasound therapy is provided with a cylindrically focused transducer. In one embodiment, the HIFU ultrasound therapy is provided at a point focus. In one embodiment, the HIFU ultrasound therapy is provided at a line focus.

In one embodiment, the HIFU is administered to a subject having a body mass index (BMI), defined as the body mass in kg divided by the square of the body height, of at least 25 kg/m$^2$, or to a subject having severe cellulite corresponding to a total sum of scores of items (a) and (b) of the Hexsel, Dal'Forno, and Hexsel Cellulite Severity Scale (CSS) of 4, 5 or 6, wherein item (a) denotes the number of evident depressions and item (b) denotes the depth of depressions, and both item (a) and item (b) are graded from 0 to 3.

In one embodiment, the HIFU is administered concurrently, sequentially or separately with the at least one of the group consisting of: the dermal filler and the fat-reducing compound. In one embodiment, the dermal filler is administered before or after the HIFU. In one embodiment, the fat-reducing compound is administered before or after the HIFU. In one embodiment, the dermal filler and the fat-reducing compound is administered before or after the HIFU. In one embodiment, the dermal filler is administered by local injection into a dermal tissue, a subcutaneous fat tissue, or both the dermal tissue and the subcutaneous fat tissue. In one embodiment, the dermal filler is hardened by the application of HIFU. In one embodiment, the dermal filler is moved by the application of HIFU. In one embodiment, the dermal filler is stabilized by the application of HIFU. In one embodiment, the viscosity of the dermal filler is modified by the application of HIFU. In one embodiment, the dermal filler is shaped in to a designed structure by the application of HIFU. In one embodiment, the dermal filler comprises calcium (hydroxy)phosphate particles selected from the group consisting of monocalcium phosphate (MCP), dicalcium phosphate (DCP), calcium dihydrogen phosphate (CDP), tricalcium phosphate (TCP) α-, α'- and β-polymorphs, octacalcium phosphate (OCP), biphasic tricalcium phosphate (BCP), and hydroxyapatite. In several embodiments, ultrasound (such as HIFU) is used both before and after application (e.g., injection) of the dermal filler.

In one embodiment, the dermal filler comprises hydroxyapatite. In one embodiment, the fat-reducing compound is administered by local injection into a subcutaneous fat tissue. In one embodiment, the dermal filler particles have a mean size of about 20 μm to about 70 μm in diameter, or a D-ratio of equal to or greater than 0.9, or both, wherein the D-ratio is defined as the ratio of the calculated diameter of a perfect circle based on the cross sectional area of the particle to the maximum diameter measured through that cross sectional centroid. In one embodiment, the dermal filler particles are administered as an injectable composition, which is in the form of a hydrogel, and wherein the injectable composition comprises calcium (hydroxy)phosphate particles. In one embodiment, the injectable composition comprises at least one polysaccharide, the polysaccharide being crosslinked and/or non-crosslinked and optionally being selected from the group consisting of cellulose, cellulose ester and cellulose ether derivatives such as cellulose acetate (CA), carboxymethyl cellulose (CMC), carboxyethyl cellulose (CEC), carboxypropyl cellulose (CPC), carboxymethyl ethylcellulose (CMEC), methyl cellulose (MC), ethyl cellulose (EC), hydroxyethyl cellulose (HEC), hydroxyethyl methylcellulose (HEMC) and hydroxypropyl methylcellulose (HPMC), hyaluronic acid (HA), dextran, carboxymethyldextran, carboxymethylstarch, chondroitin sulfate, dermatane sulfate, keratin, keratin sulfate, chitosan, chitin, pectin, carrageenan, xanthan, heparin, heparin sulfate alginate, and mixtures therefrom, wherein the polysaccharide is selected from carboxymethyl cellulose (CMC), hyaluronic acid (HA), or a mixture thereof. In one embodiment, the calcium (hydroxy)phosphate particles are present in the injectable composition in an amount of 0.5 to 50% (w/w) or 5 to 29% (w/w). In one embodiment, the injectable composition contains one or more polyols in a total amount of 0 vol. % or 0.001 to 20 vol. %. In one embodiment, the injectable composition contains at least one additional pharmaceutically acceptable ingredient comprising a local anesthetic in an amount of 0.001 to 5 vol. %. In one embodiment, the injectable composition contains one or more polyols comprising glycerol, in a total amount of 0 vol. % or 0.001 to 20 vol. %, or contains at least one additional pharmaceutically acceptable ingredient comprising lidocaine in an amount of 0.001 to 5 vol. %, or both. In one embodiment, the injectable composition contains one or more polyols, in a total amount of 0 vol. % or 0.001 to 20 vol. %, or contains at least one additional pharmaceutically acceptable ingredient comprising a local anesthetic such as lidocaine, in an amount of 0.001 to 5 vol. %, or both.

In one embodiment, the fat-reducing compound is selected from the group consisting of (i) adipocytolytic compounds, such as polidocanol, cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA), (ii) pentacyclic triterpenoid compounds, including ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone, (iii) compounds that stimulate the β2-adrenergic pathway directly or block the activity of cellular phosphodiesterases, such as paraxanthine, caffeine, ciclostamide, amirone, tolfentrine, revizinone and enoximone, (iv) proapoptotic compounds, such as resveratol and phytoalexin, (v) compounds impairing differentiation of pre-adipocytes, such as antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin, (vi) other compounds such as fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, glabridin, and (vii) combinations of one or more of (i) to (vi).

In one embodiment, the fat-reducing compound is a adipocytolytic compound selected from the group consisting of: polidocanol, cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA). In one embodiment, the fat-reducing compound is a pentacyclic triterpenoid compound selected from the group consisting of: ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone. In one embodiment, the fat-reducing compound is a compound that stimulates the β2-adrenergic pathway directly or block the activity of cellular phosphodiesterases selected from the group consisting of: paraxanthine, caffeine, ciclostamide, amirone, tolfentrine, revizinone and enoximone. In one embodiment, the fat-reducing compound is a proapoptotic compound selected from the group consisting of: resveratrol and phytoalexin. In one embodiment, the fat-reducing compound is a compound impairing differentiation of pre-adipocytes selected from the group consisting of: antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin. In one embodiment, the fat-reducing compound is selected from the group consisting of: fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, and glabridin. In one embodiment, the fat-reducing compound is administered as an injectable composition in the form of a solution, emulsion, suspension or dispersion, comprising said fat-reducing compound and a cosmetically acceptable carrier such as an aqueous solution, an organic solvent, or a mixture of an aqueous solution and an organic solvent. In one embodiment, the fat-reducing compound is present in the injectable composition in an amount from about 0.001 wt. % to about 10 wt. %, based on the total weight of the injectable composition.

In one embodiment, the treatment of gynoid lipodystrophy comprises local injection of an injectable composition of polidocanol into the subcutis and, after said local injection of an injectable composition of polidocanol, sequential or separate local injection of an injectable hydrogel composition of calcium (hydroxy)phosphate particles into the dermis. In one embodiment, the treatment includes the injection of a cavitation-prone fluid prior to application of HIFU. In one embodiment, dimple type female gynoid lipodystrophy is treated. In one embodiment, non-dimple type female gynoid lipodystrophy is treated.

In various embodiments, a method for cosmetically treating gynoid lipodystrophy includes administering to a subject in need thereof an effective amount of HIFU energy and at least one of a dermal filler and a fat-reducing compound. In one embodiment, the HIFU is administered concurrently, sequentially or separately with dermal filler. In one embodiment, the HIFU is administered concurrently, sequentially or separately with fat-reducing compound. In one embodiment, the dermal filler comprises calcium (hydroxy)phosphate particles. In one embodiment, an effective amount of compound capable of reducing local subcutaneous fat and the calcium (hydroxy)phosphate particles are administered concurrently, sequentially or separately. In one embodiment, a kit comprising a HIFU transducer, a composition of a dermal filler, and a fat-reducing compound, and optionally instructions for use is provided. In one embodiment, the kit includes an injection guidance device and a syringe. In various embodiments, a system is configured for producing an aesthetic effect, wherein the system comprises one or more energy sources and at least one of the group consisting of: one or more dermal fillers, one or more fat-reducing compounds and one or more cavitation-prone agents. In one embodiment, the energy source comprises one, two or more of the following: ultrasound, HIFU, light, laser, radiofrequency, microwave, electromagnetic, radiation, thermal, cryogenic, electron beam, photon-based, magnetic, magnetic resonance. In one embodiment, the aesthetic effect comprises a cellulite treatment. In one embodiment, the aesthetic effect comprises reducing wrinkles, sagging and/or laxity of the skin. In one embodiment, the aesthetic effect comprises reducing fat. In one embodiment, the aesthetic effect comprises body or facial sculpting. In one embodiment, two or more energy sources are used and wherein two or more of the following are used: dermal fillers, fat-reducing compounds and cavitation-prone agents. In one embodiment, two or more dermal fillers are used. In one embodiment, the dermal filler is a lip augmentation agent. In one embodiment, a use of the system is for the treatment of a dermatological or cosmetic condition. In one embodiment, a method for cosmetically treating gynoid lipodystrophy comprises administering to a subject in need thereof at least one of HIFU ultrasound therapy and a dermal filler and a fat-reducing compound, wherein the method targets (i) a tissue in or around the dermis by providing HIFU ultrasound therapy and/or by locally administering the dermal filler, (ii) a subcutaneous fat tissue by providing HIFU ultrasound therapy and/or locally administering the fat-reducing compound to reduce the volume of the subcutaneous fat tissue, and optionally (iii) a fibrous septa by providing HIFU ultrasound, mechanical cutting, or other therapy to cut the fibrous septa. In one embodiment, a method for cosmetically treating gynoid lipodystrophy comprises administering to a subject in need thereof at least one of HIFU ultrasound therapy and a dermal filler and a fat-reducing compound, wherein the method targets (a) a tissue in or around the upper-dermis by providing HIFU ultrasound therapy, (b) a tissue in or around the deep dermis by providing HIFU ultrasound therapy and/or by local administering the dermal filler, (c) a subcutaneous fat tissue by providing HIFU ultrasound therapy and/or administering the fat-reducing compound to reduce the volume of the subcutaneous fat tissue, and optionally (d) a fibrous septa by providing HIFU ultrasound, mechanical cutting, or other therapy to cut the fibrous septa. In one embodiment, a cavitation-prone fluid is injected prior to providing HIFU ultrasound therapy to cut the fibrous septa. In one embodiment, the subcutaneous fat tissue is targeted by providing an HIFU ultrasound therapy, wherein one or more simultaneous linear focused ultrasound treatments heat up portions of the subcutaneous fat-tissue in a plane or band of treatment. In one embodiment, the dermal filler comprises calcium (hydroxy)phosphate particles. In one embodiment, the fat-reducing compound is an adipocytolytic compound.

In some embodiments, use of septa dissection comprises at least one of the group consisting of: high intensity focused ultrasound (HIFU) therapy, a dermal filler, a fat-reducing compound, or a cavitation-prone fluid in the cosmetic treatment of gynoid lipodystrophy.

The septa dissection may be targeted to a dermal tissue. The septa dissection may comprise using a chamber. The septa dissection may comprise cutting the septa on a plane parallel to an upper surface of a dermal tissue. The septa dissection may comprise cutting the septa using a cutting tool. The cutting tool may have one blade. The cutting tool may comprise two blades. The septa dissection may comprise cutting the septa using an ablation tool. The ablation tool may comprise a radiofrequency (RF) probe. The septa dissection may comprise injecting an anesthetic before dissecting the septa. The septa dissection may be directed by a guidance track. The guidance track may be interchangeable. The septa dissection may be motorized. The septa dissection may be manual. The septa dissection may be administered to a subject having a body mass index (BMI), defined as the body mass in kg divided by the square of the body height, of at least 25 kg/m$^2$. The septa dissection may be administered to a subject having severe cellulite corresponding to a total sum of scores of items (a) and (b) of the Hexsel, Dal'Forno, and Hexsel Cellulite Severity Scale (CSS) of 4, 5 or 6, item (a) denoting the number of evident depressions and item (b) denoting the depth of depressions, both item (a) and item (b) being graded from 0 to 3. The septa dissection may be administered concurrently, sequentially, or separately with the at least one of the group consisting of: HIFU therapy, a dermal filler, a fat-reducing compound, or a cavitation-prone fluid.

The HIFU therapy may be targeted to a dermal tissue. The HIFU therapy may be targeted to a dermal tissue to strengthen a connective tissue by improving a collagen-network in the dermal tissue. The HIFU therapy may be targeted to a tissue in the upper dermis. The HIFU therapy may be targeted to a tissue in the upper dermis to strengthen collagen in the upper dermal tissue. The HIFU therapy may be targeted to a dermal tissue and a subcutaneous fat tissue. The HIFU therapy may be simultaneously targeted to a dermal tissue and a subcutaneous fat tissue. The HIFU therapy may be targeted to a subcutaneous fat tissue. The HIFU therapy may be targeted to a fat lobuli within a subcutaneous fat tissue. The HIFU therapy may be targeted to a subcutaneous fat tissue to induce cell-death in adipocytes. The HIFU therapy may be targeted to a subcutaneous fat tissue to induce cell-death in adipocytes via apoptosis. The HIFU therapy may be targeted to a subcutaneous fat tissue to increase lipolysis in adipocytes resulting in reduced cell diameter of affected adipocytes. The HIFU therapy may be targeted to a fibrous septa to cut the fibrous septa. The HIFU therapy may be provided at a depth of 1.5 mm below a skin surface. The HIFU therapy may be provided at a depth of 4.5 mm and/or 3.0 mm below a skin surface. The HIFU therapy may be provided at a depth of 1.5 mm and a depth of 4.5 mm and/or 3.0 mm below a skin surface. The HIFU therapy may be provided at a depth of 1.5 mm and between 10 mm to 17 mm below a skin surface. The HIFU therapy may be provided at a depth of 1.5 mm, 4.5 mm and/or 3.0 mm, and at least 10 mm below a skin surface. The HIFU therapy may be provided at a depth of at least 10 mm below a skin surface. The HIFU therapy may be provided at a depth of 17 mm below a skin surface. The HIFU therapy may be provided at a frequency of 4 MHz. The HIFU therapy may be provided at a frequency of 7 MHz. The HIFU therapy may be provided at a frequency of 10 MHz. The HIFU therapy may be provided at a frequency of 2 MHz or less. The HIFU therapy may be provided at a power of at least 5 kW/cm². The HIFU therapy may be provided at a power of at least 10 kW/cm². The HIFU therapy may be provided at a power of at least 15 kW/cm². The HIFU therapy may be provided with a spherically focused transducer. The HIFU therapy may be provided with a cylindrically focused transducer. The HIFU therapy may be provided at a point focus. The HIFU therapy may be provided at a line focus.

The dermal filler may be administered before or after the septa dissection. The fat-reducing compound may be administered before or after the septa dissection. The dermal filler and the fat-reducing compound may be administered before and/or after the septa dissection. The dermal filler may be administered by local injection into a dermal tissue, a subcutaneous fat tissue, or both the dermal tissue and the subcutaneous fat tissue. The dermal filler may be hardened or otherwise cured or altered (e.g., chemically altered) by the application of HIFU. The dermal filler may be moved by the application of HIFU. The dermal filler may be stabilized by the application of HIFU. The viscosity of the dermal filler may be modified by the application of HIFU. The dermal filler may be shaped in to a designed structure by the application of HIFU. The dermal filler may comprise calcium (hydroxy)phosphate particles selected from the group consisting of monocalcium phosphate (MCP), dicalcium phosphate (DCP), calcium dihydrogen phosphate (CDP), tricalcium phosphate (TCP) including its α-, α'- and β-polymorphs, octacalcium phosphate (OCP), biphasic tricalcium phosphate (BCP), and hydroxyapatite. The dermal filler may comprise hydroxyapatite. The fat-reducing compound may be administered by local injection into a subcutaneous fat tissue. The dermal filler particles may have a mean size of about 20 μm to about 70 μm in diameter, or a D-ratio of equal to or greater than 0.9, or both, wherein the D-ratio is defined as the ratio of the calculated diameter of a perfect circle based on the cross sectional area of the particle to the maximum diameter measured through that cross sectional centroid. The dermal filler particles may be administered as an injectable composition. In several embodiments, ultrasound (such as HIFU) is used both before and after application (e.g., injection) of the dermal filler.

The injectable composition may be in the form of a hydrogel. The injectable composition may comprise calcium (hydroxy)phosphate particles. The injectable composition may comprise at least one polysaccharide, the polysaccharide being crosslinked and/or non-crosslinked and optionally being selected from the group consisting of cellulose, cellulose ester and cellulose ether derivatives such as cellulose acetate (CA), carboxymethyl cellulose (CMC), carboxyethyl cellulose (CEC), carboxypropyl cellulose (CPC), carboxymethyl ethylcellulose (CMEC), methyl cellulose (MC), ethyl cellulose (EC), hydroxyethyl cellulose (HEC), hydroxyethyl methylcellulose (HEMC) and hydroxypropyl methylcellulose (HPMC), hyaluronic acid (HA), dextran, carboxymethyldextran, carboxymethylstarch, chondroitin sulfate, dermatane sulfate, keratin, keratin sulfate, chitosan, chitin, pectin, carrageenan, xanthan, heparin, heparin sulfate alginate, and mixtures therefrom, wherein the polysaccharide is selected from carboxymethyl cellulose (CMC), hyaluronic acid (HA), or a mixture thereof. The calcium (hydroxy)phosphate particles may be present in the injectable composition in an amount of 0.5 to 50% (w/w) or 5 to 29% (w/w). The injectable composition may contain one or more polyols in a total amount of 0 vol. % or 0.001 to 20 vol. %. The injectable composition may contain at least one additional pharmaceutically acceptable ingredient comprising a local anesthetic in an amount of 0.001 to 5 vol. %. The injectable composition may contain one or more polyols comprising glycerol, in a total amount of 0 vol. % or 0.001 to 20 vol. %, or contains at least one additional pharmaceutically acceptable ingredient comprising lidocaine in an amount of 0.001 to 5 vol. %, or both. The injectable composition may contain one or more polyols, in a total amount of 0 vol. % or 0.001 to 20 vol. %, and/or may contain at least one additional pharmaceutically acceptable ingredient comprising a local anesthetic such as lidocaine, in an amount of 0.001 to 5 vol. %, or both.

The fat-reducing compound may be selected from the group consisting of (i) adipocytolytic compounds, such as polidocanol, cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA), (ii) pentacyclic triterpenoid compounds, including ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone, (iii) compounds that stimulate the β2-adrenergic pathway directly or block the activity of cellular phosphodiesterases, such as paraxanthine, caffeine, ciclostamide, amirone, tolfentrine, revizinone and enoximone, (iv) proapoptotic compounds, such as resveratol and phytoalexin, (v) compounds impairing differentiation of pre-adipocytes, such as antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin, (vi) other compounds such as fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, glabridin, or (vii) combinations of one or more of (i) to (vi). The fat-reducing compound may be a adipocytolytic compound selected from the group consisting of: polidocanol, cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA), The fat-reducing compound may be a pentacyclic triterpenoid compound selected from the group consisting of: ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone, The fat-reducing compound may be a compound that stimulates the β2-adrenergic pathway directly or block the activity of cellular phosphodiesterases selected from the group consisting of: paraxanthine, caffeine, ciclostamide, amirone, tolfentrine, revizinone and enoximone. The fat-reducing compound may be a proapoptotic compound selected from the group consisting of: resveratrol and phytoalexin. The fat-reducing compound may be a compound impairing differentiation of pre-adipocytes selected from the group consisting of: antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin. The fat-reducing compound may be selected from the group consisting of: fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, and glabridin. The fat-reducing compound may be administered as an injectable composition in the form of a solution, emulsion, suspension or dispersion, comprising said fat-reducing compound and a cosmetically acceptable carrier such as an aqueous solution, an organic solvent, or a mixture of an aqueous solution and an organic solvent. The fat-reducing compound may be present in the injectable composition in an amount from about 0.001 wt. % to about 10 wt. %, based on the total weight of the injectable composition.

The treatment of gynoid lipodystrophy may comprise local injection of an injectable composition of polidocanol into the subcutis and, after said local injection of an injectable composition of polidocanol, sequential or separate local injection of an injectable hydrogel composition of calcium (hydroxy)phosphate particles into the dermis. The use may further comprise the injection of a cavitation-prone fluid prior to application of HIFU. Dimple type female gynoid lipodystrophy may be treated. Non-dimple type female gynoid lipodystrophy may be treated.

In some embodiments, a method for cosmetically treating gynoid lipodystrophy comprises, or alternatively consists essentially of, administering to a subject in need thereof a septa dissection and at least one of an effective amount of HIFU energy, a dermal filler, a fat-reducing compound, or a cavitation-prone fluid.

The septa dissection may be administered concurrently, sequentially, and/or separately with HIFU energy. The HIFU energy may be administered concurrently, sequentially, and/or separately with the cavitation-prone fluid. The septa dissection may be administered concurrently, sequentially, and/or separately with dermal filler. The septa dissection may be administered concurrently, sequentially, and/or separately with fat-reducing compound. The method for cosmetically treating gynoid lipodystrophy of claim 170, wherein the septa dissection may be administered concurrently, sequentially or separately with cavitation-prone fluid. The dermal filler may comprise calcium (hydroxy)phosphate particles. An effective amount of compound capable of reducing local subcutaneous fat and the calcium (hydroxy) phosphate particles may be administered concurrently, sequentially, and/or separately.

In some embodiments, a kit comprises, or alternatively consists essentially of, a septa dissection system and at least one of a HIFU transducer, a dermal filler, a fat-reducing compound, a cavitation-prone fluid, or instructions for use.

The kit may further comprise an injection guidance device. The kit may further comprise a syringe.

In some embodiments, a system for producing an aesthetic effect comprises, or alternatively consists essentially of, a septa dissection device and at least one of the group consisting of: one or more energy sources, one or more dermal fillers, one or more fat-reducing compounds, one or more cavitation-prone fluids.

The energy source may comprise one, two or more of the following: ultrasound, HIFU, light, laser, radio-frequency, microwave, electromagnetic, radiation, thermal, cryogenic, electron beam, photon-based, magnetic, magnetic resonance. The aesthetic effect may comprise a cellulite treatment. The aesthetic effect may comprise reducing wrinkles, sagging, and/or laxity of the skin. The aesthetic effect may comprise reducing fat. The aesthetic effect may comprise body or facial sculpting. Two or more energy sources may be used. Two or more of the following may be used: dermal fillers, fat-reducing compounds, and cavitation-prone fluids. Two or more dermal fillers may be used. The dermal filler may be a lip augmentation agent. The system may be used for the treatment of a dermatological or cosmetic condition.

In some embodiments, a method for cosmetically treating gynoid lipodystrophy comprises, or alternatively consists essentially of, administering to a subject in need thereof septa dissection and at least one of HIFU therapy, a dermal filler, a fat-reducing compound, or a cavitation-prone fluid. The method targets (i) a tissue in or around the dermis by providing HIFU therapy and/or by locally administering the dermal filler, (ii) a subcutaneous fat tissue by providing HIFU therapy and/or locally administering the fat-reducing compound to reduce the volume of the subcutaneous fat tissue, and optionally (iii) a fibrous septa by providing septa dissection and/or HIFU therapy to cut the fibrous septa.

In some embodiments, a method for cosmetically treating gynoid lipodystrophy comprises, or alternatively consists essentially of, administering to a subject in need thereof septa dissection and at least one of HIFU therapy, a dermal filler, a fat-reducing compound, or a cavitation-prone fluid. The method targets (a) a tissue in or around the upper-dermis by providing HIFU therapy, (b) a tissue in or around the deep dermis by providing HIFU therapy and/or by local administering the dermal filler, (c) a subcutaneous fat tissue by providing HIFU therapy and/or administering the fat-reducing compound to reduce the volume of the subcutaneous fat tissue, and optionally (d) a fibrous septa by providing septa dissection and/or HIFU therapy to cut the fibrous septa.

The cavitation-prone fluid may be injected prior to providing HIFU therapy to cut the fibrous septa. The subcutaneous fat tissue may be targeted by providing an HIFU therapy. One or more simultaneous linear focused ultrasound treatments may heat up portions of the subcutaneous fat-tissue in a plane or band of treatment. The dermal filler may comprise calcium (hydroxy)phosphate particles. The fat-reducing compound may be an adipocytolytic compound.

In some embodiments, a method for cosmetically treating gynoid lipodystrophy comprises, or alternatively consists essentially of, administering to a subject at least one therapy to target a dermal layer and at least one therapy to target a fat layer.

The at least one therapy to target the dermal layer may comprise at least one of septa dissection, HIFU therapy without a cavitation-prone fluid, HIFU therapy with a cavitation-prone fluid, or a dermal filler. The at least one therapy to target the dermal layer may comprise at least two of septa dissection, HIFU therapy without a cavitation-prone fluid, HIFU therapy with a cavitation-prone fluid, or a dermal filler. The at least one therapy to target the dermal layer may comprise at least three of septa dissection, HIFU therapy without a cavitation-prone fluid, HIFU therapy with a cavitation-prone fluid, or a dermal filler. The at least one therapy to target the dermal layer may comprise each of septa dissection, HIFU therapy without a cavitation-prone fluid, HIFU therapy with a cavitation-prone fluid, and a dermal filler. The at least one therapy to target the fat layer may comprise at least one of HIFU therapy without a cavitation-prone fluid, HIFU therapy with a cavitation-prone fluid, or a fat-reducing compound. The at least one therapy to target the fat layer may comprise at least two of HIFU therapy without a cavitation-prone fluid, HIFU therapy with a cavitation-prone fluid, or a fat-reducing compound. The at least one therapy to target the fat layer may comprise each of HIFU therapy without a cavitation-prone fluid, HIFU therapy with a cavitation-prone fluid, and a fat-reducing compound.

A kit for treating cellulite with a septa dissection system may have one or more of the features described in the foregoing description.

BRIEF DESCRIPTION OF THE DRAWINGS

The drawings described herein are for illustration purposes only and are not intended to limit the scope of the present disclosure in any way. Embodiments of the invention will become more fully understood from the detailed description and the accompanying drawings wherein:

FIG. 19A is a plot showing an embodiment of Efficacy of Filler (y-axis) and Amount of Filler (x-axis) for Filler Only and Filler Plus EBD is shown. FIG. 19B is a plot showing an embodiment of Safety of Filler (y-axis) and Amount of Filler (x-axis) for Filler Only and Filler Plus EBD is shown. FIG. 19C is a plot showing an embodiment of Efficacy of EBD (y-axis) and Amount of Energy (x-axis) for EBD Only and EBD Plus Filler is shown. FIG. 19D is a plot showing an embodiment of Safety of Filler (y-axis) and Amount of Energy (x-axis) for EBD Only and EBD Plus Filler is shown.

FIG. 20 illustrates a table of a combined cellulite treatment according to embodiments in Example 6.

FIG. 21 illustrates a table of skin firmness measurements according to embodiments of cellulite treatment of Example 6 according to FIG. 20.

DETAILED DESCRIPTION

Figure 1A:
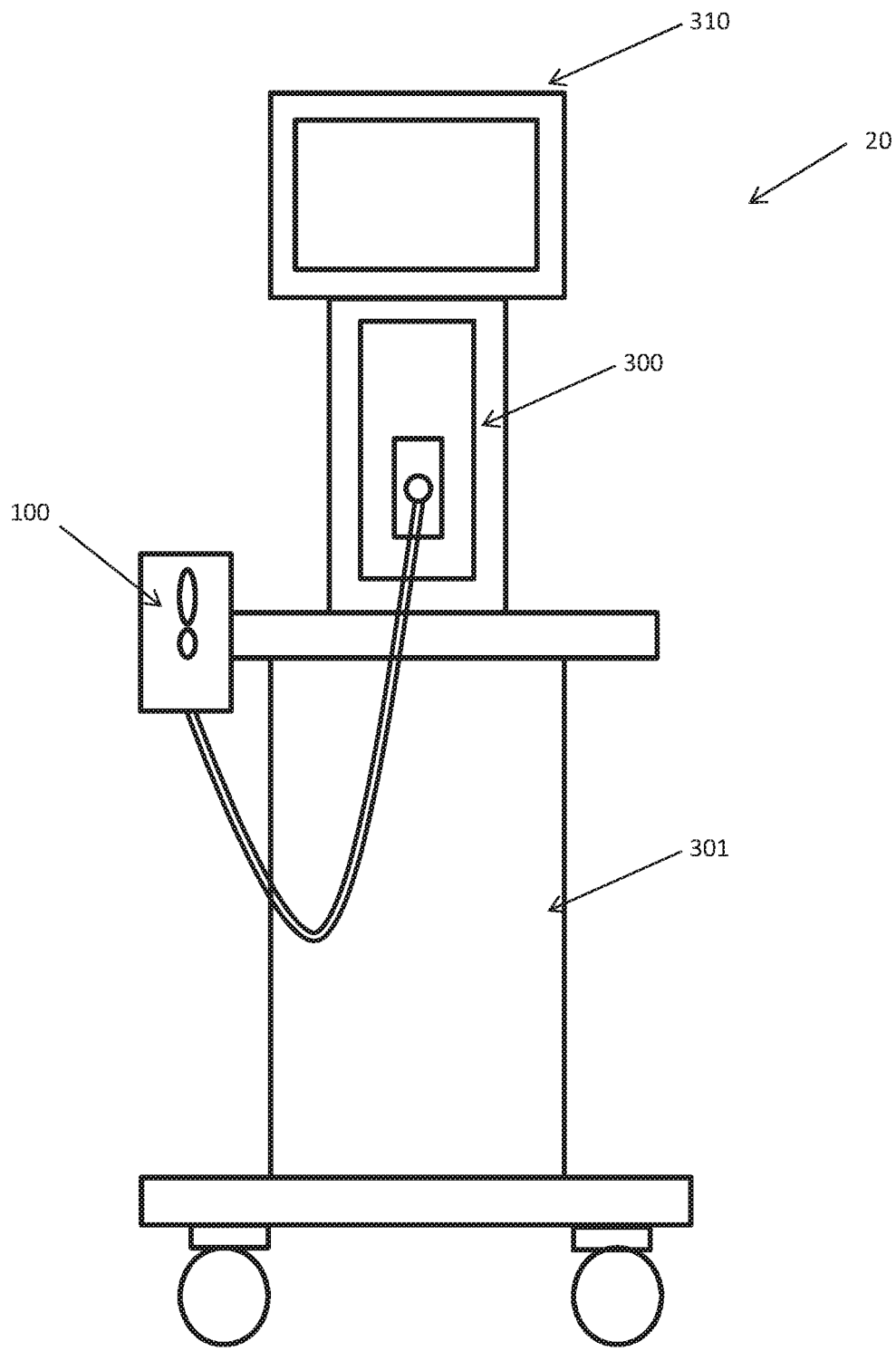
FIG. 1A is a schematic illustration of an ultrasound system according to various embodiments of the invention.

The following description sets forth examples of embodiments, and is not intended to limit the invention or its teachings, applications, or uses thereof. It should be understood that throughout the drawings, corresponding reference numerals indicate like or corresponding parts and features. The description of specific examples indicated in various embodiments of the invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

According to several embodiments of the invention, energy is used in combination with one or more agents to provide a synergistic aesthetic effect. In some embodiments, the energy is non-invasive ultrasound and the agent includes a dermal filler, a fat-reducing compound, a cavitation-prone fluid, a highly reflective, and/or absorptive fluid or combinations thereof. Although cellulite is treated in some embodiments, other treatments of tissue are also provided, including invasive/surgical methods, minimal-invasive methods and non-invasive, topical methods. In various embodiments, a combination of energy (such as HIFU) and one or more agents (compounds, fillers, gels, drugs, topicals, injectibles, lipolytics, etc.) is configured for one or more of the following: (i) improving lines and wrinkles in the skin, (ii) reducing fat, (iii) decreasing skin laxity or sagging tissue, (iv) increasing/enhancing collagen-network (e.g., collagen, elastin, fibronectin and laminin), and (iv) facial or body sculpting. This combination treatment is useful for the face or on locations below the face (e.g., the neck, décolletage, buttocks, thighs, upper arms, etc.). In some embodiments, a system is provided for both reducing fat and subsequently treating the loose, lax or sagging skin that results from fat reduction.

For example, although cellulite is described below, the embodiments described herein can also be used to treat wrinkles, reduce laxity, and/or achieve a plumping effect using ultrasound (such as HIFU) and a dermal filler (such as Radiesse). Lips can also be treated in some embodiments using a combination of energy (such as ultrasound) and lip fillers (such as hyaluronic acid, fat, collagen, etc.). As with other locations on the face and body, non-focused ultrasound may be used on the lips in one embodiment.

In other embodiments, fat and cellulite are treated on the body using energy (e.g., such as energy based devices (EBD), such as embodiments with ultrasound devices, and in one embodiment, HIFU, including HIFU at reduced intensity or defocused to enable the modification of an agent in the tissue) in combination with a pharmaceutical agent and/or dermal filler and a fat-reducing compound. The reduction of both fat and reinforcement of the connective tissue may result in an overall improved appearance of the cellulite phenotype and significant increased patient satisfaction.

Cellulite

Several embodiments of the invention provide medical devices and combinations for use in an improved treatment of tissue, for example, e.g., gynoid lipodystrophy (also known as cellulite), in particular a treatment that is effective, results in the desired aesthetic effects over a longer period, and is well tolerated. As used herein, the term "gynoid lipodystrophy" is interchangeably used with the term "cellulite." Gynoid lipodystrophy (or cellulite) generally refers to a condition that gives the skin an uneven, dimpled, orange peel-like appearance. The appearance of cellulite is derived from a combination of tissue laxity, structural fibrotic bands and fat. In a more specific sense, "gynoid lipodystrophy" means the herniation of subcutaneous fat within fibrous connective tissue, in particular in the subdermal layer (subcutis) of the skin, which usually manifests topographically as skin dimpling and nodularity, often on the pelvic region (specifically the buttocks), lower limbs, and abdomen.

While not pathological, cellulite represents a significant cosmetic appearance problem in general and in particular for severely affected individuals. Some of the co-existing factors that trigger, perpetuate or exacerbate cellulite include, among others, changes in metabolism of adipose tissue, gender specific dimorphic skin architecture, alteration of connective tissue structure, (e.g., altered fibrous tissue bands), sex-specific expansion of subcutaneous fat, skin laxity, as well as hormonal and genetic factors. Among these factors, changes in adipose tissue metabolism as well as changes in the dermal architecture are thought to be major factors for the formation of cellulite. Metabolic alterations result in an imbalance between generation of storage-fat (lipogenesis) and breakdown of storage-fat (lipolysis) within adipocytes. This leads to the formation of large adipocytes containing an increased amount of triglycerides which are typical of cellulite, giving the skin the dimpled appearance when pushing upwards within the degree of freedom defined by the network of dermal extra-cellular matrix forming the protruding fat lobuli. A lumped, textured appearance with of cellulite can be caused by the variations in the structures of multiple fat lobuli that push and distort the connective tissues beneath the skin; resulting protrusions and depressions of connective tissue anchor points create the appearance of cellulite. The changes in skin structure associated with cellulite develop in the subcutaneous layer of the skin (subcutis), which is located below the dermis and the epidermis. The fat cells of the subcutaneous fat layer below the dermis layer are arranged in chambers (e.g., lobuli) surrounded by bands of fibrous connective tissue called "septa." In non-cellulite adipose tissue, the fibrous septa are postulated to be arranged in higher numbers and/or an overlapping criss-cross pattern, creating greater strength of the tissue. In cellulitic tissue, on the other hand, the fibrous septa are arranged in parallel to each other, and perpendicular to the skin surface. This cellulitic structure is weaker and allows for the focal herniation of adipose tissue. Herniation of adipose tissue means that fat cells that are encased within the perimeters defined by the septa expand with weight gain or water gain, thereby stretching the connective tissue. The connective tissue contracts and hardens holding the skin at a non-flexible length, while the chambers or lobuli between the septa continue to expand. This results in the displacement of subcutaneous fat (herniation) and areas of the skin being pulled down while adjacent sections bulge outward, resulting in skin dimpling and the "orange peel" appearance.

In certain clinical morphological features of cellulite can be described with dimpling (e.g., a mattress phenomenon), Flattisch protrusion and linear depressions of skin surface due to irregular retraction of the skin, "Orange Peel" skin, and/or enlarged and hyperkeratotic follicular orifices due to the tumefaction of the epidermis and dilation of follicular pores, and/or laxity in the tissue. In particular situations, single dermal septa can form a prominent and local rigid perpendicular structure in the dermis. This local strong connective tissue structure holds the skin down while surround skin can be expanded by expanding subcutaneous fat tissue. In such situation, in addition to a general dimpling (e.g., orange peel), at focal locations distinct depressions are easily visible as prominent large dimples. Several embodiments described herein are designed to address the factors that contribute to the underlying causes of cellulite and the undesired appearance. In one embodiment, a device for cutting (e.g., tissue disruption/dissection device, subcision device) is used in a treatment of prominent cellulite dimples.

One major pathophysiological origin of cellulite can be traced back to architectural alterations in the subject's skin and subcutaneous fat tissue. Some specialized connective tissue structure has fibers which are perpendicular to the skin (more parallel to the skin surface) forming thus a network of compartments in which fat cells are located (e.g., visible as lobuli or fat lobuli). In many post-pubertal women this connective tissue structure can become weak. Thus, adipocytes are pushed upwards into the dermis leading to skin dimpling and nodular characteristics which leads to the clinical appearance of cellulite. This process of pushing the fat cells upwards through the "roof" of these fat cell lobuli compartments can be referred to as herniation of adipocytes into the dermis. According to several embodiments, architectural alterations are addressed by the combination of energy (such as HIFU) and anti-cellulite agents.

In one embodiment, an orange-peel cellulite phenomenon is described on histopathology grounds associated with alteration of adipocytes (anisopoikilocytosis) associated with lymphatic stasis and proliferation of fibrocytes. In one embodiment, an orange-peel cellulite phenomenon is described on histopathology grounds associated with fibroplasia, neocollagenesis, capillary neoformation, focal microhemorrhage and follicular hyperkeratosis with mild dermal oedema for an orrange peel appearance. In one embodiment, an orange-peel cellulite phenomenon is described on histopathology grounds associated with sclerosis of fibrous septae of the subcutaneous tissue and deep dermis, causing a mattress phenomenon.

In accordance with several embodiments of the invention, the subject to be treated has cellulite, e.g., is an individual subject in need of a cellulite treatment. Furthermore, in some embodiments, the subject may be a subject afflicted with severe cellulite. Within the meaning of some embodiments of the invention, "severe cellulite" corresponds to a total sum of scores of items (a) and (b) of the Hexsel, Dal'Forno, and Hexsel Cellulite Severity Scale (CSS) (Hexsel et al., A validated photonumeric cellulite severity scale, J. Eur. Acad. Dermatol. Venereol. 2009, 23: 523-528, herein incorporated by reference) of 4, 5 or 6, wherein item (a) denotes the number of evident depressions and item (b) denotes the depth of depressions, and both items (a) and (b) are graded from 0 to 3.

According to several embodiments of the invention, cellulite treatment is achieved by administering HIFU ultrasound treatment with a dermal filler and/or a fat-reducing compound that is capable of reducing local subcutaneous fat to a subject having gynoid lipodystrophy. This combined treatment approach addresses both the "connective tissue aspect" and the "fat cell aspect" and will provide improved treatment results while being well tolerated in several embodiments. Specifically, the combination treatment, in several embodiments, reduces the unwanted appearance of cellulite, increases the patient satisfaction, and improves the patient's quality of life. As discussed in further detail below, several embodiments of the invention comprise several combination treatments with energy-based devices with any one or more of an anti-cellulite agent, including for example any one or more of (i) dermal fillers, (ii) fat-reducing compounds, and (iii) cavitation, reflective and/or absorptive prone fluids.

In some embodiments, treatment addresses a connective tissue aspect of cellulite by remodeling, strengthening, or otherwise altering the shape of fat lobuli compartments (e.g., treating the structural wall, floor, and/or roof of the fat lobuli compartments and/or tissue proximate to one or more fat lobuli under the skin surface). As used herein, the term "connective tissue aspect" refers to the architectural alterations in the subject's subcutaneous connective tissue in connection with cellulite, e.g., the weakening of the skin's specialized connective tissue forming a network of compartments (septa, fat lobuli), and the upward pushing of the fat cells into the dermis leading to skin dimpling and nodular characteristics accounting for the clinical appearance of cellulite. In various embodiments, certain treatment methods of the invention address a structural, connective tissue aspect associated with cellulite via a subcision/tissue dissection treatment which breaks down/cuts the fibrous septa of cellulite (e.g., with energy configured for cutting septa a one or more targeted depths, with mechanical cutting) thus target the "connective tissue aspect." In accordance with several embodiments, the subcision/dissection treatment is used if a single dermal septa forms a prominent and local rigid perpendicular structure in the dermis.

In some embodiments for treatment of cellulite, treatments addressing the "fat cell aspect" of cellulite reduce or remove the volume of fat in the network of fat lobuli compartments. The term "fat cell aspect," as used herein, refers to a metabolic shift of adipocytes in favor of lipogenesis as well as to alterations of adipocytes associated with cellulite, such as an increased adipocyte size and an increased content of triglycerides (triacylglycerides), as well as to the cellular aspect concerning the number of fat cells. The term "addressing," as used herein with respect to the different aspects of gynoid lipodystrophy, refers to the utility of a treatment for improving the different conditions causing and/or being associated with cellulite. In one embodiment, treatment of a fat cell aspect involves reducing the volume of fat underlying the appearance of cellulite.

The term "treatment," as used herein, is intended to refer to any treatment carried out for cosmetic purposes. The term "cosmetic," as used herein, may be interchangeably used with "aesthetic." Furthermore, the term "subcutaneous fat," as used herein with respect to reducing local subcutaneous fat, is to be construed and particularly relates to fat, fat tissue or fat layer, or a fat deposit in the subcutis or subcutaneous layer (subdermal layer) of skin. The term "fat" within the meaning of some embodiments of the invention broadly relates to fat and fat constituents, especially triglycerides (triacylglycerides), as well as fat cells (adipocytes). The term "reducing," as used herein with respect to a compound capable of reducing local subcutaneous fat or fat-reducing compound, is intended to mean removing, decreasing, diminishing or minimizing local subcutaneous fat. Thus, the term "reducing" is intended to refer to removing, or decreasing (or diminishing or minimizing) the size, volume or amount of fat, a fat deposit, fat cells, a fat layer, a subcutaneous fat layer, a subdermal fat layer, and the like. It should further be appreciated that the term "reducing" does not imply any restrictions regarding the mechanism of fat reduction. Therefore, it includes, for example, decreasing the size or content of fat cells and/or decreasing the number of fat cells. Reducing in size may be a decrease of the volume of the local subcutaneous fat by at least 5%, at least 10%, at least 25%, at least 30%, at least 40%, at least 50%, at least 60%, at least 70%, at least 80%, at least 90%, or at least 95% in volume, particularly a decrease of the volume of the local subcutaneous fat in the range of 25% to 70%, more particularly in the range of 30% to 65% or 35% to 60%, and most particularly in the range of 40% to 55%. Where percentages are provided for agents, ingredients and compounds, they can be % m/m, % m/w, % w/w, % m/v, % v/v and variations thereof with respect to the formulation as a whole, unless otherwise indicated.

Dermal Fillers

In various embodiments, the use of a HIFU system 20 in combination with a dermal filler 800 provides an improved treatment of skin tissue, such as for the cosmetic reduction of the appearance of cellulite.

In various embodiments, a dermal filler 800 is collagen, hyaluronic acids, and/or calcium (hydroxy)phosphate (e.g., calcium hydroxyapatite, hydroxyapatite particles, calcium hydroxyapatite, calcium hydroxyapatite microspheres), and combinations of 2, 3 or more thereof. One non-limiting example of a dermal filler 800 includes RADIESSE® (a registered trademark of Merz North America, Inc.). In one embodiment, an undiluted formulation of Radiesse comprises or other dermal filler, consists essentially of, or consists of a solution containing 54-58% (w/w) (+/−0.5%) of specified particles. In one embodiment, an undiluted formulation of Radiesse or other dermal filler comprises, consists essentially of, or consists of a solution containing 56.3% (w/w) (+/−2%) of specified particles. In one embodiment, an undiluted formulation of Radiesse comprises, consists essentially of, or consists of a solution containing about 30% w/v of CaHAP particles. In one embodiment, an undiluted formulation of Radiesse comprises, consists essentially of, or consists of a solution containing about 30% v/v of CaHAP particles. In one embodiment, a Radiesse-dilute formulation would be any formulation generated from an undiluted Radies se-formulation by addition of a physiological solvent suitable for injection. As used herein, a "dilution" mentioned with a ratio (e.g., 1:1; 1:2, etc.) refers to a dilution ratio. In various embodiments, the dilution (ratio) may range from 1:0.1-1:1000 more specifically 1:0.5-1:100 and in particular 1:1-1:10. In one embodiment, a 1:1 dilution of the standard Radies se-formulation is used. In some embodiments, a dilution greater than 1:1 (e.g., 1:15, 1:2, 1:3, 1:4, or more) is used. In one embodiment, the dermal filler 800 is calcium (hydroxy)phosphate (e.g., hydroxyapatite) particles for an improved treatment of gynoid lipodystrophy. Some embodiments of the dermal filler 800 are described as referring to "hydroxyapatite" or "hydroxyapatite particles" (e.g., in one embodiment, "calcium (hydroxy)phosphate" or "calcium (hydroxy) phosphate particles"). The term "calcium (hydroxy)phosphate," as used in the context of some of the embodiments of the invention, includes, e.g., (1) calcium phosphates, such as monocalcium phosphate (MCP) (e.g., $Ca(H_2PO_4)_2$), dicalcium phosphate (DCP) (e.g., $CaHPO_4$), calcium dihydrogen phosphate (CDP) (e.g., $Ca(H_2PO_4)_2$), tricalcium phosphate (TCP) (e.g., $Ca_3(PO_4)_2$) including its α-, α'- and β-polymorphs, octacalcium phosphate (OCP) (e.g., $Ca_8H_2(PO_4)·6.5H_2O$), biphasic tricalcium phosphate (BCP; a mixture of two phases: hydroxyapatite (HA) and β-tricalcium phosphate (β-TCP)), and (2) calcium hydroxyphosphates, such as hydroxyapatite. In some embodiments, dermal filler 800 particles made of calcium (hydroxy)phosphate that have a defined particle size, e.g., a mean particle diameter of about 10 μm to about 100 μm, preferably about 20 μm to about 70 μm. In one embodiment, dermal filler 800 is calcium phosphate is a tricalcium phosphate (TCP), e.g., β-TCP. In one embodiment, dermal filler 800 is a calcium hydroxyphosphate, such as e.g., calcium hydroxyapatite (CaHAP) ($Ca_5(PO_4)_3(OH)$), which can be written as $Ca_{10}(PO_4)_6(OH)_2$. In various embodiments of dermal filler 800, suitable hydroxyapatite particles are any particles of a given size made of hydroxyapatite. In some embodiments, a filler such as hydroxyapatite is made with a mean particle size such as CaHAP or a particle with a maximum size or a particle with a minimum size in order to achieve a certain acoustic characteristic such as amount attenuation, reflection, back scatter intensity, back scatter directionality, etc. In some cases, the filler has a certain specified CaHAP in the fluid. "Hydroxyapatite" refers to a mineral species of the phosphate family with the formula $Ca_5(PO_4)_3(OH)$, usually written as $Ca_{10}(PO_4)_6(OH)_2$ to stress the fact that the lattice of the crystalline structure contains two molecules. Hydroxyapatite belongs to the crystallographic apatite family, which are isomorphic compounds having the same hexagonal structure. In one embodiment, dermal filler 800 comprises hydroxyapatite particles with an atomic ratio of calcium to phosphorus of 1.67±0.03.

In several embodiments of a dermal filler 800, hydroxyapatite particles are spherical or essentially spherical particles. In several embodiments of a dermal filler 800, the hydroxyapatite particles have a D-ratio of greater or equal to 0.9. The D-ratio is defined as the ratio of the calculated diameter of a perfect circle based on the cross sectional area of the particle to the maximum diameter measured through that cross sectional centroid. In several embodiments of a dermal filler 800, the mean size of the dermal filler 800 particles in diameter is usually less than 200 μm, preferably in the range of about 10 μm to 100 μm, more preferably in the range of about 20 μm to about 70 μm, and most preferably in the range of about 25 μm to about 45 μm in diameter. In addition, the hydroxyapatite particles may not comprise more than 10 wt. % of particles having a diameter of 20 μm or less, or more than 5 wt. % of particles having a diameter of 25 μm or less, and/or more than 5 wt. % of particles having a diameter of 45 μm or greater, or more than 2 wt. % of particles having a diameter of 70 μm or greater. In several embodiments of a dermal filler 800, the particles have a BET surface area of equal to or less than 0.10 $m^2/g$.

In accordance with several embodiments of the invention, the dermal filler 800 is administered as an injectable composition, in particular as an injectable composition, e.g., in the form of a hydrogel (hydrogel composition). In several embodiments of a dermal filler 800, the injectable composition comprises dermal filler particles and a pharmaceutically acceptable carrier such as an aqueous solution, an organic solvent, a mixture of an aqueous solution and an organic solvent, or a gel. In one embodiment, the pharmaceutically acceptable carrier generally serves as solvent or suspending agent for the dermal filler particles. The term "pharmaceutically acceptable," as used herein, refers to materials or substances that are suitable for use in contact with the tissues of humans and mammals without undue toxicity, irritation, allergic response, and the like. The term "gel" or "hydrogel," as used herein, generally refers to a water-swollen three-dimensional network consisting of crosslinked or non-crosslinked polymer chains. Within several embodiments of the invention, the gel is a cohesive gel, e.g., a gel having the capacity not to dissociate, because of the affinity of its polymer chains for each other. Cohesivity is used in some embodiments for the solid and fluid phases of a gel to remain intact, and thus forming a stable gel.

In several embodiments of a dermal filler 800, the injectable composition comprises hydroxyapatite particles is in the form of a hydrogel comprising the hydroxyapatite particles and at least one polysaccharide. The polysaccharide gel provides a (carrier) matrix for suspending or dispersing the hydroxyapatite particles. The "polysaccharide" is not particularly limited and may include, for example, cellulose, cellulose ester and cellulose ether derivatives such as cellulose acetate (CA), carboxymethyl cellulose (CMC), carboxyethyl cellulose (CEC), carboxypropyl cellulose (CPC), carboxymethyl ethylcellulose (CMEC), methyl cellulose (MC), ethyl cellulose (EC), hydroxyethyl cellulose (HEC), hydroxyethyl methylcellulose (HEMC) and hydroxypropyl methylcellulose (HPMC), hyaluronic acid (HA), dextran, carboxymethyldextran, carboxymethylstarch, chondroitin sulfate, dermatane sulfate, keratin, keratin sulfate, chitosan, chitin, pectin, carrageenan, xanthan, heparin, heparin sulfate and alginate. In one embodiment, the polysaccharide is selected from the group consisting of hyaluronic acid (HA), carboxylated cellulose derivatives (e.g., carboxymethyl cellulose (CMC)), and mixtures thereof. In various embodiments, polysaccharide(s) of the gel matrix may be crosslinked and/or non-crosslinked. A "crosslinked gel" or "crosslinked gel matrix" within the context of various embodiments of the invention refers to a (hydro)gel or (hydro)gel matrix which is covalently crosslinked using a crosslinking agent. Optionally, the injectable composition may contain one or more non-crosslinked polysaccharides which may be the same as or different to the crosslinked polysaccharide(s). The term "crosslinking agent" or "crosslinker," as used herein, refers to a compound having at least two functional groups (e.g., two, three or more epoxide functional groups) capable of reacting with polysaccharide polymers (e.g., hyaluronic acid) to form covalent (intra- and/or intermolecular) crosslinks. The term "crosslinking agent" or "crosslinker" is not specifically limited within some embodiments of the invention. In one embodiment, the crosslinker is a diepoxide crosslinker, e.g., 1, 4-butanediol diglycidyl ether (BDDE). Other suitable diepoxid crosslinkers include, but are not limited to ethylene glycol diglycidyl ether (EGDGE), 1, 6-hexanediol diglycidyl ether, polyethylene glycol diglycidyl ether, polypropylene glycol diglycidyl ether, polytetramethylene glycol digylcidyl ether, neopentyl glycol digylcidyl ether, polyglycerol polyglycidyl ether, 1, 2, 7, 8-diepoxyoctane, 3-(bis(glycidoxymethyl)-methoxy)-1, 2-propanediol, 1, 4-cyclohexanedimethanol diglycidyl ether, 4-vinyl-1-cyclohexene diepoxide, 1, 2, 5, 6-diepoxycyclooctane, and bisphenol A diglycidyl ether. In several embodiments of a dermal filler 800, the injectable composition comprises only one type of polysaccharide or a mixture of two different polysaccharide types (e.g., CMC and/or HA). The term a "type of polysaccharide," as used herein, also includes mixtures of materials of the same polysaccharide but having a different mean molecular weight and/or a mixture of the same polysaccharide in crosslinked and/or non-crosslinked form. Advantageously, in some embodiments, the at least one polysaccharide is selected from crosslinked or uncrosslinked carboxymethylcellulose, crosslinked or uncrosslinked hyaluronic acid, or a mixture thereof, in particular (uncrosslinked) carboxymethylcellulose or crosslinked hyaluronic acid, or a mixture thereof. In several embodiments of a dermal filler 800, the mean molecular weight of the hyaluronic acid is in the range of about $2.5 \times 10^5$ Da and $4 \times 10^6$ Da, more preferably in the range of about $1 \times 10^6$ Da and $3 \times 10^6$ Da. In several embodiments of a dermal filler 800, hyaluronic acid is crosslinked with a diepoxide crosslinker, e.g., BDDE. In several embodiments of a dermal filler 800, the particles may be present in the injectable composition in an amount of about 5 to 45 vol. %, preferably 10 to 40 vol. %, more preferably 15 to 35 vol. %, and most preferably 20 to 30 vol. %. Furthermore, in several embodiments, the at least one polysaccharide may be present in the injectable composition in a total amount of about 0.01% to 5.0% (mass/volume), about 0.1% to 4.0% (mass/volume), about 0.5% to 3.0% (mass/volume), about 1.0% to 2.5% (mass/volume) or 1.5 to 2.0% (mass/volume).

In various embodiments, a dermal filler 800 is administered by local cutaneous injection, e.g., by injection into the skin (e.g., into the dermis, the subcutis, or both the dermis and subcutis, and some embodiments, to the deep dermis, upper subcutis, or the deep dermis and upper subcutis). The term "deep dermis" generally refers to the reticular region of the dermis, e.g., a region lying deep in the papillary region and being usually much thicker than the papillary region, which is located between the epidermis and the reticular region. The reticular region of the dermis is composed of dense irregular connective tissue, and has its name from the dense concentration of collagenous, elastic, and reticular fibers. In some embodiments, a dermal filler 800 is administered more than once in a single treatment session for administration of a given amount of dermal filler 800 particles, the distance between two punctures (spacing of the punctures) is at least 0.25 cm, e.g., 0.25 cm to 3.0 cm, 0.25 cm to 2.5 cm or 0.5 cm to 2.0 cm, and 0.75 cm to 1.25 cm or about 1 cm, and any values or ranges therein. In various embodiments, there are not more than 4 punctures per square centimeter ($cm^2$), not more than 2 punctures per $cm^2$, not more than 1 puncture per $cm^2$ or even less such as not more than 0.5 or not more than 0.25 or not more than 0.1 punctures per $cm^2$. In several embodiments, an injectable composition of dermal filler 800 particles may further comprise at least one additional pharmaceutically acceptable active ingredient. Said additional pharmaceutically acceptable ingredient may be selected from the group of ingredients promoting collagen biosynthesis. In several embodiments of a dermal filler 800, additional pharmaceutically acceptable active ingredients promoting collagen biosynthesis can be selected from the group consisting of retinol, rhamnose, saponins, petroselinic acid, conjugated linoleic acid, hibamata extract, pentapeptides, hexapeptides, polycaprolactone, and poly-L-lactic acid. In several embodiments of a dermal filler 800, the injectable composition of particles may further comprise an anesthetic and/or anti-inflammatory agent. In some embodiments, the anesthetic is a local anesthetic, preferably lidocaine, in a concentration of, for example, 0.05 wt. % to 5.0 wt. %, 0.1 wt. % to 4.0 wt. %, 0.2 wt. % to 3.0 wt. %, 0.3 wt. % to 2.0 wt. %, or 0.4 wt. % to 1.0 wt. %. In several embodiments of a dermal filler 800, the injectable composition of particles may comprise one or more compounds selected from the group consisting of polyols, vitamins, amino acids, metals, antioxidants, and mineral salts. Suitable polyols for use herein include, but are not limited to, glycerin, mannitol, sorbitol, propylene glycol, erythritol, xylitol, maltitol, and lactitol. Particularly suitable for use herein is mannitol and glycerol. Preferably, the polyol is glycerol, optionally in combination with one or more of the aforementioned polyol compounds, in particular mannitol. The polyol(s) may, for example, be included in the injectable dermal filler composition in a concentration of 0% (no polyol) to 20% (volume/volume), 0.1% to 19% (volume/volume), 1% to 18%, 2% to 17%, or 3% to 13% (volume/volume), in particular in a concentration of 5% to 12% or 7% to 10% (volume/volume).

In one embodiment, an injectable dermal filler 800 composition of hydroxyapatite particles is a sterile, non-pyrogenic injectable composition of spherical hydroxyapatite particles in an aqueous based gel carrier, the composition consisting of about 55.7 wt. % calcium hydroxyapatite particles having a diameter of from about 25 μm to about 45 μm, 36.6 wt. % sterile water for injection (USP), 6.4 wt. % glycerin (USP), and 1.3 wt. % sodium carboxymethyl cellulose (USP). In one embodiment, an injectable dermal filler 800 composition of hydroxyapatite particles for use is the soft tissue filler RADIESSE or diluted versions thereof. RADIESSE comprises calcium hydroxyapatite microspheres, a CMC gel matrix and glycerol.

In various embodiments, a dermal filler 800 is a biostimulatory dermal filler promoting collagen biosynthesis. As used herein, a "biostimulatory filler" is any injectable, bio-compatible material which can be used to compensate volume loss and or stimulates regenerative processes in the skin (e.g. stimulation of collagen syntheses, restructuring of extra-cellular-matrix network) resulting in a phenotype which resembles youthful-skin by reverting or compensating age related changes in the skin. In one embodiment, a dermal filler 800 comprises calcium (hydroxy) phosphate particles as described herein. In various embodiments, a dermal filler 800 is a suitable biostimulatory dermal filler that is useful and may be selected as one or more from the group consisting of polycaprolactone and poly-L-lactic acid.

HIFU in Combination with Dermal Filler

The dermal fillers 800 described herein are used in combination with energy delivery in several embodiments. For example, ultrasound (for example, as further described below) is used in conjunction with a dermal filler 800. In one embodiment, a combination of ultrasound (e.g., HIFU) and dermal filler significantly reduces the unwanted appearance of cellulite, is well tolerated and leads to increased patient satisfaction and improvement of the patient's quality of life. In some embodiments, one dermal filler is used. In other embodiments, two, three or more dermal fillers are used. Non-focused ultrasound or non-ultrasound energy (laser, radiofrequency, thermal energy, etc.) may be used in alternative embodiments (instead of or in addition to HIFU).

In one embodiment, the combination of ultrasound (e.g., HIFU system 20) treatment with an injection of dermal filler 800 improves the skin firmness, laxity and flaccidity, and reduces the cosmetic appearance of cellulite. Without being bound by theory, it is believed that the combined effect of the HIFU 20 treatment with the injected dermal filler 800 increases in situ synthesis of extracellular matrix in general, and stimulates collagen synthesis in particular, thereby increasing the firmness or "strength" of the skin and providing beneficial long-lasting treatment effects.

In one embodiment, the combination of energy (e.g., HIFU) and a dermal filler treatment is used to address the "connective tissue aspect" by strengthening tissue structure, e.g., the skin connective tissue. In one embodiment, the HIFU system 20 treatment creates thermal coagulation zones in the dermis, which coagulates collagen and initiates new collagen formation in the dermis, strengthening and tightening the dermal tissue and structure on the top, or roof, of fat lobuli, thereby flattening the bulges in the tops/roofs of the fat lobuli, and reducing the appearance of cellulite. In one embodiment, the HIFU system 20 treatment interacts with the dermal filler 800 to strengthen, flatten, and/or tighten the dermal tissue and structure on the top, or roof, of fat lobuli, thereby flattening the bulges in the tops/roofs of the fat lobuli, and reducing the appearance of cellulite. In one embodiment, the HIFU system 20 treatment interacts with the dermal filler 800 to heat the tissue to direct the dermal filler 800 to particular ultrasound targeted locations, resulting in strengthening, flattening, and/or tightening the dermal tissue and structure on the top, or roof, of fat lobuli, thereby flattening the bulges in the tops/roofs of the fat lobuli, and reducing the appearance of cellulite. In one embodiment, the HIFU system 20 treatment heats the dermal filler 800 to more quickly move, stabilize, and/or harden the dermal filler 800 at particular ultrasound targeted locations, resulting in strengthening, flattening, and/or tightening the dermal tissue and structure on the top, or roof, of fat lobuli, thereby flattening the bulges in the tops/roofs of the fat lobuli, and reducing the appearance of cellulite. In various embodiments, the HIFU system 20 heats the dermal filler 800 to move, stabilize, and/or harden between 5-100% (e.g., 5%, 10%, 20%, 25%, 30%, 40%, 50%, 60%, 70%, 75%, 80%, 90%, 95%, 100%, or any values or ranges therein) faster than curing at body temperature. In one embodiment, the HIFU system 20 treatment heats the dermal filler 800 to move, stabilize, and/or harden the dermal filler 800 in a designed ultrasound targeted structure, thereby forming one or more struts, posts, grids, matrices, webs, ribs, supports, or other designed structures formed in vivo in the body, to provide a dermal filler 800 structure.

In one embodiment, the combination of energy (e.g., HIFU) and dermal filler is used to address both the "connective tissue aspect" and the "fat cell aspect" of cellulite by strengthening tissue structure, e.g., the skin connective tissue with HIFU and dermal filler's at the tissue structure underlying cellulite, and by heating the fat cells to reduce the volume of fat inside the lobuli via ablation, lysing, coagulation, and/or adipocytotis using varying power and/or temperature levels of heat treatment. In one embodiment, the HIFU system 20 treatment creates thermal heating zones leading to the reduced volume of fat cells in the subcutaneous fat tissue and in a further embodiment in the fat lobuli compartments, thereby deflating the bulges in the fat lobuli, and reducing the appearance of cellulite. In one embodiment, the HIFU system 20 treatment reduces fat volume and the dermal filler 800 strengthens, flattens, and/or tightens the dermal tissue and structure on the top, or roof, of fat lobuli, thereby reducing the volume of fat and flattening the bulges in the tops/roofs of the fat lobuli, and reducing the appearance of cellulite. In some embodiments, the use of energy (such as HIFU) with at least one dermal filler reduces the amount of dermal filler needed to achieve a comparable effect by at least 10%, 20%, 30%, 50%, and overlapping ranges therein, or more. In some embodiments, the use of energy (such as HIFU) with at least one dermal filler expedites or enhances the desired aesthetic effect by at least 10%, 20%, 30%, 50%, and overlapping ranges therein, or more. These effects are compared to the use of the same or similar dermal filler without energy. In one embodiment, the dermal filler reduces the amount/time of energy (e.g., HIFU) needed or enhances the effects of the energy by at least 10%, 20%, 30%, 50%, and overlapping ranges therein, or more (as compared to the energy used alone, without dermal filler).

Fat-Reducing Compounds

In various embodiments, the use of energy (e.g., a HIFU system 20) in combination with a compound capable of reducing local subcutaneous fat, also referred to herein as a "fat-reducing compound" 820 provides an improved treatment of skin tissue, such as for the cosmetic reduction of the appearance of cellulite. In some embodiments, one fat-reducing compound is used. In other embodiments, two, three or more fat-reducing compounds are used. Non-focused ultrasound or non-ultrasound energy (laser, radiofrequency, thermal energy, etc.) may be used in alternative embodiments (instead of or in addition to HIFU).

In various embodiments, a fat-reducing compound 820 may be selected from the group consisting of:

(i) adipocytolytic compounds (e.g., compounds destroying directly or indirectly adipocytes), such as polidocanol (hydroxypolyethoxydodecan), cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA), (ii) pentacyclic triterpenoid compounds, including ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone, (iii) compounds that stimulate the β2-adrenergic pathway directly or block the activity of cellular phosphodiesterases, such as paraxanthine, caffeine, ciclostamide, amirone, tolfentrine, revizinone and enoximone, (iv) proapoptotic compounds, such as resveratol and phytoalexin, (v) compounds impairing differentiation of pre-adipocytes, such as antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin, (vi) other compounds such as fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, glabridin, and (vii) combinations of one or more of (i) to (vi).

In various embodiments, a fat-reducing compound 820 is selected from the group consisting of polidocanol, fluoxetine, pentacyclic triterpenoid compounds, obeticholic acid and deoxycholic acid. In one embodiment, a fat-reducing compound 820 is polidocanol (hydroxypolyethoxydodecan).

In various embodiments, pentacyclic triterpenoid compounds exhibit, in addition to the desired adipocytolytic effect, pharmaceutically acceptable supportive activities (e.g., pro-lipolytic activity and apoptosis-inducing capacity) enhancing the desired fat-tissue reducing effect. In some embodiments, the suggested compounds can be safely purified from plants, thereby avoiding the use of material from animal sources and eliminating the risk of animal transmitted diseases. In one embodiment of a fat-reducing compound 820, the pentacyclic triterpenoid compounds have the following structure according to formula (I)

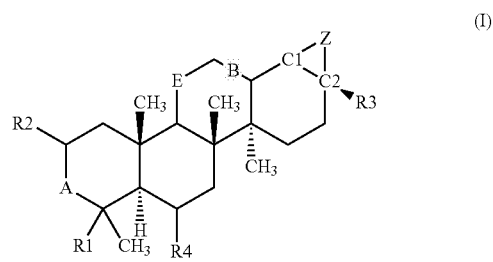

wherein:
R1 is selected from the group consisting of —$CH_3$, —$CH_2OH$, and —$COO^-X^+$, wherein $X^+$ is a proton or a pharmaceutically acceptable cation;
R2 is hydrogen or —OH;
R3 is selected from the group consisting of —$COO^-X^+$, —$CH_3$, and —COORa, wherein $X^+$ is a proton or a pharmaceutically acceptable cation and wherein Ra is a $C_{1-4}$-alkyl residue; in particular R3 is —$COO^-X^+$
R4 is hydrogen or —OH;
C1 and C2 are each a carbon atom wherein the valency of C1 is replenished by hydrogen when the bond to z is a single bond;
z represents a bivalent residue selected from the groups consisting of

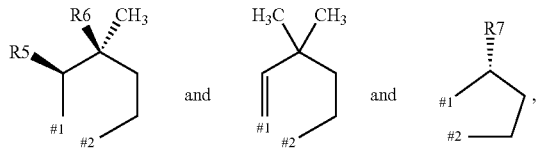

wherein
1 represents the binding site to the carbon atom C1 of the remaining structure according to formula (I),
2 represents the binding site to the carbon atom C2 of the remaining structure according to formula (I),
R5 is —$CH_3$ or hydrogen; R6 is —$CH_3$, hydrogen, or —$COO^-X^+$, and
R7 is a $C_{2-4}$ alkenyl residue or a $C_{1-4}$ alkyl residue, preferably a $C_{2-4}$ alkenyl residue;
A is a bivalent residue selected from the groups consisting of —CH(OH)—, —CH(OAc)—, —CO—, and —$CH_2$—, where Ac is an acyl group, in particular an acetyl group (—CO—$CH_3$) or a succinyl group (—CO—$CH_2CH_2$—COOH); and
B represents a double or a single bond; E represents —$CH_2$— or —CO—,
in particular wherein one of R1, R3 or R6 is —$COO^-X^+$, wherein $X^+$ is a proton or a pharmaceutically acceptable cation.

In several embodiments, a "pharmaceutically acceptable salt" is any salt that exhibits a comparably low toxicity and is acceptable for pharmaceutical purposes. Examples of pharmaceutically acceptable salts may comprise a cation selected from the group consisting of an alkali metal (in particular, $Na^+$ and/or $K^+$), a proton (e.g., $H^+$), an alkaline earth metal (in particular, $Mg^{2+}$ and/or $Ca^{2+}$), ammonium ($NH_4^+$), $Fe^{2+}$, $Fe^{3+}$, $Zn^{2+}$, $Sn^{2+}$, and an organic amine cation, or may comprise an anion selected from the group consisting of a halogen (in particular $Cl^-$, $Br^-$, $I^-$ and/or $F^-$), $OH^-$, $H_2PO_4^-$, $HPO_4^{2-}$, $PO_4^{3-}$, $SO_4^{2-}$, an anion of an organic acid (e.g., acetate, methanoate, propionate, a salt of a fatty acid, gluconate, lactate, citrate, etc.), an organic sulfonate, an organic sulfate, and organic phosphate. In one embodiment, carbon atoms C1 and C2 together with the bivalent residue z form a 5- or 6-membered ring, optionally substituted one, two or three times by —$CH_3$ and substituent(s) R5, R6 and/or R7 as indicated above. Thereby the triterpenoid compound becomes a pentacyclic triterpenoid compound. The core structure (scaffold) of the pentacyclic triterpenoid structure of several embodiments of the invention may be an ursane (alpha-Amryn), an oleanane (beta-Amryn) or a lupane ring structure. In embodiments of the above structure, $X^+$ may be any proton or a pharmaceutically acceptable cation. In one embodiment, $X^+$ is a one-fold positively charged ion. For example, the cation may be selected from the group consisting of an alkali metal (in particular, $Na^+$ and/or $K^+$), an alkaline earth metal (in particular, $Mg^{2+}$ and/or $Ca^{2+}$), ammonium ($NH_4^+$), $Fe^{2+}$, $Fe^{3+}$, $Zn^{2+}$, $Sn^{2+}$, and an organic amine. In one embodiment, the cation is a proton ($H^+$) or an alkali metal (in particular, $Na^+$ and/or $K^+$). In one embodiment, at least one of R1, R3 or R6 is —$COO^-X^+$, wherein $X^+$ is a proton or a pharmaceutically acceptable cation. In one embodiment, R7 is —C(=$CH_2$)—$CH_3$ and/or A is —CH(OH)— or —CO—. In one embodiment, one of R1, R3 and R6 is —$COO^-X^+$, wherein $X^+$ is a proton or a pharmaceutically acceptable cation. Then, in various embodiments, the other residues do not comprise a carboxyl group. In one embodiment, R1 is —$CH_3$. In one embodiment, in the pentacyclic triterpenoid compound according to formula (I), in group z, R7 is —C(=$CH_2$)—$CH_3$. In one embodiment, in the pentacyclic triterpenoid compound according to formula (I), A is —CH(OH)—, —CH(OAc)— (wherein "Ac" represents an acetyl moiety (—CO—$CH_3$) or a succinyl group (—CO—$CH_2CH_2$—COOH)), or —CO—. In one embodiment, in the pentacyclic triterpenoid compound according to formula (I), B represents a double or a single bond.

In one embodiment, the triterpenoid compound has the following structure according to formula (II)

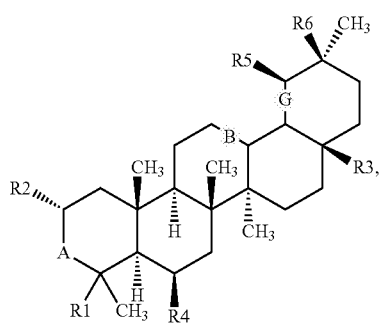

(II)

wherein the residues R1 to R6, A and B are as defined above and wherein G is a single or a double bond.

In one embodiment, the triterpenoid compound has the following structure according to formula (III)

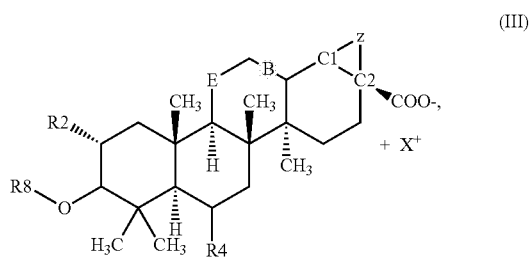

(III)

wherein:

C1 and C2 are each a carbon atom;

R2 is hydrogen or —OH;

R4 is hydrogen or —OH, in particular hydrogen;

R5 is —$CH_3$ or hydrogen;

R6 is —$CH_3$, hydrogen, or —$COO^-X^+$; and

R8 is hydrogen or —CO—$CH_3$; or

R8 is Ac, where Ac is an an acyl group, in particular an acetyl group (—$COCH_3$) or a succinyl group (—CO—$CH_2CH_2$—COOH); and z represents a bivalent residue selected from the group consisting of

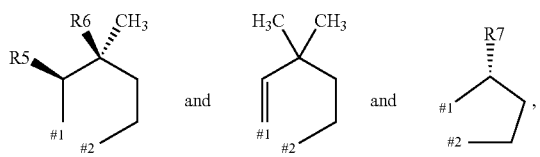

wherein

1 represents the binding site to the carbon atom C1 of the remaining structure according to formula III,

2 represents the binding site to the carbon atom C2 of the remaining structure according to formula III, and B represents a double or a single bond; and $X^+$ is a proton or a pharmaceutically acceptable cation.

In one embodiment, the triterpenoid compound has a structure according to any of formulae (IV) to (VII):

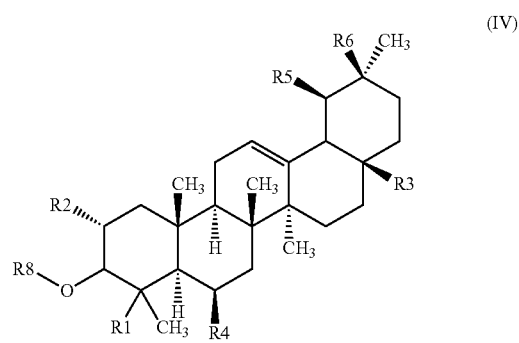

(IV)

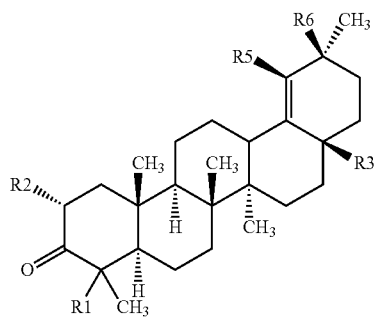
(V)

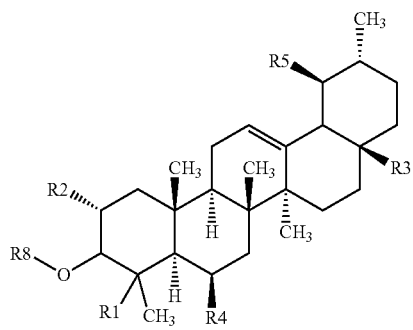
(VII)

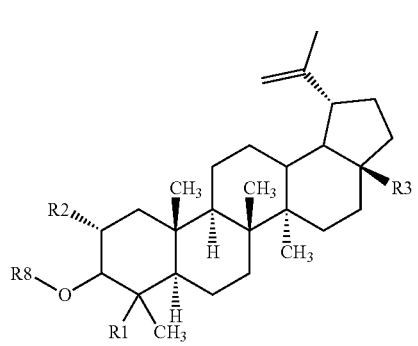
(VI)

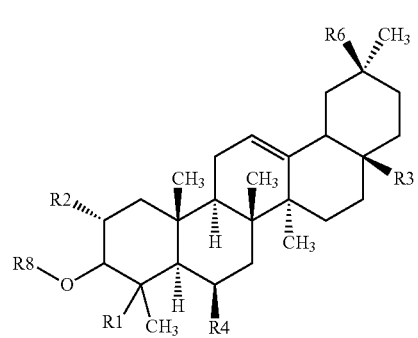
(IX)

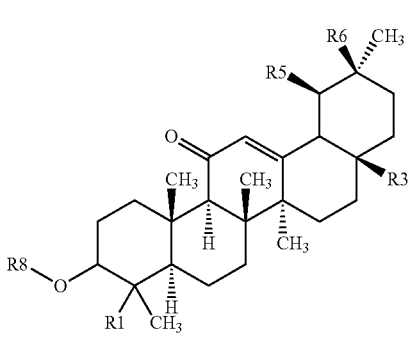
(VII)

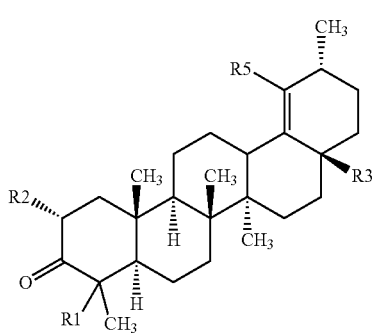
(X)

wherein:

R1 is —CH₃, —CH₂—OH, or —COO⁻X⁺, wherein X⁺ is a proton or a pharmaceutically acceptable cation, in particular wherein R1 is —CH₃;

R2 is hydrogen or —OH;

R3 is —COO⁻X⁺ or —CH₃, wherein X⁺ is a proton or a pharmaceutically acceptable cation, in particular wherein R6 is —COO⁻X⁺;

R4 is hydrogen or —OH;

R5 is —CH₃ or hydrogen;

R6 is —CH₃, hydrogen, or —COO⁻X⁺, and

R8 is hydrogen or —CO—CH₃ or —CO—CH₂CH₂—COOH wherein one of R1, R3 or R6 is —COO⁻X⁺, wherein X⁺ is a proton or a pharmaceutically acceptable cation.

In one embodiment, the triterpenoid compound has a structure according to any of formulae (VII) to (XII):

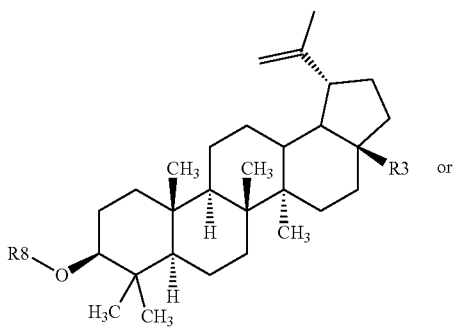
(XI)

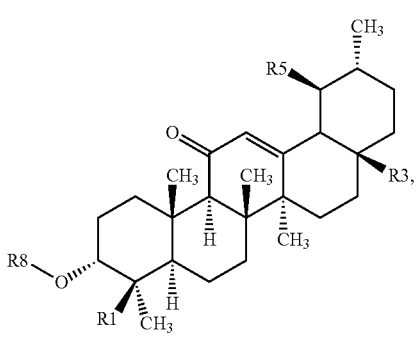

(XII)

wherein the residues R1 to R6 and R7 are as defined as above.

In one embodiment, pentacyclic triterpenoid compounds are used which are obtainable from plants. In one embodiment, the triterpenoid compound is selected from the group consisting of: ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, and pharmaceutically acceptable salts thereof. In one embodiment, asiatic acid is for use herein. In various embodiments, enoxolone and carbenoxolone are suitable compounds.

Ursolic acid is also known as (1S, 2R, 4aS, 6aR, 6aS, 6bR, 8aR, 10S, 12aR, 14bS)-10-hydroxy-1, 2, 6a, 6b, 9, 9, 12a-heptamethyl-2, 3, 4, 5, 6, 6a, 7, 8, 8a, 10, 11, 12, 13, 14b-tetra-decahydro-1H-picene-4a-carboxylic acid, prunol, malol, beta-ursolic acid, NSC4060, CCRIS 7123, TOS-BB-0966, and 3-beta-hydroxyurs-12-en-28-oic acid. It is, for example, found in and extractable from the peels of a variety of fruits as well as in herbs and spices like rosemary and thyme.

Betulinic acid is known as (3(3)-3-hydroxy-lup-20(29)-en-28-oic acid, 3α-hydroxy-methyl-1-isopropenyl-5α, 5β, 8, 8, 11α-pentamethyl-icosahydrocyclopenta[a]-chryse-nic acid, betulic acid and mairin. It is, for example, found in and extractable from the bark of a variety of plants such as, e.g., from the bark of the white birch *Betula pubescens*.

Moronic acid is also known as (4aS, 6aR, 6aS, 6bR, 8aS, 12aS, 14aS)-2, 2, 6a, 6b, 9, 9, 12a-heptamethyl-10-oxo-4, 5, 6, 6a, 7, 8, 8a, 11, 12, 13, 14, 14a-dodeca-hydro-3H-picene-4a-carboxylic acid, ambronic acid and 3-oxooleаn-18-en-28-oic acid, and oleanolic acid. It is, for example, found in and extractable from *Rhus javanica* and mistletoe *Phoradendron reichenbachianum*.

Oleanolic acid is also known as (4aS, 6aR, 6aS, 6bR, 8aR, 10S, 12aR, 14bS)-10-hydroxy-2, 2, 6a, 6b, 9, 9, 12a-heptamethyl-1, 3, 4, 5, 6, 6a, 7, 8, 8a, 10, 11, 12, 13, 14b-tetra-decahydropicene-4a-carboxylic acid and oleanic acid. It is, for example, found in and extractable from, e.g., olive oil, American pokeweed (*Phytolacca americana*), garlic, and *Syzygium* species.

Maslinic acid is also known as (4aS, 6aR, 6aS, 6bR, 8aR, 10R, 11R, 12aR, 14bS)-10,11-dihydroxy-2, 2, 6a, 6b, 9, 9, 12a-heptamethyl-1, 3, 4, 5, 6, 6a, 7, 8, 8a, 10, 11, 12, 13, 14b-tetradecahydropicene-4a-carboxylic acid, 2α-hydroxyoleanolic acid and (2α,3β)-2, 3-dihydroxyolean-12-en-28-oic acid. It is, for example, found in and extractable from olive oil. However, the in vivo activity is lower than that of, e.g., asiatic acid or carbenoxolone.

Asiatic acid is known as (1S, 2R, 4aS, 6aR, 6aS, 6bR, 8aR, 9R, 10R, 11R, 12aR, 14bS)-10, 11-dihydroxy-9-(hydroxymethyl)-1, 2, 6a, 6b, 9, 12a-hexamethyl-2, 3, 4, 5, 6, 6a, 7, 8, 8a, 10, 11, 12, 13, 14b-tetradecahydro-1H-picene-4a-carboxylic acid. It is, for example, found in and extractable from *Centella asiatica* or *Syzygium claviflorum* and is particularly suited for use herein. It can be formulated in a broad range of concentrations, has a high stability over a long period of time (months) and particularly good in-vitro and in-vivo activity. Furthermore, compositions comprising asiatic acid do not lead to nerve injury. The compositions are particularly stable over a long period of time and have particularly good in vitro and in vivo activity.

Corosolic acid is also known as (1S, 2R, 4aS, 6aR, 6aS, 6bR, 8aR, 10R, 11R, 12aR, 14bS)-10, 11-Dihydroxy-1, 2, 6a, 6b, 9, 9, 12a-heptamethyl-2, 3, 4, 5, 6, 6a, 7, 8, 8a, 10, 11, 12, 13, 14b-tetradecahydro-1H-picene-4a-carboxylic acid, glucosol, corsolic acid, colosic acid and 2α-hydroxyursolic acid. It is, for example, found in and extractable from *Lagerstroemia speciosa*.

Enoxolone is also known as 18ß-glycyrrhenic acid (the aglycon of glycyrrhizic acid), glycyrrhetic acid or (2S, 4aS, 6aS, 6bR, 8aR, 10S, 12aS, 12bR, 14bR)-10-hydroxy-2, 4a, 6a, 6b, 9, 9, 12a-heptamethyl-13-oxo-1, 2, 3, 4, 4a, 5, 6, 6a, 6b, 7, 8, 8a, 9, 10, 11, 12, 12a, 12b, 13, 14b-icosahydropicene-2-carboxylic acid. The corresponding succinate ester is carbenoxolone (CAS 5697-56-3), which has a high stability over a long period of time and particularly good in vitro and in vivo activity.

Arjunolic acid is also known as 2, 3, 2, 3-Trihydroxyolean-12-en-28-oic acid or (2α, 3β, 4α)-2, 3, 23-Trihydroxy-olean-12-en-28-oic acid. It is, for example, found in and extractable from *Terminalia arjuna*, *Combretum nelsonii* and/or *Leandra chaeton*. Madecassic acid is also known as Brahmic acid or (1S, 2R, 4aS, 6aR, 6aS, 6bR, 8R, 8aR, 9R, 10R, 11R, 12aR, 14bS)-8, 10, 11-trihydroxy-9-(hydroxymethyl)-1, 2, 6a, 6b, 9, 12a-hexamethyl-2, 3, 4, 5, 6, 6a, 7, 8, 8a, 10, 11, 12, 13, 14b-tetradecahydro-1H-picene-4a-carboxylic acid. It is, for example, found in from *Centella asiatica*.

Beta-boswellic acid is also known as (3α, 4β)-3-Hydroxyurs-12-en-23-oic acid, 3α-Hydroxyurs-12-en-24-oic acid. It is, for example, found in from *Boswellia* species such as, e.g., *Boswellia serrata*. Alpha boswellic acid is also known as (3α,4β)-3-Hydroxyolean-12-en-23-oic acid, 3α-Hydroxyolean-12-en-24-oic acid. It is, for example, found in and extractable from *Boswellia* species such as, e.g., *Boswellia serrata*. Likewise, also acetyl beta-boswellic acid, acetyl keto beta-boswellic acid, and acetyl alpha-boswellic acid are each exemplarily found and extractable from *Boswellia* species such as, e.g., *Boswellia serrata*. Further, the respective non-acetylated precursors may also be acetylated synthetically by means of standard methods.

In various embodiments of fat-reducing compounds 820, pentacyclic triterpenoid compounds include compounds having an ursane core structure (alpha-Amryn) selected from the group consisting of ursolic acid, beta boswellic acid, corosolic acid, asiatic acid, madecassic acid, acetyl beta boswellic acid, acetyl keto beta boswellic acid, and pharmaceutically acceptable salts thereof. Suitable embodiments of pentacyclic triterpenoid compounds include compounds having an oleanane core structure (beta-Amryn) selected from the group consisting of maslinic acid, oleanolic acid, moronic acid, arjunolic acid, alpha boswellic acid, acetyl alpha boswellic acid, acetyl keto alpha boswellic acid, enoxolone, and pharmaceutically acceptable salts thereof. Carbenoxolone is also of interest. Suitable embodiments of pentacyclic triterpenoid compounds include compound having a lupan core structure such as betulinic acid or a pharmaceutically acceptable salt thereof.

HIFU in Combination with Fat-Reducing Compound

The fat-reducing compounds 820 described herein are used in combination with energy delivery in several embodiments. For example, ultrasound (for example, as further described below) is used in conjunction with one or more fat-reducing compounds 820. In one embodiment, a combination of energy (such as HIFU) and a fat-reducing compound reduces the unwanted appearance of cellulite, is well tolerated and leads to increased patient satisfaction and improvement of the patient's quality of life. In some embodiments, the use of energy (such as HIFU) with at least one fat-reducing compound reduces the amount of the fat-reducing compound needed to achieve a comparable effect by at least 10%, 20%, 30%, 50%, and overlapping ranges therein, or more. In some embodiments, the use of energy (such as HIFU) with at least one fat-reducing compound expedites or enhances the desired aesthetic effect by at least 10%, 20%, 30%, 50%, and overlapping ranges therein, or more. These effects are compared to the use of the same or similar fat-reducing compound without energy. In one embodiment, the fat-reducing compound reduces the amount/time of energy (e.g., HIFU) needed or enhances the effects of the energy by at least 10%, 20%, 30%, 50%, and overlapping ranges therein, or more (as compared to the energy used alone, without a fat-reducing compound).

The compound capable of reducing local subcutaneous fat addresses the "fat cell aspect" of cellulite and adds benefit to the use of energy, such as HIFU. Specifically, the compound is believed to support and complement the action of the HIFU by removing subcutaneous local fat, thereby leading to noticeable results that are relatively quickly visible. Furthermore, the fat-reducing compound is believed to add to, enhance, or synergistically improve the effects brought about by the HIFU system 20.

Unexpectedly, the combination of HIFU system 20 treatment with an injection of a fat-reducing compound 820 improves the cosmetic appearance of cellulite by reducing the volume of fat underlying the cellulite. Without being bound by theory, it is believed that the combined effect of the HIFU 20 treatment with the injected fat-reducing compound 820 reduces fat volume and increases the in situ synthesis of extracellular matrix in general, and stimulates collagen synthesis in particular, thereby increasing the firmness or "strength" of the skin and providing beneficial long-lasting treatment effects. In various embodiments, fat-tissue underlying the appearance of cellulite is reduced by HIFU system 20 treatment combined with the injection of one, two, three, or more fat-reducing compounds 820.

In one embodiment, the combination of energy (such as HIFU) and a fat-reducing is used to address the "fat cell aspect" by reducing the volume of fat cells in fat lobuli compartments underlying the appearance of cellulite. In various embodiments, energy (e.g., HIFU 20) heats fat cells to reduce the volume of fat inside the lobuli via ablation, lysing, coagulation, and/or apoptosis using varying power and/or temperature levels of heat treatment. In one embodiment, the HIFU system 20 treatment creates thermal heating zones leading to the reduced volume of fat cells in the subcutaneous fat tissue and in a further embodiment in the fat lobuli compartments, thereby deflating the bulges in the fat lobuli, and reducing the appearance of cellulite. In one embodiment, the HIFU system 20 treatment reduces fat volume in conjunction with the fat-reducing compound 820, thereby reducing the volume of fat and reducing the appearance of cellulite. In one embodiment, the HIFU system 20 treatment heats the tissue to direct the fat-reducing compound 820 to particular ultrasound targeted location in the fat, resulting in targeting fat for reduction of the appearance of cellulite.

In one embodiment, the combination of HIFU and a fat-reducing compound treatment is used to address both the "connective tissue aspect" and the "fat cell aspect" of cellulite by strengthening tissue structure, e.g., the skin connective tissue with HIFU. In one embodiment, the HIFU system 20 treatment creates thermal coagulation zones in the dermis, which coagulates collagen and initiates new collagen formation in the dermis, strengthening and tightening the dermal tissue and structure on the top, or roof, in general in the dermal skin layer and in particular of protruding fat lobuli, thereby flattening the bulges in the tops/roofs of the fat lobuli, and reducing the appearance of cellulite. In one embodiment, a treatment depth below a skin surface is 1.5 mm. In one embodiment, a treatment depth below a skin surface is 3.0 mm. In one embodiment, a treatment depth below a skin surface is 4.5 mm. In one embodiment, the HIFU system 20 treatment interacts with the fat-reducing compound 820 to reducing the appearance of cellulite. In one embodiment, the HIFU system 20 treatment interacts with the dermal filler 800 to heat the tissue to direct the dermal filler 800 to particular ultrasound targeted locations, resulting in strengthening, flattening, and/or tightening the dermal tissue and structure on the top, or roof, of fat lobuli, thereby flattening the bulges in the tops/roofs of the fat lobuli, and reducing the appearance of cellulite. In one embodiment, the HIFU system 20 treatment heats the dermal filler 800 to more quickly move, stabilize, and/or harden he dermal filler 800 at particular ultrasound targeted locations, resulting in strengthening, flattening, and/or tightening the dermal tissue and structure on the top, or roof, of fat lobuli, thereby flattening the bulges in the tops/roofs of the fat lobuli, and reducing the appearance of cellulite.

Combined Dermal Fillers and Fat-Reducing Compounds

In several embodiments, a dermal filler and a fat-reducing compound are used together with energy delivery (including but not limited to ultrasound). In one embodiment, the invention relates to the use of ultrasound (e.g., HIFU 20) in combination with at least one dermal filler 800 and at least one fat-reducing compound 820 in the treatment of gynoid lipodystrophy. The dermal filler 800 for strengthening the connective tissue may be sequentially or separately administered in the form of injectable compositions by local injection into the lower dermis/upper subcutis and the subcutis, respectively. In one embodiment, the dermal filler 800 is administered in the form of a hydrogel composition, and a fat-reducing compound 820 is administered as an injectable composition. In various embodiments, combined HIFU treatments focus on consecutive or parallel treatment of one or two, or more target tissues aiming for (i) tightening of dermal and/or fat lobuli structure and (ii) local volume reduction of subcutaneous fat tissue by adipo-cytolysis using HIFU at target-tissue matched focus point depth, focus geometry and wavelength. In various embodiments, a modular HIFU cellulite treatment approach offers to treatment professionals and patients a broad repertoire of effective treatment combinations starting with dermal and/or skin restoration, extendable to more general restructuring of dermal extracellular matrix up to efficiently reducing a major driving force of nodular appearance of female skin: the subcutaneous adipose tissue (e.g., white adipose tissue). Several embodiments of the invention provide energy based medical devices 20 (or EBD 20) used in combination with treatment agents for use in an improved treatment of tissue, in particular a treatment that is effective, results in the desired aesthetic effects over a longer period, and is well tolerated. Embodiments include combination treatments with energy-based devices for noninvasive treatments with any one or more of dermal fillers 800, fat-reducing compounds 820, and/or cavitation-prone fluids 810.

Injection Guidance Device

In several embodiments, an injectable agent such as a dermal filler 800, cavitation-prone fluid 810, and/or fat-reducing compound 820 are used in combination with HIFU system 20 treatments. The HIFU energy treatment is administered with a HIFU device 20. In various embodiments, cellulite treatment agents (dermal filler 800, cavitation-prone fluid 810, and/or fat-reducing compound 820) are locally injected using a syringe and an injection needle 700 having a suitable diameter and length. For example, in various embodiment, a syringe with a 30G, 28G, 27G, or 25G injection needle 700 is used for injection of dermal filler 800. For example, in one embodiment, a syringe with a 33G needle is used for injection of the fat-reducing compound 820. The injection needles 700 may suitably have a length of between ~20-50 mm (e.g., 25 mm, 40 mm, etc.). Furthermore, it is also contemplated that injection of the hydroxyapatite particles and/or the at least one fat-reducing compound is carried out using needles 700 that are filled with the substance or composition to be administered and are bioresorbable. After implantation of the bioresorbable needles into the skin, each needle is separated from its carrier by contact with the body fluids. It is further contemplated that injection of the injectable agent is carried out by means of a micro-needle system, wherein the micro-needle system comprises a flexible base layer into which micro-needles of different lengths are integrated such that the tips of the micro-needles perpendicularly project from the plane of the base layer. Suitably, in various embodiments, the micro-needles of said micro-needle system have two different lengths, wherein the shorter micro-needles are filled with or are intended to be filled with an injectable composition comprising dermal filler 800 and wherein the longer micro-needles are filled with or are intended to be filled with an injectable composition comprising the at-reducing compound 820, such that the dermal filler 800 particles are delivered into the dermis, e.g., the deep dermis, wherein the fat-reducing compound 820 is delivered into the subcutis, e.g., into the subdermal fat layer.

In one embodiment, the tip of at least one of the micro needles 700, is made of a bio-resorbable material such as, for example, poly-lactide (PLA) or poly-hydroxybutyrate (PHB). Further, the micro-needle device 700 may be configured such that the bio-resorbable micro-needles can be separated from the base layer upon contact with the body fluids. In one embodiment, the tip of the needle 700 itself may be formed of dermal filler 800 (e.g., hydroxyapatite) with a biodegradable bridge made from, e.g. PLA. Using this configuration, the needle tip 700 itself will be released in the tissue after application of the micro-needle patch.

Figure 6A:
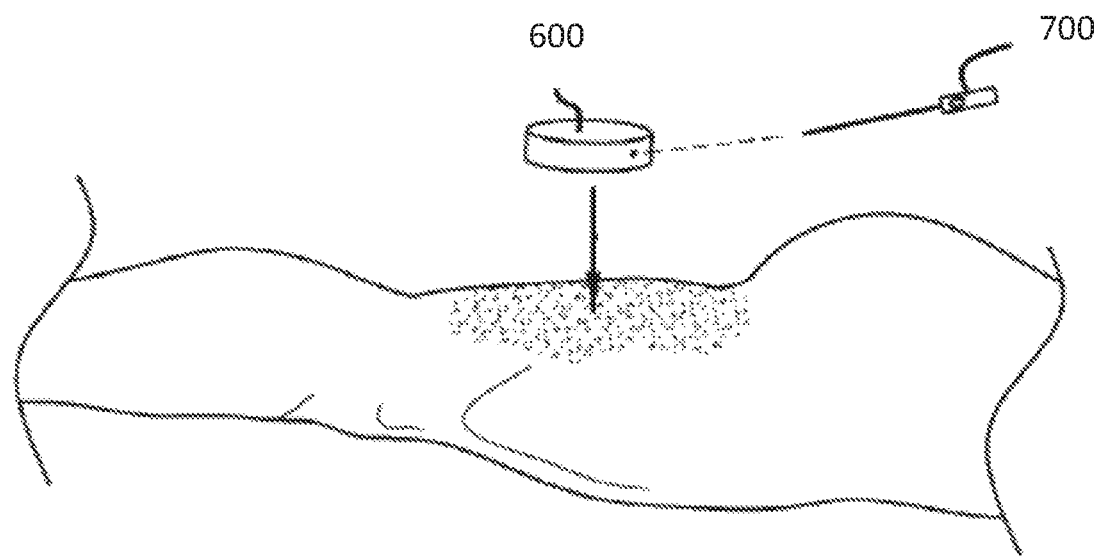
FIGS. 6A-6C illustrate schematic isometric side views of an injection guidance device according to various embodiments of the invention.
Figure 6B:
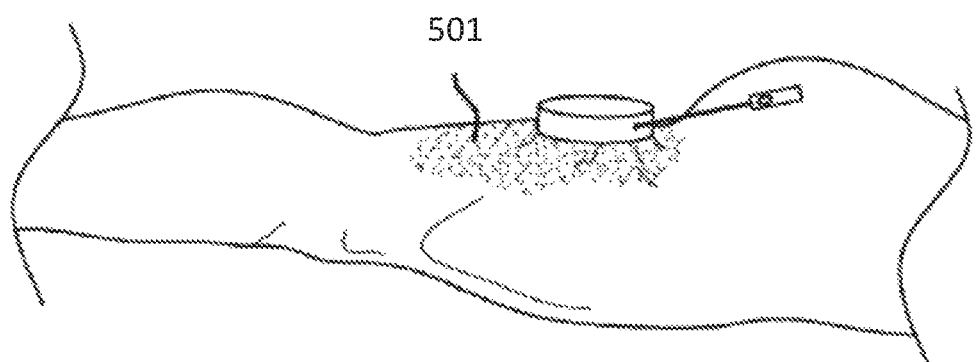
Figure 6C:
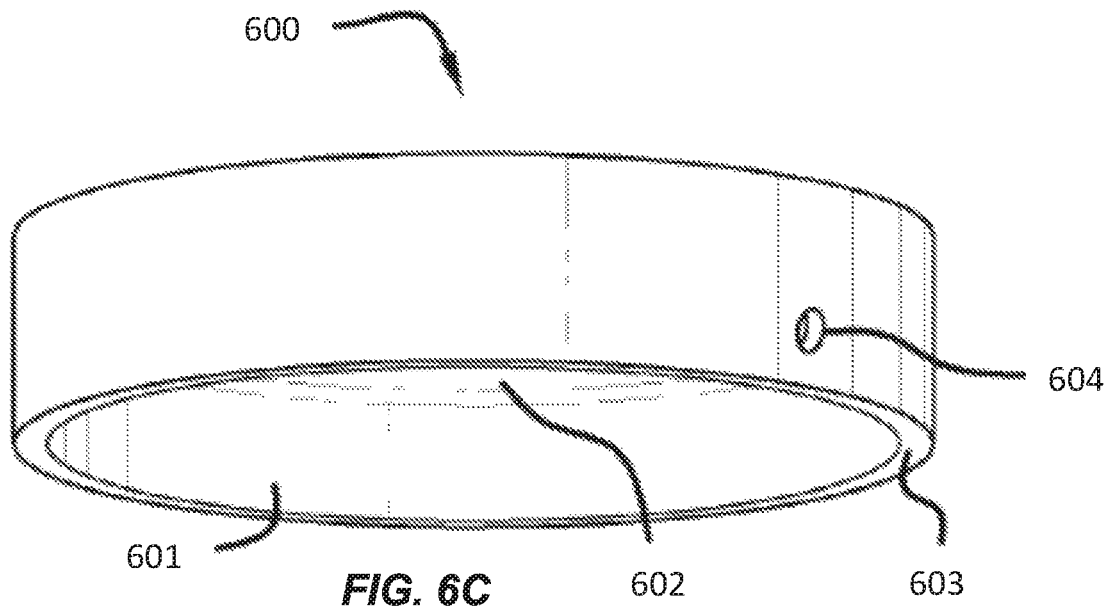

As illustrated in FIGS. 6A-6C, an embodiment of an injection guidance device 600 is used to target specific tissue depth injection with an injection device 700. In one embodiment, the injection guidance device 600 comprises a housing 603 forming a chamber 602 with a wall 601. In one embodiment, the injection guidance device 600 is connected to a low pressure of vacuum to suck a skin surface into the chamber 600. In one embodiment, the wall 601 comprises a port 604 at a specific distance (e.g., height above the remaining skin surface) configured for precise injection at a specific tissue depth with the injection device 700. In various embodiments, the injection guidance device 600 can be used to optimally and precisely delivery injectable media to a specific, targeted tissue location.

Furthermore, if any of the treatment embodiments is administered in the form of injectable compositions, the volume of the liquid or semi-solid (e.g., viscous) composition injected into a subject per injection may be in the range of several microliters to several milliliters. The amount injected per injection site (puncture) may be in the range of 5 µl to 1000 µl, particularly in the range of 10 µl to 300 µl. The hydroxyapatite particles are preferably injected in an amount of 10 µl to 75 µl, more preferably 15 µl to 50 µl or 20 µl to 30 µl, per injection site. The at least one fat-reducing compound is preferably administered in an amount of 30 µl to 300 µl, more preferably 50 µl to 200 µl or 75 µl to 150 µl, per injection site. A person skill in the art is readily able to determine appropriate amounts or volumes for the individual case.

Ultrasound Therapy

Ultrasound is one example of an energy-based treatment that is used in combination with one or more anti-cellulite agents.

In various embodiments, an ultrasound system 20 is configured for focusing ultrasound to produce focused, localized, mechanical motion within tissues and cells for the purpose of producing either localized heating for tissue coagulation or for mechanical cellular membrane disruption intended for non-invasive aesthetic use. In various embodiments, ultrasound treatment affects the structural integrity of tissues including, but not limited to, fat lobuli, fat cells, and dermis. In one embodiment, ultrasound treatment improves the structural integrity of the connective tissue aspect by strengthening or forming collagen to contain fat compartments in the skin, e.g., by building a stronger roof, foundation, and/or walls to keep the bulges of fat lobuli to a minimum and reduce the appearance of cellulite. In one embodiment, ultrasound treatment alters the structural integrity of the connective tissue aspect by piercing the roof, wall, and/or foundation of fat lobuli to release fat cells, e.g., by destroying the walls containing the fat compartments in the skin and reducing the bulges of fat lobuli and reduce the appearance of cellulite. In various embodiments, ultrasound treatment reduces the volume of fat (e.g., fat cell aspect of cellulite) via induces elimination of adipocytes (necrotic and/or apoptotic cell death) by heating fat tissue, e.g., inducing elimination of adipocytes (e.g., necrotic and/or apoptotic fat cell death). In several embodiments, HIFU systems 20 treat both a connective tissue aspect and a fat cell aspect of cellulite. In several embodiments, provided are systems and methods that successfully achieve an aesthetic effect using targeted and precise ultrasound (e.g., HIFU) to cause a visible and effective cosmetic result via a thermal pathway with one, two, three, four, or more simultaneous ultrasound focal zones for performing various treatment and/or imaging procedures in the dermis, fat, and in, on, or near the fat lobuli walls and roof. In several embodiments, provided are systems and methods that successfully achieve an aesthetic effect using targeted and precise ultrasound (e.g., HIFU) to cause a visible and effective cosmetic result via a thermal pathway with a focal point or focal line, which when moved produces a plane or band of ultrasound focused treatment. Several embodiments of the invention use high intensity micro- and macro-focused ultrasound in combination with optional ultrasound imaging for proper targeting aiming to induce in the treated skin area the desired biological effect in a defined specific target depth. In one embodiment, high intensity micro focused ultrasound in or near the epidermis, dermis, fascia, muscle, and/or fat for tightening the skin structure by inducing restructuring and reinforcement of the extracellular matrix or ECM) network. The HIFU pulses generate in the target depth thermal-coagulation-zones (or TCZs). This denaturation of extracellular matrix proteins results in an immediate tightening of the dermis and induces a repair process which replaces weak or missing extracellular matrix structure by new fibers. In several embodiments, non-invasive ultrasound is used to achieve one or more of the following effects: fat-reduction (e.g., treatment of adipose and/or cellulite), cellulite treatment (e.g., dimple or non-dimple type female gynoid lipodystrophy), a buttock lift (e.g., buttock tightening), a skin laxity treatment (e.g., treatment of tissue for tightening or an abdominal laxity treatment).

In various embodiments, HIFU increases the strength of a roof, foundation, and/or wall of fat lobuli by 5%-90% (e.g., 5%, 10%, 15%, 20%, 30%, 40%, 50%, 60%, 70%, 80%, 90% and any ranges and values therein). In various embodiments, HIFU increases the strength of a collagen in the dermis proximate a fat lobuli by 5%-90% (e.g., 5%, 10%, 15%, 20%, 30%, 40%, 50%, 60%, 70%, 80%, 90% and any ranges and values therein). In various embodiments, HIFU pierces a roof, foundation, and/or wall of fat lobuli with one or more holes in the size of 0.1 mm-1 mm in a dimension (e.g., 0.1, 0.2, 0.3, 0.4, 0.5, 0.6, 0.7, 0.8, 0.9, 1.0 mm and any values or ranges therein). In various embodiments, HIFU heats a volume of fat cells in fat lobuli to affect the viability of the fat cells by increasing the temperature of the fat cells to 40° C. to 100° C. (e.g., 40° C.-50° C., 50° C.-65° C., 65° C.-75° C., 75° C.-100° C., and any values and ranges therein).

In various embodiments, cellulite (e.g., dimple or non-dimple type gynoid lipodystrophy) reduction or amelioration of one or more characteristics (such as dimples, nodularity, "orange peel" appearance, etc., is improved by about 10-20%, 20-40%, 40-60%, 60-80% or higher (as well as overlapping ranging therein) through the use of HIFU in combination with one or more anti-cellulite agents. This percentage improvement is achieved as compared to untreated tissue, tissue treated with just the anti-cellulite agent, or tissue treated with just ultrasound alone In some embodiments, two, three or more beneficial effects are achieved during the same treatment session, and may be achieved simultaneously.

In various embodiments, transducer module 200 comprises one or more transduction elements. The transduction element(s) can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In various embodiments, in addition to, or instead of, a piezoelectrically active material, transducer modules can comprise any other materials adapted to and/or configured for generating radiation and/or acoustical energy. In various embodiments, transducer modules can be adapted to and/or configured to operate at different frequencies and treatment depths. Transducer properties can be defined by an outer diameter ("OD") and focal length ($F_L$). In one embodiment, a transducer can be adapted to and/or configured to have OD=19 mm and $F_L$=15 mm. In other embodiments, other suitable values of OD and $F_L$ can be used, such as OD of less than about 19 mm, greater than about 19 mm, etc. and $F_L$ of less than about 15 mm, greater than about 15 mm, etc. Transducer modules can be adapted to and/or configured to apply ultrasonic energy at different target tissue depths. As described herein, in several embodiments, transducer modules comprise movement mechanisms adapted to and/or configured to direct ultrasonic treatment in a linear or substantial liner sequence of individual thermal coagulation zones with a treatment spacing between individual thermal coagulation zones. For example, treatment spacing can be about 1.1 mm, 1.5 mm, etc. In several embodiments, transducer modules can further comprise movement mechanisms adapted to and/or configured to direct ultrasonic treatment in a sequence so that thermal coagulation zones are formed in linear or substantially linear sequences separated by a treatment spacing. For example, a transducer module can be adapted to and/or configured to form thermal coagulation zones along a first linear sequence and a second linear sequence separated by treatment spacing between about 2 mm and 3 mm from the first linear sequence. In one embodiment, a user can manually move the transducer modules across the surface of a treatment area so that adjacent linear sequences of thermal coagulation zones are created. In one embodiment, a movement mechanism can automatically move the transducer modules across the surface of a treatment area so that adjacent linear sequences of thermal coagulation zones are created.

In various embodiments, HIFU targets the dermis and/or fibrous septa under cellulite for the purposes of controlled mechanical tissue fractionation. In one embodiment, the fractionation depths will include 6 mm and 10 mm. Other depths may be used depending on the benefit (e.g., 1.5 mm-25 mm, 1.5 mm, 3 mm, 4.5 mm, 5 mm, 6 mm, 10 mm, 17 mm, 18 mm, 19 mm, 20 mm, 25 mm and any value or ranges therein). The suggested approach can be used by involving HIFU only or in combination with a dermal filler for supporting the tightening of the dermal skin layer. Furthermore, HIFU which fractionates tissue may be used to selectively create low mechanical resistance channels to improve the localization of the composition (e.g., a dermal filler), which increases the probability to achieve the intended outcome. For example, in some non-limiting embodiments transducers can be configured for a tissue depth of 0.5 mm, 1.0 mm, 1.5 mm, 2 mm, 3 mm, 4.5 mm, 6 mm, less than 3 mm, between 0.5 mm and 5 mm, between 1.5 mm and 4.5 mm, more than more than 4.5 mm, more than 6 mm, and anywhere in the ranges of 0.1 mm-3 mm, 0.1 mm-4.5 mm, 0.1 mm-25 mm, and any depths therein (e.g., 6 mm, 10 mm, 13 mm, 15 mm, 17 mm). In several embodiments, tissue is treated at a depth below a skin surface and the skin surface is not impaired. Instead, the therapeutic effect achieved at the depth below the skin surface results in a favorable cosmetic appearance of the skin surface. In other embodiments, the skin surface is treated with ultrasound (e.g., at a depth less than 0.5 mm). In various embodiments, high intensity macro focused ultrasound target the subcutaneous fat-layer in a target depth between e.g., 5 mm-25 mm, (e.g., 10 mm-17 mm, 13 mm-25 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, and any depths or ranges therein). In some embodiments, one or more simultaneous linear focused ultrasound treatments will heat up larger portions of the subcutaneous fat-tissue in a plane or band of treatment, via inducing the elimination of adipocytes (necrotic and preferentially apoptotic cell death).

In several embodiments, the HIFU system 20 further includes a movement mechanism configured to be programmed to provide constant or variable spacing between the plurality of individual cosmetic treatment zones. In one embodiment, a sequence of individual cosmetic treatment zones has a treatment spacing in a range from about 0.01 mm to about 50 mm (e.g., 0.1, 0.5, 1, 2, 5, 10, 15, 19, 20, 25, 30, 35, 40, 45, 49 mm or any range or value therein). In one embodiment, a sequence of individual cosmetic treatment zones has a treatment spacing in a range from about 0.01 mm to about 100 mm (e.g., 0.1, 0.5, 1, 2, 3, 4, 5, 6, 7, 8, 9, 10, 15, 20, 25, 30, 35, 40, 50, 100 mm or any range or value therein). In one embodiment, treatment zones are provided along a distance of about 25 mm. In one embodiment, treatment zones are provided along a distance of about 50 mm. In various embodiments, treatment zones are provided along a distance of 5 mm to 100 mm (e.g., 10 mm, 20 mm, 25 mm, 35 mm, 50 mm, 75 mm, 100 mm, and any amounts or ranges therein. In various embodiments, treatment zones are provided along a linear and/or curved distance.

One benefit of a motion mechanism is that it can provide for a more efficient, accurate and precise use of an ultrasound transducer, for imaging and/or therapy purposes. One advantage this type of motion mechanism has over conventional fixed arrays of multiple transducers fixed in space in an housing is that the fixed arrays are a fixed distance apart. In one embodiment, the transducer module is configured to provide an acoustic power of the ultrasonic therapy in a range of between about 1 W to about 100 W or 100 W to 1000 W (e.g., 3-30 W, 7-30 W, 21-33 W, 200 W, 500 W, 750 W, 900 W) or more and a frequency of about 1 MHz to about 20 MHz to thermally heat the tissue to cause coagulation. In one embodiment, the transducer module is configured to provide an acoustic power of the ultrasonic therapy in a range of between about 1 W to about 500 W for peak or average energy, (e.g., 3-30 W, 7-30 W, 21-33 W, 100 W, 220 W, or more) and a frequency of about 1 MHz to about 20 MHz to thermally heat the tissue to cause coagulation. In some embodiments, an instantaneous energy is delivered. In some embodiments, an average energy is delivered. In one embodiment, the acoustic power can be from a range of 1 W to about 100 W in a frequency range from about 1 MHz to about 20 MHz (e.g., 1 MHz, 3 MHz, 4 MHz, 4.5 MHz, 7 MHz, 10 MHz, 2-12 MHz, 15 MHz, 18 MHz, 2-18 MHz), or from about 10 W to about 50 W at a frequency range from about 3 MHz to about 8 MHz (e.g., 3 MHz, 4 MHz, 4.5 MHz, 7 MHz). In one embodiment, the acoustic power can be from a range of 1 W to about 500 W in a frequency range from about 1 MHz to about 12 MHz (e.g., 1 MHz, 4 MHz, 7 MHz, 10 MHz, 2-12 MHz), or from about 10 W to about 220 W at a frequency range from about 3 MHz to about 8 MHz, or 3 MHz to 10 MHz. In one embodiment, the acoustic power and frequencies are about 40 W at about 4.3 MHz and about 30 W at about 7.5 MHz. An acoustic energy produced by this acoustic power can be between about 0.01 joule ("J") to about 10 J or about 2 J to about 5 J. An acoustic energy produced by this acoustic power can be between about 0.01 J to about 60,000 J (e.g., via bulk heating, for body shaping, submental fat, abdomen and/or flanks, arms, inner thigh, outer thigh, buttocks, abdominal laxity, cellulite), about 10 J or about 2 J to about 5 J. In one embodiment, the acoustic energy is in a range less than about 3 J. In various embodiments, a treatment power is 1 kW/cm$^2$ to 100 kW/cm$^2$, 15 kW/cm$^2$ to 75 kW/cm$^2$, 1 kW/cm$^2$ to 5 kW/cm$^2$, 500 W/cm$^2$ to 10 kW/cm$^2$, 3 kW/cm$^2$ to 10 kW/cm$^2$, 15 kW/cm$^2$ to 50 kW/cm$^2$, 20 kW/cm$^2$ to 40 kW/cm$^2$, and/or 15 kW/cm$^2$ to 35 kW/cm$^2$.

In one embodiment, thermal coagulation zones can be created in a linear or substantially linear, curved or substantially curved, zone or sequence, with each individual thermal coagulation zone separated from neighboring thermal coagulation zones by a treatment spacing. In one embodiment, multiple sequences of thermal coagulation zones can be created in a treatment region. For example, thermal coagulation zones can be formed along a first sequence and a second sequence separated by a treatment distance from the first sequence. Although treatment with therapeutic ultrasound can be administered through creation of individual thermal coagulation zones in a sequence and sequences of individual thermal coagulation zones, it may be desirable to reduce treatment time and corresponding risk of pain and/or discomfort experienced by a patient. Therapy time can be reduced by forming multiple thermal coagulation zones simultaneously, nearly simultaneously, or sequentially. In some embodiments, a treatment time can be reduced 10%, 20%, 25%, 30%, 35%, 40%, 45%, 50%, 55%, 60%, 65%, 70%, 75%, 80% or more by creating multiple thermal coagulation zones.

Figure 1B:
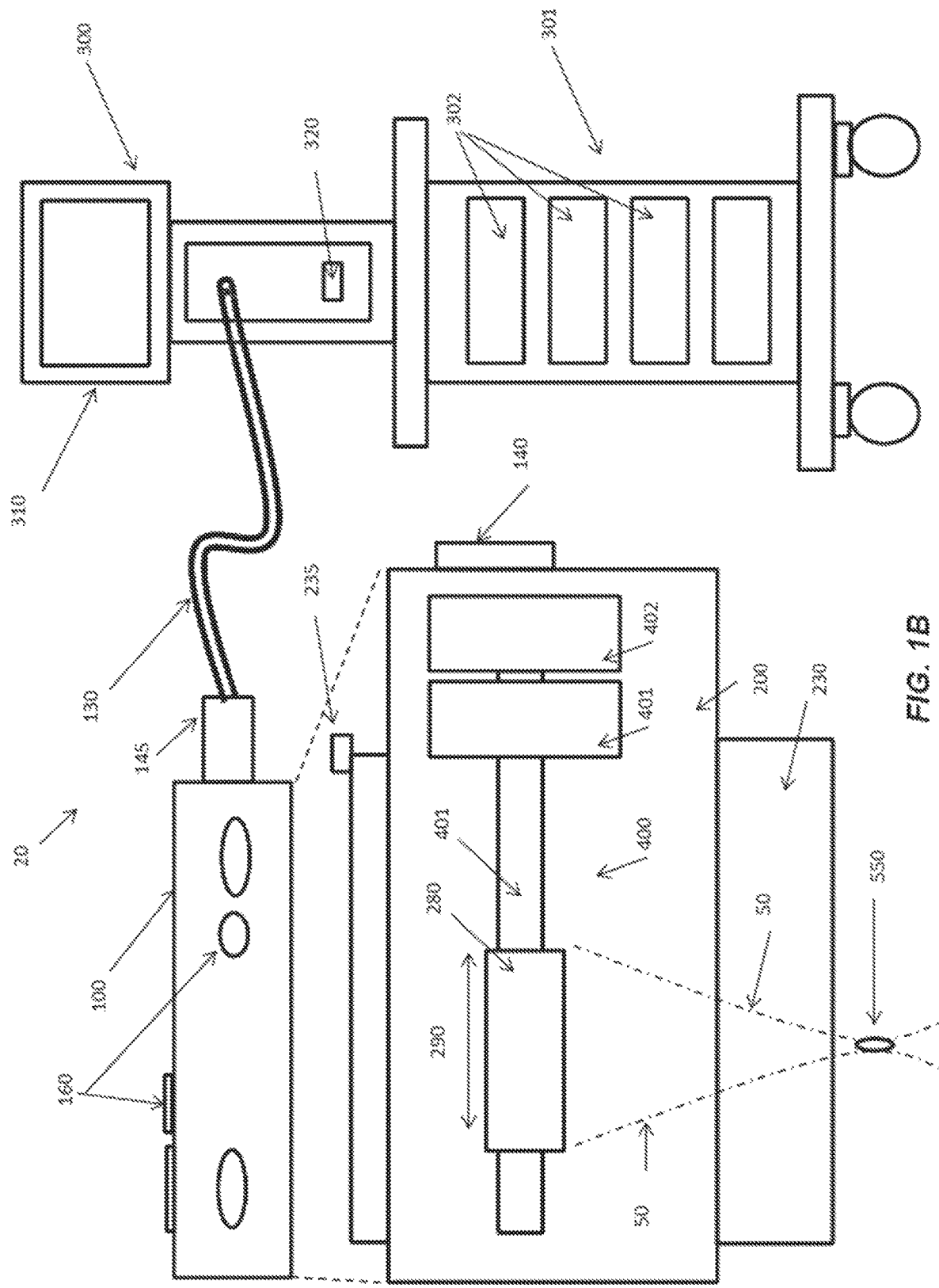
FIG. 1B is a schematic illustration of an ultrasound system according to various embodiments of the invention.
Figure 1C:
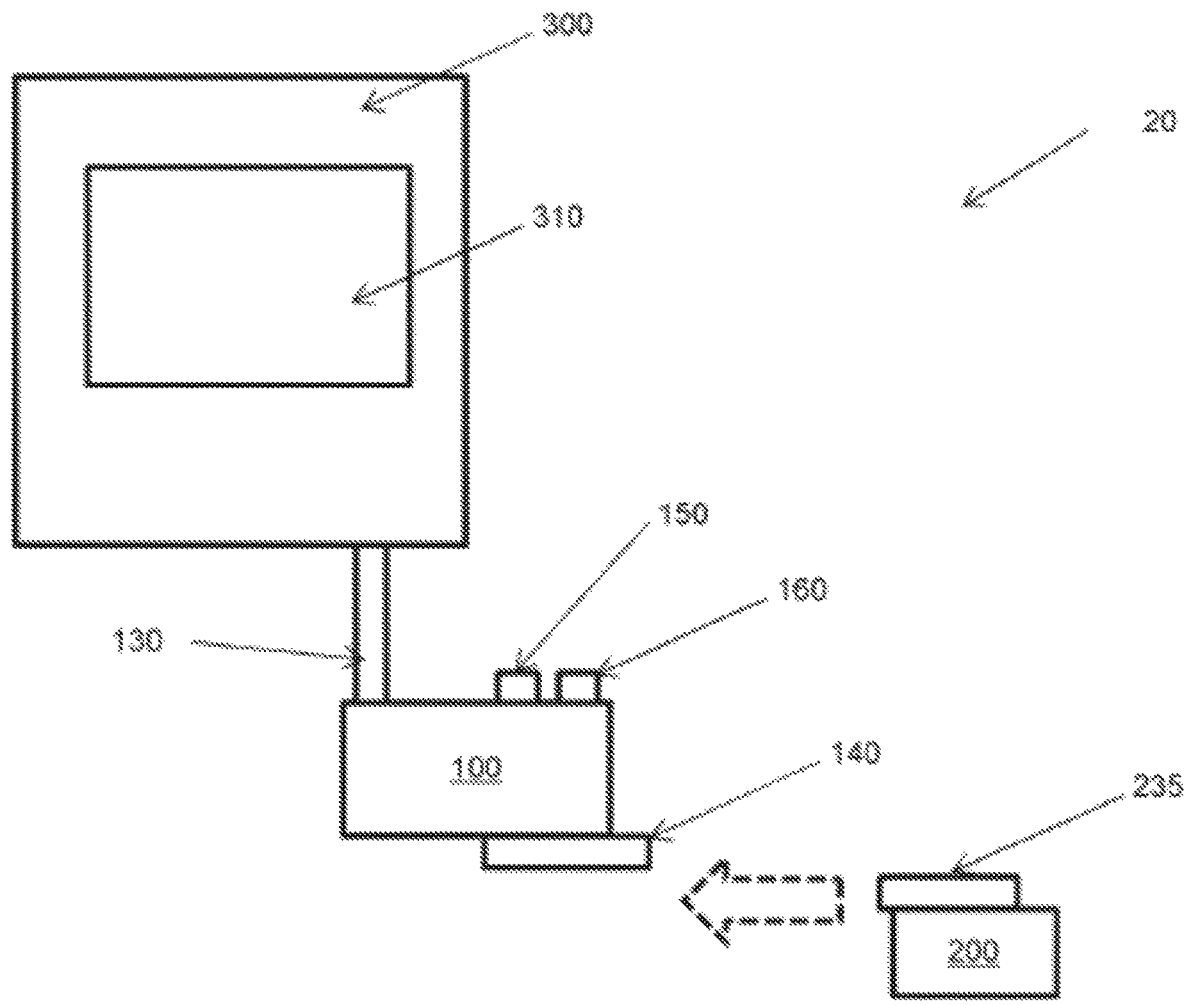
FIG. 1C is a schematic illustration of an ultrasound system according to various embodiments of the invention.

Various embodiments of a HIFU ultrasound treatment device 20 that are used in combination with an agent (such as an anti-cellulite agent) are described in U.S. application Ser. No. 12/996,616, which published as U.S. Publication No. 2011/0112405 on May 12, 2011, which is incorporated in its entirety by reference, herein. With reference to the illustration in FIGS. 1A, 1B, and 1C, various embodiments of HIFU system 20 include a hand wand (e.g., handpiece) 100, module (e.g., transducer module, cartridge, probe) 200, and a controller (e.g., console) 300. In some embodiments, a console 300 comprises a communication system (e.g., Wi-Fi, Bluetooth, modem, etc. to communicate with another party, a manufacturer, a supplier, a service provider, the Internet, and/or a cloud. In some embodiments, a cart 301 provides mobility and/or position of the system 20, and can include wheels, surfaces to write on or place components, and/or compartments 302 (e.g., drawers, containers, shelves, etc.) to, for example, store or organize components. In some embodiments, the cart has a power supply, such as a power connection to a battery and/or one or more cords to connect power, communications (e.g., Ethernet) to the system 20. In some embodiments, the system 20 comprises a cart 301. In some embodiments, the system 20 does not comprise a cart 301. The hand wand 100 can be coupled to the controller 300 by an interface 130, which may be a wired or wireless interface. The interface 130 can be coupled to the hand wand 100 by a connector 145. The distal end of the interface 130 can be connected to a controller connector on a circuit 345 (not shown). In one embodiment, the interface 130 can transmit controllable power from the controller 300 to the hand wand 100. In an embodiment, the system 20 has multiple imaging channels (e.g., 8 channels) for ultra-clear HD (high definition) visualization of subcutaneous structures to improve imaging. In an embodiment, the system 20 multiple therapy channels (e.g., 8 channels) and a precision linear-drive motor that doubles treatment accuracy while increasing speed (e.g., by 25%, 40%, 50%, 60%, 75%, 100% or more). Together, these features establish one of the most versatile system platforms in the industry and provide a foundation for unprecedented future possibilities. In various embodiments, the controller 300 can be adapted to and/or configured for operation with the hand wand 100 and the module 200, as well as the overall ultrasound system 20 functionality. In various embodiments, multiple controllers 300, 300', 300", etc. can be adapted to and/or configured for operation with multiple hand wands 100, 100', 100", etc. and or multiple modules 200, 200', 200", etc. The controller 300 can include connectivity to one or more interactive graphical display 310, which can include a touchscreen monitor and Graphic User Interface (GUI) that allows the user to interact with the ultrasound system 20. In one embodiment, a second smaller, more mobile display that allows the user to more easily position and view the treatment screen. In one embodiment, a second display is included that allows the system user to view a treatment screen (e.g., on a wall, on a mobile device, large screen, remote screen). In one embodiment, the graphical display 310 includes a touch-screen interface 315 (not shown). In various embodiments, the display 310 sets and displays the operating conditions, including equipment activation status, treatment parameters, system messages and prompts, and ultrasound images. In various embodiments, the controller 300 can be adapted to and/or configured to include, for example, a microprocessor with software and input/output devices, systems and devices for controlling electronic and/or mechanical scanning and/or multiplexing of transducers and/or multiplexing of transducer modules, a system for power delivery, systems for monitoring, systems for sensing the spatial position of the probe and/or transducers and/or multiplexing of transducer modules, and/or systems for handling user input and recording treatment results, among others. In various embodiments, the controller 300 can include a system processor and various analog and/or digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software running on the system process may be adapted to and/or configured to control all initialization, timing, level setting, monitoring, safety monitoring, and all other ultrasound system functions for accomplishing user-defined treatment objectives. Further, the controller 300 can include various input/output modules, such as switches, buttons, etc., that may also be suitably adapted to and/or configured to control operation of the ultrasound system 20.

In one embodiment, the hand wand 100 includes one or more finger activated controllers or switches, such as 150 and 160. In various embodiments, one or more thermal treatment controllers 160 (e.g., switch, button) activates and/or stops treatment. In various embodiments, one or more imaging controllers 150 (e.g., switch, button) activates and/or stops imaging. In one embodiment, the hand wand 100 can include a removable module 200. In other embodiments, the module 200 may be non-removable. In various embodiments, the module 200 can be mechanically coupled to the hand wand 100 using a latch or coupler 140. In various embodiments, an interface guide 235 or multiple interface guides 235 can be used for assisting the coupling of the module 200 to the hand wand 100. The module 200 can include one or more ultrasound transducers 280. In some embodiments, an ultrasound transducer 280 includes one or more ultrasound elements. The module 200 can include one or more ultrasound elements. The hand wand 100 can include imaging-only modules, treatment-only modules, imaging-and-treatment modules, and the like. In various embodiments, the ultrasound transducer 280 is movable in one or more directions 290 within the module 200. The transducer 280 is connected to a motion mechanism 400. In various embodiments, the motion mechanism comprises zero, one, or more bearings, shafts, rods, screws, lead screws 401, encoders 402 (e.g., optical encoder to measure position of the transducer 280), motors 403 (e.g., a step motor) to help ensure accurate and repeatable movement of the transducer 280 within the module 200. In various embodiments, module 200 can include a transducer 280 which can emit energy through an acoustically transparent member 230. In one embodiment, the control module 300 can be coupled to the hand wand 100 via the interface 130, and the graphic user interface 310 can be adapted to and/or configured for controlling the module 200. In one embodiment, the control module 300 can provide power to the hand wand 100. In one embodiment, the hand wand 100 can include a power source. In one embodiment, the switch 150 can be adapted to and/or configured for controlling a tissue imaging function and the switch 160 can be adapted to and/or configured for controlling a tissue treatment function. In various embodiments, delivery of emitted energy 50 at a suitable focal depth, distribution, timing, and energy level is provided by the module 200 through controlled operation by the control system 300 of the transducer 280 to achieve the desired therapeutic effect with a thermal coagulation zone 550 ("TCZ" e.g., a thermal coagulation zone or line).

In one embodiment, the module 200 can be coupled to the hand wand 100. The module 200 can emit and receive energy, such as ultrasonic energy. The module 200 can be electronically coupled to the hand wand 100 and such coupling may include an interface which is in communication with the controller 300. In one embodiment, the interface guide 235 can be adapted to and/or configured to provide electronic communication between the module 200 and the hand wand 100. The module 200 can comprise various probe and/or transducer configurations. For example, the module 200 can be adapted to and/or configured for a combined dual-mode imaging/therapy transducer, coupled or co-housed imaging/therapy transducers, separate therapy and imaging probes, and the like. In one embodiment, when the module 200 is inserted into or connected to the hand wand 100, the controller 300 automatically detects it and updates the interactive graphical display 310. In some embodiments, an access key 320 (e.g., a secure USB drive, key) is connected (e.g., removably) to a system 20 to permit the system 20 to function. In various embodiments, the access key is programmed to be customer specific, and serves multiple functions, including system security, country/region specific access to treatment guidelines and functionality, software upgrades, support log transfers and/or credit transfer and/or storage. In various embodiments, the system 20 has internet and/or data connectivity. In an embodiment, connectivity provides a method by which data is transferred between the system 20 provider and the customer. In various embodiments, data includes credits, software updates and support logs. Connectivity is divided into different model embodiments, based on how a user's console is connected to the internet. In one embodiment, Disconnected Model connectivity comprises a console that is disconnected from the internet and customer doesn't have internet access. Credit transfers and software upgrades are conducted by shipping access key(s), (e.g., USB keys) to the customer. In one embodiment, Semi-Connected Model connectivity comprises a console that is disconnected from the internet but customer has internet access. Credit transfers, software upgrades and support log transfers are conducted using the customer's personal computer, smart phone, or other computing device in conjunction with the system access key to transfer data. In one embodiment, Fully-Connected Model connectivity comprises a console that is wirelessly connected to the internet using Wi-Fi, cellular modem, Bluetooth, or other protocol. Credit transfers, software upgrades and support log transfers are made directly between the console and the cloud. In various embodiments, the system 20 connects to an online portal, for streamlined inventory management, on-demand treatment purchases and business analytics insights to drive customer aesthetic treatment business to the next level.

Figure 2:
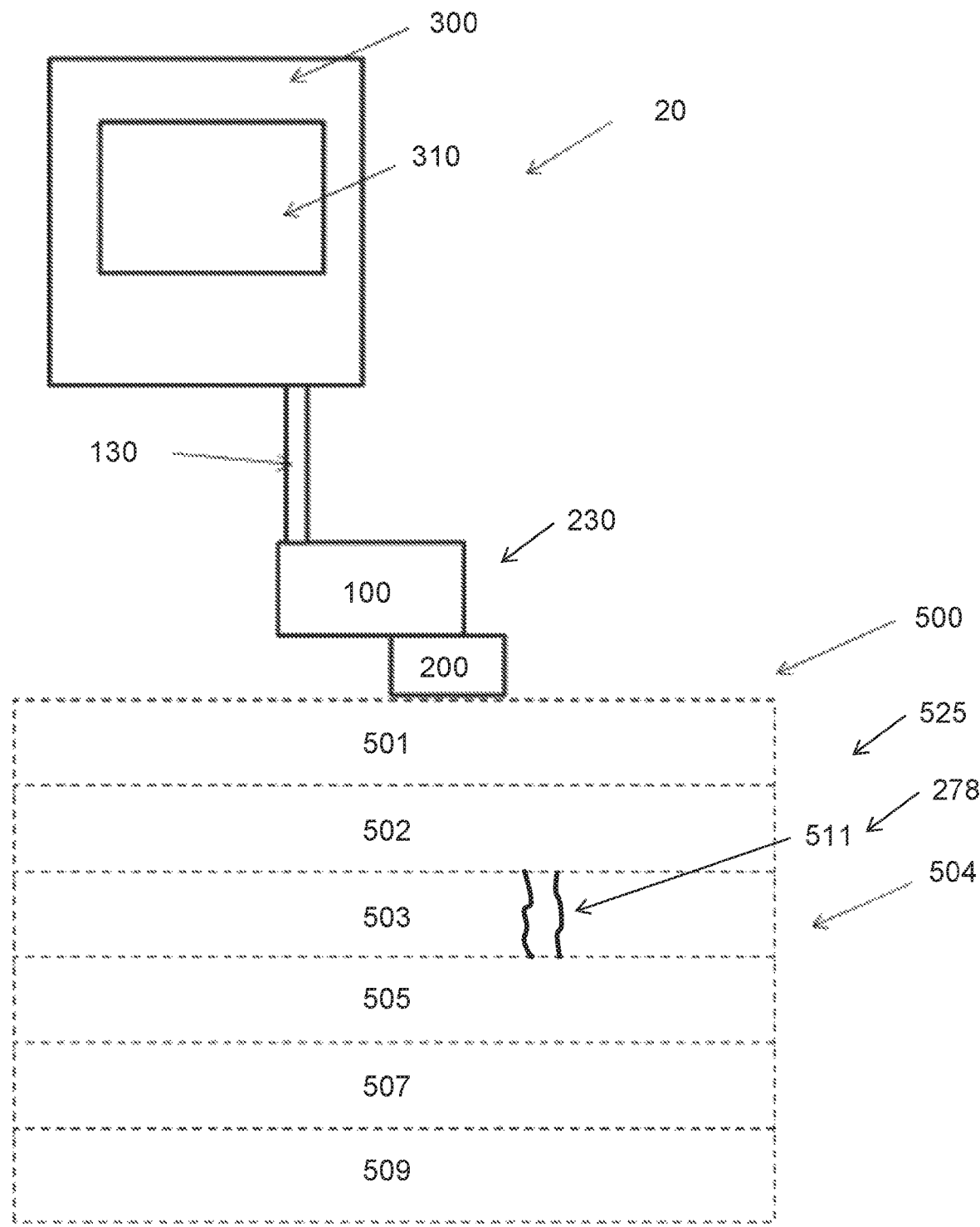
FIG. 2 is a schematic illustration of an ultrasound system coupled to a region of interest according to various embodiments of the invention.

FIG. 2 is a schematic illustration of the ultrasound system 20 coupled to a region of interest 10. In various embodiments, tissue layers of the region of interest 10 can be at any part of the body of a subject. In one embodiment, the tissue layers are in the head and face region of the subject. The cross-sectional portion of the tissue of the region of interest 10 includes a skin surface 501, an epidermal layer 502, a dermal layer 503, a fat layer 505, a superficial muscular aponeurotic system 507, and a muscle layer 509. The tissue can also include the hypodermis 504, which can include any tissue below the dermal layer 503. The combination of these layers in total may be known as subcutaneous tissue 510. Also illustrated in FIG. 2 is a treatment zone 525 which is below the surface 501. In one embodiment, the surface 501 can be a surface of the skin of a subject 500. Although an embodiment directed to therapy at a tissue layer may be used herein as an example, the system can be applied to any tissue in the body. In various embodiments, the system and/or methods may be used on tissue (including but not limited to one or a combination of muscles, fascia, SMAS, dermis, epidermis, fat, adipose cells, cellulite, which may be called gynoid lipodystrophy, (e.g., non-dimple type female gynoid lipodystrophy), collagen, skin, blood vessels, of the face, neck, head, arms, legs, or any other location on or in the body (including bodily cavities). In various embodiments, cellulite (e.g., non-dimple type female gynoid lipodystrophy) reduction is achieved in an amount of 2%, 5%, 10%, 15%, 20%, 25%, 30%, 40%, 50%, 75%, 80%, 90%, 95%, and any ranges therein. With reference to the illustration in FIG. 2, an embodiment of the ultrasound system 20 includes the hand wand 100, the module 200, and the controller 300. In one embodiment, the module 200 includes a transducer 280.

Figure 3:
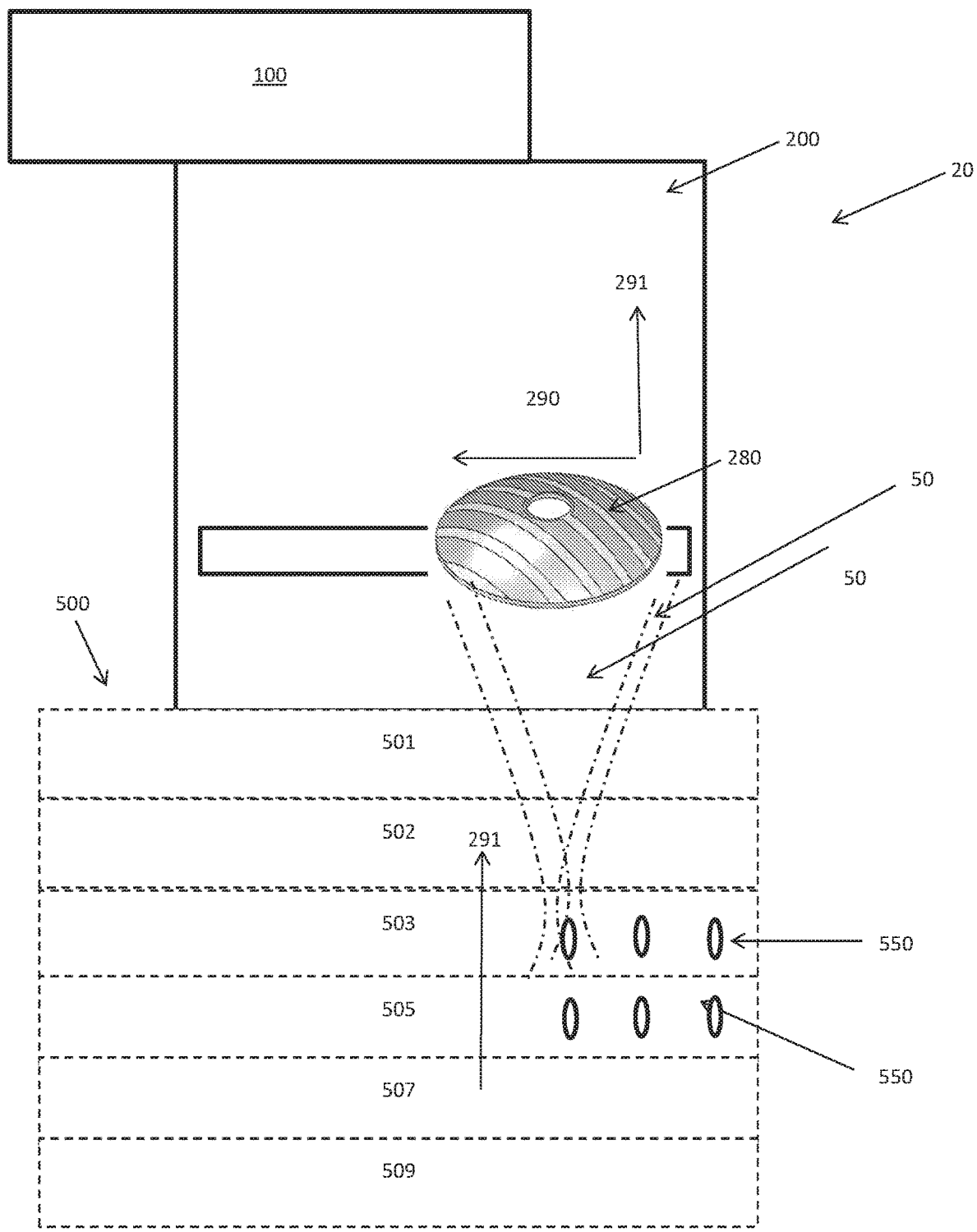
FIG. 3 is a schematic illustration of a portion of a transducer according to various embodiments of the invention.

FIG. 3 illustrates an embodiment of an ultrasound system 20 with a transducer 280 adapted to and/or configured to treat tissue at multiple focal locations 278 (e.g., focal depths, focal positions). Various embodiments of HIFU ultrasound systems configured for simultaneous ultrasound treatment at multiple locations in tissue are described in U.S. application Ser. No. 14/193,234, which published as U.S. Publication No. 2014/0257145 on Sep. 11, 2014, which is incorporated in its entirety by reference, herein. In one embodiment, the focal depth 278 is a distance between the transducer 280 and the target tissue for treatment. In one embodiment, a focal depth 278 is fixed for a given transducer 280. In one embodiment, a focal depth 278 is variable for a given transducer 280. In one embodiment, a transducer 280 is configured to treat simultaneously at multiple depths below a skin surface (e.g., 1.5 mm, 3.0 mm, 4.5 mm, or other depths). With reference to the illustration in FIG. 4, the module 200 can include a transducer 280 which can emit energy through an acoustically transparent member 230. In various embodiments, a depth may refer to the focal depth 278. In one embodiment, the transducer 280 can have an offset distance (or standoff distance) 270, which is the distance between the transducer 280 and a surface of the acoustically transparent member 230. In one embodiment, the focal depth 278 of a transducer 280 is a fixed distance from the transducer. In one embodiment, a transducer 280 may have a fixed offset distance 270 from the transducer to the acoustically transparent member 230. In one embodiment, an acoustically transparent member 230 is adapted to and/or configured at a position on the module 200 or the ultrasound system 20 for contacting the skin surface 501. In various embodiments, the focal depth 278 exceeds the offset distance 270 by an amount to correspond to treatment at a target area located at a tissue depth 279 below a skin surface 501. In various embodiments, when the ultrasound system 20 placed in physical contact with the skin surface 501, the tissue depth 279 is a distance between the acoustically transparent member 230 and the target area, measured as the distance from the portion of the hand wand 100 or module 200 surface that contacts skin (with or without an acoustic coupling gel, medium, etc.) and the depth in tissue from that skin surface contact point to the target area. In one embodiment, the focal depth 278 can correspond to the sum of an offset distance 270 (as measured to the surface of the acoustically transparent member 230 in contact with a coupling medium and/or skin 501) in addition to a tissue depth 279 under the skin surface 501 to the target region. In various embodiments, the acoustically transparent member 230 is not used.

Various embodiments of the invention relate to devices or methods of splitting an ultrasonic energy beam into multiple beams. In one embodiment, a HIFU 20 ultrasound treatment is directed to the dermis 503 and the fat layer 505. In one embodiment, a simultaneous HIFU 20 treatment is configured to strengthen collagen structure near the dermis 503—fat 505 interface at the "roof" of a fat lobuli, and to reduce volume of fat by apoptosis heating within the fat 505 layer. In various embodiments, devices or methods can be used to alter the delivery of ultrasound acoustic energy in any procedures such as, but not limited to, therapeutic ultrasound, diagnostic ultrasound, ultrasonic welding, any application that involves coupling mechanical waves to an object, and other procedures. Generally, with therapeutic ultrasound, a tissue effect is achieved by concentrating the acoustic energy using focusing techniques from the aperture. In some instances, high intensity focused ultrasound is used for therapeutic purposes in this manner. In one embodiment, a tissue effect created by application of therapeutic ultrasound at a particular depth to can be referred to as creation of a thermal coagulation zone. In some embodiments, a zone can include a point. In some embodiments, a zone is a line, plane, band, spherical, elliptical, cubical, or other one-, two-, or three-dimensional shape. It is through creation of thermal coagulation zones at particular positions that thermal and/or mechanical ablation of tissue can occur non-invasively or remotely. Various embodiments of the invention address potential challenges posed by administration of ultrasound therapy. In various embodiments, time for effecting the formation of thermal coagulation zones for a desired cosmetic and/or therapeutic treatment for a desired clinical approach at a target tissue is reduced. In various embodiments, treating tissue, such as skin tissue, with multiple beams provides one or more advantages, such as, for example, reducing treatment time, creating unique heating patterns, leveraging multiple channels for greater power, the option to treat skin at two or more depths with the same or different power levels, (e.g., a thermal coagulation zone in the superficial muscular aponeurotic system and another defocused energy at the surface of the skin, or other combinations), optional simultaneous treatment at different depths (e.g., such as at depths below a skin surface of 1.5 mm, 3 mm and/or 4.5 mm thermal coagulation zones simultaneously or in an overlapping time period); and/or treatment with one, two, or more simultaneous linear or line focuses, such as at different depths below the skin surface or spaced apart. In some embodiments simultaneous multi-focus therapy uses dithering. In some embodiments, dithering (e.g., electronic dithering) of multiple and/or split ultrasound beam apertures using frequency modulation provide treatment zones or points in multiple locations. In some embodiments, dithering relates to intentional movement of the position/location of a focal point of an energy beam. For example, in one embodiment, dithering involves shaking, moving, vibrating, altering the location and/or position of a single focal zone, and/or a relative spacing between two or more focal zones. In various embodiments, the relative position of a focal zones is dithered by 1-50% (e.g., 1%, 5%, 10%, 15%, 20%, 25%, 30%, 35%, 40%, 45%, 50% and any range therein, such as a percentage of a mean location by a certain percentage). In various embodiments, spacing between focal zones is dithered by a range of between 1-50% (e.g., 1%, 5%, 10%, 15%, 20%, 25%, 30%, 35%, 40%, 45%, 50% and any range therein). In some embodiments, dithering may be achieved through mechanical, electronic, or combinations of mechanical and electronic means depending on the system design. In one embodiment of mechanical dithering, the ultrasound beam is moved locally around the intended thermal coagulation zone center through a mechanical translation or tilt of the therapy transducer or patient or any combination thereof. The mechanical translation and/or tilt enable(s) the spread of the acoustic energy such that thermal conduction limitations of tissue are overcome. This creates a flatter temperature profile in tissue to either reduce the total acoustic energy to create the same effected tissue volume or have the same total acoustic energy to increase the effected tissue volume when compared to a stationary ultrasound therapy device. In various embodiments of electronic dithering, frequency, phase, amplitude modulations or time based techniques are used to in combination with a uniquely defined transducer to move the ultrasound beam in tissue without any mechanical movement. In one embodiment, electronic movement of the ultrasound beam occurs significantly faster than mechanical movement to overcome the thermal conductivity limitation of tissue. In various embodiments, a ratio of relative focal zone positioning via dithering is 1:1000, 1:500, 1:200; 1:100, 1:50, 1:25, 1:10, 1:2 or any ratio between 1:1000 and 1:1. In various embodiments, a ratio of spacing between relative focal zone positioning via dithering is 1:1000, 1:500, 1:200; 1:100, 1:50, 1:25, 1:10, 1:2 or any ratio between 1:1000 and 1:1. For example, in some embodiments, a focal zone is activated at "1" and an open spacing ratio of untreated tissue is provided in the second number of the ratio. For example, in one embodiment, a dithering spacing is e.g., 1 mm, and a dithering distance is 0.1 mm, so a ratio is 1:10. In various embodiments, a ratio of spacing between focal zones via dithering is 1:1000, 1:500, 1:200; 1:100, 1:50, 1:25, 1:10, 1:2 or any ratio between 1:1000 and 1:1. In some embodiments, the spacing of simultaneous focal zones is dithered. In some embodiments, the treatment points and/or zones are formed simultaneously in tissue. In various embodiments, dithering for performing various treatment and/or imaging procedures is with modulated and/or multiphased with controlled variance in frequency. Some embodiments relate to splitting an ultrasound therapy beam to two, three, four, or more focal zones for performing various treatments with, for example, dithering, poling, phasing, and/or modulation techniques and/or imaging procedures.

In accordance with various embodiments, a cosmetic ultrasound treatment system and/or method can non-invasively produce single or multiple dithered cosmetic treatment zones and/or thermal coagulation zones where ultrasound is focused in one or more locations in a region of treatment in tissue under a skin surface, and moved via changes in frequency (e.g., via frequency modulation). Some systems and methods provide cosmetic treatment at different locations in tissue, such as at different depths, heights, widths, and/or positions. In one embodiment, a method and system comprise a multiple depth/height/width transducer system configured for providing ultrasound treatment to one or more region of interest, such as between at least one depth of treatment region of interest, a superficial region of interest, and/or a subcutaneous region of interest. In one embodiment, a method and system comprise a transducer system configured for providing ultrasound treatment to more than one region of interest, such as between at least two points in various locations (e.g., at one or more fixed or variable depths, heights, widths, and/or orientations, etc.) in a region of interest in tissue. Some embodiments can split a beam to focus at two, three, four, or more focal points (e.g., multiple focal points, multi-focal points) for cosmetic treatment zones and/or for imaging in a region of interest in tissue. Position and/or dithering of the focal points can be positioned axially, laterally, or otherwise within the tissue. Some embodiments can be configured for spatial control, such as by the location and/or dithering of a focus point, changing the distance from a transducer to a reflecting surface, and/or changing the angles of energy focused or unfocused to the region of interest, and/or configured for temporal control, such as by controlling changes in the frequency, drive amplitude and timing of the transducer. In some embodiments the position and/or dithering of multiple treatment zones or focal points is achieved with poling, phasic poling, biphasic poling, and/or multi-phasic poling. In some embodiments the position of multiple treatment zones or focal points with phasing, such as in one embodiment, electrical phasing. As a result, changes in the location of the treatment region, the number, shape, size and/or volume of treatment zones or lesions in a region of interest, as well as the thermal conditions, can be dynamically controlled over time.

In accordance with various embodiments, a cosmetic ultrasound treatment system and/or method can create multiple cosmetic treatment zones using one or more of frequency modulation, phase modulation, poling, nonlinear acoustics, and/or Fourier transforms to create any spatial periodic pattern with one or multiple ultrasound portions. In one embodiment, a system simultaneously or sequentially delivers single or multiple treatment zones using poling at a ceramic level. In one embodiment, a poling pattern is function of focal depth and frequency, and the use of odd or even functions. In one embodiment, a poling pattern, which can be a combination of odd or even functions, is applied, and based on focal depth and/or frequency. In one embodiment, a process can be used in two or more dimensions to create any spatial periodic pattern. In one embodiment, an ultrasound beam is split axially and laterally to significantly reduce treatment time through the use of nonlinear acoustics and Fourier transforms. In one embodiment, modulation from a system and amplitude modulation from a ceramic or a transducer can be used to place multiple treatments zones in tissue, either sequentially or simultaneously. In one embodiment, an aesthetic imaging and treatment system includes an ultrasonic probe that includes an ultrasound transducer configured to apply ultrasonic therapy to tissue at a plurality of locations at a focal depth with electronic dithering of multiple energy beam apertures with frequency modulation. In one embodiment, the system includes a control module coupled to the ultrasonic probe for controlling the ultrasound transducer. In one embodiment, the system includes dithering configured to provide variable spacing between a plurality of individual cosmetic treatment zones. In various embodiments, an ultrasound treatment system for dithering multiple simultaneous focus points from an ultrasound transducer includes an ultrasonic probe and a control module coupled to the ultrasonic probe for controlling the ultrasound transducer. The ultrasonic probe includes an ultrasound transducer with a single transduction element adapted to simultaneously apply ultrasonic therapy to tissue at a plurality of spaced locations at a focal depth. The ultrasound transducer is poled with at least a first poling configuration and a second poling configuration. The control module modifies the spacing between the spaced locations via dithering of a first focal zone and a second focal zone, such that dithering via modulation of a frequency precisely moves a position of a beam focus point at the spaced locations.

Figure 4:
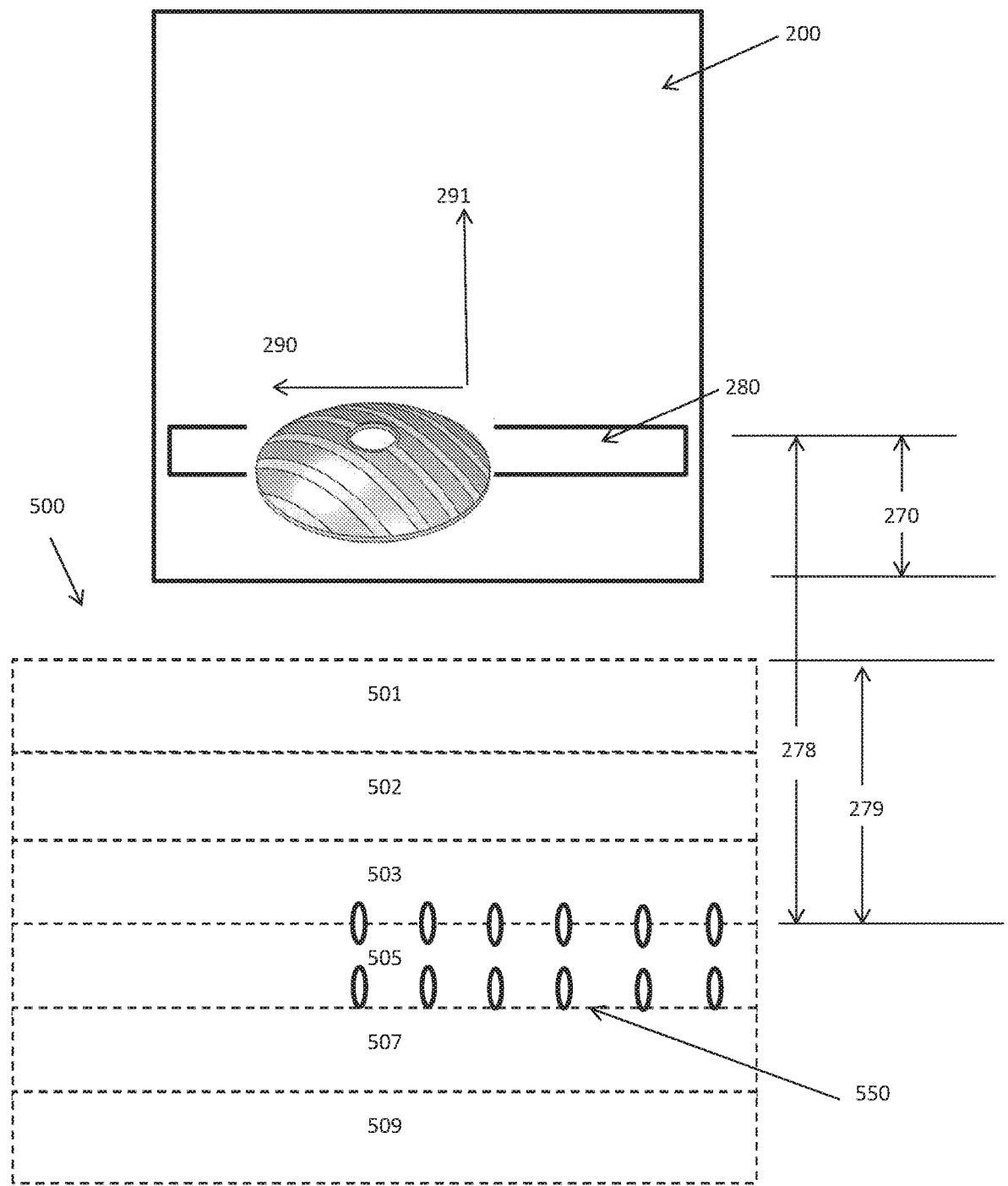
FIG. 4 is a partial cut away side view of an ultrasound system according to various embodiments of the invention.

As illustrated in FIGS. 3 and 4, in various embodiments of a HIFU system 20, delivery of emitted energy 50 at one or more suitable focal depths 278, distribution, timing, and energy level is provided by the module 200 through controlled operation by the control system 300 to achieve the desired therapeutic effect of controlled thermal injury to treat at least one of the epidermis layer 502, dermis layer 503, fat layer 505, the SMAS layer 507, the muscle layer 509, and/or the hypodermis 504. FIGS. 3 and 4 illustrate various embodiments of a HIFU 20 treatment at multiple depths. In various embodiments, the depth can correspond to any tissue, tissue layer, skin, epidermis, dermis, hypodermis, fat, SMAS, muscle, blood vessel, nerve, or other tissue. During operation, the module 200 and/or the transducer 280 can also be mechanically and/or electronically scanned along the surface 501 to treat an extended area. Before, during, and after the delivery of ultrasound energy 50 to at least one of the epidermis layer 502, dermis layer 503, hypodermis 504, fat layer 505, the SMAS layer 507 and/or the muscle layer 509, monitoring of the treatment area and surrounding structures can be provided to plan and assess the results and/or provide feedback to the controller 300 and the user via a graphical interface 310. In one embodiment, an ultrasound system 20 generates ultrasound energy which is directed to and focused below the surface 501. This controlled and focused ultrasound energy 50 creates the thermal coagulation zone or zone 550. In one embodiment, the ultrasound energy 50 creates a void in subcutaneous tissue 510. In various embodiments, the emitted energy 50 targets the tissue below the surface 501 which cuts, ablates, coagulates, micro-ablates, manipulates, and/or causes a thermal coagulation zone 550 in the tissue portion 10 below the surface 501 at a specified focal depth 278. In one embodiment, during the treatment sequence, the transducer 280 moves in a direction denoted by the arrow marked 290 at specified intervals 295 to create a series of treatment zones 254 each of which receives an emitted energy 50 to create one or more thermal coagulation zones 550. In one embodiment, an arrow marked 291 illustrates an axis or direction that is orthogonal or parallel to arrow 290, and a spacing of thermal coagulation zones 550 show thermal coagulation zones can be spaced orthogonally or parallel to the motion direction of the transducer 280. In some embodiments, an orientation of the spaced thermal coagulation zones can be set at any angle 0-180 degrees from arrow 290. In some embodiments, an orientation of the spaced thermal coagulation zones can be set at any angle 0-180 degrees based on the orientation of poled areas on the transducer 280.

Figure 5A:
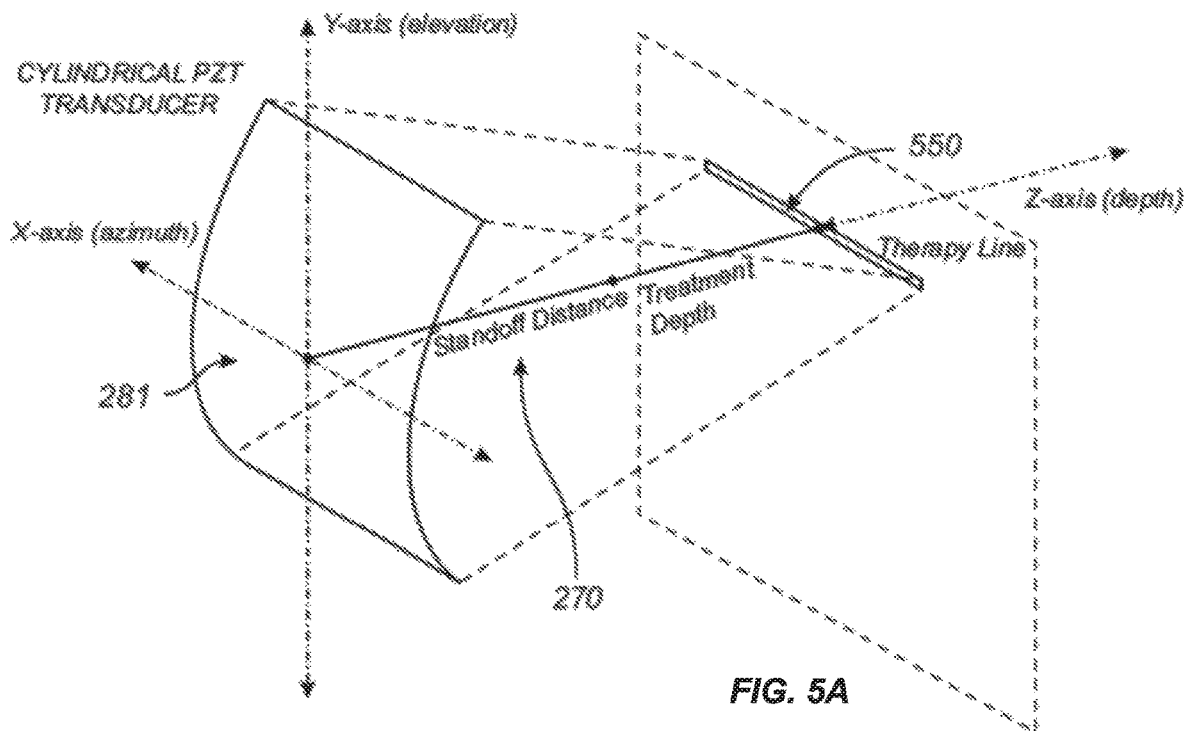
FIGS. 5A-5B illustrate a schematic isometric side view of a cylindrical transducer being moved by a motion mechanism in a cosmetic treatment system, wherein the thermal coagulation zone sweeps a treatment area, according to an embodiment.
Figure 5B:
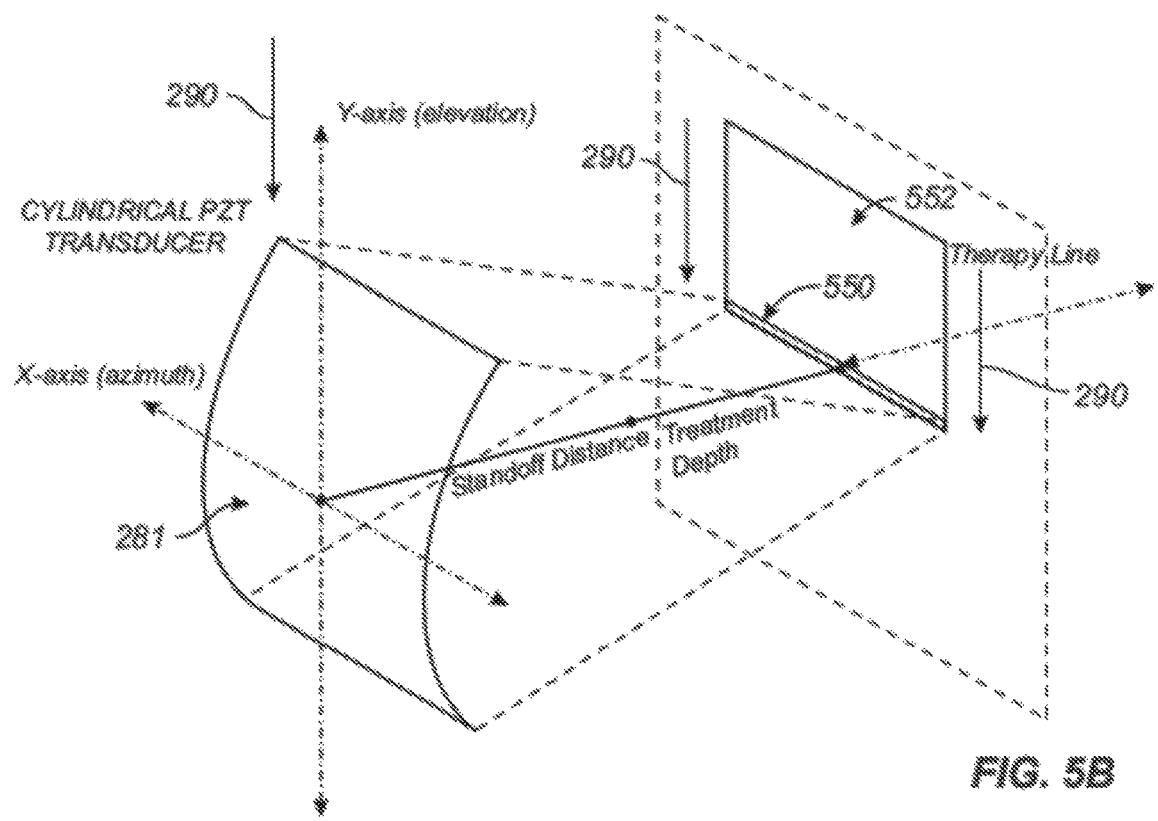

In some embodiments, as illustrated in FIGS. 5A and 5B, a transducer 280 comprises a cylindrical transduction element 281 which creates a line or band of focused ultrasound treatment. In one embodiment, a cylindrical transduction element 281 has a concave surface 282 and a convex surface 283. The cylindrical transduction element 281 extends linearly along its longitudinal axis (X-axis, azimuth) with a curved cross section along a Y-axis (elevation). In one embodiment, the cylindrical surface has a radius at a focal depth (z-axis) at the center of the curvature of the cylindrical surface, such that the thermal coagulation zone 550 is focused at the center of the radius. For example, in one embodiment, cylindrical transduction element 281 has a concave surface that extends like a cylinder that produces a focus zone that extends along a line, such as a therapy line, such as thermal coagulation zone 550. The focus zone thermal coagulation zone 550 extends along the width (along the X-axis, azimuth) of the cylindrical transduction element 281, in a line parallel to the longitudinal axis of the cylindrical transduction element 281. In various embodiments, a thermal coagulation zone 550 as illustrated in FIG. 3 or 4 can be a line extending in and/or out of the page. In various embodiments of the cylindrical transduction element 281, a concave surface directs ultrasound energy to a linear thermal coagulation zone 550. Cylindrical transduction element 281 need not be cylindrical; in some embodiments, element 281 is a transduction element having one or more curved or non-linear portions. Various embodiments of band ultrasound treatment with a thermal line or plane of treatment in tissue are described in U.S. application Ser. No. 15/302,436, which published as U.S. Publication No. 2017/0028227 on Feb. 2, 2017, which is incorporated in its entirety by reference, herein.

As illustrated in FIGS. 5A-5B in several embodiments, a system may comprise a movement mechanism 285 configured to move a transducer 280 comprising a cylindrical transduction element 281 in one, two, three or more directions. In one embodiment, a motion mechanism 285 can move in a linear direction, one or both ways, denoted by the arrow marked 290 in order move a thermal coagulation zone 550 through tissue. In various embodiments, the motion mechanism 285 can move the transducer in one, two, and/or three linear dimensions and/or one, two, and/or three rotational dimensions. In one embodiment, a motion mechanism 285 can move in up to six degrees of freedom. Movement of the thermal coagulation zone 550 can be with the transducer continuously delivering energy to create a treatment area 552. In one embodiment, a movement mechanism 285 can automatically move the cylindrical transduction element 281 across the surface of a treatment area so that the thermal coagulation zone 550 can form a treatment area 552.

HIFU Treatment Combined with Dermal Fillers and/or Fat-Reducing Compounds

In several embodiments, HIFU is used in conjunction with a dermal filler, a fat-reducing compound, or both, to provide synergistic results. The HIFU can be administered before or after the agents in some embodiments. In one embodiment, simultaneous application of HIFU and the agent(s) is provided.

In one embodiment, a HIFU treatment (e.g., building the dermal roof) comprises HIFU 20 treatment in or around the dermis (e.g., target depth between 1.5 mm and 4.5 mm) for tightening the dermal/skin structure by inducing restructuring and reinforcement of the extracellular matrix network. In one embodiment, a dual or triple HIFU treatment approach with HIFU at multiple depths comprises HIFU in or around the dermis for tightening the dermal/skin structure by inducing restructuring and reinforcement of the extracellular matrix network. In one embodiment, parallel or consecutive application of a HIFU—dermal filler combination comprises HIFU 20 in or around the upper-dermis (e.g., target depth 1.5 mm) and/or the lower-dermis (e.g., target depth 3.0-4.5 mm) in combination with dermal filler 800 in or around the deep-dermis for tightening the dermal structure by inducing restructuring and reinforcement of the extracellular matrix network. In one embodiment, a dual or triple depth HIFU approach comprises high intensity macro focused ultrasound for targeting the subcutaneous fat layer in a target depth e.g., between 10-17 mm for reduction of subcutaneous fat tissue by adipocytolysis.

In one embodiment, combined HIFU+Injection lipolysis treatment comprises HIFU in or around the dermis (e.g., target depth 1.5 and 4.5 mm) for tightening the dermal/skin structure by inducing restructuring and reinforcement of the extracellular matrix network and injection of a fat-reducing compound (e.g., adipo-cytolytic compound, polidocanol) into the subcutaneous fat-layer for reduction of subcutaneous fat tissue.

In one embodiment, a triple combined approach is provided. For example, HIFU 20, dermal filler 800, and fat-reducing compound 820 (e.g., injection lipolysis) are all used on a given subject. In one embodiment, this approach comprises HIFU in or around the upper-dermis (e.g., target depth 1.5 mm) in combination with, a dermal filler 800 (e.g., calcium hydroxyapatite microspheres in a gel-matrix, RADIESSE) in or around the deep-dermis for tightening the dermal structure by inducing restructuring and reinforcement of the extracellular matrix network, and the injection of an adipo-cytolytic compound into the subcutaneous fat-layer for reduction of a fat-reducing compound (e.g., adipo-cytolytic compound, polidocanol) into the subcutaneous fat-layer for reduction of subcutaneous fat tissue.

In some embodiments, by precisely reinforcing the dermal extracelluar matrix network in the dermis, the missing "roof" in a dermal fiber network can be (re)formed and thus treat, improve, and/or cure a central anthological factor for cellulite. In some embodiments, depending on the severity of cellulite in addition the extracellular matrix in the deep dermis can be reinforced. This deep dermal enforcement can be reached by HIFU treatment at a depth of e.g., 4.5 mm, and/or by application of dermal filler 800. In several embodiments, the HIFU treatments are provided using applicant's technology marked under the brands ULTHERAPY®, DEEPSEE®, and/or OCTAVE™.

Although ultrasound is described above, several embodiments of the invention include other energy sources in addition to or instead of ultrasound. For example, the following may be used, alone or in combination: light, laser, radio-frequency (RF), microwave, electromagnetic, radiation, thermal, cryogenic, electron beam, photon-based, magnetic, magnetic resonance, and/or other energy forms. Although HIFU is described in several embodiments, non-focused ultrasound can instead be used for some applications. In one embodiment, both HIFU and non-focused ultrasound are employed (together with the agents described herein). In another embodiment, ultrasound is used in combination with radiofrequency, mechanical lysis, laser, or microwave energy, along with the agents described herein.

HIFU with Cavitation-Prone Fluids

In various embodiments, the use of a HIFU system 20 in combination with a cavitation-prone fluid 810 provides an improved treatment of skin tissue. In various embodiments, the treatment of skin tissue is for wrinkles, aged looking skin, skin laxity, skin lifting, fat, cellulite, and in one particular example, provides an improved treatment of gynoid lipodystrophy. In one embodiment, the cavitation-prone fluid 810 increases adipocytolytic efficiency of ultrasound treatment by prior application of the cavitation-prone fluid 810 into the targeted fat-tissue. In one embodiment, the ultrasound generated cavitation bubbles would increase the disruption of adipocytes. More specifically, in one embodiment, the use of HIFU and a cavitation-prone fluid reduces the unwanted appearance of cellulite, is well tolerated and leads to increased patient satisfaction. According to some embodiments, a cavitation-prone fluid is used with either a dermal filler, a fat-reducing compound, or both to achieve enhanced effects.

Examples of cavitation-prone fluids that are used with energy-based devices (such as laser, RF, lights, ultrasound, HIFU) include but are not limited water, an aqueous solution of Ethanol, and an aqueous solution of Glycerol. With respect to cavitation-prone fluids, the application of ultrasound energy amplifies a cavitation, or bubble bursting effect, which can reduce the volume of fat cells in lobuli compartments underlying the appearance of cellulite.

Disruption of Local, Distinct Dermal Septa

Referring again to the skin of the subject 500 illustrated in FIG. 2, distinct fibrous connective bands or septa 511 extend between the epidermal layer 502 and the fat layer 505. As described herein, the septa can contribute to the appearance of cellulite because the non-flexible length does not accommodate an increase in fat cells. As a result, the septa impart tension to the underside of the skin layer, e.g., the epidermal layer, while the skin surrounding the septa is raised as a result of increase fat volume, leading to dimples or depressions in the skin surface. This results in a more or less evenly distributed irregularity over large areas of the skin in general. However, at specific sites, single dermal septa form a prominent and local rigid perpendicular structure in the dermis. This local strong connective tissue structure holds the skin down while surround skin can be expanded to a larger extent by expanding subcutaneous fat tissue. In such situation, in addition to a general dimpling, at focal locations distinct depressions are easily visible. Systems and methods for dissecting (e.g., severing, cutting, or otherwise disrupting) the septa 511 can be combined with other treatment methods and devices described herein, including HIFU, dermal fillers, cavitation-prone fluids, and/or fat-reducing compounds. While described methods for reducing the fat-cell aspect and reinforcement of the dermal connective tissue will be used for treatment of generalized cellulite phenotype on large skin areas, the dermal-dissecting methods can address specific local, prominent skin depression. As described herein, in some embodiments, septae can be dissected using a suitable HIFU device, with or without a cavitation-prone fluid. Other ablation modalities are also used in some embodiments (e.g., radiofrequency, microwave, laser, thermal, cryogenic, combinations thereof, and the like).

In some embodiments, systems and methods for dissecting, or otherwise disrupting septae can include a minimally-invasive mechanical cutting device. For example, as described in U.S. application Ser. No. 12/852,029, which published as U.S. Publication No. 2011/0028898 on Feb. 3, 2011, and U.S. application Ser. No. 12/975,966, which published as U.S. Publication No. 2012/0165725 on Jun. 28, 2012, each of which is incorporated its entirety by reference, herein, the skin of the subject can be suctioned into and/or isolated by a chamber by, for example, the application of negative pressure (or elevated by an alternative force, such as a downward force on the chamber), for example to stabilize the tissue. A wall at least partially defining the chamber can include an aperture for insertion of instruments such as a needle, a cutting blade, etc. The cutting blade can be moved proximally and distally along a longitudinal cutting axis. In some embodiments, the cutting blade can also or alternatively be moved lateral to the longitudinal cutting axis. In some embodiments, a guide or template (e.g., connectable to the chamber in a fixed position) can guide movement of the cutting blade in a particular pattern or motion. The cutting of the band might be performed with suitable cutting devices "free-hand" or more preferentially by using tissue stabilized guided dissection. In some embodiments, the guide can direct the cutting blade to be a certain height in the dermal layer. Movement of the cutting blade can dissect one septa or multiple septae, releasing the epidermal layer from the fat layer at one or more non-flexible distances.

In some embodiments, the device used to dissect septae or parts thereof may also be used to target a desired skin- or fat-compartment for stimulation of neo-collagenesis and/or application of adipocytolytic compounds. For example, the aperture in the chamber can be used to guide a needle, for example for delivering anesthesia and/or other medicaments (e.g., dermal fillers, cavitation-prone fluids, fat reducing compounds, etc.) before and/or after dissecting septae. In some embodiments, a guide can direct the needle to be a certain height in the dermal layer and/or the fat layer. For example, as described herein, certain cosmetic treatments can be combined, and a single chamber with multiple templates can be used for multiple treatments.

Figure 7A:
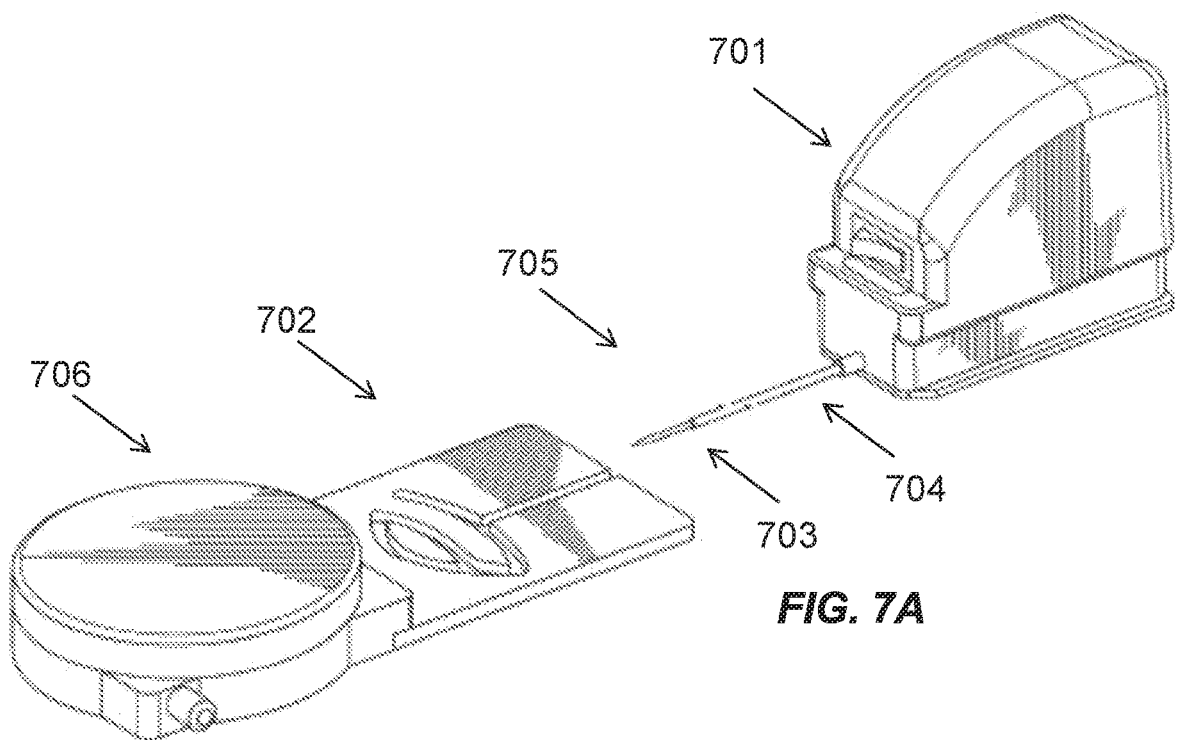
FIG. 7A illustrates a schematic isometric side view of a septa dissecting device according to various embodiments of the invention.

FIG. 7A illustrates a schematic isometric side view of a septa dissecting device or system according to various embodiments of the invention. The dissection system may include a cutting module 701 (e.g., a motor-controlled cutting module, a manual cutting module) and a guidance track 702 operably connectable to the cutting module 701 and/or another cutting module or cutting handpiece. In the embodiment illustrated in FIG. 7A, the cutting module 701 includes an embodiment of cutting tool 705 (a reciprocating cutting blade 703 disposed in a sleeve 704) and a housing and a base. The guidance track 702 is coupled to a chamber 706. The chamber 706 may be the same as or different than the chamber 600. In some embodiments, the guidance tract 702 may be detachably coupled to the chamber 706. The guidance track 702 is generally configured to constrain a portion of a cutting module guide pin in contact with the guidance track 702 to move along a predetermined path. Thus, a distal end of the cutting tool 705, passing through an entry hole (e.g., the port 604), cooperatively moves in a plane substantially parallel to the guidance track 702 and in a predetermined shape defined by the predefined path. Motor operation of cutting module 701 is preferably controlled manually by an electric switch or button, but may also or alternatively be activated by electrical or other contact means, for example within the guidance track 702.

Figure 7B:
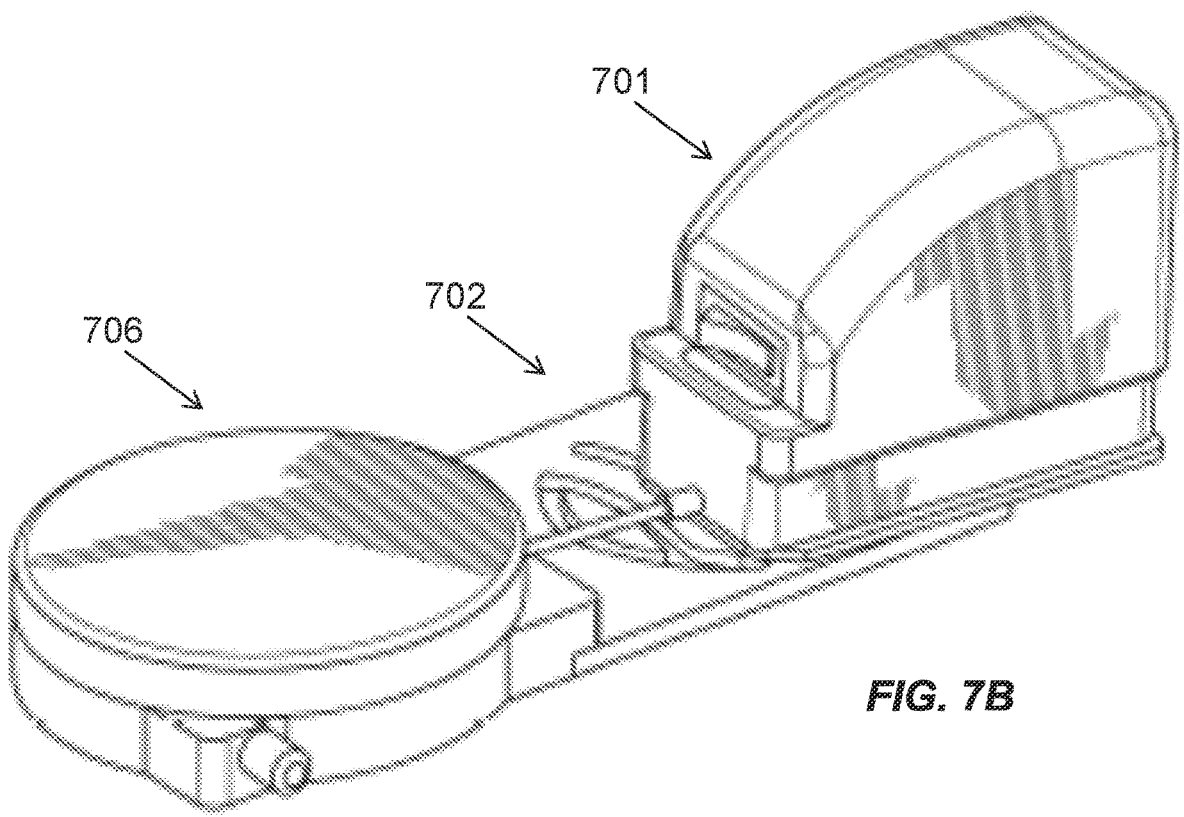
FIG. 7B illustrates a schematic isometric side view of a septa dissecting device according to various embodiments of the invention.

FIG. 7B illustrates a schematic isometric side view of a septa dissecting device according to various embodiments of the invention. The cutting module 701 is coupled to the guidance track 702. For example, a projection extending downward from the cutting module 701 may reside in the grooves of the guidance track 702. In some embodiments, a magnet, optical guidance, or other means of following the guidance track 702 may be used. In the position shown in FIG. 7B, the cutting blade 703 is inserted through an aperture of the chamber 706. The sleeve 704 passes through entry hole of the chamber 706, effectively creating a pivot at the point of contact with the skin.

Figure 7C:
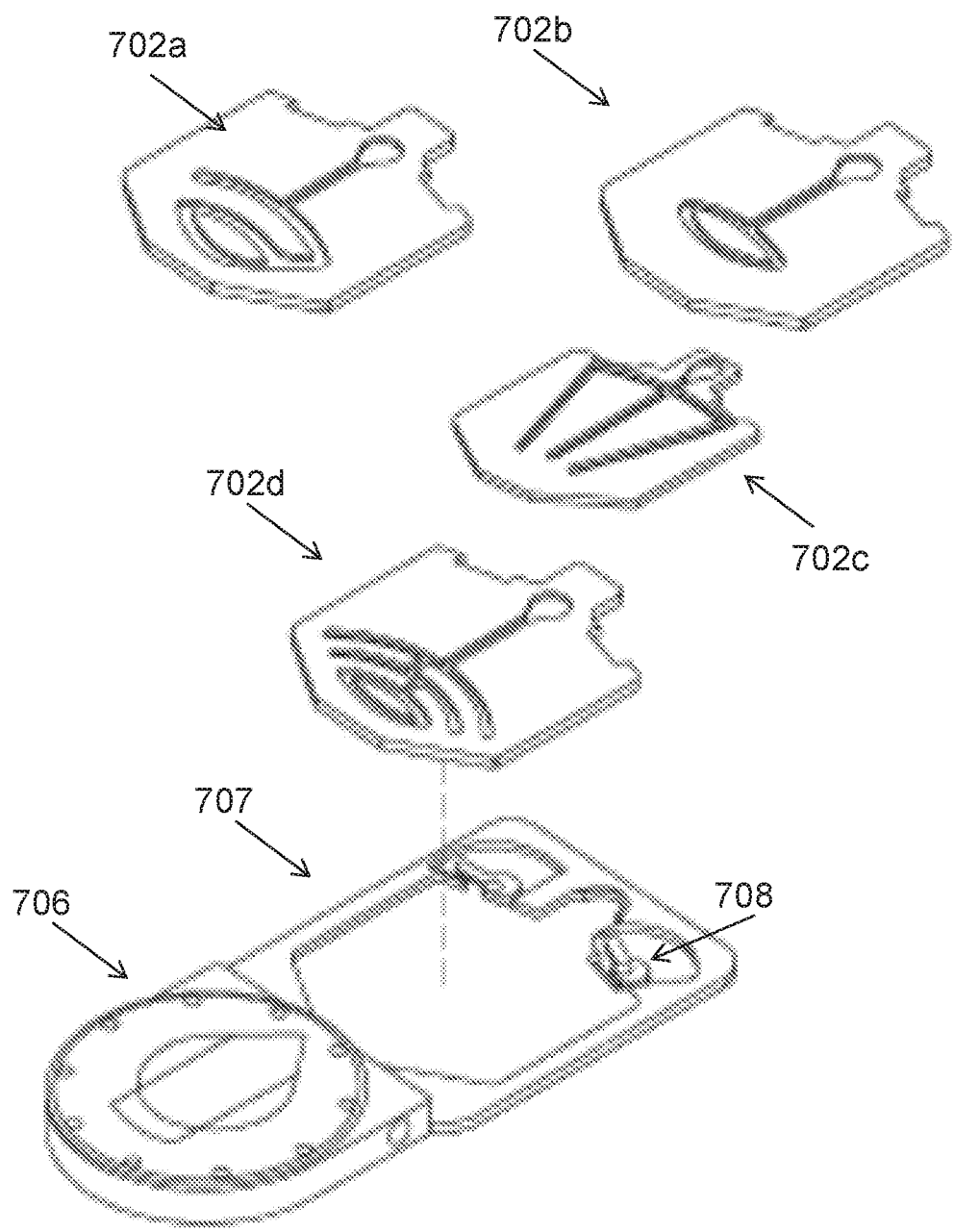
FIG. 7C illustrates schematic isometric side views of insertable movement guides usable with a septa dissecting device according to various embodiments of the invention.

FIG. 7C illustrates schematic isometric side views of insertable movement guides usable with a septa dissecting device according to various embodiments of the invention. The guidance tract 702a is one of multiple possible guidance tracks or guidance track inserts 702a, 702b, 702c, 702d insertable into a guidance track holder 707. The guidance track holder 707 is coupled to a chamber 706. The chamber 706 may be the same as or different than the chamber 600. In some embodiments, the guidance tract holder 707 may be detachably coupled to the chamber 706.

In one embodiment, the path of guidance track 702a is defined by a central channel passing through multiple arcs, the arcs each having a radius measured from a center point located beyond the guidance track 702a in a direction toward the portion of the cutting tool that will provide the cutting action. Moving toward the center point, each successive arc decreases in length and grows smaller. In this embodiment, the penultimate arc is joined with a final inverted arc of the same size to create a closed loop between the penultimate arc and final inverted arc. In one embodiment, the central channel does not intersect with the inverted arc; rather, a guide pin can move along the path of the central channel will move into the final inverted arc by traveling along and beyond an end of the penultimate arc. In the depicted embodiment, there are three primary arcs, the last joining the inverted arc. The central channel also has an enlarged opening at its starting position, furthest from the arcs, wherein the central channel is in the form of an elongated substantially straight track moving toward the arcs. This straightened portion allows the cutting module 701 to be positioned within the guidance track 702a at its beginning and to move in a forward direction to insert the cutting tool 705 through the conduit and entry point and into the recessed area. The central channel is also staggered between the first and second arcs and between the second and third arcs to inhibit or prevent a cutting module traveling along the guidance track from slipping further forward to the last arc before providing the operator of the cutting module the opportunity to move the cutting module 701 in the entire range of the predefined guidance path 702a. In embodiments in which the guide pin has an enlarged head, an enlarged opening of the center channel may be suitable for receiving the enlarged head, and the guidance track 702a can include an enlarged underside for passage of the enlarged head along the guidance path 702 while inhibitor or preventing the cutting module 701 from being lifted off the guidance track 702 and/or supports the cutting module 701 at a predefined planar orientation relative to guidance track 702. In some embodiments, the arcs of guidance track 702a are connected at the outer edges to allow alternate movements of the cutting module 701 between the arcs. This may be particularly useful, for example, once the dissection is complete so that the cutting module 701 can be easily moved from the last inverted arc to the central channel.

In alternate embodiments, with continued reference to FIG. 7B, the guidance track 702a may be removable and replaced with a different guidance track 702b, 702c, 702d, etc., which creates a different dissection profile. For instance, a variety of guidance tracks or guidance track inserts 702a, 702b, 702c, 702d may be provided so the operator can tailor the procedure to the patient's anatomy, the size of the lesion to be created, etc. The guidance track 702 may be inserted into a guidance track holder 707 and optionally constrained by a locking mechanism 708. The locking mechanism 708 may include, for example, pivoting arms or levers that rotate within an indentation to overlap a portion of guidance track 702 to constrain the guidance track 702 in the guidance track holder 707. FIG. 7B depicts an embodiment including a predetermined path for use with an injection device to coordinate movement of a complementary device having a hypodermic needle or other injection device to inject a solution within a tissue disposed within the recessed area in a treatment area defined by the predefined path. For example, the guidance track 702c can be used to inject dermal fillers, cavitation-prone fluids, fat reducing compounds, anesthetics, etc. Such a system can be advantageous for the combinations of treatments described herein. Guidance track inserts 702 having different thicknesses can be used to target different layers (e.g., the dermal layer, the fat layer) and heights therein. Different guidance tracks 702 can be used instead of a guidance track holder and guidance track inserts. In some embodiments, the chamber 706 may comprise a plurality of entry holes at different distances from a tissue apposition surface (tissue facing surface) of the chamber 706, which is defined by a top wall 720 and perimeter wall 722 of the chamber 706 (see, e.g., FIG. 9). For example, a first entry hole configured to allow passage tools for injecting fluid may be positioned between about 1.5 mm and about 4.5 mm from the apposition surface, to correspond to certain depths below the skin surface. For another example, a second entry hole configured to allow passage of tools configured to dissect septa may have a height between about 10 mm and about 20 mm from the tissue apposition surface. Accordingly, in several embodiments, the depth anesthesia delivery and/or tissue dissection can range from about 1.0 to about 30 mm below an epidermal surface, for example, about 3-5 mm, about 5-7 mm, about 7-10 mm, about 10-15 mm, about 15-20, about 3-20 mm and any depth therebetween, including endpoints. Additionally, depending on the embodiment, a plurality of depths may be used, either for anesthesia delivery and/or for tissue dissection. For example, anesthesia may be delivered at a first site at a first depth and a second site at a second depth. In several embodiments, the first and second depths are the same, while in some embodiments the first and second depths are different. Likewise, in several embodiments, the depth of tissue dissection at a first and second (and further) sites may be the same or may be different.

Figure 8A:
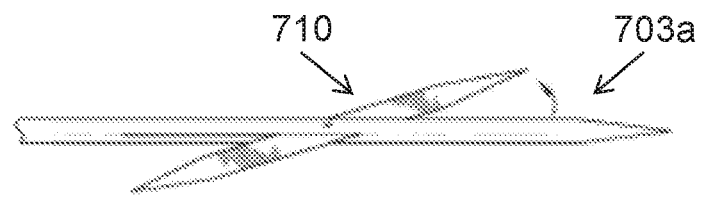
FIGS. 8A-8C illustrates schematic isometric side views of cutting blades usable with a septa dissecting device according to various embodiments of the invention.
Figure 8B:
Figure 8C:
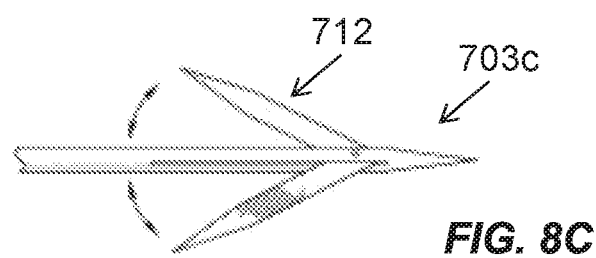

FIGS. 8A-8C illustrates schematic isometric side views of cutting blades usable with a septa dissecting device according to various embodiments of the invention. In one embodiment, depicted by FIG. 8A, a single blade member 710 is pivotably associated at or near a distal end of the cutting tool 703a such that when the blade member 710 is in a collapsed or retracted state, the blade member 710 is parallel to the longitudinal axis of the cutting tool 703a, and, when the blade member 710 is deployed, the ends of the blade member 710 extend laterally away from the longitudinal axis of the cutting tool 703a. The blade member 710 may have two sharp surfaces (e.g., the proximal facing surfaces in the deployed state, the distal facing surfaces in the deployed state). The blade member 710 may have four sharp surfaces (e.g., the proximal and distal facing surfaces in the deployed state).

In another embodiment, as shown by FIG. 8B, a single blade member 711 is pivotably connected at a proximal pivot point of the blade member 711 such that the blade member 711 foldably pivots from a closed position wherein the unconnected (distal) end is inside the cutting tool 703b to an open position wherein the unconnected end of the blade member 711 extends outward from the pivot point. The blade member 711 may have one sharp surface (e.g., the proximal facing surface in the deployed state, the distal facing surface in the deployed state). The blade member 711 may have two sharp surfaces (e.g., the proximal and distal facing surfaces in the deployed state).

In a further embodiment, as shown by FIG. 8C, the device includes two blade members 712 pivotably connected at an end of each blade member 712 such that the blade members 712 foldably pivot from a closed position wherein the unconnected ends are proximate to each other, to an open position wherein the unconnected ends extend outward from pivot point. In one aspect of this embodiment, the two blade members 712 are connected together at common pivot point. In another aspect, the blade members 712 may be connected at independent pivot points (each blade having its own pivot point) attached to, or associated with, a common rigid member or separate deployment members. As shown by the illustrative embodiments, the one or more blade members may be collapsed to and from subdermal catheter by way of an elongated opening on each respective side of the cutting tool 703c.

Figure 7D:
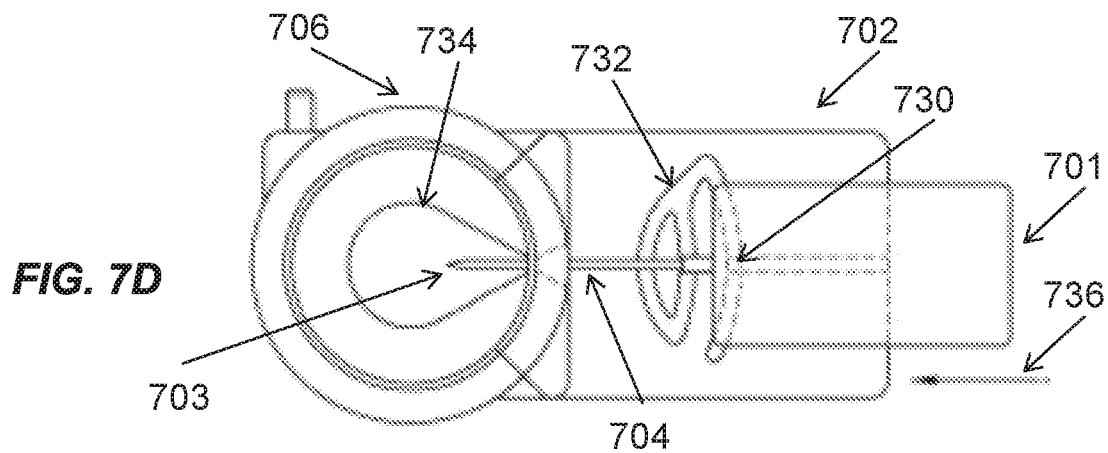
FIGS. 7D-7F illustrate schematic top plan views depicting the operational range of a guided septa dissecting device according to various embodiments of the invention.
Figure 7E:
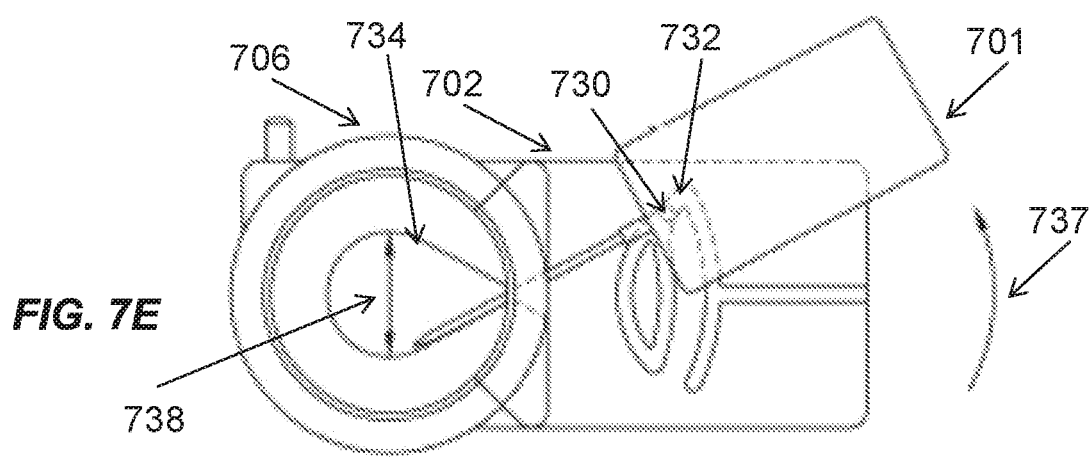
Figure 7F:
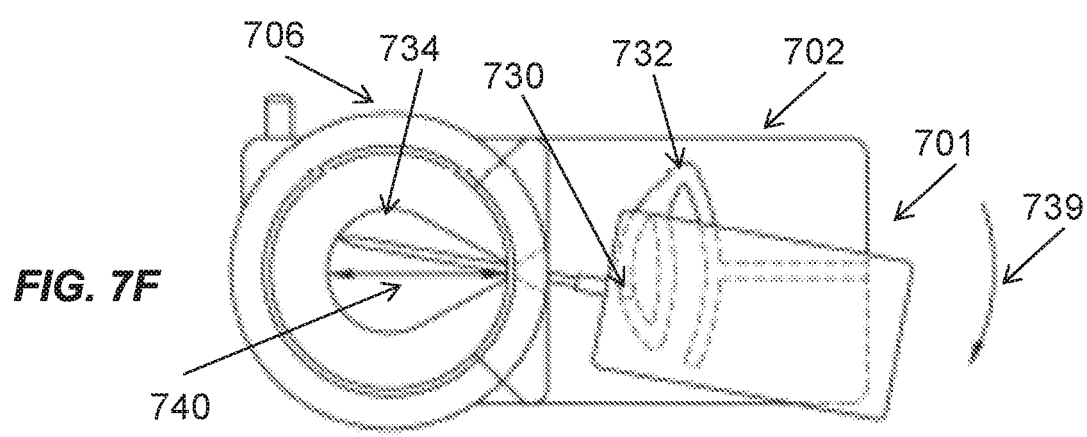

FIGS. 7D-7F illustrate schematic top plan views depicting the operational range of a guided septa dissecting device according to various embodiments of the invention. A guide pin 730 on the underside of cutting module 701 is engaged into a groove 732 of the guidance track 702. Accordingly, the bottom of cutting module 701 remains in contact with platform guidance track 702 during operation, thus constraining the cutting module 701 to operate only in a plane at a desired depth. Engagement between the pin 730 and the guidance track 702, combined with pivot at the shaft entry hole, constrains the cutting module 701 to only operate within a cutting region 734. The guidance track 702 may be constructed in any number of ways consistent with the practice of the invention. The shape of guidance track 702 is not limited to those illustrated by the accompanying figures herein. In some embodiments, the guidance track 702 may be undercut and the guide pin 730 may include a flange such that the interface between the flange and the undercut inhibits or prevents cutting module 701 from being lifted off the guidance track 702 or relative to the chamber 706. The cutting device 701 is constrained by the guide pin 730 to move along the guidance track 702. Accordingly, the cutting device 701 moves in a side to side fashion to allow a distal end of the device (including a cutting device (e.g., needle, blade, RF cutter, water jet, laser, ultrasonic or harmonic scalpel)) to move along the maximum boundary (laterally and longitudinally) of the cutting region 734.

FIG. 7D shows the cutting blade 703 entering into cutting region 734. The guide pin 730 is engaged in the guidance track 702 as the cutting module 701 is advanced in the y-direction, as indicated by the arrow 736, until the guide pin 730 reaches the proximal arc of the guidance track 702. At this point, the cutting blade 703 is through the skin and a motor can be energized to commence reciprocation of the cutting blade 703. In further embodiments, the guidance track 702 incorporates a contact (e.g., a sensor) to inhibit or prevent premature powering of a motor module, or automated powering of a motor module when the motor module has reached the appropriate position on the guidance track 702.

As the cutter module 701 is advanced toward the chamber 706, the guide pin 730 moves along, and is restricted by, the maze-like path of the guidance track 702, such that, as depicted by FIGS. 7E and 7F, as the guide pin 730 moves within the guidance track 702, a distal end of the cutting tool 703 moves from side to side inside cutting region S02 in a controlled fashion. The path of the guidance track 702 defines the size and shape of cutting region 734. In embodiments in which the cutting tool 703 comprises extending blades, energy ablation, etc., the path of the guidance track 702 may at least partially define the size and shape of cutting region 734. Taking the z-axis (into and out of the page) as the centerline of the cutting module 701 from top to bottom, the path of the guidance track 702 preferably restricts movement of the cutting module 701, and, thus, the cutting tool 703 moves in x- and y-directions within a plane parallel to the top of the chamber 706. The interaction between the guide pin 730 and the guidance track 702 defines a maximum x-direction width 738 and a maximum y-direction width 740. A physician can move the cutting module 701 along the guidance track 702 by beginning the cutting just inside the skin and, following the track to work inward, the fixed (non-cutting) portion of the shaft 704 is always within a region where the tissue is separated; otherwise, the unseparated tissue can inhibit or prevent the shaft 704 from pivoting freely over the desired region.

As shown in FIG. 7F, the path of the guide track 702 preferably defines the region 734 in which the cutting tool 703 will move within the recessed area of the chamber 706. The geometry of the guidance track 702 in conjunction with the dimensions and other parameters of the cutting tool 703 and reciprocation stroke defines the dissection area. After following the entire track, the motor is turned off and the cutting tool 703 is removed from the chamber 706. After the power is turned off and prior to removal of the cutting tool 703, the dissection can be confirmed by retracing the path with the motor module off. The power may be turned back on to cut any areas not previously released. The entire cutting module 701 could be manually operated. The cutting module 701 could be partially manually operated (e.g., manually moved along the guidance track 702 but having motor-based reciprocation of the cutting tool 703). The cutting module 701 could be variably motor operated (e.g., a motor to move along the guidance track 702 but having motor-based reciprocation of the cutting tool 703 only at certain times as may be automatically caused or manually caused). These same methods could apply to any cutting instrument disclosed herein. In the depicted embodiment, the overall resulting region 734 is tear-dropped shaped. The path of guidance track 702, entry point, etc. can be altered to modify the shape of region 734 to take any shape.

An alternate range of motion may be enabled by selection of the guidance tracks 702b, 702c, 702d illustrated in FIG. 7C. A physician may also choose to restrict the motor module within the multiple arcs 702a, 702b, 702c, 702d and not complete the outer regions of any one of the arcs. A staggered central track may be used to advance the cutting module 701 toward a final inverted arc. In a further method, the physician may choose to not complete successive arc(s). Thus, by these methods, a reduced area of dissection can be created.

Figure 9:
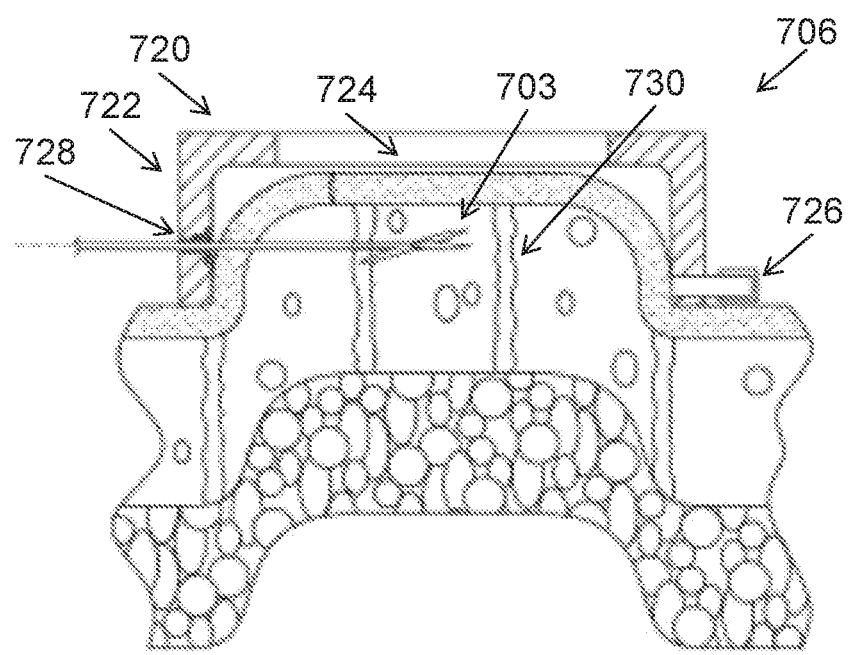
FIG. 9 is a schematic illustration of a septa dissecting device coupled to a region of interest according to various embodiments of the invention.
Figure 10A:
FIGS. 10A-10F illustrate embodiments of a treatment sequence between a HIFU device 20 treatment with one of dermal fillers 800, cavitation-prone fluids 810, and fat-reducing compounds 820.
Figure 10B:
Figure 10C:
Figure 10D:
Figure 10E:
Figure 10F:
Figure 11A:
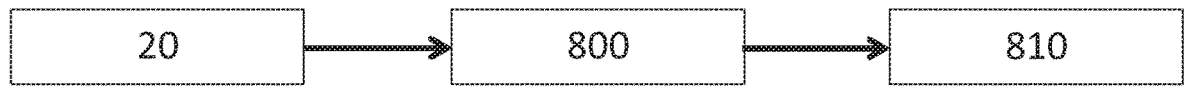
FIGS. 11A-11F illustrate embodiments of a treatment sequence starting with a HIFU device 20 treatment followed by two treatments among treatments with dermal fillers 800, cavitation-prone fluids 810, and fat-reducing compounds 820.
Figure 11B:
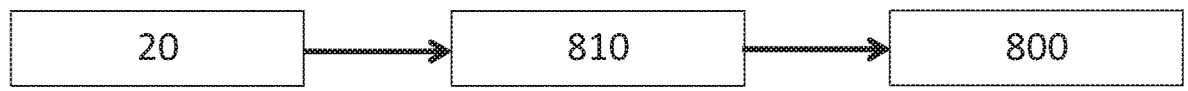
Figure 11C:
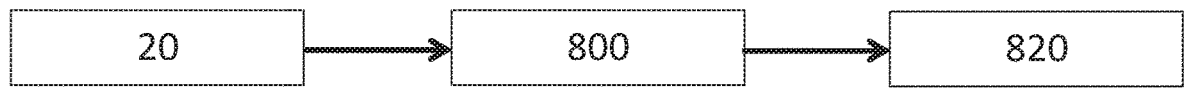
Figure 11D:
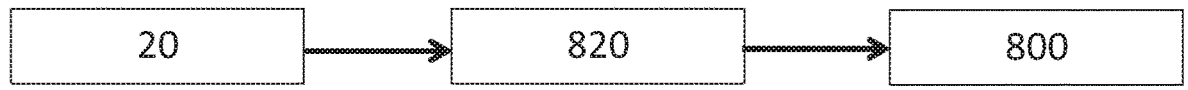
Figure 11E:
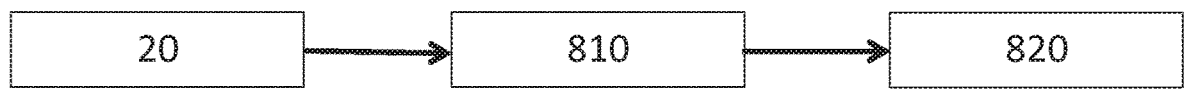
Figure 11F:
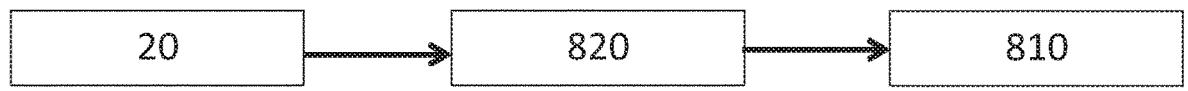
Figure 12A:
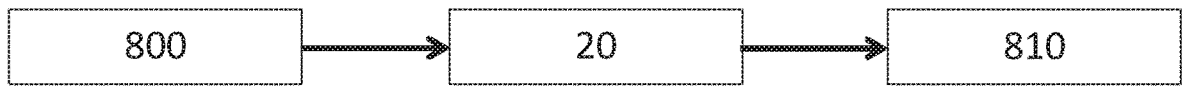
FIGS. 12A-12F illustrate embodiments of a treatment sequence with a HIFU device 20 treatment preceded and followed by two treatments among treatments with dermal fillers 800, cavitation-prone fluids 810, and fat-reducing compounds 820.
Figure 12B:
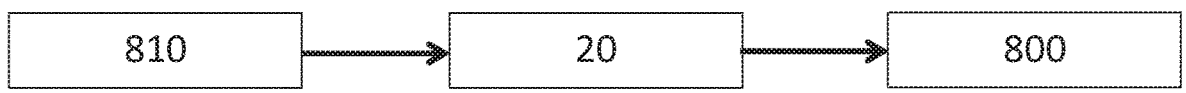
Figure 12C:
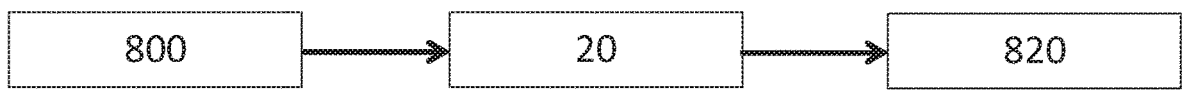
Figure 12D:
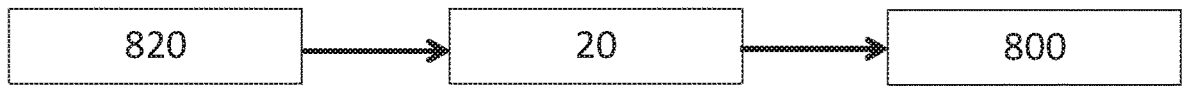
Figure 12E:
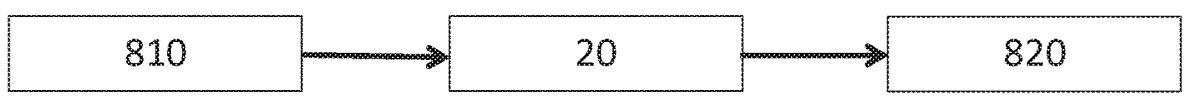
Figure 12F:
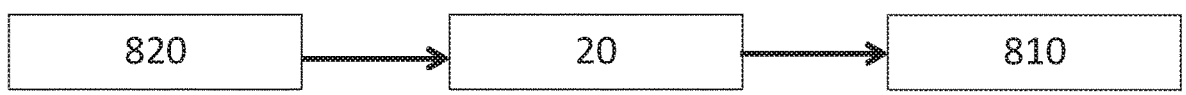
Figure 13A:
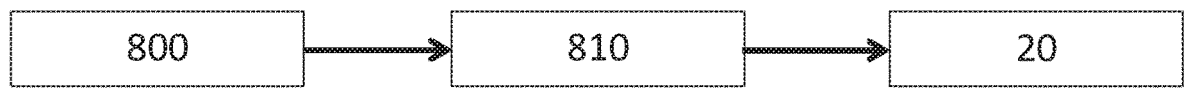
FIGS. 13A-13F illustrate embodiments of a treatment sequence with a HIFU device 20 treatment preceded by two treatments among treatments with dermal fillers 800, cavitation-prone fluids 810, and fat-reducing compounds 820.
Figure 13B:
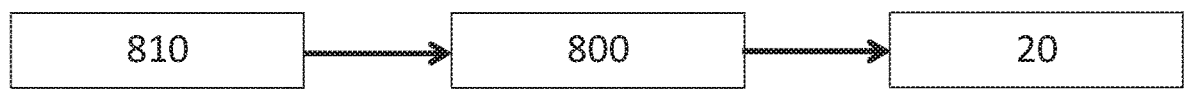
Figure 13C:
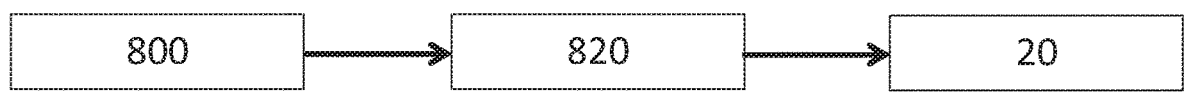
Figure 13D:
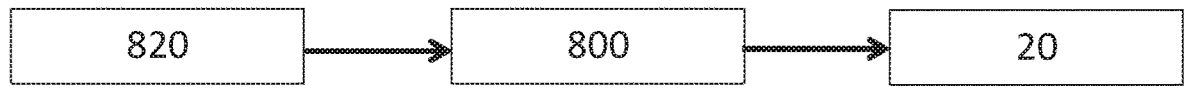
Figure 13E:
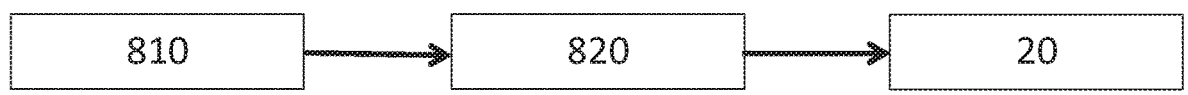
Figure 13F:
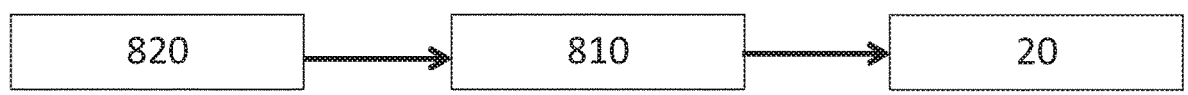
Figure 14A:
FIGS. 14A-14F illustrate embodiments of a treatment sequence with a HIFU device 20 treatment followed by three treatments in various orders with dermal fillers 800, cavitation-prone fluids 810, and fat-reducing compounds 820. In various other contemplated embodiments, the HIFU device 20 treatment can be second, third, or fourth in the sequence of the four treatments.
Figure 14B:
Figure 14C:
Figure 14D:
Figure 14E:
Figure 14F:
Figure 15A:
FIGS. 15A-15D illustrate embodiments of a treatment sequence including a septa dissecting treatment 830 and one of a HIFU device 20 treatment, treatments with dermal fillers 800, treatments with cavitation-prone fluids 810, and treatments with fat-reducing compounds 820.
Figure 15B:
Figure 15C:
Figure 15D:
Figure 16A:
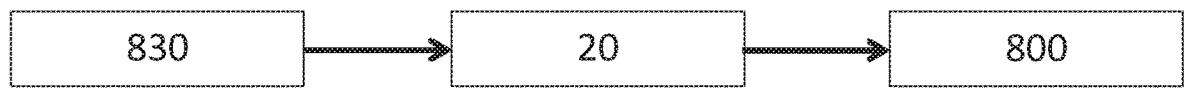
FIGS. 16A-16F illustrate embodiments of a treatment sequence including a septa dissecting treatment 830 and two of a HIFU device 20 treatment, treatments with dermal fillers 800, treatments with cavitation-prone fluids 810, and treatments with fat-reducing compounds 820.
Figure 16B:
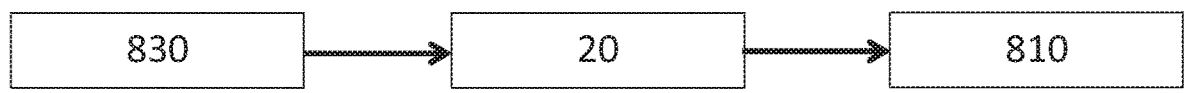
Figure 16C:
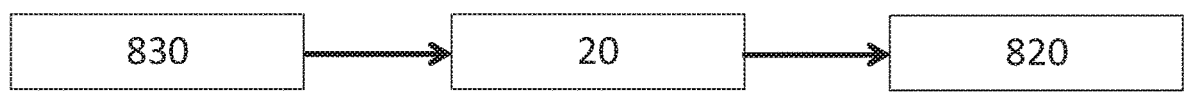
Figure 16D:
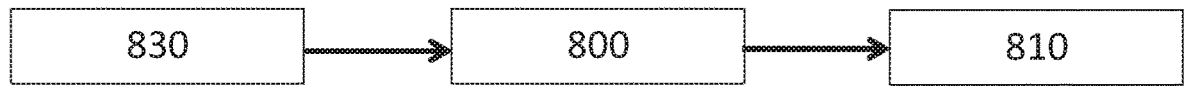
Figure 16E:
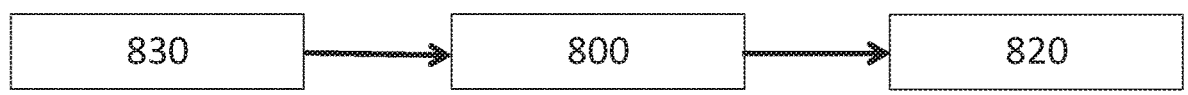
Figure 16F:
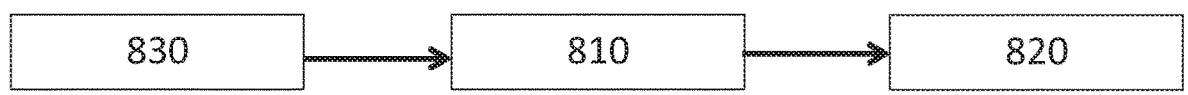
Figure 17A:
FIGS. 17A-17D illustrate embodiments of a treatment sequence including a septa dissecting treatment 830 and three of a HIFU device 20 treatment, treatments with dermal fillers 800, treatments with cavitation-prone fluids 810, and treatments with fat-reducing compounds 820.
Figure 17B:
Figure 17C:
Figure 17D:

FIG. 9 is a schematic illustration of a septa dissecting device coupled to a region of interest according to various embodiments of the invention. A top wall 720 and perimeter wall 722 define a tissue apposition surface (tissue facing surface) facing into recessed area. The tissue apposition surface may be curved inward to the handpiece, or concave, or recessed, so that when chamber 706 is disposed against an epidermis, further pressure against the chamber 706 will cause the chamber 706 to encompass a subcutaneous level of tissue, particularly the subdermal fat layer below the epidermis and dermis layers, wherein these layers will be positioned within the recessed area. In some embodiments, the tissue apposition surface includes perimeter wall 722 as a relatively small inner wall around the perimeter of recessed area. In some embodiments, the chamber 706 may include a transparent cover 724 so that a physician can clearly see and verify that the dermis is properly positioned within the dissection region. In the depicted embodiment, the perimeter walls (sidewalls) 722 of the chamber 706 are shown generally circular. However, one of ordinary skill in the art will appreciate that the chamber 706 can be any shape.

The chamber 706 further allows for three-dimensional control of treatment or anesthetic solution delivery and dissection of subcutaneous tissues. The chamber 706 can controls a depth between about 4 mm and about 20 mm below the surface of skin (measured orthogonally from the dermis); depths less than about 4 mm or greater than about 20 mm are also contemplated. The depth is generally defined as being measured downward from tissue apposition surface. For the purpose of this disclosure, the depth is measured when the epidermis is flush against apposition surface, and the thickness of epidermis is considered negligible. As such, the depth can also be considered to be a depth below the surface of the skin or a depth below the epidermis. The range of motion in the lateral direction is controlled by the length and movement of the injection needle, cutting blade, RF probe, etc., and can encompass a length of between about 2 mm and about 100 mm in either direction. As the needle/blade/probe is disposed further into the skin, larger arcs can be achieved. Generally, the chamber 706 is pressed against the tissue to move the subcutaneous layer into the recessed area and against the tissue apposition surface.

In some embodiments, vacuum (negative pressure, suction) is used to enhance the capture of the tissue. A vacuum source may be placed in fluid connection with chamber 706 via an optional vacuum port 726. The vacuum source may include a vacuum pump in fluid communication with the recessed area. The vacuum pump can supply suction to the recessed area to pull tissue snugly and securely therein. In some embodiments, the vacuum pump is configured to communicate with a microprocessor and a gauge (e.g., in a graphical user interface) to display a vacuum pressure. The system may further include a display indicating the elapsed amount of time that the vacuum was supplied to the chamber 706 by the vacuum pump. The vacuum pump may modulate the suction such that a higher suction force is applied initially to pull the tissue into the recess, and a somewhat lower suction force is used to maintain/hold the tissue in place thereafter. The vacuum port 726 may be located in the top wall 720 and/or the perimeter wall 722 of the chamber 706. In some embodiments, the tissue apposition surface includes two or more vacuum ports 726 disposed on its surface and configured to apply suction from the vacuum source to the recessed area and to the tissue from different locations of the chamber 706.

In the embodiment depicted by FIG. 9, the chamber 706 is seen in use with a vacuum pressure (suction) applied to a portion of skin. Suction applied at the vacuum port 726 causes the skin to be pulled up into contact with the apposition surface of the chamber 706. By applying a sufficient suction force, a portion of epidermis is pulled into the chamber 706 and conforms to the inner recessed area. While the surface of the skin is tightly positioned against the top wall 720 and perimeter wall 722 of the recessed area, the fat layer (subcutaneous tissue) is also drawn into the chamber 706. A cutting tool 703 (e.g., a needle, cutting blade, RF probe, etc.), can be inserted through an entry hole of a conduit 728 in a side of the chamber 706, through the skin, and into the subcutaneous tissue. The chamber 706 can enable the cutting tool to 703 be consistently inserted at desired treatment depth. The chamber 706 thus provides for precise control of the depth of the dissection plane and allows for cutting and/or movement of the cutting tool 703 substantially parallel to the surface of the tissue along a plane.

A membrane formed of a flexible and resilient material may also be applied to the perimeter wall (sidewall) 722 across the proximal (away from the recessed area) or distal ends (closer to the recessed area) of the conduit 728 to reduce or minimize vacuum leakage therethrough (although in several embodiments, a membrane is not included, as the presence/pressure of the skin raised within the chamber forms a seal against the perimeter wall). The membrane preferably is sufficiently resilient to seal around the cutting tool 703 as the cutting tool 703 pierces (self-sealing) therethrough and reduce or minimize vacuum leakage. In one embodiment, the membrane comprises silicone. The self-sealing membrane may additionally or alternatively comprise other materials. The conduit 728 is disposed in sidewall 722 of the chamber 706, preferably, adjacent bottom or side portion of tissue apposition surface. In some embodiments, the conduit 728 is a through hole defined in perimeter wall 722 or in top wall 720. In other embodiments, the conduit 728 is a tube-like member inserted into and/or mounted to a through hole in the perimeter wall 722 or top wall 720. The conduit 728 is configured to allow passage of a hypodermic needle, subdermal catheter, cutting tool (as described above), deployment applicator, or other appropriately configured tool through the conduit 728 and into recessed area of the chamber 706. The tool may pass through the conduit 728 just enough to penetrate the tissue.

The conduit 728 is preferably located proximate a bottom edge of perimeter wall (sidewall) 722 to allow a cutting tool 703, needle, etc. to be inserted into the tissue (captured in the recessed area) in a plane parallel to the dermis. In some embodiments, the conduit 728 supplies an angle of penetration so that the tool inserted through the conduit 728 will penetrate into tissue disposed within the recessed area, and substantially parallel to the surface of the tissue and parallel to the surface of top wall 720 at a particular depth. Specifically, this configuration may provide stability of the tool to maintain an even level, e.g., when the cutting tool is cutting the fibrous structures 730 between the epidermis (and dermis) and the subdermal fat. In some embodiments, the conduit 728 provides an angle of entry to bias the plane of dissection toward or away from the dermis. In several embodiments, a plurality of conduits are provided, at various distances from the apposition surface, thereby allowing for a single device to achieve a variety of corresponding depths of insertion of a dissection tool and/or needle, depending on which conduit is utilized.

As depicted in FIG. 9, the entry hole for the conduit 728 is preferably disposed on an inner side of the conduit 728 and facing the recessed area. The conduit 728 preferably widens outward toward an outer side of the perimeter elevation such that a distal end of the cutting tool 703 inserted through the entry hole moves in one direction when a proximal end of the cutting tool 703 outside the conduit 728 moves in an opposite direction. The entry hole thereby can at least partially define a cutting tool pivot point when a distal end of the cutting tool 703 is inserted through conduit 728 and into the recessed area, and the cutting tool 703 moves primarily in an x-y plane parallel to the top surface of the chamber 706. In some embodiments, the entry hole may include an optional locking mechanism that locks the tool 703 in place upon insertion into the conduit 728. In some embodiments in which a vacuum is supplied to the recessed area, an optional gasket or seal may be placed within, in front of, behind, or around the entry hole to reduce or minimize vacuum leakage.

In some embodiments, the conduit 728 can constrain side-to-side movement of a tool such that movement of the tool through the conduit 728 is limited to a backward direction and a forward direction. In some embodiments, the conduit 728 can constrain upward and downward movement of a tool to maintain movement of the tool in a plane parallel to the surface of the skin. In other embodiments, the conduit 728 is configured to allow the cutting tool to be moved in an arc parallel to the recessed area of the tissue facing (apposition) surface so as to allow cutting within a subdermal area substantially the size of the recessed surface area. Thus, in several embodiments, the movement of the tool is in forward, reverse, and side-to-side directions within a dissection plane and with the conduit/entry hole serving as a pivot point for the tool.

In some embodiments, the conduit 728 includes a tool control mechanism which allows the cutting tool 703 or other tool to be controlled by a microprocessor. In such an embodiment, the chamber 706 and/or the microprocessor can control the cutting device 703 to precisely cut an area of tissue disposed within the recessed area. The area being cut is predetermined and programmed into the microprocessor by the operator of the device.

Cosmetic Treatment Combinations

In accordance with several embodiments of the invention, the energy (such as HIFU) is administered before the agent. For example, in a single treatment session (in a single day), a subject is treated with HIFU and the agent is applied within minutes or hours. The HIFU can optionally be reapplied. Alternatively, the HIFU is applied on one day and the agent is applied on a different, subsequent, day.

According to another embodiment, the energy (such as HIFU) is administered together with the agent at substantially the same time.

In yet another embodiment, the energy (such as HIFU) is administered after the agent is applied. For example, in a single treatment session (in a single day), a subject is treated with one or more agents, and the HIFU is applied within minutes or hours. The agent(s) can optionally be reapplied. Alternatively, the agent is applied on one day and the HIFU is applied on a different, subsequent, day.

Some subjects will see improvement in one treatment session. Multiple treatments may be needed in some embodiments. Treatments can be performed at intervals of days, weeks and months. HIFU and one or more anti-cellulite agents can be applied on a single day or on different days. In one embodiment, a solo treatment of either energy or an agent is used to maintain effects once the combination treatment has been performed. As an example, HIFU and a dermal filler are applied in combination; thereafter, the dermal filler is used for maintenance (e.g., weeks or months after the combination treatment is applied).

FIGS. 10A-10F illustrate embodiments of a treatment sequence between a HIFU device 20 treatment with one of dermal fillers 800, cavitation-prone fluids 810, and fat-reducing compounds 820. FIGS. 11A-11F illustrate embodiments of a treatment sequence starting with a HIFU device 20 treatment followed by two treatments among treatments with dermal fillers 800, cavitation-prone fluids 810, and fat-reducing compounds 820. FIGS. 12A-12F illustrate embodiments of a treatment sequence with a HIFU device 20 treatment preceded and followed by two treatments among treatments with dermal fillers 800, cavitation-prone fluids 810, and fat-reducing compounds 820. FIGS. 13A-13F illustrate embodiments of a treatment sequence with a HIFU device 20 treatment preceded by two treatments among treatments with dermal fillers 800, cavitation-prone fluids 810, and fat-reducing compounds 820. FIGS. 14A-14F illustrate embodiments of a treatment sequence with a HIFU device 20 treatment followed by three treatments in various orders with dermal fillers 800, cavitation-prone fluids 810, and fat-reducing reducing compounds 820. In various other contemplated embodiments, the HIFU device 20 treatment can be second, third, or fourth in the sequence of the four treatments. In various embodiments, a sequence of treatment provides advantageous results.

FIGS. 15A-15D illustrate embodiments of a treatment sequence including a septa dissecting treatment 830 and one of a HIFU device 20 treatment, treatments with dermal fillers 800, treatments with cavitation-prone fluids 810, and treatments with fat-reducing compounds 820. The septa dissecting treatment 830 may comprise using at least one of a cutting blade or dermal layer HIFU with cavitation-prone fluids injected proximate the septa. Although illustrated as being the septa dissecting treatment 830 followed by one of a HIFU device 20 treatment, treatments with dermal fillers 800, treatments with cavitation-prone fluids 810, and treatments with fat-reducing compounds 820, the opposite order (e.g., one of a HIFU device 20 treatment, treatments with dermal fillers 800, treatments with cavitation-prone fluids 810, and treatments with fat-reducing compounds 820 followed by a septa dissecting treatment 830) is also possible. In various embodiments, a sequence of treatment provides advantageous results (including, but not limited to one or more of the following, decreased bruising, enhanced aesthetic effects, shorter recovery time, shorter treatment time, longer lasting aesthetic effects, and reduced discomfort).

FIGS. 16A-16F illustrate embodiments of a treatment sequence including a septa dissecting treatment 830 and two of a HIFU device 20 treatment, treatments with dermal fillers 800, treatments with cavitation-prone fluids 810, and treatments with fat-reducing compounds 820. The septa dissecting treatment 830 may comprise using at least one of a cutting blade or dermal layer HIFU with cavitation-prone fluids injected proximate the septa. Although illustrated as being the septa dissecting treatment 830 followed by two of a HIFU device 20 treatment, treatments with dermal fillers 800, treatments with cavitation-prone fluids 810, and treatments with fat-reducing compounds 820, the opposite order (e.g., two of a HIFU device 20 treatment, treatments with dermal fillers 800, treatments with cavitation-prone fluids 810, and treatments with fat-reducing compounds 820 followed by a septa dissecting treatment 830) or an order including a septa dissecting treatment 830 between one of a HIFU device 20 treatment, treatments with dermal fillers 800, treatments with cavitation-prone fluids 810, and treatments with fat-reducing compounds 820 and one of a HIFU device 20 treatment, treatments with dermal fillers 800, treatments with cavitation-prone fluids 810, and treatments with fat-reducing compounds 820 are also possible. Although illustrated as being a septa dissecting treatment 830 followed by a specific one of a HIFU device 20 treatment, treatments with dermal fillers 800, treatments with cavitation-prone fluids 810, and treatments with fat-reducing compounds 820 followed by another specific one of a HIFU device 20 treatment, treatments with dermal fillers 800, treatments with cavitation-prone fluids 810, and treatments with fat-reducing compounds 820, the order of the two of a HIFU device 20 treatment, treatments with dermal fillers 800, treatments with cavitation-prone fluids 810, and treatments with fat-reducing compounds 820 can be swapped. For example, in FIG. 16F, a septa dissecting treatment 830 may be followed by treatments with fat reducing compounds 820, which may be followed by treatments with cavitation-prone fluids 810. In various embodiments, a sequence of treatment provides advantageous results.

FIGS. 17A-17D illustrate embodiments of a treatment sequence including a septa dissecting treatment 830 and three of a HIFU device 20 treatment, treatments with dermal fillers 800, treatments with cavitation-prone fluids 810, and treatments with fat-reducing compounds 820. The septa dissecting treatment 830 may comprise using at least one of a cutting blade or dermal layer HIFU with cavitation-prone fluids injected proximate the septa. Although illustrated as being the septa dissecting treatment 830 followed by three of a HIFU device 20 treatment, treatments with dermal fillers 800, treatments with cavitation-prone fluids 810, and treatments with fat-reducing compounds 820, the opposite order (e.g., three of a HIFU device 20 treatment, treatments with dermal fillers 800, treatments with cavitation-prone fluids 810, and treatments with fat-reducing compounds 820 followed by a septa dissecting treatment 830) or an order including a septa dissecting treatment 830 between one or two of a HIFU device 20 treatment, treatments with dermal fillers 800, treatments with cavitation-prone fluids 810, and treatments with fat-reducing compounds 820 and one of a HIFU device 20 treatment, treatments with dermal fillers 800, treatments with cavitation-prone fluids 810, and treatments with fat-reducing compounds 820 are also possible. Although illustrated as being a septa dissecting treatment 830 followed by a specific order of three of a HIFU device 20 treatment, treatments with dermal fillers 800, treatments with cavitation-prone fluids 810, and treatments with fat-reducing compounds 820, the order of the three of a HIFU device 20 treatment, treatments with dermal fillers 800, treatments with cavitation-prone fluids 810, and treatments with fat-reducing compounds 820 can be mixed. For example, in FIG. 17C, a HIFU device 20 treatment may be followed by a septa dissecting treatment 830, which may be followed by treatments with fat reducing compounds 820, which may be followed by treatments with cavitation-prone fluids 810. In various embodiments, a sequence of treatment provides advantageous results (as described herein).

Figure 18:
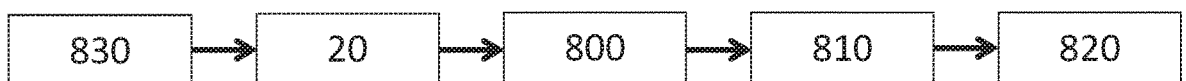
FIG. 18 illustrates embodiments of a treatment sequence including a septa dissecting treatment 830 and each of a HIFU device 20 treatment, treatments with dermal fillers 800, treatments with cavitation-prone fluids 810, and treatments with fat-reducing compounds 820.
Figure 19A:
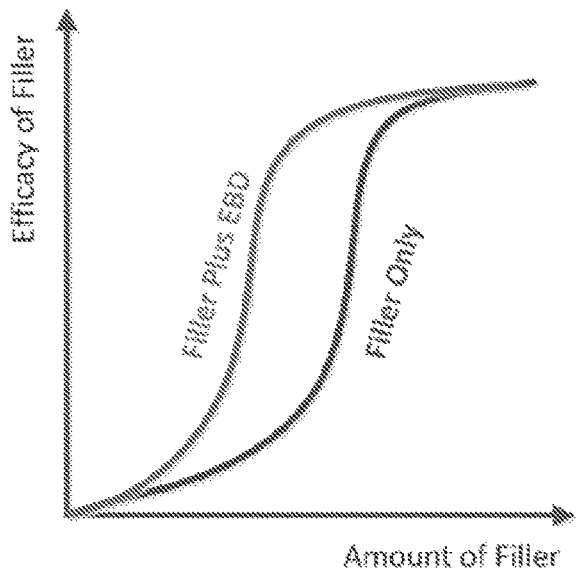
FIGS. 19A-19D illustrate embodiments of treatments with Filler or EBD alone or in combination.
Figure 19B:
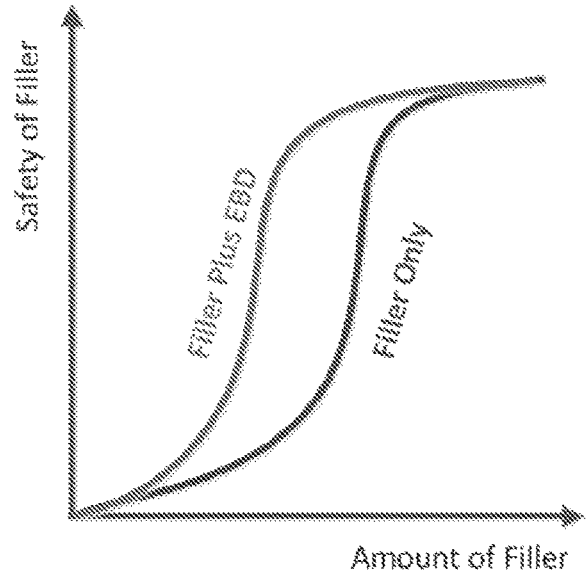
Figure 19C:
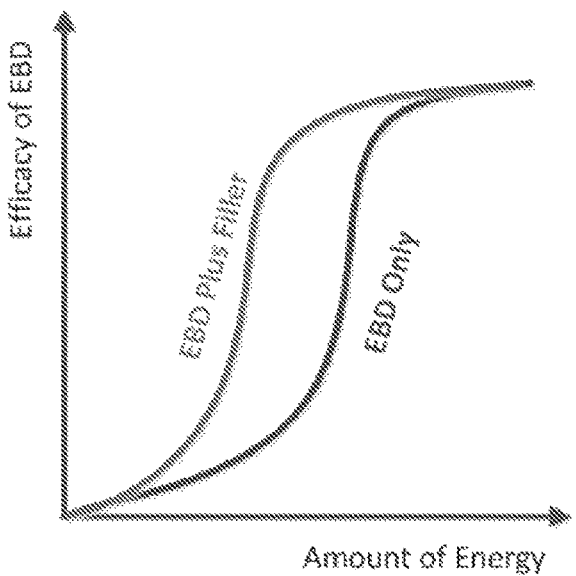
Figure 19D:
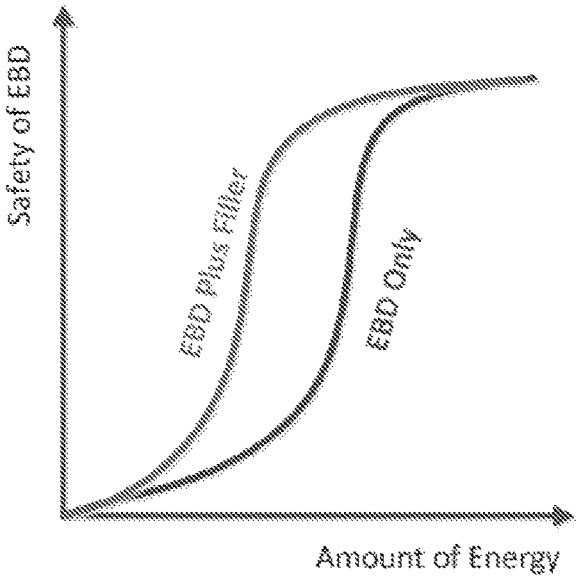

FIG. 18 illustrates embodiments of a treatment sequence including a septa dissecting treatment 830 and each of a HIFU device 20 treatment, treatments with dermal fillers 800, treatments with cavitation-prone fluids 810, and treatments with fat-reducing compounds 820. The septa dissecting treatment 830 may comprise using at least one of a cutting blade or dermal layer HIFU with cavitation-prone fluids injected proximate the septa. Although illustrated as being the septa dissecting treatment 830 followed by each of a HIFU device 20 treatment, treatments with dermal fillers 800, treatments with cavitation-prone fluids 810, and treatments with fat-reducing compounds 820, the opposite order (e.g., each of a HIFU device 20 treatment, treatments with dermal fillers 800, treatments with cavitation-prone fluids 810, and treatments with fat-reducing compounds 820 followed by a septa dissecting treatment 830) or an order including a septa dissecting treatment 830 between one, two, or three of a HIFU device 20 treatment, treatments with dermal fillers 800, treatments with cavitation-prone fluids 810, and treatments with fat-reducing compounds 820 and one of a HIFU device 20 treatment, treatments with dermal fillers 800, treatments with cavitation-prone fluids 810, and treatments with fat-reducing compounds 820 are also possible. Although illustrated as being a septa dissecting treatment 830 followed by a specific order of each of a HIFU device 20 treatment, treatments with dermal fillers 800, treatments with cavitation-prone fluids 810, and treatments with fat-reducing compounds 820, the order of the three of a HIFU device 20 treatment, treatments with dermal fillers 800, treatments with cavitation-prone fluids 810, and treatments with fat-reducing compounds 820 can be mixed. For example, a HIFU device 20 treatment may be followed by a septa dissecting treatment 830, which may be followed by treatments with fat reducing compounds 820, which may be followed by treatments with dermal fillers 800, which may be followed by treatments with cavitation-prone fluids 810. In various embodiments, a sequence of treatment provides advantageous results (as described herein).

One or more of the members of the treatment sequences described herein may be repeated in a sequence. For example, with reference to FIG. 16F, a septa dissecting treatment 830 may be followed by treatments with cavitation-prone fluids 810, which may be followed by treatments with fat reducing compounds 820, which may be followed by treatments with cavitation-prone fluids 810. Permutations of the treatments described herein, including repetition of one or more treatments within a sequence, are contemplated.

Cosmetic Treatment Kits

In one embodiment, a kit is provided comprising at least one ultrasound transducer 200, at least one dermal filler 800 and/or at least one fat-reducing compound 820, and optionally instructions for use. In one embodiment an injection guidance device 600, and optionally instructions for use are also included. A cavitation-prone fluid may also be provided.

In another variation of the kit, the composition containing dermal filler 800 and/or the fat-reducing compound 820 are not present in a form ready for being injectable, e.g., in liquid form, but as a powder, in form of granules or as a tablet. In one embodiment for use, the powder, granules or tablets is to be dissolved or suspended in a solvent before being administrable by injection. In one embodiment, the kit further comprises at least one vial containing a solvent for dissolving or suspending the composition containing dermal filler 800 and/or the fat-reducing compound 820. This provides the advantage that the amount and/or concentration of the dermal filler 800 and/or the fat-reducing compound 820 can be adjusted to the patient's needs prior to its administration. A cavitation-prone fluid is provided in some embodiments.

Furthermore, in various embodiments, the kit comprises one or more devices for administering the composition(s). In one embodiment, administering one or both of the compositions comprises use of at least two syringes 700, each provided with or to be provided with an injection needle of specific length for targeting the desired tissue. It is also within the scope of an embodiment of the invention that such application means are configured as a specific application device, which allows for the simultaneous delivery of the two different compositions in different depths of the skin of a patient. In a specific embodiment, the means are configured such that the amount to be delivered to the patient is individually adjustable for each composition. In particular, the kit may comprise the micro-needle system described above in connection with an embodiment of the invention. The syringe(s) and the micro-needle systems may be present in the kit as such, e.g., empty, or may be pre-filled with an injectable composition of dermal filler 800 and/or the fat-reducing compound 820.

Example Embodiments

The following examples are non-limiting embodiments.

In several embodiments, a method of treating gynoid lipodystrophy includes applying high intensity focused ultrasound (HIFU) therapy to a tissue region below a skin surface; injecting a first compound into the tissue region treated by the HIFU; wherein the first compound comprises a dermal filler, wherein the dermal filler comprises calcium hydroxyapatite, and injecting a second compound into the tissue region treated by the HIFU; wherein the second compound comprises a fat-reducing compound, wherein the fat-reducing compound comprises polidocanol, thereby treating gynoid lipodystrophy. The method may further include reapplying HIFU after the dermal filler is injected to harden the dermal filler. In one embodiment, the method further includes focusing the HIFU at a depth 1.5 mm below the skin surface, wherein the HIFU therapy is applied at 10 MHz, wherein the calcium hydroxyapatite is provided in a final concentration of 25-31% w/w, and wherein the polidocanol is provided in a final concentration of 0.5% w/v. The method may further comprise administering a second treatment 90+/−10 days later, including focusing the HIFU at a depth 1.5 mm below the skin surface, wherein the HIFU therapy is applied at 10 MHz, wherein the calcium hydroxyapatite is injected in a dermis layer below the skin surface, wherein the calcium hydroxyapatite is provided in a final concentration of 25-31% w/w, wherein the polidocanol is injected in a subcutaneous fat below the skin surface, and wherein the polidocanol is provided in a final concentration of 0.5% w/v. In one embodiment, the calcium hydroxyapatite is provided in a final concentration of 25-31% w/w and wherein the polidocanol is provided in a final concentration of 0.5% w/v. The method may further include reapplying HIFU after the dermal filler is injected, thereby modifying a viscosity of the dermal filler by the application of HIFU, and shaping the dermal filler in to a designed structure by the application of HIFU. The method may further include focusing the HIFU at a depth 1.5 mm below the skin surface; and wherein the HIFU therapy is applied at 10 MHz. In one embodiment, the method further includes focusing the HIFU at a depth 3.0 mm below the skin surface; and wherein the HIFU therapy is applied at 7 MHz. The method may further include focusing the HIFU at a depth 4.5 mm below the skin surface; and wherein the HIFU therapy is applied at 4 MHz. In one embodiment, the method further includes the calcium hydroxyapatite being provided in a concentration (e.g., a final concentration) of 56.3% (w/w) (+/−2%) diluted with 2% aqueous lidocaine. In one embodiment, the method further includes the calcium hydroxyapatite being provided in a concentration (e.g., a final concentration) of 25-31% w/w (e.g., resulting from a 1:1 dilution ratio of RADIESSE (about 56.3% w/w)). The method may further include having the polidocanol provided in a concentration (e.g., a final concentration) of 1% w/v diluted with 2% aqueous lidocaine. The method may further include having the polidocanol provided in a concentration (e.g., a final concentration) of 0.5% w/v. In one embodiment, the method further includes reapplying HIFU after the dermal filler is injected, wherein the dermal filler is any one or more of the group consisting of: hardened by the application of HIFU, moved by the application of HIFU, stabilized by the application of HIFU, modifies viscosity by the application of HIFU, and shaped in to a designed structure by the application of HIFU. The method may further include further comprising dissecting at least one septa in the dermal layer with a septae dissection technology. In one embodiment, the method further includes administering the dermal filler by local injection into a dermal tissue, a subcutaneous fat tissue, or both the dermal tissue and the subcutaneous fat tissue. The method may further include focusing the HIFU at fat tissue, wherein two or more simultaneous focused ultrasound treatments heat up portions of the fat tissue. Percentages herein may also be % m/m, % m/w, % w/w, % m/v, % v/v with respect to, for example, the total formulation injected or applied.

In several embodiments, the use of high intensity focused ultrasound (HIFU) therapy with at least one of the group consisting of: a dermal filler, or a fat-reducing compound in the cosmetic treatment of gynoid lipodystrophy. In one embodiment, the HIFU therapy is targeted to a dermal tissue. The HIFU therapy may be targeted to a dermal tissue to strengthen a connective tissue by improving a collagen-network in the dermal tissue. In one embodiment, the HIFU therapy is targeted to a tissue in the upper dermis. The HIFU therapy may be targeted to a tissue in the upper dermis to strengthen collagen in the upper dermal tissue. In one embodiment, the HIFU therapy is targeted to a dermal tissue and a subcutaneous fat tissue. The HIFU therapy may be simultaneously targeted to a dermal tissue and a subcutaneous fat tissue. In one embodiment, the HIFU therapy is targeted to a subcutaneous fat tissue. The HIFU therapy may be targeted to a fat lobuli within a subcutaneous fat tissue. In one embodiment, the HIFU therapy is targeted to a subcutaneous fat tissue to induce cell-death in adipocytes. The HIFU therapy may be targeted to a subcutaneous fat tissue to induce cell-death in adipocytes via apoptosis. In one embodiment, the HIFU therapy is targeted to a subcutaneous fat tissue to increase lipolysis in adipocytes resulting in reduced cell diameter of affected adipocytes. The HIFU therapy may be targeted to a fibrous septa to cut the fibrous septa. In one embodiment, the HIFU therapy is provided at a depth of 1.5 mm below a skin surface. The HIFU therapy may be provided at a depth of 4.5 mm and/or 3.0 mm below a skin surface. In one embodiment, the HIFU therapy is provided at a depth of 1.5 mm and a depth of 4.5 mm and/or 3.0 mm below a skin surface. The HIFU therapy may be provided at a depth of 1.5 mm and between 10 mm to 17 mm below a skin surface. In one embodiment, the HIFU therapy is provided at a depth of 1.5 mm, 4.5 mm and/or 3.0 mm, and at least 10 mm below a skin surface. The HIFU therapy may be provided at a depth of at least 10 mm below a skin surface. In one embodiment, the HIFU therapy is provided at a depth of 17 mm below a skin surface. The HIFU therapy may be provided at a frequency of 4 MHz. In one embodiment, the HIFU therapy is provided at a frequency of 7 MHz. The HIFU therapy may be provided at a frequency of 10 MHz. In one embodiment, the HIFU therapy is provided at a frequency of 2 MHz or less. The HIFU therapy may be provided at a power of at least 5 kW/cm$^2$. In one embodiment, the HIFU therapy is provided at a power of at least 10 kW/cm$^2$. The HIFU therapy may be provided at a power of at least 15 kW/cm$^2$. In one embodiment, the HIFU therapy is provided with a spherically focused transducer. The HIFU therapy may be provided with a cylindrically focused transducer. In one embodiment, the HIFU therapy is provided at a point focus. The HIFU therapy may be provided at a line focus. In one embodiment, the HIFU is administered to a subject having a body mass index (BMI), defined as the body mass in kg divided by the square of the body height, of at least 25 kg/m2, or to a subject having severe cellulite corresponding to a total sum of scores of items (a) and (b) of the Hexsel, Dal'Forno, and Hexsel Cellulite Severity Scale (CSS) of 4, 5 or 6, wherein item (a) denotes the number of evident depressions and item (b) denotes the depth of depressions, and both item (a) and item (b) are graded from 0 to 3. The HIFU may be administered concurrently, sequentially or separately with the at least one of the group consisting of: the dermal filler and the fat-reducing compound. In one embodiment, the dermal filler is administered before or after the HIFU. The fat-reducing compound may be administered before or after the HIFU. In one embodiment, the dermal filler and the fat-reducing compound is administered before or after the HIFU. The dermal filler may be administered by local injection into a dermal tissue, a subcutaneous fat tissue, or both the dermal tissue and the subcutaneous fat tissue. In one embodiment, the dermal filler is hardened by the application of HIFU. The dermal filler may be moved by the application of HIFU. In one embodiment, the dermal filler is stabilized by the application of HIFU. The viscosity of the dermal filler may be modified by the application of HIFU. In one embodiment, the dermal filler is shaped in to a designed structure by the application of HIFU. The dermal filler comprises calcium (hydroxy)phosphate particles selected from the group consisting of monocalcium phosphate (MCP), dicalcium phosphate (DCP), calcium dihydrogen phosphate (CDP), tricalcium phosphate (TCP) including its α-, α'- and β-polymorphs, octacalcium phosphate (OCP), biphasic tricalcium phosphate (BCP), and hydroxyapatite. In one embodiment, the dermal filler comprises hydroxyapatite. The fat-reducing compound may be administered by local injection into a subcutaneous fat tissue. In one embodiment, the dermal filler particles have a mean size of about 20 μm to about 70 μm in diameter, or a D-ratio of equal to or greater than 0.9, or both, wherein the D-ratio is defined as the ratio of the calculated diameter of a perfect circle based on the cross sectional area of the particle to the maximum diameter measured through that cross sectional centroid. The dermal filler particles may be administered as an injectable composition, which may be in the form of a hydrogel, and wherein the injectable composition comprises calcium (hydroxy)phosphate particles. In one embodiment, the injectable composition comprises at least one polysaccharide, the polysaccharide being crosslinked and/or non-crosslinked and optionally being selected from the group consisting of cellulose, cellulose ester and cellulose ether derivatives such as cellulose acetate (CA), carboxymethyl cellulose (CMC), carboxyethyl cellulose (CEC), carboxypropyl cellulose (CPC), carboxymethyl ethylcellulose (CMEC), methyl cellulose (MC), ethyl cellulose (EC), hydroxyethyl cellulose (HEC), hydroxyethyl methylcellulose (HEMC) and hydroxypropyl methylcellulose (HPMC), hyaluronic acid (HA), dextran, carboxymethyldextran, carboxymethylstarch, chondroitin sulfate, dermatane sulfate, keratin, keratin sulfate, chitosan, chitin, pectin, carrageenan, xanthan, heparin, heparin sulfate alginate, and mixtures therefrom, wherein the polysaccharide is selected from carboxymethyl cellulose (CMC), hyaluronic acid (HA), or a mixture thereof. The calcium (hydroxy)phosphate particles may be present in the injectable composition in an amount of 0.5 to 50% (w/w) or 5 to 29% (w/w). In one embodiment, the injectable composition contains one or more polyols in a total amount of 0 vol. % or 0.001 to 20 vol. %. The injectable composition may contain at least one additional pharmaceutically acceptable ingredient comprising a local anesthetic in an amount of 0.001 to 5 vol. %. In one embodiment, the injectable composition contains one or more polyols comprising glycerol, in a total amount of 0 vol. % or 0.001 to 20 vol. %, or contains at least one additional pharmaceutically acceptable ingredient comprising lidocaine in an amount of 0.001 to 5 vol. %, or both. The injectable composition may contain one or more polyols, in a total amount of 0 vol. % or 0.001 to 20 vol. %, or contains at least one additional pharmaceutically acceptable ingredient comprising a local anesthetic such as lidocaine, in an amount of 0.001 to 5 vol. %, or both. In one embodiment, the fat-reducing compound is selected from the group consisting of (i) adipocytolytic compounds, such as polidocanol, cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA), (ii) pentacyclic triterpenoid compounds, including ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone, (iii) compounds that stimulate the β2-adrenergic pathway directly or block the activity of cellular phosphodiesterases, such as paraxanthine, caffeine, ciclostamide, amirone, tolfentrine, revizinone and enoximone, (iv) proapoptotic compounds, such as resveratol and phytoalexin, (v) compounds impairing differentiation of pre-adipocytes, such as antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin, (vi) other compounds such as fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, glabridin, and (vii) combinations of one or more of (i) to (vi). The fat-reducing compound may be a adipocytolytic compound selected from the group consisting of: polidocanol, cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA). In one embodiment, the fat-reducing compound is a pentacyclic triterpenoid compound selected from the group consisting of: ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone, The fat-reducing compound may be a compound that stimulates the J32-adrenergic pathway directly or block the activity of cellular phosphodiesterases selected from the group consisting of: paraxanthine, caffeine, ciclostamide, amirone, tolfentrine, revizinone and enoximone. In one embodiment, the fat-reducing compound is a proapoptotic compound selected from the group consisting of: resveratrol and phytoalexin. The fat-reducing compound may be a compound impairing differentiation of pre-adipocytes selected from the group consisting of: antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin. In one embodiment, the fat-reducing compound is selected from the group consisting of: fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, and glabridin. The fat-reducing compound may be administered as an injectable composition in the form of a solution, emulsion, suspension or dispersion, comprising said fat-reducing compound and a cosmetically acceptable carrier such as an aqueous solution, an organic solvent, or a mixture of an aqueous solution and an organic solvent. In one embodiment, the fat-reducing compound is present in the injectable composition in an amount from about 0.001 wt. % to about 10 wt. %, based on the total weight of the injectable composition. The treatment of gynoid lipodystrophy may comprise local injection of an injectable composition of polidocanol into the subcutis and, after said local injection of an injectable composition of polidocanol, sequential or separate local injection of an injectable hydrogel composition of calcium (hydroxy)phosphate particles into the dermis. In one embodiment, the method further comprises the injection of a cavitation-prone fluid prior to application of HIFU. The dimple type female gynoid lipodystrophy may be treated. In one embodiment, non-dimple type female gynoid lipodystrophy is treated.

In several embodiments, a method for cosmetically treating gynoid lipodystrophy comprising administering to a subject in need thereof an effective amount of HIFU energy and at least one of a dermal filler and a fat-reducing compound. In one embodiment, the HIFU is administered concurrently, sequentially or separately with dermal filler. The HIFU may be administered concurrently, sequentially or separately with fat-reducing compound. In one embodiment, the dermal filler comprises calcium (hydroxy)phosphate particles. An effective amount of compound capable of reducing local subcutaneous fat and the calcium (hydroxy) phosphate particles may be administered concurrently, sequentially or separately. In several embodiments, a kit comprising a HIFU transducer, a composition of a dermal filler, and a fat-reducing compound, and optionally instructions for use. In one embodiment, the kit further comprising an injection guidance device and a syringe.

In several embodiments, a system for producing an aesthetic effect, wherein the system comprises one or more energy sources and at least one of the group consisting of: one or more dermal fillers, one or more fat-reducing compounds and one or more cavitation-prone agents. In one embodiment, the energy source comprises one, two or more of the following: ultrasound, HIFU, light, laser, radiofrequency, microwave, electromagnetic, radiation, thermal, cryogenic, electron beam, photon-based, magnetic, magnetic resonance. The aesthetic effect may comprise a cellulite treatment. In one embodiment, the aesthetic effect comprises reducing wrinkles, sagging and/or laxity of the skin. The aesthetic effect may comprise reducing fat. In one embodiment, the aesthetic effect comprises body or facial sculpting. Two or more energy sources may be used and wherein two or more of the following are used: dermal fillers, fat-reducing compounds and cavitation-prone agents. In one embodiment, two or more dermal fillers are used. The dermal filler may be a lip augmentation agent. In one embodiment, the treatment of a dermatological or cosmetic condition.

In several embodiments, a method for cosmetically treating gynoid lipodystrophy comprising administering to a subject in need thereof at least one of HIFU therapy and a dermal filler and a fat-reducing compound, wherein the method targets (i) a tissue in or around the dermis by providing HIFU therapy and/or by locally administering the dermal filler, (ii) a subcutaneous fat tissue by providing HIFU therapy and/or locally administering the fat-reducing compound to reduce the volume of the subcutaneous fat tissue, and optionally (iii) a fibrous septa by providing HIFU therapy to cut the fibrous septa.

In several embodiments, a method for cosmetically treating gynoid lipodystrophy comprising administering to a subject in need thereof at least one of HIFU therapy and a dermal filler and a fat-reducing compound, wherein the method targets (a) a tissue in or around the upper-dermis by providing HIFU therapy, (b) a tissue in or around the deep dermis by providing HIFU therapy and/or by local administering the dermal filler, (c) a subcutaneous fat tissue by providing HIFU therapy and/or administering the fat-reducing compound to reduce the volume of the subcutaneous fat tissue, and optionally (d) a fibrous septa by providing HIFU therapy to cut the fibrous septa. In one embodiment, a cavitation-prone fluid is injected prior to providing HIFU therapy to cut the fibrous septa. The subcutaneous fat tissue may be targeted by providing an HIFU therapy, wherein one or more simultaneous linear focused ultrasound treatments heat up portions of the subcutaneous fat-tissue in a plane or band of treatment. In one embodiment, the dermal filler comprises calcium (hydroxy)phosphate particles. The fat-reducing compound may be an adipocytolytic compound.

In several embodiments, a kit for treating cellulite with an ultrasound transducer having one or more of the features described in the foregoing description.

In several embodiments, use of septa dissection include at least one of the group consisting of: high intensity focused ultrasound (HIFU) therapy, a dermal filler, a fat-reducing compound, or a cavitation-prone fluid in the cosmetic treatment of gynoid lipodystrophy. In one embodiment, the septa dissection is targeted to a dermal tissue. The septa dissection may comprise using a chamber. In one embodiment, the septa dissection comprises cutting the septa on a plane parallel to an upper surface of a dermal tissue. The septa dissection may comprise cutting the septa using a cutting tool. In one embodiment, the cutting tool has one blade. The cutting tool may comprise two blades. In one embodiment, the septa dissection comprises cutting the septa using an ablation tool. The ablation tool may comprise a radiofrequency (RF) probe. In one embodiment, the septa dissection comprises injecting an anesthetic before dissecting the septa. The septa dissection may be directed by a guidance track. In one embodiment, the guidance track is interchangeable. The septa dissection may be motorized. In one embodiment, the septa dissection is manual. The septa dissection may be administered to a subject having a body mass index (BMI), defined as the body mass in kg divided by the square of the body height, of at least 25 kg/m$^2$, or to a subject having severe cellulite corresponding to a total sum of scores of items (a) and (b) of the Hexsel, Dal'Forno, and Hexsel Cellulite Severity Scale (CSS) of 4, 5 or 6, wherein item (a) denotes the number of evident depressions and item (b) denotes the depth of depressions, and both item (a) and item (b) are graded from 0 to 3. In one embodiment, the septa dissection is administered concurrently, sequentially, or separately with the at least one of the group consisting of: HIFU therapy, a dermal filler, a fat-reducing compound, or a cavitation-prone fluid. The HIFU therapy may be targeted to a dermal tissue. In one embodiment, the HIFU therapy is targeted to a dermal tissue to strengthen a connective tissue by improving a collagen-network in the dermal tissue. The HIFU therapy may be targeted to a tissue in the upper dermis. In one embodiment, rein the HIFU therapy is targeted to a tissue in the upper dermis to strengthen collagen in the upper dermal tissue. The HIFU therapy may be targeted to a dermal tissue and a subcutaneous fat tissue. In one embodiment, the HIFU therapy is simultaneously targeted to a dermal tissue and a subcutaneous fat tissue. The HIFU therapy may be targeted to a subcutaneous fat tissue. In one embodiment, the HIFU therapy is targeted to a fat lobuli within a subcutaneous fat tissue. The HIFU therapy may be targeted to a subcutaneous fat tissue to induce cell-death in adipocytes. In one embodiment, the HIFU therapy is targeted to a subcutaneous fat tissue to induce cell-death in adipocytes via apoptosis. The HIFU therapy is targeted to a subcutaneous fat tissue to increase lipolysis in adipocytes resulting in reduced cell diameter of affected adipocytes. In one embodiment, the HIFU therapy is targeted to a fibrous septa to cut the fibrous septa. The HIFU therapy may be provided at a depth of 1.5 mm below a skin surface. In one embodiment, the HIFU therapy is provided at a depth of 4.5 mm and/or 3.0 mm below a skin surface. The HIFU therapy may be provided at a depth of 1.5 mm and a depth of 4.5 mm and/or 3.0 mm below a skin surface. In one embodiment, the HIFU therapy is provided at a depth of 1.5 mm and between 10 mm to 17 mm below a skin surface. The HIFU therapy may be provided at a depth of 1.5 mm, 4.5 mm and/or 3.0 mm, and at least 10 mm below a skin surface. In one embodiment, the HIFU therapy is provided at a depth of at least 10 mm below a skin surface. The HIFU therapy may be provided at a depth of 17 mm below a skin surface. In one embodiment, the HIFU therapy is provided at a frequency of 4 MHz. The HIFU therapy may be provided at a frequency of 7 MHz. In one embodiment, the HIFU therapy is provided at a frequency of 10 MHz. The HIFU therapy may be provided at a frequency of 2 MHz or less. In one embodiment, the HIFU therapy is provided at a power of at least 5 kW/cm$^2$. The HIFU therapy may be provided at a power of at least 10 kW/cm$^2$. In one embodiment, the HIFU therapy is provided at a power of at least 15 kW/cm$^2$. The HIFU therapy may be provided with a spherically focused transducer. In one embodiment, the HIFU therapy is provided with a cylindrically focused transducer. The HIFU therapy may be provided at a point focus. In one embodiment, the HIFU therapy is provided at a line focus. The dermal filler may be administered before or after the septa dissection. In one embodiment, the fat-reducing compound is administered before or after the septa dissection. The dermal filler and the fat-reducing compound may be administered before or after the septa dissection. In one embodiment, the dermal filler is administered by local injection into a dermal tissue, a subcutaneous fat tissue, or both the dermal tissue and the subcutaneous fat tissue. The dermal filler may be hardened by the application of HIFU. In one embodiment, the dermal filler is moved by the application of HIFU. The dermal filler may be stabilized by the application of HIFU. In one embodiment, the viscosity of the dermal filler is modified by the application of HIFU. The dermal filler may be shaped in to a designed structure by the application of HIFU. In one embodiment, the dermal filler comprises calcium (hydroxy)phosphate particles selected from the group consisting of monocalcium phosphate (MCP), dicalcium phosphate (DCP), calcium dihydrogen phosphate (CDP), tricalcium phosphate (TCP) including its α-, α'- and β-polymorphs, octacalcium phosphate (OCP), biphasic tricalcium phosphate (BCP), and hydroxyapatite. The dermal filler may comprise hydroxyapatite. In one embodiment, the fat-reducing compound is administered by local injection into a subcutaneous fat tissue. The dermal filler particles may have a mean size of about 20 μm to about 70 μm in diameter, or a D-ratio of equal to or greater than 0.9, or both, wherein the D-ratio is defined as the ratio of the calculated diameter of a perfect circle based on the cross sectional area of the particle to the maximum diameter measured through that cross sectional centroid. In one embodiment, the dermal filler particles are administered as an injectable composition, which is in the form of a hydrogel, and wherein the injectable composition comprises calcium (hydroxy)phosphate particles. The injectable composition may comprise at least one polysaccharide, the polysaccharide being crosslinked and/or non-crosslinked and optionally being selected from the group consisting of cellulose, cellulose ester and cellulose ether derivatives such as cellulose acetate (CA), carboxymethyl cellulose (CMC), carboxyethyl cellulose (CEC), carboxypropyl cellulose (CPC), carboxymethyl ethylcellulose (CMEC), methyl cellulose (MC), ethyl cellulose (EC), hydroxyethyl cellulose (HEC), hydroxyethyl methylcellulose (HEMC) and hydroxypropyl methylcellulose (HPMC), hyaluronic acid (HA), dextran, carboxymethyldextran, carboxymethylstarch, chondroitin sulfate, dermatane sulfate, keratin, keratin sulfate, chitosan, chitin, pectin, carrageenan, xanthan, heparin, heparin sulfate alginate, and mixtures therefrom, wherein the polysaccharide is selected from carboxymethyl cellulose (CMC), hyaluronic acid (HA), or a mixture thereof. In one embodiment, the calcium (hydroxy)phosphate particles are present in the injectable composition in an amount of 0.5 to 50% (w/w) or 5 to 29% (w/w). The injectable composition may contain one or more polyols in a total amount of 0 vol. % or 0.001 to 20 vol. %. In one embodiment, the injectable composition contains at least one additional pharmaceutically acceptable ingredient comprising a local anesthetic in an amount of 0.001 to 5 vol. %. The injectable composition may contain one or more polyols comprising glycerol, in a total amount of 0 vol. % or 0.001 to 20 vol. %, or contains at least one additional pharmaceutically acceptable ingredient comprising lidocaine in an amount of 0.001 to 5 vol. %, or both. In one embodiment, the injectable composition contains one or more polyols, in a total amount of 0 vol. % or 0.001 to 20 vol. %, or contains at least one additional pharmaceutically acceptable ingredient comprising a local anesthetic such as lidocaine, in an amount of 0.001 to 5 vol. %, or both. The fat-reducing compound may be selected from the group consisting of (i) adipocytolytic compounds, such as polidocanol, cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA), (ii) pentacyclic triterpenoid compounds, including ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone, (iii) compounds that stimulate the J32-adrenergic pathway directly or block the activity of cellular phosphodiesterases, such as paraxanthine, caffeine, ciclostamide, amirone, tolfentrine, revizinone and enoximone, (iv) proapoptotic compounds, such as resveratol and phytoalexin, (v) compounds impairing differentiation of pre-adipocytes, such as antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin, (vi) other compounds such as fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, glabridin, or (vii) combinations of one or more of (i) to (vi). In one embodiment, the fat-reducing compound is a adipocytolytic compound selected from the group consisting of: polidocanol, cationic-amphiphilic compounds, trifluoperazine, nebivolol, duloxetine, phosphatidylcholine (PC), bile acids including deoxycholate (DC), chenodeoxycholic acid (CDCA), ursodeoxycholate (UDCA) and lithocholic acid (LCA). The fat-reducing compound may be a pentacyclic triterpenoid compound selected from the group consisting of: ursolic acid, betulinic acid, moronic acid, oleanolic acid, maslinic acid, asiatic acid, corosolic acid, alpha boswellic acid, beta boswellic acid, acetyl alpha boswellic acid, acetyl beta boswellic acid, acetyl keto alpha boswellic acid, acetyl keto beta boswellic acid, madecassic acid, arjunolic acid, enoxolone, enoxolone, and carbenoxolone, In one embodiment, the fat-reducing compound is a compound that stimulates the β2-adrenergic pathway directly or block the activity of cellular phosphodiesterases selected from the group consisting of: paraxanthine, caffeine, ciclostamide, amirone, tolfentrine, revizinone and enoximone. The fat-reducing compound may be a proapoptotic compound selected from the group consisting of: resveratrol and phytoalexin. In one embodiment, the fat-reducing compound is a compound impairing differentiation of pre-adipocytes selected from the group consisting of: antagonists of the peroxisome proliferator-activated receptor-gamma such as an antagonist of the peroxisome proliferator-activated receptor-gamma of herbal origin, particularly naringenin, luteolin, phenylacrylic acid (rosmarinic acid), diosmetin and poncirin. The fat-reducing compound may be selected from the group consisting of: fluoxetine, glycyrrhizic acid, maslinic acid, ginsenoide Rh2, betulinic acid, moronic acid, deoxycholic acid, obeticholic acid, erythrodoil, ursolic acid, uvaol, betulinic acid, becarben, carbenoxolone, and glabridin. In one embodiment, the fat-reducing compound is administered as an injectable composition in the form of a solution, emulsion, suspension or dispersion, comprising said fat-reducing compound and a cosmetically acceptable carrier such as an aqueous solution, an organic solvent, or a mixture of an aqueous solution and an organic solvent. The fat-reducing compound is present in the injectable composition in an amount from about 0.001 wt. % to about 10 wt. %, based on the total weight of the injectable composition. In one embodiment, the treatment of gynoid lipodystrophy comprises local injection of an injectable composition of polidocanol into the subcutis and, after said local injection of an injectable composition of polidocanol, sequential or separate local injection of an injectable hydrogel composition of calcium (hydroxy)phosphate particles into the dermis. The treatment may comprise the injection of a cavitation-prone fluid prior to application of HIFU. In one embodiment, dimple type female gynoid lipodystrophy is treated. Non-dimple type female gynoid lipodystrophy may be treated.

In several embodiments, a method for cosmetically treating gynoid lipodystrophy comprising administering to a subject in need thereof a septa dissection and at least one of an effective amount of HIFU energy, a dermal filler, a fat-reducing compound, or a cavitation-prone fluid. In one embodiment, the septa dissection is administered concurrently, sequentially or separately with HIFU energy. The HIFU energy may be administered concurrently, sequentially or separately with the cavitation-prone fluid. In one embodiment, the septa dissection is administered concurrently, sequentially or separately with dermal filler. The septa dissection may be administered concurrently, sequentially or separately with fat-reducing compound. In one embodiment, the septa dissection is administered concurrently, sequentially or separately with cavitation-prone fluid. The dermal filler may comprise calcium (hydroxy)phosphate particles. In one embodiment, an effective amount of compound capable of reducing local subcutaneous fat and the calcium (hydroxy)phosphate particles are administered concurrently, sequentially or separately.

In several embodiments, a kit comprising a septa dissection system and at least one of a HIFU transducer, a dermal filler, a fat-reducing compound, a cavitation-prone fluid, or instructions for use. In one embodiment, the kit further comprises an injection guidance device and a syringe.

In several embodiments, a system for producing an aesthetic effect, wherein the system comprises a septa dissection device and at least one of the group consisting of: one or more energy sources, one or more dermal fillers, one or more fat-reducing compounds, one or more cavitation-prone fluids. The energy source may comprise one, two or more of the following: ultrasound, light, laser, radio-frequency, microwave, electromagnetic, radiation, thermal, cryogenic, electron beam, photon-based, magnetic, magnetic resonance. In one embodiment, the aesthetic effect comprises a cellulite treatment. The aesthetic effect comprises reducing wrinkles, sagging and/or laxity of the skin. In one embodiment, the aesthetic effect comprises reducing fat. The aesthetic effect may comprise body or facial sculpting. In one embodiment, two or more energy sources are used and wherein two or more of the following are used: dermal fillers, fat-reducing compounds, and cavitation-prone fluids. Two or more dermal fillers may be used. In one embodiment, the dermal filler is a lip augmentation agent. The system may used for the treatment of a dermatological or cosmetic condition.

In several embodiments, a method for cosmetically treating gynoid lipodystrophy comprising administering to a subject in need thereof septa dissection and at least one of HIFU therapy, a dermal filler, a fat-reducing compound, or a cavitation-prone fluid, wherein the method targets (i) a tissue in or around the dermis by providing HIFU therapy and/or by locally administering the dermal filler, (ii) a subcutaneous fat tissue by providing HIFU therapy and/or locally administering the fat-reducing compound to reduce the volume of the subcutaneous fat tissue, and optionally (iii) a fibrous septa by providing septa dissection and/or HIFU therapy to cut the fibrous septa.

In several embodiments, a method for cosmetically treating gynoid lipodystrophy comprising administering to a subject in need thereof septa dissection and at least one of HIFU therapy, a dermal filler, a fat-reducing compound, or a cavitation-prone fluid, wherein the method targets (a) a tissue in or around the upper-dermis by providing HIFU therapy, (b) a tissue in or around the deep dermis by providing HIFU therapy and/or by local administering the dermal filler, (c) a subcutaneous fat tissue by providing HIFU therapy and/or administering the fat-reducing compound to reduce the volume of the subcutaneous fat tissue, and optionally (d) a fibrous septa by providing septa dissection and/or HIFU therapy to cut the fibrous septa. In one embodiment, the cavitation-prone fluid is injected prior to providing HIFU therapy to cut the fibrous septa. The subcutaneous fat tissue may be targeted by providing an HIFU therapy, wherein one or more simultaneous linear focused ultrasound treatments heat up portions of the subcutaneous fat-tissue in a plane or band of treatment. In one embodiment, the dermal filler comprises calcium (hydroxy)phosphate particles. The fat-reducing compound may be an adipocytolytic compound. In several embodiments, a method for cosmetically treating gynoid lipodystrophy comprising administering to a subject at least one therapy to target a dermal layer and at least one therapy to target a fat layer. In one embodiment, the at least one therapy to target the dermal layer comprises at least one of septa dissection, HIFU therapy without a cavitation-prone fluid, HIFU therapy with a cavitation-prone fluid, or a dermal filler. At least one therapy may be used to target the dermal layer comprises at least two of septa dissection, HIFU therapy without a cavitation-prone fluid, HIFU therapy with a cavitation-prone fluid, or a dermal filler. In one embodiment, the at least one therapy to target the dermal layer comprises at least three of septa dissection, HIFU therapy without a cavitation-prone fluid, HIFU therapy with a cavitation-prone fluid, or a dermal filler. The at least one therapy to target the dermal layer may comprise each of septa dissection, HIFU therapy without a cavitation-prone fluid, HIFU therapy with a cavitation-prone fluid, and a dermal filler. In one embodiment, the at least one therapy to target the fat layer comprises at least one of HIFU therapy without a cavitation-prone fluid, HIFU therapy with a cavitation-prone fluid, or a fat-reducing compound. The at least one therapy to target the fat layer may comprise at least two of HIFU therapy without a cavitation-prone fluid, HIFU therapy with a cavitation-prone fluid, or a fat-reducing compound. In one embodiment, the at least one therapy to target the fat layer comprises each of HIFU therapy without a cavitation-prone fluid, HIFU therapy with a cavitation-prone fluid, and a fat-reducing compound.

In several embodiments, a kit for treating cellulite with a septa dissection system having one or more of the features described in the foregoing description.

In several embodiments, a use for treating cellulite having one or more of the features described in the foregoing description.

In several embodiments, a method of treating cellulite having one or more of the features described in the foregoing description.

In several embodiments, a cellulite treatment system having one or more of the features described in the foregoing description.

Further, areas of applicability will become apparent from the description provided herein. It should be understood that the description and specific examples are intended for purposes of illustration only and are not intended to limit the scope of the embodiments disclosed herein. In some embodiments, the system comprises various features that are present as single features (as opposed to multiple features). Multiple features or components are provided in alternate embodiments. In various embodiments, the system comprises, consists essentially of, or consists of one, two, three, or more embodiments of any features or components disclosed herein. In some embodiments, a feature or component is not included and can be negatively disclaimed from a specific claim, such that the system is without such feature or component.

Some embodiments and the examples described herein are examples and not intended to be limiting in describing the full scope of compositions and methods of these invention. Equivalent changes, modifications and variations of some embodiments, materials, compositions and methods can be made within the scope of an embodiment of the invention, with substantially similar results. The methods summarized above and set forth in further detail below describe certain actions taken by a practitioner; however, it should be understood that they can also include the instruction of those actions by another party. In several of the embodiments described herein, the procedure is entirely cosmetic and not a medical act. For example, in one embodiment, the methods described herein need not be performed by a doctor, but at a spa or other aesthetic institute. In some embodiments, a system can be used for the non-invasive cosmetic treatment of skin.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "treating cellulite with an ultrasonic probe" include "instructing the treatment of a cellulite with an ultrasonic probe." The ranges disclosed herein also encompass any and all overlap, sub-ranges, and combinations thereof. Language such as "up to," "at least," "greater than," "less than," "between," and the like includes the number recited. Numbers proceeded by a term such as "about" or "approximately" include the recited numbers. For example, "about 25 mm" includes "25 mm." Where an indefinite or definite article is used when referring to a singular noun, e.g., "a," "an," "the," this includes a plural of that noun unless something else is specifically stated.

EXAMPLES

The following examples are provided for ease of understanding of several embodiments of the invention and are included only for illustrative purposes without imposing any undue limitations upon the claimed invention. For example, although a specific dermal filler such as CaHAP may be described below in certain embodiments, one or more other dermal fillers can also be used instead of or in addition to CaHAP in other embodiments.

Example 1

Ex Vivo Preliminary Tests

The ex vivo preliminary tests described in this example are carried out to establish suitable parameters for clinical development and involve application if HIFU energy from a HIFU device 20 and the injection of a dermal filler 800 and a fat-reducing compound 820 into the thigh of a dead female mammalian body, and an assessment of their tissue distribution and treatment effects. In this example, the dermal filler 800 comprises hydroxyapatite particles. In this example, the fat-reducing compound 820 comprises polidocanol.

After the application of microfocused ultrasound (ULTHERAPY) HIFU device 20 of focused ultrasound delivery at a depth of 4.5 mm below the skin surface, small deposits of hydroxyapatite particles are provided in the lower dermis/upper subcutis by injecting a composition comprising about 55.7 wt. % calcium hydroxyapatite particles (mean diameter of 25-45 μm), 36.6 wt. % sterile water for injection (USP), 6.4 wt. % glycerin (USP) and 1.3 wt. % sodium carboxymethyl cellulose (USP), supplemented with a red dye for improved visualization.

The composition is injected in a volume of 0.03 ml to 0.05 ml per injection point into the thigh at a depth of 5 mm, 8 mm or 10 mm and at an angle of about 60° using a 25G, 27G or 30G injection needle in a injection guidance device 600. Injections are spaced apart from each other by about 0.5 cm, 1.0 cm or 2.0 cm. Likewise small amounts (0.05 ml or 0.1 ml) of 0.5% or 2% polidocanol in aqueous methylene blue are injected into the upper subcutaneous tissue of the other thigh, the injections being spaced apart from each other by about 0.5 cm, 1.0 cm, 1.5 cm, 2.0 cm or 3.0 cm.

About 30 minutes after injection, macrosections are prepared and the distribution of the red or blue dye within the tissue is determined. It some embodiments, the red dye of the hydroxyapatite composition is present within the superficial fat lobules of the subcutis. The blue dye representing polidocanol, on the other hand, is hardly present in the fat lobules, but is observed to accumulate in the septa between the fat lobules. The preparation is very evenly distributed in the dermis. In view of these results, it is concluded that (1) the needle used for injecting polidocanol into the upper subcutis should have a length of about 8-10 mm, (2) the preparation comprising 2% polidocanol shows better distribution characteristics than the preparation comprising 0.5% polidocanol, and (3) the distance between individual injections is most suitably about 1 cm since this distance results in a confluent and even distribution throughout the tissue in some embodiments. Furthermore, regarding the injection of hydroxyapatite particles, it is concluded that (1) the injection should preferably occur in a depth of at most 5 mm for reaching the lower dermis, (2) a distance of about 1 cm between individual injections is most suitable for obtaining an even distribution throughout the tissue. In addition, the capability of placing thermal coagulations points or focus areas (TCP) in the envisaged target depth of 4.5 mm and desired and reproducible spacing of 1.5 mm TCPs is confirmed.

Example 2

Patient Study

Materials and Methods
Patients

Healthy skin patients of legal age with moderately severe cellulite on buttocks (total score of 6 to 10 on the Cellulite Severity Scale (CSS) according to Hexsel et al., (the "Hexsel, Dal'Forno, and Hexsel Cellulite Severity Scale"; see Hexsel et al., A validated photonumeric cellulite severity scale, J. Eur. Acad. Dermatol. Venereol. 2009, 23: 523-528), a body mass index (BMI) below 30, and a waist-hip ratio of <0.6 are included in the patient study.
Products High Intensity Focused Ultrasound (HIFU) device 20.

Radiesse® (Merz, Frankfurt a. M., Germany) is a soft tissue dermal filler 800 which comprises calcium hydroxyapatite (CaHAP) particles dispersed in a carrier gel of carboxymethyl cellulose (CMC) that further includes glycerol.

Aethoxysklerol® 0.5% is an injection solution which contains polidocanol as active agent in a concentration of 0.5% w/v (10 mg in 2 ml of injection solution) of a fat-reducing compound 820.
Therapy Regimen At day 0, and optionally at day 45±3 days, a HIFU treatment is directed to the posterior buttocks, lateral buttocks, and posterior thighs using at least one of the following transducers: a 10 MHz transducer at 1.5 mm, a 4 MHz transducer at a focal depth of 4.5 mm, a 7 MHz transducer at a depth of 3.0 mm, (using 75 lines per transducer for each side—25 lines per buttock or thigh treatment site), and a 2 MHz transducer at a depth of 13 mm.

At day 0, day 45±3 days, and optionally day 90±4 days, 2 ml of a diluted Aethoxysklerol® solution (Aethoxysklerol® 1% diluted 1:1 with 2% aqueous lidocaine) is subcutaneously injected in each buttock adjacent the thigh. At day 45, calcium hydroxyapatite particles is administered by deep intradermal injection of 3 ml diluted RADIESSE (RADIESSE diluted 1:1 with 2% aqueous lidocaine) in each buttock adjacent the thigh.

The injections are performed by serial, selective injection on the first, second and third appointment. Before the injections, a tattoo mask is applied to the areas of the thighs to be treated for the standardization of injection points (150 points with spacing of 1 cm). The injection depth is sonographically controlled. A 25G, 27G, 30G or 33G injection needle is used for Aethoxysklerol® and calcium hydroxyapatite (RADIESSE), respectively. The volume per injection point is 0.1 ml for Aethoxysklerol® and between 0.015 ml to 0.02 ml for RADIESSE. The treatment is well tolerated with no or reduced side-effects in several embodiments.

Data is collected at day 0, the days of treatment, after 6 months and after 9 months using the test methods described below.

Test Methods

Cutometry: The elasticity of skin is measured using a commercial cutometer. The measuring principle is based on the so-called suction method. A negative pressure is produced in the measuring head, and the skin is drawn inside the instrument, and after a defined time released again. An optical measuring system measures the light intensity, which varies in accordance with the degree of skin penetration. The resistance of the skin to the negative pressure (firmness) and its ability to return into its original position (elasticity) are displayed as curves (penetration depth in mm/time) in real time during the measurement.

The parameters determined from the measurement curves included, inter alia, the R2 (gross elasticity), R5 (the net elasticity), and R6 (viscoelasticity) parameters. R2 is a measure of the gross elasticity of the skin (resistance versus ability of returning). The closer R2 is to 100%, the more elastic the skin. Likewise, the closer the value of R5 (net elasticity, e.g., the elastic portion of the suction part versus the elastic portion of the relaxation part) is to 100%, the more elastic the skin. The parameter R6 (viscoelasticity) indicates the portion of the viscoelasticity of the curve. The smaller this value is, the higher the elasticity of skin.

Sonography: The thickness of the dermis (often referred to as "skin thickness") and the skin density is assessed by 20 MHz ultrasound examination using a DUB® ultrasound scanner (tpm, Luneburg, Germany).

Cellulitis severity rating: The severity of cellulite is rated using the total score from the Hexsel, Dal'Forno, and Hexsel Cellulite Severity Scale (CSS) (Hexsel et al. (2009), supra). The Hexsel et al. rating score consists of the following criterions: (a) number of evident depressions, (b) depth of depressions, (c) morphological appearance of skin surface alterations, (d) grade of laxity, flaccidity or sagging skin, (e) classification scale by the Nürnberger-Müller scale. The rating is carried out by the patients themselves and by a blinded expert. Each item is graded from 0 to 3, allowing final classification of cellulite as mild (1-5 points), moderate (6-10 points), and severe (11-15 points).

Patient questionnaire on quality of life: The quality of life (QoL or Qol) is assessed using a patient questionnaire (CelluQol®) (Hexsel D, Weber M, Tabord M L, Fonte de Souza J., Preliminary results of the elaboration of a new instrument to evaluate quality of life in patients with cellulite-CelluQol®, Poster AAD 2012). Each question is rated from 1 to 5 as follows: 1=not bothered at all, 2=not bothered most of the time, 3=no feelings either way, 4=bothered most of the time, 5=bothered all the time Results The results show that the combined use of Ultherapy HIFU treatment, Aethoxysklerol® 0.5%, and RADIESSE leads to a significant improvement of skin elasticity and skin firmness, as evidenced by the positive change of the cutometry parameters, as well as to a stabilization of the dermis, as evidenced by the results of high-frequency ultrasound measurements. Furthermore, the reduced body weight and circumference of thighs results in a significantly slimmer silhouette, in line with the positive evaluation in this respect by the patient. Also, the quality of life is clearly improved. Overall, the patient's expectation is met and the patient is satisfied with the combined treatment outcome.

Thus, the results show that the treatment with HIFU in combination with calcium hydroxyapatite particles (RADIESSE) and polidocanol (Aethoxysklerol® 0.5%) is efficient in the treatment of cellulite (gynoid lipodystrophy), and thus offers a new promising treatment option.

Example 3

Materials and Methods

Patients

Healthy skin patients of legal age with moderately severe cellulite and concomitant advanced skin laxity and/or enhanced BMI. The cellulite appears on buttocks (total score of 6 to 10 on the Cellulite Severity Scale (CSS) according to Hexsel et al., (the "Hexsel, Dal'Forno, and Hexsel Cellulite Severity Scale"; see Hexsel et al., A validated photonumeric cellulite severity scale, J. Eur. Acad. Dermatol. Venereol. 2009, 23: 523-528), a body mass index (BMI) between 25 to 40, and a waist-hip ratio of <0.6 are included in the patient study.

Products

Ultherapy® (Ulthera, Inc., Mesa, Ariz.) is a High Intensity Focused Ultrasound (HIFU) device 20.

Radiesse® (Merz, Frankfurt a. M., Germany) is a soft tissue dermal filler 800 which comprises calcium hydroxyapatite (CaHAP) particles dispersed in a carrier gel of carboxymethyl cellulose (CMC) that further includes glycerol.

Therapy Regimen

At day 0, a HIFU treatment is directed to the posterior buttocks, lateral buttocks, and posterior thighs using a 10 MHz transducer at 1.5 mm and 150 lines for each side. Immediately thereafter calcium hydroxyapatite particles are administered by deep intradermal injection of 3 ml diluted RADIESSE (1.5 ml RADIESSE diluted 1:1 with 1.5 ml 2% aqueous lidocaine) in each buttock adjacent the thigh. Microinjection technique is used with an amount of approx. 0.05 ml per droplet with a sharp needle of 27G into the dermal-subdermal layer. The mean number of injection points is 60, spaced 1 cm apart. Baseline is documented by taking a standardized photo of skin surface, measuring skin thickness (sonography), measuring density and measuring elasticity (Cutometrie).

At day 90±4 days, 3 months after initial treatment, a HIFU treatment is directed to the posterior buttocks, lateral buttocks, and posterior thighs using the 10 MHz transducer at 1.5 mm and 150 lines for each side. Immediately thereafter calcium hydroxyapatite particles are administered by deep intradermal injection of 3 ml diluted RADIESSE (1.5 ml RADIESSE diluted 1:1 with 1.5 ml 2% aqueous lidocaine) in each buttock adjacent the thigh. Microinjection technique is used with an amount of approx. 0.05 ml per droplet with a sharp needle of 27G into the dermal-subdermal layer. The mean number of injection points is 60, spaced 1 cm apart. Take a standardized photo of skin surface, measure skin thickness (sonography), measure density, measure elasticity (Cutometrie). At day 180±8 days, after 6 months, take a standardized photo of skin surface, measure skin thickness (sonography), measure density, and measure elasticity (Cutometrie). At day 270±12 days, after 9 months, take a standardized photo of skin surface, measure skin thickness (sonography), measure density, and measure elasticity (Cutometrie).

Results

The results show that the combined use of Ultherapy HIFU treatment and RADIESSE leads to a significant improvement of skin elasticity and skin firmness, as evidenced by the positive change of the cutometry parameters, as well as to a stabilization of the dermis, as evidenced by the results of high-frequency ultrasound measurements. Also, the quality of life is clearly improved. Overall, the patient's expectation is met and the patient is satisfied with the combined treatment outcome.

Thus, the results show that the treatment with HIFU in combination with calcium hydroxyapatite particles (RADIESSE) is efficient in the treatment of cellulite (gynoid lipodystrophy), and thus offers a new promising treatment option.

Example 4

Materials and Methods

Patients

Healthy skin patients of legal age with moderately severe cellulite and concomitant advanced skin laxity and/or enhanced BMI. The cellulite appears on buttocks (total score of 6 to 10 on the Cellulite Severity Scale (CSS) according to Hexsel et al., (the "Hexsel, Dal'Forno, and Hexsel Cellulite Severity Scale"; see Hexsel et al., A validated photonumeric cellulite severity scale, J. Eur. Acad. Dermatol. Venereol. 2009, 23: 523-528), a body mass index (BMI) between 25 to 40, and a waist-hip ratio of <0.6 are included in the patient study.

Products

Ultherapy® (Ulthera, Inc., Mesa, Ariz.) is a High Intensity Focused Ultrasound (HIFU) device 20.

Radiesse® (Merz, Frankfurt a. M., Germany) is a soft tissue dermal filler 800 which comprises calcium hydroxyapatite (CaHAP) particles dispersed in a carrier gel of carboxymethyl cellulose (CMC) that further includes glycerol.

Aethoxysklerol® 0.5% is an injection solution which contains polidocanol as active agent in a concentration of 0.5% w/v (10 mg in 2 ml of injection solution) of a fat-reducing compound 820.

Therapy Regimen

At day 0, a HIFU treatment is directed to the posterior buttocks, lateral buttocks, and posterior thighs using a 10 MHz transducer at 1.5 mm and 150 lines for each side. Patients receive 8 ml of a diluted Aethoxysklerol® solution (2×2 ml Aethoxysklerol® 1% diluted 1:1 with 4 ml 2% aqueous lidocaine) per treatment side. Through microinjection technique 0.1 ml per droplet is injected with a sharp needle of 30 G into the subcutaneous fat. The mean number of injection points is 80, spaced 1 cm apart. Per treatment side patients receive calcium hydroxyapatite particles being administered by deep intradermal injection of 3 ml diluted RADIESSE (1.5 ml RADIESSE diluted 1:1 with 1.5 ml 2% aqueous lidocaine) in total. Microinjection technique is used with an amount of approx. 0.05 ml per droplet with a sharp needle of 27 G into the dermal-subdermal layer. The mean number of injection points is 60, spaced 1 cm apart. Baseline is documented by taking a standardized photo of skin surface, measuring skin thickness (sonography), measuring density and measuring elasticity (Cutometrie).

At 45 days (±3 days), after 1.5 months, patients receive 8 ml of a diluted Aethoxysklerol® solution (2×2 ml Aethoxysklerol® 1% diluted 1:1 with 4 ml 2% aqueous lidocaine) per treatment side. Through microinjection technique 0.1 ml per droplet is injected with a sharp needle of 30 G into the subcutaneous fat. The mean number of injection points is 80, spaced 1 cm apart. Take a standardized photo of skin surface, measure skin thickness (sonography), measure density, measure elasticity (Cutometrie).

At day 90 (±4 days), after 3 months, a HIFU treatment is directed to the posterior buttocks, lateral buttocks, and posterior thighs using the 10 MHz transducer at 1.5 mm and 150 lines for each side. Per treatment side patients receive 8 ml of a diluted Aethoxysklerol® solution (2×2 ml Aethoxysklerol® 1% diluted 1:1 with 4 ml 2% aqueous lidocaine) in total. Through microinjection technique 0.1 ml per droplet is injected with a sharp needle of 30 G into the subcutaneous fat. The mean number of injection points is 80, spaced 1 cm apart. Per treatment side patients receive calcium hydroxyapatite particles being administered by deep intradermal injection of 3 ml diluted RADIESSE (1.5 ml RADIESSE diluted 1:1 with 1.5 ml 2% aqueous lidocaine) in total. Microinjection technique is used with an amount of approx. 0.05 ml per droplet with a sharp needle of 27 G into the dermal-subdermal layer. The mean number of injection points is 60, spaced 1 cm apart. Take a standardized photo of skin surface, measure skin thickness (sonography), measure density, measure elasticity (Cutometrie).

At day 180±8 days, after 6 months, take a standardized photo of skin surface, measure skin thickness (sonography), measure density, and measure elasticity (Cutometrie). At day 270±12 days, after 9 months, take a standardized photo of skin surface, measure skin thickness (sonography), measure density, and measure elasticity (Cutometrie).

Results

The results show that the combined use of Ultherapy HIFU treatment, Aethoxysklerol® 0.5%, and RADIESSE leads to a significant improvement of skin elasticity and skin firmness, as evidenced by the positive change of the cutometry parameters, as well as to a stabilization of the dermis, as evidenced by the results of high-frequency ultrasound measurements. Furthermore, the reduced body weight and circumference of thighs results in a significantly slimmer silhouette, in line with the positive evaluation in this respect by the patient. Also, the quality of life is clearly improved. Overall, the patient's expectation is met and the patient is satisfied with the combined treatment outcome.

Thus, the results show that the treatment with HIFU in combination with calcium hydroxyapatite particles (RADIESSE) and polidocanol (Aethoxysklerol® 0.5%) is efficient in the treatment of cellulite (gynoid lipodystrophy), and thus offers a new promising treatment option.

Example 5

Materials and Methods

Patients

Healthy skin patients of legal age with moderately severe cellulite and concomitant advanced skin laxity and/or enhanced BMI. The cellulite appears on buttocks (total score of 6 to 10 on the Cellulite Severity Scale (CSS) according to Hexsel et al., (the "Hexsel, Dal'Forno, and Hexsel Cellulite Severity Scale"; see Hexsel et al., A validated photonumeric cellulite severity scale, J. Eur. Acad. Dermatol. Venereol. 2009, 23: 523-528), a body mass index (BMI) between 25 to 40, and a waist-hip ratio of <0.6 are included in the patient study.

Products

Cellfina® System (Ulthera, Inc., Mesa, Ariz.) is used for a septa dissecting treatment 830.

Ultherapy® (Ulthera, Inc., Mesa, Ariz.) is a High Intensity Focused Ultrasound (HIFU) device 20.

Radiesse® (Merz, Frankfurt a. M., Germany) is a soft tissue dermal filler 800 which comprises calcium hydroxyapatite (CaHAP) particles dispersed in a carrier gel of carboxymethyl cellulose (CMC) that further includes glycerol.

Aethoxysklerol® 0.5% is an injection solution which contains polidocanol as active agent in a concentration of 0.5% w/v (10 mg in 2 ml of injection solution) of a fat-reducing compound 820.

Therapy Regimen

At day 0, a Cellfina® System is used to dissect septae in the dermal layer. The septae are dissected in portions of the posterior buttocks, lateral buttocks, and posterior thighs leading to release of dimples. The portions are drawn into a chamber using negative pressure, then a needle extending into the chamber delivers anesthesia (lidocaine). Once sensation is sufficiently abated, a cutting tool guided by a guidance track is used to cut septa(e) in that portion. Cutting the shortened fibrous septa associated to skin-dimples and thereby reducing the retraction of the skin in the treated areas are part of this effective and long-lasting combination treatment in several embodiments.

Also at day 0, a HIFU treatment is directed to the posterior buttocks, lateral buttocks, and posterior thighs using a 10 MHz transducer at 1.5 mm and 150 lines for each side. Patients receive 8 ml of a diluted Aethoxysklerol® solution (2×2 ml Aethoxysklerol® 1% diluted 1:1 with 4 ml 2% aqueous lidocaine) per treatment side. Through microinjection technique, 0.1 ml per droplet is injected with a sharp needle of 30 G into the subcutaneous fat. The mean number of injection points is 80, spaced 1 cm apart. Per treatment side, patients receive calcium hydroxyapatite particles being administered by deep intradermal injection of 3 ml diluted RADIESSE (1.5 ml RADIESSE diluted 1:1 with 1.5 ml 2% aqueous lidocaine) in total. Microinjection technique is used with an amount of approx. 0.05 ml per droplet with a sharp needle of 27 G into the dermal-subdermal layer. The mean number of injection points is 60, spaced 1 cm apart. Subdermal application using a vectored (e.g., fanning) approach may be an option depending on individual patient modalities. Baseline is documented by taking a standardized photo of skin surface, measuring skin thickness (sonography), measuring density, and measuring elasticity (Cutometrie).

At 45 days (±3 days), after 1.5 months, patients receive 8 ml of a diluted Aethoxysklerol® solution (2×2 ml Aethoxysklerol® 1% diluted 1:1 with 4 ml 2% aqueous lidocaine) per treatment side. Through microinjection technique, 0.1 ml per droplet is injected with a sharp needle of 30 G into the subcutaneous fat. The mean number of injection points is 80, spaced 1 cm apart. Take a standardized photo of skin surface, measure skin thickness (sonography), measure density, and measure elasticity (Cutometrie).

At day 90 (±4 days), after 3 months, a HIFU treatment is directed to the posterior buttocks, lateral buttocks, and posterior thighs using the 10 MHz transducer at 1.5 mm and 150 lines for each side. Per treatment side, patients receive 8 ml of a diluted Aethoxysklerol® solution (2×2 ml Aethoxysklerol® 1% diluted 1:1 with 4 ml 2% aqueous lidocaine) in total. Through microinjection technique 0.1 ml per droplet is injected with a sharp needle of 30 G into the subcutaneous fat. The mean number of injection points is 80, spaced 1 cm apart. Per treatment side, patients receive calcium hydroxyapatite particles being administered by deep intradermal injection of 3 ml diluted RADIESSE (1.5 ml RADIESSE diluted 1:1 with 1.5 ml 2% aqueous lidocaine) in total. Microinjection technique is used with an amount of approx. 0.05 ml per droplet with a sharp needle of 27 G into the dermal-subdermal layer. The mean number of injection points is 60, spaced 1 cm apart. Take a standardized photo of skin surface, measure skin thickness (sonography), measure density, and measure elasticity (Cutometrie).

At day 180 (±8 days), after 6 months, take a standardized photo of skin surface, measure skin thickness (sonography), measure density, and measure elasticity (Cutometrie). At day 270 (±12 days), after 9 months, take a standardized photo of skin surface, measure skin thickness (sonography), measure density, and measure elasticity (Cutometrie).

As each intervention targets different sites and pathomechanisms in the dermis and subcutaneous layers, the suggested combination of these treatments resembles an effective, holistic treatment approach for cellulite over a broad range of severity.

According to several embodiments, the combination of tissue stabilized guided subcision/tissue dissection with two interventions to enhance neocollagenesis (micro-focussed ultrasound and diluted hydroxyl apatite) and reduction of the subcutaneous fat-layer (by ultrasound or combination with injection of adipocytolytic compounds) will result in a more pronounced and even improvement of clinical appearance of skin affected by cellulite phenotype.

Results

The results show that the combined use of septa dissection using a Cellfina System, Ultherapy HIFU treatment, Aethoxysklerol® 0.5%, and RADIESSE leads to a significant improvement of skin elasticity and skin firmness, as evidenced by the positive change of the cutometry parameters, as well as to a stabilization of the dermis, as evidenced by the results of high-frequency ultrasound measurements. Local obvious skin depressions can be released very efficiently and for the long-term. Furthermore, the reduced body weight and circumference of thighs results in a significantly slimmer silhouette, in line with the positive evaluation in this respect by the patient. Also, the quality of life is clearly improved. Overall, the patient's expectation is met and the patient is satisfied with the combined treatment outcome.

Thus, the results in one embodiment show that the treatment with the combination of Cellfina System treatment, HIFU, calcium hydroxyapatite particles (RADIESSE), and polidocanol (Aethoxysklerol® 0.5%) is efficient in the treatment of cellulite (gynoid lipodystrophy), and thus offers a new promising treatment option.

In the multiple examples provided above, although specific trade names of technologies are described, they should not be construed as overly limiting. For instance, Cellfina is one example of how septae may be cut. Other septae dissection technology may also be used, including but not limited to fluid dissection, ultrasound dissection, other energy-based dissection, scalpels, chemical or enzymatic agents, etc. In some embodiments, energy-based technology other than that commercialized under the trade name Ultherapy is used including, but not limited to other ultrasound technology (focused or non-focused), radiofrequency, laser, microwave, cryotherapy, etc. In some embodiments, alternatives to RADIESSE are used, including but not limited to hydroxyapatite derivatives, calcium microspheres, and other dermal fillers. For example, PLLA (poly-L-lactic acid) may be used. In some embodiments, alternatives to Aethoxysklerol are used, including but not limited to polidocanol derivatives and sclerotherapy compounds.

Example 6

Materials and Methods
Patients
Skin-Healthy patients of legal age (women aged 37 to 48) with moderate cellulite on upper thighs and concomitant skin laxity and increased BMI are treated with (i) an injection of diluted calcium hydroxyapatite CaHAP particles only as mono treatment; (ii) a combination of calcium hydroxyapatite CaHAP injections and micro focused ultrasound ("MFU") at a depth of 1.5 mm under the skin surface as dual combination treatment; or (iv) a combination of calcium hydroxyapatite CaHAP injections and MFU at 1.5 mm plus Aethoxysklerol as triple combination treatment.

Assessment of different skin parameters have been recorded prior treatment (day 0) as well as 90 days (+/−10 days), 180 days (+/−10 days), and 270 days (+/−10 days) after treatment. As overall assessment parameter the Merz Aesthetic scale cellulite dimples and skin laxity—both at rest—have been used.
Products
Ultherapy® (Ulthera, Inc., Mesa, Ariz.) is a High Intensity Focused Ultrasound (HIFU) device 20, used for MFU.

Radiesse® (Merz, Frankfurt a. M., Germany) is a soft tissue dermal filler 800 which comprises calcium hydroxyapatite (CaHAP) particles dispersed in a carrier gel of carboxymethyl cellulose (CMC) that further includes glycerol. For the injection into the subcutaneous fat tissue, in one embodiment, Radiesse® is diluted in a ratio of 1:1 with 2% aqueous lidocaine.

Aethoxysklerol® 1% is used in one embodiment and is an injection solution which contains polidocanol, a fat-reducing compound 820, as active agent in a concentration of 1% w/v. For the injection into the subcutaneous fat tissue Aethoxysklerol® 1% is diluted in a ratio of 1:1 with 2% aqueous lidocaine.
Therapy Regimen
The therapy regimen is summarized at the Table at FIG. 20.
Results
While both treatments (Radiesse (CaHAP) alone or in combination with Ultherapy (MFU)) show a one-point improvement (from 2 to 1) in both Merz Aesthetic scales for cellulite dimples and skin laxity—(both at rest)—however, the onset of this improvement was measurable after the dual combination treatment already after 90 days while it was measurable after monotherapy only on day 180.

The triple combination treatment did not obviously impact the dimple scale but also resulted in an early (detectable already at day 90) one-point improvement in the skin laxity scale.

Figures 22, 23:
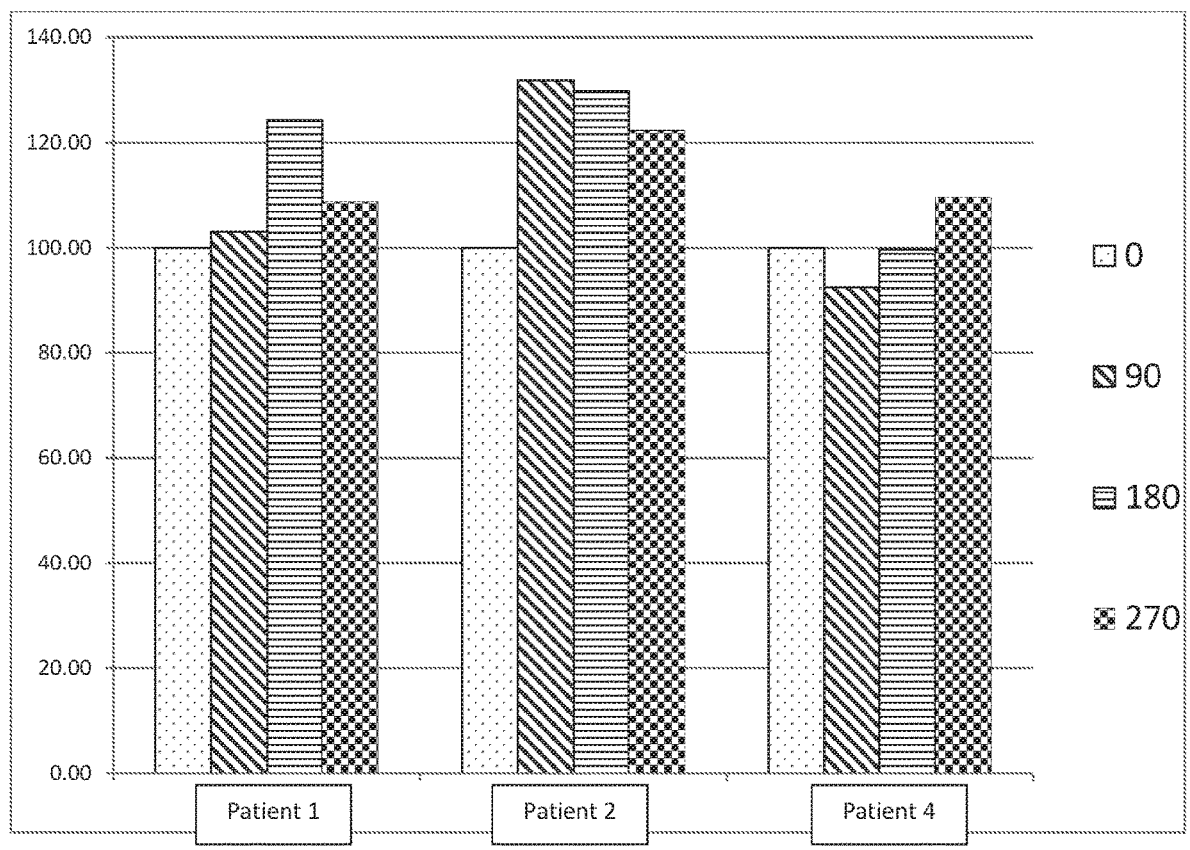
FIG. 22 illustrates a table of skin firmness measurements according to embodiments of cellulite treatment of Example 6 according to FIG. 20.
FIG. 23 illustrates a graph of skin firmness measurements according to embodiments of cellulite treatment of Example 6 according to FIG. 20.

Skin Elasticity
Elasticity of the skin is impacted by elastic and plastic properties resulting in capability to stretch and come back to the original shape. These bending and reshaping curves can be determined numerically using defined suction stretch and digital measurement of skin movement by cutometrie. Determined parameters are the gross-elasticity (R2) and the skin firmness (R0).
Skin Firmness (R0)
Skin firmness was measured on the upper back thigh. See FIGS. 21, 22, and 23.

The mono-treatment with diluted CaHAP resulted in a clear improved R0-value and shows on day 180 after treatment an improvement of about 24% over starting value. On day 270 skin firmness was still improved over starting value but was reduced to an improvement of about 9%.

The dual combo-treatment (patient 2) shows a stronger and faster improvement of the skin firmness as determined by R0 value. On day 90 after treatment an improvement of about 32% of the starting value was determined. Also here this maximum improvement declines thereafter but still exceeds the effect of the mono-treatment with still about 22% improvement after 270 days.

Each patient tested presents an individual cellulite phenotype not fully represented by a single test parameter. However used test-parameter can be used to judge general efficacy of evaluated treatment combination.

Figures 24, 25:
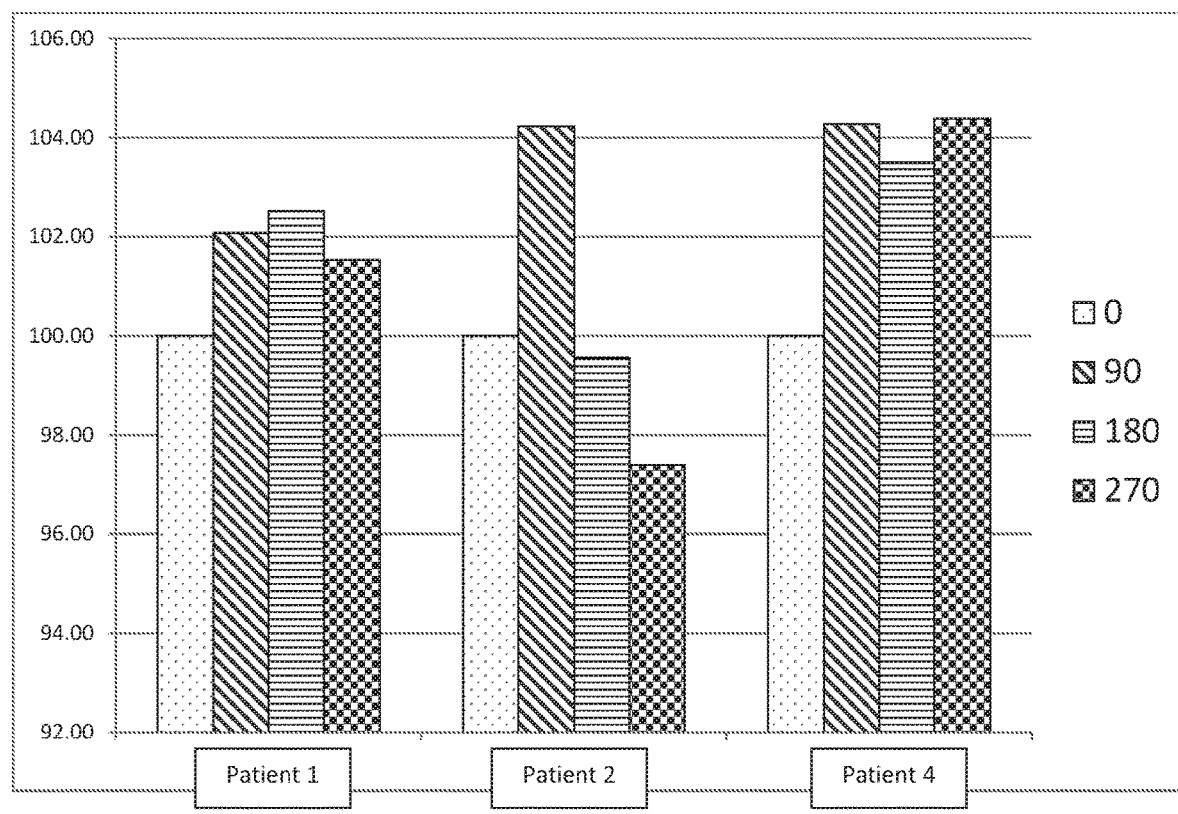
FIG. 24 illustrates a table of gross skin elasticity measurements according to embodiments of cellulite treatment of Example 6 according to FIG. 20.
FIG. 25 illustrates a graph of skin elasticity measurements according to embodiments of cellulite treatment of Example 6 according to FIG. 20.

Also the triple-combination treatment resulted in an improvement of skin firmness. The re-modulation of the fat-cell compartment after treatment with polidocanol resulted in a transient reduction of skin firmness but finally (day 270) resulted also in roughly 10% improvement of skin firmness. While non-inferior to the mono-treatment the effect reached by the triple-combo treatment appears to be more sustainable since skin firmness still not declined within the observation period.
Gross Elasticity (R2)
The gross elasticity was measured at the back of the upper thighs. See FIG. 24.

Figure 26:
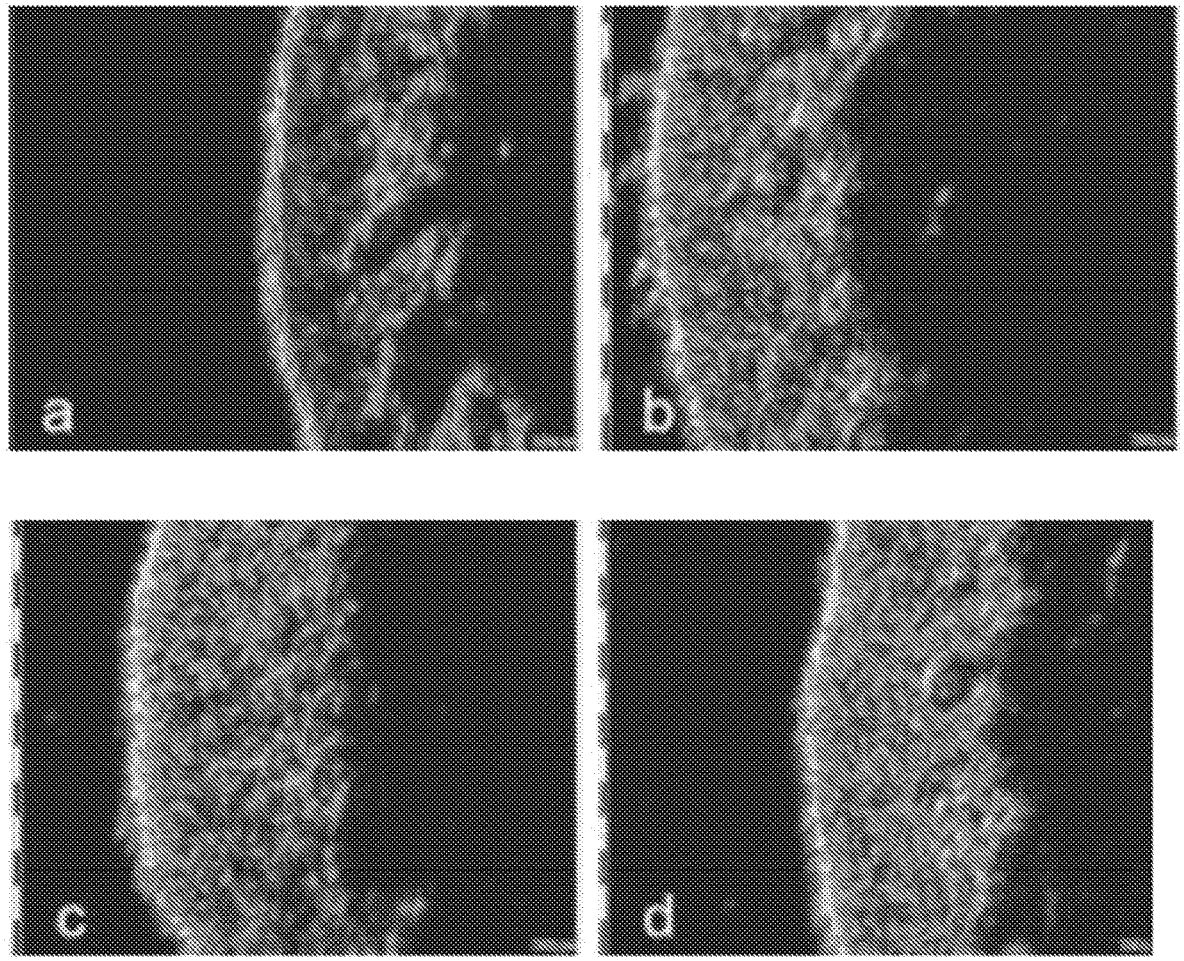
FIG. 26 illustrates images of skin over a period of 0, 90, 180, and 270 days according to embodiments of cellulite treatment of Example 6 according to FIG. 20.
Figure 27:
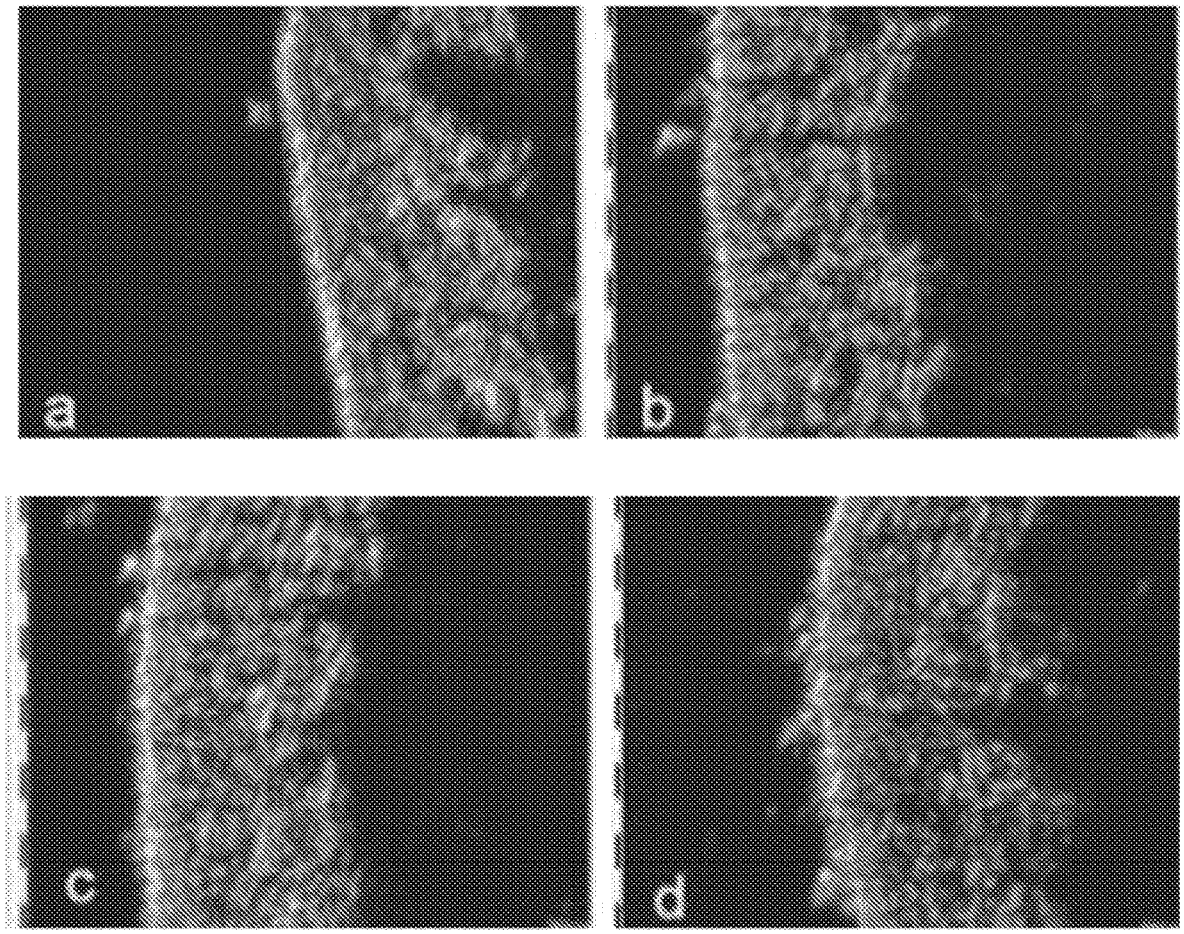
FIG. 27 illustrates images of skin according to embodiments of cellulite treatment of Example 6 according to FIG. 20.

The mono and dual-combo therapy resulted only in a transient improvement of this skin parameter. In contrast the triple-combo therapy resulted in a fast (detectable from day 90 on) and sustainable improvement of the R2-value over a period of 270 days. See FIG. 25.
Skin Thickness
As assessed via 20 MHz sonographic measurements the dual and triple combination therapy improved the skin density (dermis) clearly. Furthermore the fat-protrusions at the dermal-subdermal border are visibly reduced. See FIGS. 26 and 27.

What is claimed is:
1. A method of treating gynoid lipodystrophy, the method comprising:
applying high intensity focused ultrasound (HIFU) therapy to a tissue region below a skin surface;
injecting a first compound into the tissue region treated by the HIFU;
wherein the first compound comprises a dermal filler, wherein the dermal filler comprises calcium hydroxyapatite, and
injecting a second compound into the tissue region treated by the HIFU;
wherein the second compound comprises a fat-reducing compound,
wherein the fat-reducing compound comprises polidocanol,
administering a second treatment 90±10 days later, comprising:

focusing the second HIFU at a depth 1.5 mm below the skin surface,
wherein the second HIFU therapy is applied at 10 MHz,
wherein the second calcium hydroxyapatite is injected in a dermis layer below the skin surface,
wherein the second calcium hydroxyapatite is provided in a final concentration of 25-31% w/w,
wherein the second polidocanol is injected in a subcutaneous fat below the skin surface, and
wherein the second polidocanol is provided in a final concentration of 0.5% w/v;
thereby treating gynoid lipodystrophy.

2. The method of claim 1, further comprising reapplying HIFU after the dermal filler is injected to harden the dermal filler.

3. The method of claim 1, further comprising
focusing the HIFU at a depth 1.5 mm below the skin surface,
wherein the HIFU therapy is applied at 10 MHz,
wherein the calcium hydroxyapatite is provided in a final concentration of 25-31% w/w,
wherein the polidocanol is provided in a final concentration of 0.5% w/v.

4. The method of claim 1,
wherein the second calcium hydroxyapatite is provided in a final concentration of 25% w/w.

5. The method of claim 1, wherein the calcium hydroxyapatite is provided in a final concentration of 25-31% w/w and wherein the polidocanol is provided in a final concentration of 0.5% w/v.

6. The method of claim 1, further comprising reapplying HIFU after the dermal filler is injected, thereby modifying a viscosity of the dermal filler by the application of HIFU, and shaping the dermal filler into a designed structure by the application of HIFU.

7. The method of claim 1, further comprising dissecting at least one septa in the dermis layer with a septae dissection technology.

8. The method of claim 1, further comprising
administering the dermal filler by local injection into a dermal tissue, a subcutaneous fat tissue, or both the dermal tissue and the subcutaneous fat tissue.

9. The method of claim 1, further comprising
focusing the HIFU at fat tissue, wherein two or more simultaneous focused ultrasound treatments heat up portions of the fat tissue.

10. A method for cosmetically treating gynoid lipodystrophy comprising:
administering to a subject in need thereof an effective amount of HIFU energy and at least one of a dermal filler and a fat-reducing compound,
administering a second treatment 90±10 days later a second HIFU energy and a dermal filler comprising calcium hydroxyapatite and a fat-reducing compound comprising polidocanol, comprising:
focusing the second HIFU energy at a depth 1.5 mm below a skin surface,
wherein the second HIFU therapy is applied at 10 MHz,
wherein the calcium hydroxyapatite is injected in a dermis layer below the skin surface,
wherein the calcium hydroxyapatite is provided in a final concentration of 25-31% w/w,
wherein the polidocanol is injected in a subcutaneous fat below the skin surface, and
wherein the polidocanol is provided in a final concentration of 0.5% w/v.

11. The method for cosmetically treating gynoid lipodystrophy of claim 10, wherein the HIFU is administered concurrently, sequentially or separately with at least one of the group consisting of: a dermal filler and a fat-reducing compound.

12. The method for cosmetically treating gynoid lipodystrophy of claim 10, wherein the dermal filler comprises calcium (hydroxy)phosphate particles.

13. The method for cosmetically treating gynoid lipodystrophy of claim 10, wherein the fat-reducing compound and the calcium hydroxyapatite are administered concurrently, sequentially or separately.

14. A method for producing an aesthetic ultrasound effect, comprising:
applying ultrasound to a tissue region below a skin surface;
injecting a first compound into the tissue region treated by the ultrasound;
wherein the first compound comprises a dermal filler,
wherein the dermal filler comprises calcium hydroxyapatite, and
injecting a second compound into the tissue region treated by the ultrasound;
wherein the second compound comprises a fat-reducing compound,
wherein the fat-reducing compound comprises polidocanol
administering a second treatment 90±10 days later, comprising:
focusing the second ultrasound at a depth 1.5 mm below the skin surface,
wherein the second ultrasound is applied at 10 MHz,
wherein the second calcium hydroxyapatite is injected in a dermis layer below the skin surface,
wherein the second calcium hydroxyapatite is provided in a final concentration of 25-31% w/w,
wherein the second polidocanol is injected in a subcutaneous fat below the skin surface, and
wherein the second polidocanol is provided in a final concentration of 0.5% w/v.

15. The method of claim of 14, further comprising applying a cavitation-prone agent to the tissue region treated by the ultrasound.

16. The method of claim of 14, further comprising applying an additional energy source to the tissue region treated by the ultrasound.

17. The method of claim 16, wherein the additional energy source comprises one or more of the group consisting of: visible light, laser, radio-frequency, microwave, electromagnetic, cryogenic, electron beam, and magnetic energy.

18. The method of claim 14, wherein said ultrasound comprises high intensity focused ultrasound (HIFU).

19. The method of claim 14, wherein the dermal filler comprises calcium (hydroxy)phosphate particles selected from the group consisting of: monocalcium phosphate (MCP), dicalcium phosphate (DCP), calcium dihydrogen phosphate (CDP), tricalcium phosphate (TCZ) including its α-, α'- and β-polymorphs, octacalcium phosphate (OCP), biphasic tricalcium phosphate (BCP), and hydroxyapatite.

20. The method of claim 14, wherein the aesthetic ultrasound effect comprises at least one of the group consisting of: a cellulite treatment, reducing wrinkles, sagging and/or laxity of the skin, reducing fat, body sculpting, and facial sculpting.

* * * * *